(12) United States Patent
Roberts et al.

(10) Patent No.: US 11,312,971 B2
(45) Date of Patent: *Apr. 26, 2022

(54) ENHANCED ACYLTRANSFERASE POLYNUCLEOTIDES, POLYPEPTIDES AND METHODS OF USE

(71) Applicant: Agresearch Limited, Hamilton (NZ)

(72) Inventors: Nicholas John Roberts, Feilding (NZ); Amy Christina Curran, San Diego, CA (US); Somrutai Winichayakul, Palmerston North (NZ); Marissa Roldan, Palmerston North (NZ); Richard William Scott, Palmerston North (NZ)

(73) Assignee: Agresearch Limited, Hamilton (NZ)

(*) Notice: Subject to any disclaimer, the term of this patent is extended or adjusted under 35 U.S.C. 154(b) by 391 days.

This patent is subject to a terminal disclaimer.

(21) Appl. No.: 14/438,758

(22) PCT Filed: Oct. 22, 2013

(86) PCT No.: PCT/IB2013/059524
§ 371 (c)(1),
(2) Date: Apr. 27, 2015

(87) PCT Pub. No.: WO2014/068437
PCT Pub. Date: May 8, 2014

(65) Prior Publication Data
US 2015/0275223 A1    Oct. 1, 2015

Related U.S. Application Data

(60) Provisional application No. 61/720,069, filed on Oct. 30, 2012.

(51) Int. Cl.
*C12N 15/82* (2006.01)
*C12N 9/10* (2006.01)
*C12P 7/64* (2022.01)

(52) U.S. Cl.
CPC .... *C12N 15/8247* (2013.01); *C12Y 203/0102* (2013.01); *C12N 9/1029* (2013.01); *C12P 7/64* (2013.01)

(58) Field of Classification Search
CPC ............ C12Y 203/0102; C12N 15/8247
See application file for complete search history.

(56) References Cited

U.S. PATENT DOCUMENTS

| | | |
|---|---|---|
| 4,795,855 A | 1/1989 | Fillatti et al. |
| 4,943,674 A | 7/1990 | Houck et al. |
| 5,004,863 A | 4/1991 | Umbeck |
| 5,086,169 A | 2/1992 | Mascarenhas |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,412,085 A | 5/1995 | Allen et al. |
| 5,416,011 A | 5/1995 | Hinchee et al. |
| 5,463,174 A | 10/1995 | Moloney et al. |
| 5,536,653 A | 7/1996 | Barry et al. |
| 5,545,169 A | 8/1996 | Yarger |
| 5,545,546 A | 8/1996 | Allen et al. |
| 5,563,055 A | 10/1996 | Townsend et al. |
| 5,569,834 A | 10/1996 | Hinchee et al. |
| 5,591,616 A | 1/1997 | Hiei et al. |
| 5,608,150 A | 3/1997 | Conner |
| 5,639,952 A | 6/1997 | Quail et al. |
| 5,656,496 A | 8/1997 | Quail et al. |
| 5,750,385 A | 5/1998 | Shewmaker et al. |
| 5,750,871 A | 5/1998 | Moloney et al. |
| 5,792,935 A | 8/1998 | Arntzen et al. |
| 5,795,855 A | 8/1998 | Schneider et al. |
| 5,824,877 A | 10/1998 | Hinchee et al. |
| 5,837,848 A | 11/1998 | Ely et al. |

(Continued)

FOREIGN PATENT DOCUMENTS

WO   WO 1998/055631 A1   12/1998
WO   WO 2000/001713 A2   1/2000

(Continued)

OTHER PUBLICATIONS

Xu et al (Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content. Plant Biotechnology Journal 6:799-818, 2008).*
Yen et al (DGAT enzymes and triacylglycerol biosynthesis. Journal of Lipid Research vol. 49, 2283-2301, 2008).*
McFie et al (Topological Orientation of Acyl-CoA:Diacylglycerol Acyltransferase-1 (DGAT 1) and Identification of a Putative Active Site Histidine and the Role of the N Terminus in Dimer/Tetramer Formation. The Journal of Biological Chemistry vol. 285, No. 48, pp. 37377-37387, Nov. 26, 2010).*
Ling (Oleosin fusion expression systems for the production of recombinant proteins. Biologia, Bratislava, 62/2: 119-123, 2007).*
Xu et al (Cloning and characterization of an acyl-CoA-dependent diacylglycerol acyltransferase 1 (DGAT1) gene from Tropaeolum majus, Plant Biotechnology Journal 6:799-818, 2008) (Year: 2008).*

(Continued)

*Primary Examiner* — Bratislav Stankovic
*Assistant Examiner* — Wayne Zhong
(74) *Attorney, Agent, or Firm* — Leydig, Volt & Mayer, Ltd.

(57) ABSTRACT

The invention provides modified DGAT1 proteins that are modified in the N-terminal region upstream of the acyl-Co A binding site. The modified DGAT proteins show enhanced activity, without reduced protein accumulation when expressed in cells. The modified DGAT1 proteins of the invention can be expressed in cells to increase cellular lipid accumulation and/or modify the cellular lipid profile. The invention also provides polynucleotides encoding the modified DGAT1 proteins, cells and compositions comprising the polynucleotides or modified DGAT proteins, and methods using the modified DGAT1 proteins to produce oil.

27 Claims, 9 Drawing Sheets

Specification includes a Sequence Listing.

(56) References Cited

U.S. PATENT DOCUMENTS

| | | | |
|---|---|---|---|
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 6,100,077 | A | 8/2000 | Sturley et al. |
| 6,127,179 | A | 10/2000 | DellaPenna et al. |
| 6,184,443 | B1 | 2/2001 | Pedersen et al. |
| 6,228,643 | B1 | 5/2001 | Greenland et al. |
| 6,229,067 | B1 | 5/2001 | Sonnewald et al. |
| 6,342,657 | B1 | 1/2002 | Thomas et al. |
| 6,344,548 | B1 | 2/2002 | Farese, Jr. et al. |
| 7,081,565 | B2 | 7/2006 | Ohlrogge et al. |
| 7,141,424 | B2 | 11/2006 | Shin et al. |
| 7,153,953 | B2 | 12/2006 | Marraccini et al. |
| 7,371,928 | B2 | 5/2008 | Suh et al. |
| 7,405,345 | B2 | 7/2008 | Ohlrogge et al. |
| 7,629,454 | B2 | 12/2009 | Chan et al. |
| 7,642,346 | B2 | 1/2010 | Chaudhary et al. |
| 7,667,097 | B2 | 2/2010 | Scheirlinck et al. |
| 7,745,697 | B2 | 6/2010 | Perez et al. |
| 9,957,519 | B2 * | 5/2018 | Roberts ............... C12N 9/1029 |
| 2001/0047525 | A1 | 11/2001 | Bruce et al. |
| 2003/0115632 | A1 | 6/2003 | Lardizabal et al. |
| 2004/0067506 | A1 | 4/2004 | Scheres et al. |
| 2009/0094717 | A1 | 4/2009 | Troukhan et al. |
| 2010/0024079 | A1 | 1/2010 | Andersen et al. |
| 2010/0184130 | A1 * | 7/2010 | Koprowski ........ C12N 15/8247 435/41 |
| 2011/0167514 | A1 | 7/2011 | Brover et al. |
| 2011/0190165 | A1 * | 8/2011 | Weselake ............. C12N 9/1051 506/11 |
| 2012/0156360 | A1 | 6/2012 | Roesler et al. |
| 2015/0252378 | A1 * | 9/2015 | Roberts ............... C12N 9/1029 435/134 |
| 2015/0284736 | A1 | 10/2015 | Roberts et al. |

FOREIGN PATENT DOCUMENTS

| | | |
|---|---|---|
| WO | WO 2000/032756 A2 | 6/2000 |
| WO | WO 2002/000894 A2 | 1/2002 |
| WO | WO 2004/011671 A2 | 2/2004 |
| WO | WO 2006/052914 A1 | 5/2006 |
| WO | WO 2009/143397 A2 | 11/2009 |
| WO | WO 2011/053169 A1 | 5/2011 |

OTHER PUBLICATIONS

McFie et al (Topological Orientation of Acyl-CoA:Diacylglycerol Acyltransferase-1 (DGAT1) and Identification of a Putative Active Site Histidine and the Role of the N Terminus in Dimer/Tetramer Formation. The Journal of Biological Chemistry vol. 285, No. 48, pp. 37377-37387, Nov. 26, 2010) (Year: 2010).*
Yen et al (DGAT enzymes and triacylglycerol biosynthesis. Journal of Lipid Research vol. 49, 2283-2301, 2008) (Year: 2008).*
Schnable et al (The B73 Maize Genome: Complexity, Diversity, and Dynamics. Science. 326:1112-1115, 2009). (Year: 2009).*
Ling (Oleosin fusion expression systems for the production of recombinant proteins. Biologia, Bratislava, 62/2: 119-123, 2007) (Year: 2007).*
Sun et al (Newly Identified Essential Amino Acids Affecting Chlorella ellipsoidea DGAT1 Function Revealed by Site-Directed Mutagenesis. Int. J. Mol. Sci., 19, 3462, 1-13, 2018) (Year: 2018).*
Wang et al (Cloning and comparative analysis of the gene encoding diacylglycerol acyltransferase from wild type and cultivated soybean. Theor Appl Genet 112: 1086-1097, 2006) (Year: 2006).*
Schnable et al (The B73 Maize Genome: Complexity, Diversity, and Dynamics. Science 326: 1112-1115, Jun. 2012) (Year: 2012).*
Alam et al. (1999) "Transgenic insect-resistant maintainer line (IR68899B) for improvement of hybrid rice," Plant Cell Rep. 18:572-575.
Altpeter et al. (2004) "Comparison of Transgene Expression Stability after Agrobacterium-mediated or Biolistic Gene Transfer into Perennial Ryegrass (Lolium perenne L.)," Developments in Plant Breeding. 11(7):255-260.
Altschul et al. (1997) "Gapped BLAST and PSI-BLAST: a new generation of protein database search programs," Nucleic Acids Res. 25:3389-3402.
Andrianov et al. (2009) "Tobacco as a production platform for biofuel: overexpression of Arabidopsis DGAT and LEC2 genes increases accumulation and shifts the composition of lipids in green biomass," Plant Biotechnol. J. 8:277-287.
Bairoch et al. (1994) "PROSITE: recent developments," Nucleic Acids Res. 22:3583-3589.
Baxevanis (2001) "The Molecular Biology Database Collection: an updated compilation of biological database resources," Nucleic Acids Res. 29:1-10.
Beopoulos et al. (Mar. 31, 2011) "An overview of lipid metabolism in yeasts and its impacton biotechnological processes," Appl. Microbiol. Biotechnol. 90:1193-1206.
Birch (1997) "Plant Transformations: Problems and Strategies for Practical Applications," Ann. Rev. Plant Phys. Plant Mol. Biol. 48:297-326.
Birney et al. (2004) "GeneWise and Genomewise," Genome Res. 14:988-995.
Bolton et al. (1962) "A General Method for the Isolation of RNA Complementary to DNA," Proc. Natl. Acad. Sci. USA. 48:1390-1397.
Bouvier-Navé et al. (2000) "Expression in yeast and tobacco of plant cDNAs encoding acyl CoA:diacylglycerol acyltransferase," Eur. J. Biochem. 267:85-96.
Bowie et al. (1990) "Deciphering the message in protein sequences: tolerance to amino acid substitutions," Science. 247:1306-1310.
Browse et al. (1986) "Fatty acid composition of leaf lipids determined after combined digestion and fatty acid methyl ester formation from fresh tissue," Anal. Biochem. 152:141-145.
Cahoon et al. (2007) "Engineering oilseeds for sustainable production of industrial and nutritional feedstocks: solving bottlenecks in fatty acid flux," Current Opinion in Plant Biology. 10:236-244.
Cardoza et al. (2006) "Canola (Brassica napus L.)," Methods Mol. Biol. 343:257-266.
Christou et al. (1991) "Production of Transgenic Rice (Oryza sativa L.) Plants from Agronomically Important Indica and Japonica Varieties via Electric Discharge Particle Acceleration of Exogenous DNA into Immature Zygotic Embryos," Nature Biotech. 9:957-962.
Clough et al. (1998) "Floral dip: a simplified method for Agrobacterium-mediated transformation of Arabidopsis thaliana," Plant J. 16(6):735-743.
Dan et al. (2006) "MicroTom—a high-throughput model transformation system for functional genomics," Plant Cell Reports. 25:432-441.
Durrett et al. (2008) "Plant triacylglycerols as feedstocks for the production of biofuels," Plant J. 54:593-607.
Elble (1992) "A simple and efficient procedure for transformation of yeasts," BioTechniques. 13:18-20.
Ellerström et al. (1996) "Functional dissection of a napin gene promoter: identification of promoter elements required for embryo and endosperm-specific transcription," Plant Molecular Biology. 32(6):1019-1027.
Falquet et al. (2002) "The PROSITE database, its status in 2002," Nucleic Acids Res. 30:235-238.
Feng et al. (1987) "Progressive sequence alignment as a prerequisite to correct phylogenetic trees," J. Mol. Evol. 25:351-360.
Folta et al. (2006) "Characterization of LF9, an octoploid strawberry genotype selected for rapid regeneration and transformation," Planta. 224(5):1058-1067.
Fortman et al. (2008) "Biofuel alternatives to ethanol: pumping the microbial well," Trends Biotechnol. 26:375-381.
Frohman (1993) "Rapid amplification of complementary DNA ends for generation of full-length complementary DNAs: thermal RACE," Methods Enzymol. 218:340-356.

(56) References Cited

OTHER PUBLICATIONS

GenBank (Jul. 25, 2006) "diacylglycerol acyltransferase [*Oryza sativa* Japonica Group]," Accession No. AAW47581. Accessible on the Internet at URL: http://www.ncbi.nlm.nih.gov/protein/AAW47581. [Last Accessed Dec. 17, 2015].

GenBank (Feb. 25, 2009) "unknown [*Zea mays*]," Accession No. ACN35495. Accessible on the Internet at URL: http://www.ncbi.nlm.nih.gov/protein/ACN35495. [Last Accessed Dec. 17, 2015].

Giesen et al. (1998) "A formula for thermal stability (Tm) prediction of PNA/DNA duplexes," Nucleic Acids Res. 26(21):5004-5006.

Gonzalez Padilla et al. (2003) "Early antibiotic selection and efficient rooting and acclimatization improve the production of transgenic plum plants (*Prunus domestica* L.)," Plant Cell Rep. 22(1):38-45.

Graham et al. (1995) "Agrobacterium-mediated transformation of soft fruit Rubus, Ribes, and Fragaria," Methods Mol. Biol. 44:129-133.

Guiheneuf et al. (2011) "Cloning and molecular characterization of a novel acyl-CoA:diacylglycerol acyltransferase 1-like gene (PtDGAT1) from the diatom Phaeodactylum tricornutum," The FEBS Journal. 278:3651-3666.

Halford et al. (1998) "SNF1-related protein kinases: global regulators of carbon metabolism in plants?" Plant Mol. Biol. 37:735-748.

Hellens et al. (2000) "pGreen: a versatile and flexible binary Ti vector for Agrobacterium-mediated plant transformation," Plant Mol. Biol. 42:819-832.

Hellens et al. (2005) "Transient expression vectors for functional genomics, quantification of promoter activity and RNA silencing in plants," Plant Methods. 1:13 pp. 1-14.

Herrera-Estrella et al. (1993) "Expression of chimaeric genes transferred into plant cells using a Ti-plasmid-derived vector," Nature. 303:209-213.

Hofmann et al. (1999) "The PROSITE database, its status in 1999," Nucleic Acids Res. 27:215-219.

Horsch et al. (1985) "A simple and general method for transferring genes into plants," Science. 227:1229-1231.

Huang (1994) "On Global Sequence Alignment," Computer Applications in the Biosciences. 10:227-235.

James et al. (Sep. 27, 2010) "Disruption of the *Arabidopsis* CGI-58 homologue produces Chanarin-Dorfman-like lipid droplet accumulation in plants," Proc. Natl. Acad. Sci. USA. 107:17833-17838.

Jang et al. (2006) "Functional classification, genomic organization, putatively cis-acting regulatory elements, and relationship to quantitative trait loci, of sorghum genes with rhizome-enriched expression," Plant Physiol. 142:1148-1159.

Jeanmougin et al. (1998) "Multiple sequence alignment with Clustal X," Trends Biochem. Sci. 23:403-405.

Josefsson et al. (1987) "Structure of a gene encoding the 1.7 S storage protein, napin, from *Brassica napus*," J. Biol. Chem. 262(25):12196-12201.

Kaup et al. (2002) "A role for diacylglycerol acyltransferase during leaf senescence," Plant Physiol. 129(4):1616-1626.

Krens et al. (1997) "Transgenic caraway, *Carum carvi* L.: a model species for metabolic engineering," Plant Cell Rep. 17:39-43.

Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.

Li et al. (1996) "Genetic transformation of cassava (*Manihot esculenta* Crantz)," Nat. Biotechnol. 14:736-740.

Li et al. (2003) "Transgenic rose lines harboring an antimicrobial protein gene, Ace-AMP1, demonstrate enhanced resistance to powdery mildew (*Sphaerotheca pannosa*)," Planta. 218:226-232.

Li et al. (Jan. 27, 2010) "DGAT1, DGAT2 and PDAT expression in seeds and other tissues of epoxy and hydroxy fatty acid accumulating plants," Lipids. 45:145-157.

Lung et al. (2006) "Diacylglycerol acyltransferase: a key mediator of plant triacylglycerol synthesis," Lipids. 41(12):1073-1088.

Matsuda et al. (2005) "Development of an Agrobacterium-mediated transformation method for pear (*Pyrus communis* L.) with leaf-section and axillary shoot-meristem explants," Plant Cell Rep. 24(1):45-51.

McFie et al. (Sep. 27, 2010) "Topological orientation of acyl-CoA:diacylglycerol acyltransferase-1 (DGAT1) and identification of a putative active site histidine and the role of the n terminus in dimer/tetramer formation," J. Biol. Chem. 285:37377-37387.

Michelmore et al. (1987) "Transformation of lettuce (*Lactuca sativa*) mediated by Agrobacterium tumefaciens," Plant Cell Rep. 6:439-442.

Moloney et al. (1989) "High efficiency transformation of *Brassica napus* using Agrobacterium vectors," Plant Cell Rep. 8:238-242.

Mu et al. (2008) "LEAFY COTYLEDON1 is a key regulator of fatty acid biosynthesis in *Arabidopsis*," Plant Physiol. 148:1042-1054.

Needleman et al. (1970) "A general method applicable to the search for similarities in the amino acid sequence of two proteins," J. Mol. Biol. 48:443-453.

Nielsen et al. (1991) "Sequence-selective recognition of DNA by strand displacement with a thymine-substituted polyamide," Science. 254(5037):1497-1500.

Niu et al. (1998) "Transgenic peppermint (*Mentha x piperita* L.) plants obtained by cocultivation with Agrobacterium tumefaciens," Plant Cell Rep. 17:165-171.

Notredame et al. (2000) "A novel method for fast and accurate multiple sequence alignment," J. Mol. Biol. 302:205-217.

Nykiforuk et al. (2002) "Characterization of cDNAs encoding diacylglycerol acyltransferase from cultures of *Brassica napus* and sucrose-mediated induction of enzyme biosynthesis," Biochimica et Biophysica Acta. 1580:95-109.

Ohlrogge et al. (2009) "Energy. Driving on biomass," Science. 324:1019-1020.

Oosumi et al. (2006) "High-efficiency transformation of the diploid strawberry (*Fragaria vesca*) for functional genomics," Planta. 223(6):1219-1230.

Orlikowska et al. (1995) "Factors influencing Agrobacterium tumefaciens-mediated transformation and regeneration of the safflower cultivar 'centennial,'" Plant Cell Tissue and Organ Culture. 40:85-91.

Ortiz et al. (1996) "Hygromycin resistance as an efficient selectable marker for wheat stable transformation," Plant Cell Rep. 15:877-881.

Pena et al. (1995) "High efficiency Agrobacterium-mediated transformation and regeneration of citrus," Plant Sci.104:183-191.

Potrykus et al.: Eds. (1995) Gene Transfer to Plants. Springer-Verlag. Berlin, Germany, pp. i-xxii.

Ramesh et al. (2006) "Improved methods in Agrobacterium-mediated transformation of almond using positive (mannose/pmi) or negative (kanamycin resistance) selection-based protocols," Plant Cell Rep. 25(8):821-828.

Rice et al. (2000) "EMBOSS: The European Molecular Biology Open Software Suite," Trends in Genetics. 16(6):276-277.

Rose et al. (1989) "KAR2, a karyogamy gene, is the yeast homolog of the mammalian BiP/GRP78 gene," Cell. 57:1211-1221.

Salse et al. (2008) "Identification and characterization of shared duplications between rice and wheat provide new insight into grass genome evolution," Plant Cell. 20:11-24.

Sandager et al. (2002) "Storage lipid synthesis is non-essential in yeast," The Journal of Biological Chemistry. 277:6478-6482.

Sanjaya et al. (Oct. 2011) "Increasing the energy density of vegetative tissues by diverting carbon from starch to oil biosynthesis in transgenic *Arabidopsis*," Plant Biotechnol. J. 9:874-883.

Santos-Mendoza et al. (2008) "Deciphering gene regulatory networks that control seed development and maturation in *Arabidopsis*," Plant J. 54:608-620.

Schenk et al. (2001) "Promoters for pregenomic RNA of banana streak badnavirus are active for transgene expression in monocot and dicot plants," Plant Molecular Biology. 47:399-412.

Schrott (1995) "Selectable Marker and Reporter Genes," Ch. 31 In; Potrykus et al.: Eds. Gene Transfer to Plants. Springer-Verlag. Berlin, Germany, pp. 325-336.

(56) References Cited

OTHER PUBLICATIONS

Scott et al. (Oct. 2010) "Elevation of oil body integrity and emulsion stability by polyoleosins, multiple oleosin units joined in tandem head-to-tail fusions," Plant Biotechnology Journal. 8:912-927.

Shockey et al. (2006) "Tung tree DGAT1 and DGAT2 have nonredundant functions in triacylglycerol biosynthesis and are localized to different subdomains of the endoplasmic reticulum," Plant Cell. 18:2294-2313.

Smeets et al. (1997) "Developmental Regulation of Lectin and Alliinase Synthesis in Garlic Bulbs and Leaves," Plant Physiol. 113:765-771.

Song et al. (2005) "Transformation of Montmorency sour cherry (*Prunus cerasus* L.) and Gisela 6 (*P. cerasus x P. canescens*) cherry rootstock mediated by Agrobacterium tumefaciens," Plant Cell Rep. 25(2):117-123.

Tatusova et al. (1999) "Blast 2 sequences—a new tool for comparing protein and nucleotide sequences," FEMS Microbiol. Lett. 174:247-250.

Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.

Thompson et al. (1994) "Clustal W: improving the sensitivity of progressive multiple sequence alignment through sequence weighting, position-specific gap penalties and weight matrix choice," Nucleic Acids Res. 22:4673-4680.

Triglia et al. (1988) "A procedure for in vitro amplification of DNA segments that lie outside the boundaries of known sequences," Nucleic Acids Res. 16:8186.

Wang et al. (2006) "Transformation of Actinidia eriantha: a potential species for functional genomics studies in Actinidia," Plant Cell Rep. 25(5):425-431.

Wang et al. (2009) "Maize Transformation," In; Handbook of Maize. Bennetzen, J. L.; Hake, S. C.: Eds. Springer-Verlag. New York, New York. pp. 609-639.

Wheeler et al. (2001) "Database resources of the National Center for Biotechnology Information," Nucleic Acids Res. 29:11-16.

Winichayakul et al. (2009) "Head-to-tail fusions of camelid antibodies can be expressed in planta and bind in rumen fluid," Biotechnol. Appl. Biochem. 53:111-122.

Xu et al. (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content," Plant Biotechnol. J. 6:799-818.

Yang et al. (2009) "Turnover of fatty acids during natural senescence of *Arabidopsis*, Brachypodium, and switchgrass and in *Arabidopsis* beta-oxidation mutants," Plant Physiol. 150:1981-1989.

Yao et al. (1995) "Regeneration of transgenic plants from the commercial apple cultivar Royal Gala," Plant Cell Reports. 14:407-412.

\* cited by examiner

```
   1  TGAATCCTTT TTCCTTTCTT CTTCTTCTTC TCTTCAGAGA AAACTTTGCT
  51  TCTCTTTCTA TAAGGAACCA GACACGAATC CCATTCCCAC CGATTTCTTA
 101  GCTTCTTCCT TCAATCCGCT CTTTCCCTCT CCATTAGATT CTGTTTCCTC
 151  TTTCAATTTC TTCTGCATGC TTCTCGATTC TCTCTGACGC CTCTTTTCTC
                                              M  A  I  L  D  S  A·
 201  CCGACGCTGT TTCGTCAAAC GCTTTTCGAA ATGGCGATTT TGGATTCTGC
       ·G  V  T     T  V  T  E     N  G  G     G  E  F     V  D  L  D·
 251  TGGCGTTACT ACGGTGACGG AGAACGGTGG CGGAGAGTTC GTCGATCTTG
       ·R  L  R     R  R  K     S  R  S  D     S  S  N     G  L  L
 301  ATAGGCTTCG TCGACGGAAA TCGAGATCGG ATTCTTCTAA CGGACTTCTT
        L  S  G  S     D  N  N     S  P  S     D  D  V     G  A  P  A·
 351  CTCTCTGGTT CCGATAATAA TTCTCCTTCG GATGATGTTG GAGCTCCCGC
       ·D  V  R     D  R  I  D     S  V  V     N  D  D     A  Q  G  T·
 401  CGACGTTAGG GATCGGATTG ATTCCGTTGT TAACGATGAC GCTCAGGGAA
       ·A  N  L     A  G  D     N  N  G  G     G  D  N     N  G  G
 451  CAGCCAATTT GGCCGGAGAT AATAACGGTG GTGGCGATAA TAACGGTGGT
        G  R  G  G     G  E  G     R  G  N     A  D  A     F  T  Y·
 501  GGAAGAGGCG GCGGAGAAGG AAGAGGAAAC GCCGATGCTA CGTTTACGTA
       ·R  P  S     V  P  A  H     R  R  A     R  E  S     P  L  S  S·
 551  TCGACCGTCG GTTCCAGCTC ATCGGAGGGC GAGAGAGAGT CCACTTAGCT
       ·D  A  I     F  K  Q
 601  CCGACGCAAT CTTCAAACAG GTTAAAATC TCAGAAATCT TCGAATTTGG
 651  TGTTTGCTTG TTGTTTTATA TGGAATTGAG TTTGGTGATT GTTTTGCATT
       ·Q  S  H     A  G  L  F     N  L  C     V  V  V     L  I  A  V·
 701  GCAGAGCCAT GCCGGATTAT TCAACCTCTG TGTAGTAGTT CTTATTGCTG
       ·N  S  R     L  I  I     E  N  L  M     K
 751  TAAACAGTAG ACTCATCATC GAAAATCTTA TGAAGGTTTG CTGTTACTTG
 801  TTTCTCCTTT TAGGAATTGA ATTGCTTGAA AATTTATCAG AGACGAATAA
       ·                                       Y  G  W  L  I  R  T  D
 851  CTTTGTTGTT GCTATCATTC ATGTAGTATG GTTGGTTGAT CAGAACGGAT
        F  W  F  S     S  R  S     L  R  D     W  P  L  F     M  C  W·
 901  TTCTGGTTTA GTTCAAGATC GCTGCGAGAT TGGCCGCTTT TCATGTGTTG
 951  GTAAAAGAAG ATGTTTTTTA TTTCCAGCAA TGTTACATTG TTATACGTAT
1001  AATGATGAGT TTAGTGATCA AGTTCCTCTT TGATTCTTCT TTCTTGTTGC
        I  S  L     S  I  F     P  L  A     A  F  T  V     E  K  L·
1051  AGTATATCCC TTTCGATCTT TCCTTTGGCT GCCTTTACGG TTGAGAAATT
       ·V  L  Q     K  Y  I  S     E  P
1101  GGTACTTCAG AAATACATAT CAGAACCTGT GAGTAATTAC TATTCTCCAG
1151  CCATTACTGT AATTTTATT GAAGACAAGT TTGTATCATG AAGAACTTAC
```

Figure 1

```
                                          V  V  I  F  L  H  I  I  I  ·
1201  AAGTTCTGTT TTGAAAATGC TCAAGGTTGT CATCTTTCTT CATATTATTA

·  T  M  T  E  V  L  Y  P  V  Y  V  T  L  R
1251  TCACCATGAC AGAGGTTTTG TATCCAGTTT ACGTCACCCT AAGGTGATAC

1301  TGTTTTTCTG GTCTCAGTTT GTGATACTGT TTTTAAGTTT AGTTGTCTGA

C  D  S  A  F  L  S  G  V  ·
1351  CCCGGTGATC TTGAAAATGG ACAGGTGTGA TTCTGCTTTT TTATCAGGTG

·  T  L  M  L  L  T  C  I  V  W  L  K  L  V  S  Y
1401  TCACTTTGAT GCTCCTCACT TGCATTGTGT GGCTAAAGTT GGTTTCTTAT

A  H  T  S  Y  D  I  R  S  L  A  N  A  A  D  K
1451  GCTCATACTA GCTATGACAT AAGATCCCTA GCCAATGCAG CTGATAAGGT

1501  AAAATACGAA AAAGAAGCGT ATGTATTAGT CACTTGCACT GTGTTACTGT

A  N  P  E  V  S  Y  Y  ·
1551  TTTAACCAAA CACTGTTATG AACTTTAGGC CAATCCTGAA GTCTCCTACT

·  V  S  L  K  S  L  A  Y  F  M  V  A  P  T  L  C
1601  ACGTTAGCTT GAAGAGCTTG GCATATTTCA TGGTCGCTCC CACATTGTGT

Y  Q
1651  TATCAGGTAA CTGCAAAGTG CATCAACCAT TCTTATACTT GCAAGAGTTT

P  S  Y  P  R  S  ·
1701  CTTGTCTAAA CCTCGGATCT TGCTTTTCC CCAGCCAAGT TATCCACGTT

·  A  C  I  R  K  G  W  V  A  R  Q  F  A  K  L  V
1751  CTGCATGTAT ACGGAAGGGT TGGGTGGCTC GTCAATTTGC AAAACTGGTC

I  F  T  G  F  M  G  F  I  I  E  Q
1801  ATATTCACCG GATTCATGGG ATTTATAATA GAACAAGTAC GTTTTCACAT

1851  CTTGCTTTAT TAGTTTTCCT TGGTGAAAAT CATCATCCCT GCGTTGTCAC

Y  I  N  P  I  ·
1901  CACTTGACTT CATGTTCTTT TGTTACATTT TGGCAGTATA TAAATCCTAT

·  V  R  N  S  K  H  P  L  K  G  D  L  L  Y  A  I  E  ·
1951  TGTCAGGAAC TCAAAGCATC CTTTGAAAGG CGATCTTCTA TATGCTATTG

·  R  V  L  K  L  S  V  P  N  L  Y  V  W  L  C  M
2001  AAAGAGTGTT GAAGCTTTCA GTTCCAAATT TATATGTGTG GCTCTGCATG

F  Y  C  F  F  H  L  W
2051  TTCTACTGCT TCTTCCACCT TTGGTATGCT GTGATCCCAT CTCTTTCAAA

2101  ATAATTTGCA AATTCGAAAA ACCGAAAAAG GCTAAATCTC ATACGAATTT

2151  GATATTTTTA GTTTCTTAGA GTCGGTGATG TAATTTCAGT TACTGAACGC

L  N  I  L  A  E  L  L  C  F  G  ·
2201  AAATCTCTTG TCCAAAGGTT AAACATATTG GCAGAGCTTC TCTGCTTCGG

·  D  R  E  F  Y  K  D  W  W  N  A  K  S  V  G  D
2251  GGATCGTGAA TTCTACAAAG ATTGGTGGAA TGCAAAAAGT GTGGGAGATG

2301  TGAGCTATTT TACTCAAAAG AAAACTTATG ATTTTTAATG TTGTCGTTGT

2351  TTTGGGTCA TCTAACTAAC CAAATTCATG TATTCACTGT CTTCCTTTAT
```

Figure 1 cont.

```
                   Y  W  R  M  W  N  M
2401 CAGTACTGGA GAATGTGGAA TATGGTATGG TTCTCTTCCT AAACATCACC

2451 TTCTTTTGTA CACAAAATAG AAGAAGAGAG CTAATTAAGA TCTTGTTTTC

P  V  H  K  W  M  V  R  H  I  Y  F  P  C
2501 CTTGACAGCC TGTTCATAAA TGGATGGTTC GACATATATA CTTCCCGTGC

L  R  S  K  I  P  K
2551 TTGCGCAGCA AGATACCAAA GGTGAGTGAG ATATATACCG ATATGCAATT

2601 GTCGAGATTT GTTTCTGTGA TATAAATTTA ACCCTCCACA CACTTGTTTT

T  L  A  I  I  I  A  F  L  V  S  A  V  F  H  E  ·
2651 TCAGACACTC GCCATTATCA TTGCTTTCCT AGTCTCTGCA GTCTTCATG

2701 AGGTATACAT ACTTTCTACA TTGCCCTGTC TCTAGACGCA TGAACACACG

2751 CTAGTGAAAG AAATGCTAAT ATTCAAAGCA TTGTTTTTAC TTAACGATCT

L  C  I  A  V  P  C  R  L  ·
2801 TGTGTTACAA ATTTCCTTTT GACAGCTATG CATCGCAGTT CCTTGTCGTC

·  F  K  L  W  A  F  L  G  I  M  F  Q
2851 TCTTCAAGCT ATGGGCTTTT CTTGGGATTA TGTTTCAGGT TAAAAAATTA

2901 CTAAACTGCT GCAGTCGATT TTTACTAAAC TCTAATCTCA TATTCTGACC

V  P  L  V  F  I  T  N  Y  L  Q  ·
2951 AACCAATTTG TTTGAGTAGG TGCCTTTGGT CTTCATCACA AACTATCTAC

·  E  R  F  G  S  T
3001 AGGAAAGGTT TGGCTCAACG GTATGCTCTC AAAACCCGAG AAAATAGAAC

3051 GAATAACTCT TCTTTCATA GCCTAGCCAT TTAAATCGCA ATGCTGAAAC

V  G  ·
3101 TTAATAATAA AGGTGATCTG TTTTGGAATG GGATCATATT ATTACGTGGG

·  N  M  I  F  W  F  I  F  C  I  F  G  Q  P  M  C  V  ·
3151 GAACATGATC TTCTGGTTCA TCTTCTGCAT TTTCGGACAA CCGATGTGTG

·  L  L  Y  H  D  L  M  N  R  K  G  S    M  S (SEQ ID NO: 118)
3201 TGCTTCTTTA TTACCACGAC CTGATGAACC GAAAAGGATC GATGTCATGA

3251 AACAACTGTT CAAAAAATGA CTTTCTTCAA ACATCTATGG CCTCGTTGGA

3301 TCTCCGTTGA TGTTGTGGTG GTTCTGATGC TAAAACGACA AATAGTGTTA

3351 TAACCATTGA AGAAGAAAAG AAAATTAGAG TTGTTGTATC TGCAAAAATT

3401 TTGGTAGAGA CACGCGAACC CGTTTGGATT TTGTTATGGT GTAAAGAAAT

3451 TTCAATCAAA AAACTGTTGT AATAATTGTT ACCAAAAAGA AATGCTTTTC

3501 TGGAAACGAG GGGAAAAATA GTAGTTTTGT T (SEQ ID NO: 81)
```

Figure 1 cont.

```
      M   A   P   P   P   S   M   P   A   A   S   D   R   A   G   P   G  ·
  1 ATGGCCCCGC CCCCCTCCAT GCCTGCCGCC TCCGATCGCG CCGGCCCTGG

· R   D   A   G   D   S   S   S   L   R   L   R   R   A   P   S   A  ·
 51 CCGCGACGCG GGCGACTCGT CCTCCCTTCG CCTCCGCCGC GCCCCCTCAG

· D   A   G   D   L   A   G   D   S   S   V   G   L   R   E   N
101 CCGACGCCGG CGACCTTGCC GGCGATTCCT CGGTAGGCTT GCGGGAGAAC

G   E   P   Q   P   P   T   N   P   P   P   Q   E   Q   Q   Q   Q  ·
151 GGCGAGCCGC AACCGCCGAC GAATCCGCCG CCGCAGGAGC AGCAGCAGCA

· H   E   M   L   Y   Y   R   A   S   A   P   A   H   R   R   V   K  ·
201 GCACGAGATG CTATACTACC GCGCGTCGGC GCCCGCCCAC CGCCGCGTCA

· E   S   P   L   S   S   D   A   I   F   R   Q
251 AGGAGAGCCC CCTCAGCTCT GACGCCATCT TCCGGCAGGT GAGGAGACGC

301 GAATTTTAGG CTCGCTGTTT GTAAGCGATT GTTTGATCCC CGCGCTTGTG

351 CTTCGATCCA CGCCAGTTGC AAAATCCTGC AAATTGTTTG TTGCTTCCAG

401 TCAACTCTGC CTCTGTTTTT TTTTGGTTGG TGTGTGTGTG TGTGTGTGTG

451 TTCAAATCAC ACTTTGTGCT ATCGGTAGCT TAACACTGCC GGTTGCCATC

501 TCGCGCGCAC GGATGTTTTA TTGTGGGCCT TGGGCTTCGG AATTGTGGAT

551 AGATTGTGCG CGTGTACTCG AATGGGCACA ATTCGTTTCG TGGGGGGCAT

601 ATGCTGCTGC GATTGAGGTC GGTGTTTACT TGTTTTGGGA TCAGGGGGAC

651 CAGTGCCGGT GCGCGGGTGC CAGATGCATG CCACGCAGAA TTTGGCATCG

701 GCCGGCTGAA GCAGCAAACA ACGAGCGTAA CCGTTACCAC TGGAGGAGCT

751 TTGGCTTGTC GAAACGGATG ACTGGATGAG CGAATGAATC ATTGAATTCA

801 TTGTTGGCGG TACTCACTAT AGTGATGTGG ACAGTTGTTG GGACAGCACC

851 TGCAGTGCCC CCAGTATTAT TAATGCTGAC TTTTCTAACT ACAATGCGTG

901 TTACATTGTT TGTACACCTT GGCTTTCCTG CTTGGGGCAT TGCTTCTTGT

951 TGAGGACCAT ATAACTGTGC ACCTACATAG AACTGTATTG GACCACTTGT

1001 AAGTTTTAAC TGGTTAGCCC TCCATTTTTT AATAGGTATA TTATTAGACA

1051 ATTTTTATTG TCATTGACAT TATTTTTGTT TGCTACTCTC GGAGCCCTTT

1101 TCCCAGTGTA ATCTTAATAG GGCTCAAATC ACAGCAGAAA CACGTGAGAC

1151 GTAATTTTCT AGTGATACTT TTATTAGACT TTGTTGTTTC TGCACATACT

1201 CTAAATCTGT TTTGAAGGTA GGAGTGCTTA TTTGGATGAT AAATAATCCT

1251 CTGTTAGTTG CATGAATATT TATACATCAC ATGCCTCCTA CATGGTTCCT

1301 GGGATTACAC AGTGGACAAC GCTTGATAAA TTGAGTCCAT GCTAACTTGA

1351 TTATAATATA TCAGTATTCC ATATATCATT TTATCTTGTA CTTCAACTGA

1401 GATCATCCTT ATTTTTTGCA AACCGTATTT ATTGGTTGCT CTGGAGAATT
```

Figure 2

```
                                                       S  H  A  G  L
1451  GAAGTCTTGA AACTAAGCAC TTCTCCTGAT TGCAGAGCCA TGCTGGTCTT

L  N  L  C  I  V  V  L  I  A  V  N  S  R  L  I  I ·
1501  CTGAATCTAT GCATTGTTGT TCTGATCGCA GTGAACAGCA GACTCATTAT

· E  N  L  M  K
1551  TGAGAATTTA ATGAAGGTTT ATTACTTTCT TTCTTTTTTC ATTTTCCTCA

1601  CCTTCATTTA CAGATCCCTC AATCCATCTC CTTCTGAAAT ACATCTGGTC

1651  TTCTTCCTGC GCATTTGTCT AGTGTAAATC TGACACATTC TGTGTTTTAT

Y  G  L  L  I  R  A  G  F  W  F ·
1701  TTAAATTGGC TGGTGCAGTA TGGCCTGTTG ATAAGAGCTG GATTTTGGTT

· S  A  R  S  L  G  D  W  P  L  L  M  C  W
1751  TAGTGCAAGA TCGCTGGGTG ACTGGCCCCT TCTAATGTGC TGGTAGAAAT

1801  TGTTGTCATT TTAATTCAG ATGGGTTTCA ATAAGAACT GTGGAGTAAT

L  T  L  P  V  F  P  L  V  A  L ·
1851  CAATCTGTCA ATTTCAGCCT CACTCTACCA GTTTCCCAC TAGTTGCACT

· M  A  E  K  L  I  T  R  K  L  I  G  E  H
1901  CATGGCTGAG AAGCTGATCA CAAGAAAGCT CATTGGTGAA CATGTAAGTT

1951  TGACTCACAA GATTGCGTAG TATTTTGTAG AGAAGTTCTC TTTTGTTATT

2001  TCTTAGGTAT AAGTGTTGAG GATTGAATTA GATGTAAAAC TAGACAGTCC

2051  TCTATTCTGC ATCTTCCAGG TGCCATTTAT CGTTTATGAC TTCTATACAC

V  V  I  L  L  H  I  I  I  T  T  S  A  I ·
2101  CTCTTGCAGG TGGTTATTCT ACTCCATATC ATTATTACAA CATCTGCCAT

· V  Y  P  V  V  V  T  L  K
2151  TGTCTATCCA GTTGTTGTGA CTCTTAAGTA AGCATTTCTT TCTGCTTTGC

2201  AGTTTGTTTG GATGCATCTT ATTTGACAT TCGTTGAGCT CTAGTATTTC

2251  ATGGTATGGA ATACATTCAA TTAATCTTGT TCGTAATTTG CTGTACTTCA

2301  TGGTATGGTG GCCAACTACA TTATTGTGCC CCAAACATTT AGTCTTTCCC

2351  TTCAAGATAC GTACTATACT ATGCAAATTG GGTGGATAAA AAGGTAGCTA

2401  CATAACACTT TTATTTAATT GTATCTGGTG ACTCCACACT ATAATACAAA

2451  GAAACGCAAC TCTCCAGCAT ATTCAAGAAA AAATGTATC TGGTGATAAA

2501  AATCTATTGC AAATGTTCAT TTATCTCTAG TAGAAGAAAT CCTTACTATC

2551  TTACTCTGTC TTGATCTGTT CACTGACTGC ATCTAATAGG GAAGATTTGT

2601  TAGTCCATCA ATATTGATAC ACATTTTATT ATGCAGATAT TTTGTTTCTT

2651  TCATGTAGCT TCTAGCTTGT AACCCCTTTC CTAACATGAA GCTGATCTTT

2701  CCATTGTACA AGAAAAATTG GATATATTTG TTCACATGCT TGGAAATTGA

2751  ATAAACAAAC TGTAGTATTT CTGATGTTGA TGTGCAAGTA GTAGACTTTG

2801  GTTGAGTCAA TTGTTATCTC TCAAAAGAG CCATTAGGAG CAAGTTACCT

2851  TTTCATTGAT TATATTTTCT GTGAGACTGC AAGAGTTAAG AATGTTGTAT
```

Figure 2 cont.

```
2901 GGTTGATGCC TTATGCTGTT TAGTTTAAGT TTGTTATAAT TGCCAAGAAA
2951 TGTTACTTGA AAAGATATTG TCCCATGCAT CAATTATGGA TTATCAGTTC
                                         C  D  S  A  V  L  S  G  F  ·
3001 AGTCATATTC CGAAAAATTT CAGGTGTGAC TCAGCAGTAC TATCTGGATT
     · V  L  M  F  L  A  S  I  M  W  M  K  L  V  S  Y  A  ·
3051 TGTGCTAATG TTTCTTGCGA GCATCATGTG GATGAAGCTT GTCTCTTATG
     · H  T  N  Y  D  I  R  V  L  S  K  S  T  E  K
3101 CACATACAAA TTATGATATA AGGGTATTGT CCAAAAGTAC TGAGAAGGTA
3151 ATGCATTGAC ATGTTAATCT GAATCAGTTC AAATATTTTG TTAACATGTT
3201 GCCCATTTCT CAAAATTGAT TTGTTGACGT TCAAACTTTT CTTAAAACTC
3251 CTTTTGGTGG CCAAATTTTT CTGAAGCTAG AATATCTCCC ACTTGTTTAA
3301 ACTTCTTTTC CAGTTTCATT TCATGAATGT CTTATATCTA GTTTCAATTT
3351 TTGCATAGGA TGAAATGTGG TGCCAATCAA TATACGTTAC CATCAAGAGA
3401 GTAAAAAAAT TGTTCTTAAC TTCTCATACA GTGTTTTTGT TACATGGGCT
3451 GATCATATAT ACTCTCATGT GTTAGCTTAA CTGTTAGTGT ATACCTCTAT
3501 TGTAATGGGC CTTGGTCCAC CTAACCCTGT TATATCAATG CATTCCCAAC
3551 CCTAATTAGG GTTAGGGTTT CCCTCATTCT AACTTCAGGC AACGGTAGCA
3601 TATGATTATA TCCCTTCATT TTCATTTTTC ATGCAAATAA CCACTATTGC
                                     G  A  A  Y  G  N  Y  V  D  P  E
3651 TATATTCTTA TTTTTAGGGT GCTGCATATG GAAATTATGT CGATCCTGAG
     N  M  K  D  P  T  F  K  S  L  V  Y  F  M  L  A  P  ·
3701 AATATGAAAG ATCCAACCTT TAAAAGTCTA GTGTACTTCA TGTTGGCCCC
     · T  L  C  Y  Q
3751 AACACTTTGT TACCAGGTAC TATTATTGGA CCAATGCCCC GTTTTTGTTT
3801 TTAATGTCTA CACTCTGCTT TTCTTCATCG CGTCTATCTA GTTATGCCAG
                                                     P  T  Y  ·
3851 TGACAACATG AATTTCCTGA TGTCACTTTG GCATGTTATG CAGCCAACTT
     · P  Q  T  T  C  I  R  K  G  W  V  T  Q  Q  L  I
3901 ATCCTCAAAC TACATGTATT AGAAAGGGTT GGGTGACCCA GCAACTCATA
     K  C  V  V  F  T  G  L  M  G  F  I  I  E  Q
3951 AAGTGCGTGG TTTTTACAGG CTTGATGGGC TTCATAATTG AGCAAGTGAG
4001 CCTCCTATAT TCCTTAAGTA ACTTGTATTT ATACATAACT TTGGATTAAA
                                         Y  I  N  P  I  V  K  N
4051 TTACCAATTT TTCTTCTATT TTGCAGTATA TAAACCCAAT TGTGAAGAAT
     S  K  H  P  L  K  G  N  F  L  N  A  I  E  R  V  L  ·
4101 TCCAAACATC CACTGAAAGG GAATTTTTTG AATGCTATAG AAAGAGTCTT
     · K  L  S  V  P  T  L  Y  V  W  L  C  M  F  Y  C  F  ·
4151 AAAACTCTCA GTGCCAACAT TATATGTATG GCTTTGCATG TTCTATTGCT
     · F  H  L  W
4201 TTTTTCATTT ATGGTTAGTA TCTTGCTTCA GTTCAACAGT ACCTTAAATT
```

Figure 2 cont.

```
4251  TGTGCGGCAG TGATTGGTTT ATATAACAGG TTAATTGGGT TTTGACCTGC

4301  ATGGGACTTT GATTCCATT TTCCATGGCA TTCTTGTTTG CTCTTTTGGT

L  N  I  V  A  E  L  L  C  F  G  D  R  E  ·
4351  TGGTTTCAGG CTGAACATTG TAGCTGAACT CCTCTGTTTC GGTGACCGTG

·  F  Y  K  D  W  W  N  A  K  T  V  E  E
4401  AATTCTATAA GGACTGGTGG AATGCCAAAA CTGTTGAAGA GGTGAGATGC

4451  CTGTTAAAAT TGAGTTCGTT TCTTTTGAAG TGAGAACTTT AAATAGGACT

4501  GACATCAATT ATATTCTCAT GTACTTAAAT GTGATGGTAT TTGGGGCTT

Y  W  R  M  W  N  M
4551  TACCTCAGTA CTGGAGGATC TGGAACATGG TAATCTTTTT GTTACTTCTA

4601  TATTCAGATT CTATACCCTT TTATTTAGTT GAGACTTTGT TACTTAACTA

4651  AGGACAGTTG TGATGGTAGT GGTACTCTTC TATTTAGTTA AGACTTCCTT

4701  AACTTCTGTC ACTGAGCTTG AGATATTGT CTAATAATAT CTTTCAAATA

P  V  H  K  W  I  I  R  ·
4751  ACTGACAATT AGTCTATTTT TTGTCAGCCT GTTCATAAGT GGATCATCAG

·  H  I  Y  F  P  C  I  R  K  G  F  S  R
4801  ACACATATAT TTTCCATGTA TAAGGAAAGG CTTTTCCAGG GTAATTGCTT

4851  CTATATGTGT ACAAAACTCT ACATTTGTTC TTTGCTTTTG AATTCTCCAA

4901  ATGCAGTTTA GTTTGGAACA TCGATGCAAT ATAGAATTCA CAATATACAA

4951  ATGATGTTCT TTAGAAAATG GGGAAGCAGA GCTGGACAGA GTGTTAGCAC

5001  TCAATTGTCA ATTTGTCATA ATAATAATGA ATACAACTGA ACAAGTGGCT

5051  GAAACTGTTG TGAGAAAATC AGAACACTAG TGGTCAATAT TATTTGCATA

5101  GTAAATCAAT TTGGTAATGT AAATTAAGAT ATGAAGTTCT TACTTCTTAT

5151  ATAAAGATTT ACTATGCTTG AATTTTATAG TGGCTGAAAC TTTACTGTTC

5201  TTGGATAAAG ATTTTAAATA AAAACAAAGG ATATCTAGAC TTGGCAACAA

5251  AATGCTGCCT TCTGCTGACT GGCAAAAGTA AATTAGACAA TGTGAATACA

G
5351  GATTTTCACT GCCTACTTCT CAAATTCGTA TTGTATCTAC ACTGCAGGGT

V  A  I  L  I  S  F  L  V  S  A  V  F  H  E
5401  GTAGCTATTC TAATCTCGTT TCTGGTTTCA GCTGTATTCC ATGAGGTACT

5451  TTAAGTTCTT CAGAAGCCTT TTTCATGATC GGTTCAATTT CTGTTTTTCC

5501  TAAGACATGC TATTGTTCGA ATTCCACTCA GCACATTACT AACAATACGT

5551  TTGACCTTAC GTACCAATAT ATCATCACCA CATCTCTTTT TACATTGTGA

I  C  I  A  V  P  C  H  I  F  K  F  W  A
5601  ATTCACAGAT ATGTATTGCG GTGCCGTGCC ACATTTCAA ATTCTGGGCA

F  S  G  I  M  F  Q
5651  TTTTCTGGGA TCATGTTTCA GGTATAGAAA TAACACTAAT ATATAACTAC
```

Figure 2 cont.

```
5701  TACCTCCATT CCGAATTATA AGTCTTTCTG GCTTGGCTTT TCTAGTTACA
5751  TTATACTAGG TATATATCTA GATTATAATA GTTATATATC TAGACATTGT
5801  GTATATCTAG ATGCATACCA AATGTTACCT ATCTAGAAAA TAGGATCATG
5851  GTTTCAGGTA TAGAAGTAGT AATAATATAA TAACTACTAC CTCCATTTCG
5901  AACTGTAAGT CATTATGACT TGGCTTTTAT AGATAATGCT AAGAGTTATA
5951  TATCTGGACA TTATCTAGAT GCGTAGCTAC GAATCTAGGA AAACTAGAAC
6001  GACTTGTAAT TATCCCTGCC TTTTCTTTTG AGTCCATCAG TGTCTATTCT
6051  CTTACGTTTT GATTCCATCA TTACATCCAT AAGAACAATA CTACATCTTG
6101  GATACAATGT ACCTTCCACT GTTTTCACAT AGGCTGACAC TGGTTGATGT
                I  P  L  V  F  L  T  R  Y  L  H  A  T
6151  CTGACTCACA GATACCGTTG GTATTCTTGA CAAGATATCT CCATGCTACG
       F  K  H  V  M
6201  TTCAAGCATG TAATGGTACG CTGTGTCAAT TATGTCCTTT TTTTCCCATT
                                                   V  G  N
6251  ACCTCTTGCC ACTACCTAAC CATCATCTTC TTATTGGCA GGTGGGCAAC
       M  I  F  W  F  F  S  I  V  G  Q  P  M  C  V  L  L  ·
6301  ATGATATTTT GGTTCTTCAG TATAGTCGGA CAGCCGATGT GTGTCCTTCT
       ·  Y  Y  H  D  V  M  N  R  Q  A  Q  A  S  R      (SEQ ID NO: 119)
6351  ATACTACCAT GACGTCATGA ACAGGCAGGC CCAGGCAAGT AGATAG   (SEQ ID NO: 82)
```

ENHANCED ACYLTRANSFERASE POLYNUCLEOTIDES, POLYPEPTIDES AND METHODS OF USE

CROSS-REFERENCE TO RELATED APPLICATIONS

This application is a U.S. National Stage Application filed under 35 U.S.C. § 371 of International Application No. PCT/IB2013/059524, filed Oct. 22, 2013, which claims the benefit of U.S. Provisional Patent Application No. 61/720,069, filed Oct. 30, 2012. Both of these applications are hereby incorporated by reference in their entireties.

TECHNICAL FIELD

The invention relates to compositions and methods for the manipulation of cellular lipid production and/or cellular lipid profile.

BACKGROUND

Plant oil is an economically important product not only due to its broad utilization in the food industry and as a component of feed ingredients but it also has a wide range of applications as biofuels or in the manufacture of various nutraceutical and industrial products. Within the plant itself, oil is essential to carry out a number of metabolic processes which are vital to growth and development particularly during seed germination and early plant growth stages. Considering its value, there is a growing research interest within the biotechnology field to improve plant oil production and make the supply more sustainable.

The major component of plant oil is triacylglyceride (TAG). It is the main form of storage lipid in oil seeds and the primary source of energy for seed germination and seedling development.

TAG biosynthesis via the Kennedy pathway involves sequential acylation steps starting from the precursor sn-glycerol-3-phosphate (G3P). Firstly, G3P is esterified by an acyl-CoA to form lysophosphatidic acid (LPA) in a reaction catalyzed by glycerol-3-phosphate acyltransferase (GPAT, EC 2.3.1.15). This is followed by a second acylation step catalyzed by lysophosphatidic acid acyltransferase (LPAT; EC 2.3.1.51) forming phosphatidic acid (PA), a key intermediate in the biosynthesis of glycerolipids. The PA is then dephosphorylated by the enzyme phosphatidic acid phosphatase (PAP; EC3.1.3.4) to release the immediate precursor for TAG, the sn-1,2-diacylglycerol (DAG). Finally, DAG is acylated in the sn-3 position by the enzyme diacylglycerol acyltransferase (DGAT; EC 2.3.1.20) to form TAG.

Since this last catalytic action is the only unique step in TAG biosynthesis, DGAT is termed as the committed triacylglycerol-forming enzyme. As DAG is located at the branch point between TAG and membrane phospholipid biosyntheses, DGAT potentially plays a decisive role in regulating the formation of TAG in the glycerolipid synthesis pathway (Lung and Weselake, 2006, Lipids. December 2006; 41(12):1073-88). There are two different families of DGAT proteins. The first family of DGAT proteins ("DGAT1") is related to the acyl-coenzyme A:cholesterol acyltransferase ("ACAT") and has been described in the U.S. Pat. Nos. 6,100,077 and 6,344,548. A second family of DGAT proteins ("DGAT2") is unrelated to the DGAT1 family and is described in PCT Pantention Publication WO 2004/011671 published Feb. 5, 2004. Other references to DGAT genes and their use in plants include PCT Publication Nos. WO2004/011,671, WO1998/055,631, and WO2000/001,713, and US Pat. Publication No. 20030115632.

DGAT1 is typically the major TAG synthesising enzyme in both the seed and senescing leaf (Kaup et al., 2002, Plant Physiol. 129(4):1616-26; for reviews see Lung and Weselake 2006, Lipids. December 2006; 41(12):1073-88; Cahoon et al., 2007, Current Opinion in Plant Biology. 10:236-244; and Li et al., 2010, Lipids. 45:145-157).

Raising the yield of oilseed crops (canola, sunflower, safflower, soybean, corn, cotton, linseed, flax etc) has been a major target for the agricultural industry for decades. Many approaches (including traditional and mutational breeding as well as genetic engineering) have been tried, typically with modest success (Xu et al., 2008, Plant Biotechnol J., 6:799-818 and references therein).

Although liquid biofuels offer considerable promise the reality of utilising biological material is tempered by competing uses and the quantities available. Consequently, engineering plants and microorganisms to address this is the focus of multiple research groups; in particular the accumulation of triacylglcerol (TAG) in vegetative tissues and oleaginous yeasts and bacteria (Fortman et al., 2008, Trends Biotechnol 26, 375-381; Ohlrogge et al., 2009, Science 324, 1019-1020). TAG is a neutral lipid with twice the energy density of cellulose and can be used to generate biodiesel a high energy density desirable biofuel with one of the simplest and most efficient manufacturing processes. Engineering TAG accumulation in leaves has so far resulted in a 5-20 fold increase over WT utilising a variety of strategies which includes: the over-expression of seed development transcription factors (LEC1, LEC2 and WRI1); silencing of APS (a key gene involved in starch biosynthesis); mutation of CGI-58 (a regulator of neutral lipid accumulation); and upregulation of the TAG synthesising enzyme DGAT (diacylglycerol O acyltransferase, EC 2.3.1.20) in plants and also in yeast (Andrianov et al., 2009, Plant Biotech J 8, 1-11; Mu et al., 2008, Plant Physiol 148, 1042-1054; Sanjaya et al., 2011, Plant Biotech J 9, 874-883; Santos-Mendoza et al., 2008, Plant J 54, 608-620; James et al., 2010, Proc Natl Acad Sci U.S.A. 107, 17833-17838; Beopoulos et al., 2011, Appl Microbiol Biotechnol 90, 1193-1206; Bouvier-Navé et al., 2000, Eur J Biochem 267, 85-96; Durrett et al., 2008, Plant J 54, 593-607. However, it has been acknowledged that to achieve further increases in TAG, preventing its catabolism may be crucial within non oleaginous tissues and over a range of developmental stages (Yang and Ohlrogge, 2009, Plant Physiol 150, 1981-1989).

Positively manipulating the yield and quality of triacylglycderides (TAG) in eukaryotes is difficult to achieve. The enzyme diacylglycerol-O-acyltransferase (DGAT) has the lowest specific activity of the Kennedy pathway enzymes and is regarded as a 'bottleneck' in TAG synthesis.

Attempts have been made previously to improve DGAT1 by biotechnological methods, with limited success. For example Nykiforuk et al., (2002, Biochimica et Biophysica Acta 1580:95-109) reported N-terminal truncation of the *Brassica napus* DGAT1 but reported approximately 50% lower activity. McFie et al., (2010, JBC., 285:37377-37387) reported that N-terminal truncation of the mouse DGAT1 resulted in increased specific activity of the enzyme, but also reported a large decline in the level of protein that accumulated.

Xu et al., (2008, Plant Biotechnology Journal, 6:799-818) recently identified a consensus sequence (X-Leu-X-Lys-X-X-Ser-X-X-X-Val) (SEQ ID NO: 111) within *Tropaeolum majus* (garden nasturtium) DGAT1 (TmDGAT1) sequences as a targeting motif typical of members of the SNF1-related protein kinase-1 (SnRK1) with Ser being the residue for phosphorylation. The SnRK1 proteins are a class of Ser/Thr protein kinases that have been increasingly implicated in the global regulation of carbon metabolism in plants, e.g. the inactivation of sucrose phosphate synthase by phosphorylation (Halford & Hardie 1998, Plant Mol Biol. 37:735-48. Review). Xu et al., (2008, Plant Biotechnology Journal, 6:799-818) performed site-directed mutagenesis on six putative functional regions/motifs of the TmDGAT1 enzyme. Mutagenesis of a serine residue (S197) in a putative SnRK1 target site resulted in a 38%-80% increase in DGAT1 activity, and over-expression of the mutated TmDGAT1 in *Arabidopsis* resulted in a 20%-50% increase in oil content on a per seed basis.

It would be beneficial to provide improved forms of DGAT1, which overcome one or more of the deficiencies in the prior art, and which can be used to increase cellular oil production.

It is an object of the invention to provide modified and enhanced DGAT1 proteins and methods for their use to increase cellular lipid production and/or at least to provide the public with a useful choice.

SUMMARY OF THE INVENTION

The inventors have shown that it is possible to modify the N-terminal region of DGAT1 proteins upstream of the acyl-CoA binding site, to produce a modified DGAT1 proteins with increase activity, without reduced protein accumulation seen in some modified DGAT1 proteins the prior art. The modified DGAT1 proteins of the invention can be expressed in cells to increase cellular lipid accumulation.

Polynucleotide Encoding a Polypeptide

In the first aspect the invention provides an isolated polynucleotide encoding a modified DGAT1 protein that is modified in the N-terminal region of the protein upstream of the acyl-CoA binding site.

In one embodiment the modified DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the unmodified DGAT1.

In one embodiment the N-terminal region is at least 3 amino acids upstream of the conserved motif ESPLSS (Glu-Ser-Pro-Leu-Ser-Ser) (SEQ ID NO: 112) in the acyl-CoA binding site.

In a further embodiment the N-terminal region is at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16 amino acids upstream of the conserved motif ESPLSS in the acyl-CoA binding site.

In a preferred embodiment the modified DGAT1 has an intact acyl-CoA binding site.

Modification

In one embodiment the modification is at least one of:
  a) a deletion,
  b) a substitution, and
  c) an addition
of at least amino acid.

In a further embodiment the modification is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids in the N-terminal region.

In a preferred embodiment the modification is a deletion.

Modification is a Truncation

In one embodiment the modification is truncation of one or more amino acids from the N-terminal end of the N-terminal region.

In a further embodiment the truncation is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids from the N-terminal end of the N-terminal region.

In one embodiment the modification is truncation of all of the N-terminal region.

Modification is a Truncation with a Methionine Added to the Truncated N-Terminus In a further embodiment an M (Met) residue is added to the truncated N-terminus.

The modified DGAT1 protein of this embodiment may also be regarded as having an internal deletion of one of more amino acids downstream of the N-terminal M (Met) of the unmodified DGAT1, but upstream of the acyl-CoA binding site.

In a further embodiment a flexible peptide linker is added to the truncated N-terminus.

In a preferred embodiment the flexible peptide linker is soluble.

In one embodiment the flexible peptide linker comprises the sequence (GGGS)n or (Gly-Gly-Gly-Ser; SEQ ID NO: 120)n. In one embodiment n is a number between 1 and 5.

In a further embodiment the sequence MGGGS (Met-Gly-Gly-Gly-Ser) (SEQ ID NO:113) is added to the truncated N-terminus.

In a further embodiment the polypeptide of the invention, when expressed in the cell, has altered substrate specificity relative to the unmodified DGAT1.

Constructs

In a further embodiment the invention provides a genetic construct comprising a polynucleotide of the invention.

Cells

In a further embodiment the invention provides a cell comprising a polynucleotide of the invention.

In a further embodiment the invention provides a cell comprising a genetic construct of the invention.

In a preferred embodiment the cell expresses the modified DGAT1.

In one embodiment the modified DGAT1 protein, when expressed in the cell, has at least one of:
  i) increased DGAT1 activity,
  ii) increased stability,
  iii) altered oligomerisation properties,
  iv) substantially normal cellular protein accumulation properties, and
  v) substantially normal subcellular targeting properties
relative to the unmodified DGAT1 when expressed in a cell.

In a further embodiment the cell produces more lipid than does a control cell.

In one embodiment the cell produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control cell.

In a further embodiment the cell has an altered lipid profile relative to a control cell.

In one embodiment the proportion of 16:0 in the triacylglycerol is altered relative to that in a control cell.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the proportion of 16:0 in the triacylglycerol is altered relative to that in a control cell. In one embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control cell.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control cell.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In one embodiment the altered lipid profile has a proportion of 18:1 in the triacylglycerol in the range 39% to 55%. In this embodiment the proportion of 18:1 in the triacylglycerol is altered within the range 39% to 55%.

The control cell may be any cell of the same type that is not transformed with the polynucleotide, or construct, of the invention to express the modified DGAT1.

In one embodiment the control cell is an untransformed cell. In a further embodiment the control cell is transformed cell to express the unmodified DGAT1.

Cells Also Transformed to Express an Oleosin

In one embodiment the cell is also transformed to express at least one of: an oleosin, steroleosin, caloleosin, polyoleosin, and an oleosin including at least one artificially introduced cysteine (WO2011/053169).

Plant

In a further embodiment the invention provides a plant comprising a polynucleotide of the invention.

In a further embodiment the invention provides a plant comprising a genetic construct of the invention.

In a preferred embodiment the plant expresses the modified DGAT1.

In one embodiment the modified DGAT1 protein when expressed in the plant has at least one of:
  i) increased DGAT1 activity,
  ii) increased stability,
  iii) altered oligomerisation properties,
  iv) substantially normal cellular protein accumulation properties, and
  v) substantially normal subcellular targeting properties
relative to the unmodified DGAT1.

In a further embodiment the plant produces more lipid, in at least one of its tissues or parts, than does the equivalent tissue or part in a control plant.

In one embodiment the plant produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control plant.

In one embodiment the tissue is a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monoct plant. In a further embodiment the part is a stovum (stalk and leaf blade).

In a preferred embodiment the tissue is seed tissue. In a preferred embodiment the part is a seed. In a preferred embodiment the tissue is endosperm tissue.

In a further embodiment the plant as a whole produces more lipid than does the control plant as a whole.

In a further embodiment the plant has an altered lipid profile, in at least one of its tissues or parts, relative to a control plant.

In one embodiment the proportion of 16:0 in the triacylglycerol is altered relative to that in a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, relative to that in a control plant.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control cell.

In a further embodiment the altered lipid profile has a proportion of 18:1 in the triacylglycerol in the range 39% to 55%. In this embodiment the proportion of 18:1 in the triacylglycerol is altered within the range 39% to 55%.

In one embodiment the tissue is a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monoct plant. In a further embodiment the part is a stovum (stalk and leaf blade).

In a preferred embodiment the tissue is seed tissue. In a preferred embodiment the part is a seed. In a preferred embodiment the tissue is endosperm tissue.

In a further embodiment the plant as a whole has an altered lipid profile relative to the control plant as a whole.

The control plant may be any plant of the same type that is not transformed with the polynucleotide, or construct, of the invention to express the modified DGAT1.

In one embodiment the control plant is an untransformed plant. In a further embodiment the control plant is transformed plant to express the unmodified DGAT1.

Plant Also Transformed to Express an Oleosin

In one embodiment the plant is also transformed to express at least one of: an oleosin, steroleosin, caloleosin, polyoleosin, and an oleosin including at least one artificially introduced cysteine (WO 2011/053169).

Polypeptide

In a further aspect the invention provides a modified DGAT1 protein that is modified in the N-terminal region of the protein upstream of the acyl-CoA binding site.

In one embodiment the modified DGAT1 protein has at least one of:
i) increased DGAT1 activity
ii) increased stability
ill) altered oligomerisation properties
iv) substantially normal cellular protein accumulation properties
v) substantially normal cellular targeting properties
relative to the unmodified DGAT1.

In one embodiment the N-terminal region is at least 3 amino acids upstream of the conserved motif ESPLSS (Glu-Ser-Pro-Leu-Ser-Ser) in the acyl-CoA binding site.

In a further embodiment the N-terminal region is at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16 amino acids upstream of the conserved motif ESPLSS in the acyl-CoA binding site.

In a preferred embodiment the modified DGAT1 has an intact acyl-CoA binding site.

Modification

In one embodiment the modification is at least one of:
a) a deletion,
b) a substitution, and
c) an addition
of at least amino acid.

In a further embodiment the modification is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids In a preferred embodiment the modification is a deletion.

Modification is a Truncation

In one embodiment the modification is truncation of one or more amino acids from the N-terminal end of the N-terminal region.

In a further embodiment the truncation is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids from the N-terminal end of the N-terminal region.

In one embodiment the modification is truncation of all of the N-terminal region.

Modification is a Truncation with a Methionine Added to the Truncated N-Terminus In a further embodiment an M (Met) residue is added to the truncated N-terminus.

The modified DGAT1 protein of this embodiment may also be regarded as having an internal deletion of one of more amino acids downstream of the N-terminal M (Met) of the unmodified DGAT1, but upstream of the acyl-CoA binding site.

In a further embodiment a flexible peptide linker is added to the truncated N-terminus.

In a preferred embodiment the flexible peptide linker is soluble.

In one embodiment the flexible peptide linker comprises the sequence (GGGS)n or (Gly-Gly-Gly-Ser; SEQ ID NO: 120)n. In one embodiment n is a number between 1 and 5.

In a further embodiment the sequence MGGGS (Met-Gly-Gly-Gly-Ser) (SEQ ID NO: 113) is added to the truncated N-terminus.

Method for Producing an Enhanced DGAT1

In a further aspect the invention provides a method for producing an enhanced DGAT1, the method comprising modifying the N-terminal region of the protein upstream of the acyl-CoA binding site.

In one embodiment the modified DGAT1 protein has at least one of:
  i) increased DGAT1 activity
  ii) increased stability
  iii) altered oligomerisation properties
  iv) substantially normal cellular protein accumulation properties
  v) substantially normal cellular targeting properties
relative to the unmodified DGAT1.

In one embodiment the N-terminal region is at least 3 amino acids upstream of the conserved motif ESPLSS (Glu-Ser-Pro-Leu-Ser-Ser) (SEQ ID NO:112) in the acyl-CoA binding site.

In a further embodiment the N-terminal region is at least 4, preferably at least 5, preferably at least 6, preferably at least 7, preferably at least 8, preferably at least 9, preferably at least 10, preferably at least 11, preferably at least 12, preferably at least 13, preferably at least 14, preferably at least 15, preferably at least 16 amino acids upstream of the conserved motif ESPLSS in the acyl-CoA binding site.

In a preferred embodiment the modified DGAT1 has an intact acyl-CoA binding site.

Modification

In one embodiment the modification is at least one of:
  a) a deletion,
  b) a substitution, and
  c) an addition
of at least amino acid.

In a further embodiment the modification is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids In a preferred embodiment the modification is a deletion.

Modification is a Truncation

In one embodiment the modification is truncation of one or more amino acids from the N-terminal end of the N-terminal region.

In a further embodiment the truncation is of at least 2, more preferably at least 3, more preferably at least 4, more preferably at least 5, more preferably at least 10, more preferably at least 20, more preferably at least 30, more preferably at least 40, more preferably at least 50, more preferably at least 60, more preferably at least 70, more preferably at least 80, more preferably at least 90, more preferably at least 100, more preferably at least 110, more preferably at least 120 amino acids from the N-terminal end of the N-terminal region.

In one embodiment the modification is truncation of all of the N-terminal end of the N-terminal region.

Modification is a Truncation with a Methionine Added to the Truncated N-Terminus In a further embodiment an M (Met) residue is added to the truncated N-terminus.

The modified DGAT1 protein of this embodiment may also be regarded as having an internal deletion of one of more amino acids downstream of the N-terminal M (met) of the unmodified DGAT1, but upstream of the acyl-CoA binding site.

In a further embodiment a flexible peptide linker is added to the truncated N-terminus.

In a preferred embodiment the flexible peptide linker is soluble.

In one embodiment the flexible peptide linker comprises the sequence (GGGS)n or (Gly-Gly-Gly-Ser; SEQ ID NO: 120)n. In one embodiment n is a number between 1 and 5.

In a further embodiment the sequence MGGGS (Met-Gly-Gly-Gly-Ser)(SEQ ID NO: 113) is added to the truncated N-terminus.

In a further embodiment the method comprises testing at least one of the
  i) activity
  ii) stability
  iii) oligomerisation properties
  iv) cellular protein accumulation properties
  v) cellular targeting properties
of the modified DGAT1 protein.

In a further embodiment method comprises the step of selecting a modified DGAT1 protein that has at least one of:
  i) increased DGAT1 activity
  ii) increased stability
  iii) altered oligomerisation properties
  iv) substantially normal cellular protein accumulation properties
  v) substantially normal cellular targeting properties
relative to the unmodified DGAT1 protein.

Plant Parts

In a further embodiment the invention provides a part, propagule or progeny of a plant of the invention.

In a preferred embodiment the part, propagule or progeny comprises at least one of a polynucleotide, construct or polypeptide of the invention.

In a preferred embodiment the part, propagule or progeny expresses at least one of a polynucleotide, construct or polypeptide of the invention.

In a preferred embodiment the part, propagule or progeny expresses a modified DGAT1 of the invention.

In a further embodiment the part, propagule or progeny produces more lipid than does a control part, propagule or progeny, or part, propagule or progeny of a control plant.

In one embodiment the part, propagule or progeny produces at least 5% more, preferably at least 10% more, preferably at least 15% more, preferably at least 20% more, preferably at least 25% more, preferably at least 30% more, preferably at least 35% more, preferably at least 40% more, preferably at least 45% more, preferably at least 50% more, preferably at least 55% more, preferably at least 60% more, preferably at least 65% more, preferably at least 70% more, preferably at least 75% more, preferably at least 80% more, preferably at least 85% more, preferably at least 90% more, preferably at least 95% more preferably at least 100% more, preferably at least 105% more, preferably at least 110% more, preferably at least 115% more, preferably at least 120% more, preferably at least 125% more, preferably at least 130% more, preferably at least 135% more, preferably at least 140% more, preferably at least 145% more, preferably at least 150% more lipid than does a control part, propagule or progeny, or part, propagule or progeny of a control plant.

In a further embodiment the part, propagule or progeny has an altered lipid profile relative to a control part, propagule or progeny, or part, propagule or progeny of a control plant.

In one embodiment the proportion of 16:0 in the triacylglycerol is altered relative to that in a control part, propagule or progeny, or part, propagule or progeny of a control plant.

In one embodiment the proportion of 16:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 16:0 in the triacylglycerol in the range 6% to 16%. In this embodiment the proportion of 16:0 in the triacylglycerol is altered within the range 6% to 16%.

In a further embodiment the proportion of 18:0 in the triacylglycerol is altered relative to that in a control part, propagule or progeny, or part, propagule or progeny of a control plant.

In one embodiment the proportion of 18:0 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in control part, propagule or progeny, or part, propagule or progeny of a control plant.

In a further embodiment the altered lipid profile has a proportion of 18:0 in the triacylglycerol in the range 7% to 15%. In this embodiment the proportion of 18:0 in the triacylglycerol is altered within the range 7% to 15%.

In a further embodiment the proportion of 18:1 in the triacylglycerol is altered relative to that in a control part, propagule or progeny, or part, propagule or progeny of a control plant.

In one embodiment the proportion of 18:1 in the triacylglycerol is altered by at least 1%, preferably at least 2%, more preferably at least 3%, more preferably at least 4%, more preferably at least 5%, more preferably at least 6%, more preferably at least 7%, more preferably at least 8%, more preferably at least 9%, more preferably at least 10%, more preferably at least 11%, more preferably at least 12%, more preferably at least 13%, more preferably at least 14%, more preferably at least 15%, more preferably at least 16%, more preferably at least 17%, more preferably at least 18%, more preferably at least 19%, more preferably at least 20%, relative to that in a control part, propagule or progeny, or part, propagule or progeny of a control plant.

In a further embodiment the altered lipid profile has a proportion of 18:1 in the triacylglycerol in the range 39% to 55%. In this embodiment the proportion of 18:1 in the triacylglycerol is altered within the range 39% to 55%.

The control plant may be any plant of the same type that is not transformed with the polynucleotide, or construct, of the invention to express the modified DGAT1.

In one embodiment the control plant is an untransformed plant. In a further embodiment the control plant is transformed plant to express the unmodified DGAT1.

Preferably the control the part, propagule or progeny is from a control plant as described above.

In one embodiment the part is from a vegetative tissue. In one embodiment the part is a leaf. In a further embodiment the part is a root. In a further embodiment the part is a tuber. In a further embodiment the part is a corm. In a further embodiment the part is a stalk. In a further embodiment the part is a stalk of a monocot plant. In a further embodiment the part is a stovum (stalk and leaf blade).

In a further embodiment the part is from a reproductive tissue. In a further embodiment the part is a seed. In a preferred embodiment the part is from or includes endosperm tissue.

Animal Feed

In a further aspect the invention provides an animal feedstock comprising at least one of a polynucleotide, construct, modified DGAT1 protein, cell, plant cell, plant part, propagule and progeny of the invention.

Biofuel Feedstock

In a further aspect the invention provides a biofuel feedstock comprising at least one of a polynucleotide, construct, modified DGAT1 protein, cell, plant cell, plant part, propagule and progeny of the invention.

Lipid

In one embodiment the lipid is an oil. In a further embodiment the lipid is triacylglycerol (TAG)

Methods for Producing Lipid

In a further aspect the invention provides a method for producing lipid, the method comprising expressing a modified DGAT1 protein of the invention in a cell, plant cell or plant.

In a preferred embodiment expressing the modified DGAT1 protein of the invention in the plant leads production of the lipid in the cell, plant cell or plant.

In one embodiment the method includes the step of transforming a cell, plant cell or plant with a polynucleotide of the invention encoding the modified DGAT1 protein.

In a further embodiment the method includes the step of extracting the lipid from the cell, plant cell, or plant, or from a part, propagule or progeny of the plant.

In one embodiment the lipid is an oil. In a further embodiment the lipid is triacylglycerol (TAG)

In a further embodiment the lipid is processed into at least one of:
a) a fuel,
b) an oleochemical,
c) a nutritional oil,
d) a cosmetic oil,
e) a polyunsaturated fatty acid (PUFA), and
f) a combination of any of a) to e).

In a further aspect the invention provides a method for producing lipid, the method comprising extracting lipid from at least one of a cell, plant cell, plant, plant part, propagule and progeny of the invention.

In one embodiment the lipid is an oil. In a further embodiment the lipid is triacylglycerol (TAG)

In a further embodiment the lipid is processed into at least one of:
a) a fuel,
b) an oleochemical,
c) a nutritional oil,
d) a cosmetic oil,
e) a polyunsaturated fatty acid (PUFA), and
f) a combination of any of a) to e).

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner. In some embodiments, the term "comprising" (and related terms such as "comprise and "comprises") can be replaced by "consisting of" (and related terms "consist" and "consists").

Definitions

The term "DGAT1" as used herein means acyl CoA: diacylglycerol acyltransferase (EC 2.3.1.20) DGAT1 is typically the major TAG synthesising enzyme in both the seed and senescing leaf (Kaup et al., 2002, Plant Physiol. 129 (4):1616-26; for reviews see Lung and Weselake 2006, Lipids. December 2006; 41(12):1073-88; Cahoon et al., 2007, Current Opinion in Plant Biology. 10:236-244; and Li et al., 2010, Lipids. 45:145-157).

DGAT1 contains approximately 500 amino acids and has 10 predicted transmembrane domains whereas DGAT2 has only 320 amino acids and is predicted to contain only two transmembrane domains; both proteins were also predicted to have their N- and C-termini located in the cytoplasm (Shockey et al., 2006, Plant Cell 18:2294-2313). Both DGAT1 and DGAT2 have orthologues in animals and fungi and are transmembrane proteins located in the ER.

In most dicotyledonous plants DGAT1 & DGAT2 appear to be single copy genes whereas there are typically two versions of each in the grasses which presumably arose during the duplication of the grass genome (Salse et al., 2008, Plant Cell, 20:11-24).

The term "unmodified DGAT1" as used herein typically means a naturally occurring or native DGAT1. In some cases the DGAT1 sequence may have been assembled from sequences in the genome, but may not be expressed in plants.

In one embodiment the unmodified DGAT1 polypeptide sequences have the sequence of any one of SEQ ID NO: 1 to 29 or a variant thereof. Preferably the variant has at least 70% identity to any one of SEQ ID NO: 1 to 29. In a further embodiment the unmodified DGAT1 sequences have the sequence of any one of SEQ ID NO: 1 to 29.

In one embodiment the unmodified DGAT1 polynucleotide sequences have the sequence of any one of SEQ ID NO: 30 to 58 or a variant thereof. Preferably the variant has at least 70% identity to any one of SEQ ID NO: 30 to 58. In a further embodiment the unmodified DGAT1 sequences have the sequence of any one of SEQ ID NO: 30 to 58.

The term "modified DGAT1" as used herein refers to the DGAT1 of the invention that is modified upstream of the acyl-CoA binding site, relative to an unmodified DGAT1.

In one embodiment the modified DGAT1 sequences have the sequence of any SEQ ID NO: 59 and 62 to 66 or a variant thereof. Preferably the variant has at least 70% identity to any one of SEQ ID NO: 59 and 62 to 66. In a further embodiment the modified DGAT1 sequences the sequence of any one of SEQ ID NO: 59 and 62 to 66.

In a further embodiment the modified DGAT1 polypeptide sequences have the sequence of any SEQ ID NO: 59 and 66 or a variant thereof. Preferably the variant has at least 70% identity to any one of SEQ ID NO: 59 and 66. In a further embodiment the modified DGAT1 sequences have the sequence of any one of SEQ ID NO: 59 and 66.

Although not preferred, the modified DGAT1 of the invention may include modifications additional to those upstream of the acyl-CoA binding site. Preferably the modified DGAT1 of the invention includes an intact acyl-CoA binding site.

The terms upstream and downstream are according to normal convention to mean towards the N-terminus of a polypeptide, and towards the C-terminus of a polypeptide, respectively.

Acyl-CoA Binding Site

The position of the acycl-CoA binding site in a number of DGAT1 sequences is shown if FIG. 3.

Conserved Motif ESPLSS

In a preferred embodiment the acycl-CoA binding site comprises the conserved motif ESPLSS Acyl-CoA Binding Site General Formulae In a preferred embodiment the acyl-CoA binding site has the formula:

XXXESPLSSXXIFXXXHA     (SEQ ID NO:114), where X is any amino acid.

In a preferred embodiment the acyl-CoA binding site has the formula:

XXXESPLSSXXIFXXSHA     (SEQ ID NO: 115), where X is any amino acid.

In a preferred embodiment the acyl-CoA binding site has the formula:

$X_1X_2X_3$ESPLSS$X_4X_5$IF$X_6X_7X_8$HA     (SEQ ID NO: 116), where $X_1$=R, K, V, T, A, S or G; $X_2$=A, T, V, I, N, R, S or L; $X_3$=R or K; $X_4$=D or G; $X_5$=A, T, N, or L; $X_6$=K or R; $X_7$=Q or H; and $X_8$=S or is absent.

In a preferred embodiment the acyl-CoA binding site has the formula:

$X_1X_2X_3$ESPLSS$X_4X_5$IFX$_6X_7$SHA            (SEQ ID NO: 117), where $X_1$=R, K, V, T, A, S or G; $X_2$=A, T, V, I, N, R, S or L; $X_3$=R or K; $X_4$=D or G; $X_5$=A, T, N, or L; $X_6$=K or R; and $X_7$=Q or H.

Methods for Modifying DGAT1

Methods for modifying the sequence of proteins, or the polynucleotide sequences encoding them, are well known to those skilled in the art. The sequence of a protein may be conveniently modified by altering/modifying the sequence encoding the protein and expressing the modified protein. Approaches such as site-directed mutagenesis may be applied to modify existing polynucleotide sequences. Altered polynucleotide sequences may also be conveniently synthesised in its modified form.

The phrase "increased DGAT1 activity" means increased specific activity relative to that of the unmodified DGAT1.

An art skilled worker would know how to test the "specific activity" of the chimeric DGAT1. This may typically be done by isolating, enriching and quantifying the recombinant DGAT1 then using this material to determine either the rate of triaclyglyceride formation and/or the disappearance of precursor substrates (including various forms of acyl-CoA and DAG) as per Xu et al., (2008), Plant Biotechnology Journal. 6:799-818.

The phrase "increased stability" means that the modified DGAT1 protein is more stable, when expressed in a cell, than the unmodified DGAT1. This may lead to increased accumulation of active modified DGAT1 when it is expressed in cells, relative to when unmodified DGAT1 is expressed in cells.

Those skilled in the art know how to test the "stability" of the modified DGAT1. This would typically involve expressing the chimeric DGAT1 in a cell, or cells, and expressing the first or second DGAT1 in a separate cell, or cells of the same type. Accumulation of chimeric and the first or second DGAT1 protein in the respective cells can then be measured, for example by immunoblot and/or ELISA. A higher level of accumulation of the chimeric DGAT1 relative to the first or second DGAT1, at the same time point, indicates that the chimeric DGAT1 has increased stability. Alternatively, stability may also be determined by the formation of quaternary structure which can also be determined by immunoblot analysis.

The phrase "altered oligomerisation properties" means that the way in which, or the extent to which modified DGAT1 forms oligomers is altered relative to unmodified DGAT1.

Those skilled in the art know how to test the "oligomerisation properties" of the modified DGAT1. This may typically be done by immunoblot analysis or size exclusion chromatography.

The phrase "substantially normal cellular protein accumulation properties" means that the modified DGAT1 of the invention retains substantially the same protein accumulation when expressed in a cell, as does the unmodified DGAT1. That is there is no less accumulation of modified DGAT1 than there is accumulation of unmodified DGAT1, when either are separately expressed in the same cell type.

An art skilled worker would know how to test the "cellular protein accumulation properties" of the modified DGAT1. This would typically involve expressing the modified DGAT1 in a cell, or cells, and expressing the unmodified DGAT1 in a separate cell, or cells of the same type. Accumulation of modified and unmodified DGAT1 protein in the respective cells can then be measured, for example by ELISA or immunoblot. A higher level of accumulation of the modified DGAT1 relative to the unmodified DGAT1, at the same time point, indicates that the modified DGAT1 has increased "cellular protein accumulation properties".

The phrase "substantially normal subcellular targeting properties" means that the modified DGAT1 of the invention retains substantially the same subcellular targeting when expressed in a cell, as does the unmodified DGAT1. That is the modified DGAT1 is targeted to the same subcellular compartment/s as the unmodified DGAT1, when either are separately expressed in the same cell type.

An art skilled worker would know how to test the "subcellular targeting properties" of the chimeric DGAT1. This would typically involve expressing the chimeric DGAT1 in a cell, or cells, and expressing the first or second DGAT1 in a separate cell, or cells of the same type. Subcellular targeting of chimeric and the first or second DGAT1 protein in the respective cells can then be assessed, for example by using ultracentrifugation to separate and isolating individual subcellular fractions then determining the level of DGAT1 in each fraction. Substantially similar "subcellular targeting" of the chimeric DGAT1 relative to the first or second DGAT1, at the same time point, indicates that the chimeric DGAT1 has increased "substantially normal cellular protein has "substantially normal subcellular targeting properties".

Lipid

In one embodiment the lipid is an oil. In a further embodiment the oil is triacylglycerol (TAG)

Lipid Production

In certain embodiments the cell, cells, tissues, plants and plant parts of the invention produces more lipid than control cells, tissues, plants and plant parts.

Those skilled in the art are well aware of methods for measuring lipid production. This may typically be done by quantitative fatty acid methyl ester gas chromatography mass spectral analysis (FAMES GC-MS). Suitable methods are also described in the examples section of this specification.

Substrate Specificity

In certain embodiments, the polypeptides of the invention have altered substrate specificity relative to other DGAT1 proteins. Plant DGAT1 proteins are relatively promiscuous in terms of the fatty acid substrates and DAG species they are capable of utilizing to generate TAG. As such they can be considered to have relatively low substrate specificity. However, this can be modified such that certain fatty acids become a preferred substrate over others. This leads to an increase in the proportions of the preferred fatty acids in the TAG and decreases in the proportions of the non preferred fatty acid species. Substrate specificity can be determined by in vitro quantitative analysis of TAG production following the addition of specific and known quantities of purified substrates to known quantities of recombinant DGAT, as per Xu et al., (2008), Plant Biotechnology Journal. 6:799-818.

Lipid Profile

In a further embodiment the cell, cells, tissues, plants and plant parts of the invention have an altered lipid profile relative to the control cells, tissues, plants and plant parts.

Those skilled in the art are well aware of methods for assessing lipid profile. This may involve assessing the proportion or percentage of at least one of the 16:0, 16:1, 18:0, 18:1c9 fatty acid species present in the lipid. This may typically be done by fatty acid methyl ester (FAME) analysis (Browse et al., 1986, Anal. Biochem. 152, 141-145). Suitable methods are also described in the examples section of this specification.

Cells

The modified DGAT1 of the invention, or as used in the methods of the invention, may be expressed in any cell type.

In one embodiment the cell is a prokaryotic cell. In a further embodiment the cell is a eukaryotic cell. In one embodiment the cell is selected from a bacterial cell, a yeast cell, a fungal cell, an insect cell, algal cell, and a plant cell. In one embodiment the cell is a bacterial cell. In a further embodiment the cell is a yeast cell. In one embodiment the yeast cell is a S. ceriviseae cell. In further embodiment the cell is a fungal cell. In further embodiment the cell is an insect cell. In further embodiment the cell is an algal cell. In a further embodiment the cell is a plant cell.

In one embodiment the cell is a non-plant cell. In one embodiment the non-plant is selected from E. coli, P. pastoris, S. ceriviseae, D. salina, C. reinhardtii. In a further embodiment the non-plant is selected from P. pastoris, S. ceriviseae, D. salina, C. reinhardtii.

In one embodiment the cell is a microbial cell. In another embodiment, the microbial cell is an algal cell of the division of Chlorophyta (green algae), Rhodophyta (red algae), Phaeophyceae (brown algae), Bacillariophycaeae (diatoms), or Dinoflagellata (dinoflagellates). In another embodiment, the microbial cell is an algal cell of the species Chlamydomonas, Dunaliella, Botrycoccus, Chlorella, Cypthecodinium, Gracilaria, Sargassum, Pleurochrysis, Porphyridium, Phaeodactylum, Haematococcus, Isochrysis, Scenedesmus, Monodus, Cyclotella, Nitzschia, or Parietochloris. In another embodiment, the algal cell is Chlamydomonas reinhardtii. In yet another embodiment, the cell is from the genus Yarrowia, Candida, Rhodotorula, Rhodosporidium, Cryptococcus, Trichosporon, Lipomyces, Pythium, Schizochytrium, Thraustochytrium, or Ulkenia. In yet another embodiment, the cell is a bacterium of the genus Rhodococcus, Escherichia, or a cyanobacterium. In yet another embodiment, the cell is a yeast cell. In yet another embodiment, the cell is a synthetic cell.

Plants

The unmodified DGAT1 sequences, from which the modified DGAT1 sequences are produced, may be naturally-occurring DGAT1sequences. Preferably the unmodified DGAT1 sequences are from plants. In certain embodiments the cells into which the modified DGAT1 proteins are expressed are from plants. In other embodiments the modified DGAT1 proteins are expressed in plants.

The plant cells, from which the modified DGAT1 proteins are derived, the plants from which the plant cells are derived, and the plants in which the modified DGAT1 proteins are expressed may be from any plant species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Other preferred plants are forage plant species from a group comprising but not limited to the following genera: Zea, Lolium, Hordium, Miscanthus, Saccharum, Festuca, Dactylis, Bromus, Thinopyrum, Trifolium, Medicago, Pheleum, Phalaris, Holcus, Glycine, Lotus, Plantago and Cichorium.

Other preferred plants are leguminous plants. The leguminous plant or part thereof may encompass any plant in the plant family Leguminosae or Fabaceae. For example, the plants may be selected from forage legumes including, alfalfa, clover; leucaena; grain legumes including, beans, lentils, lupins, peas, peanuts, soy bean; bloom legumes including lupin, pharmaceutical or industrial legumes; and fallow or green manure legume species.

A particularly preferred genus is Trifolium. Preferred Trifolium species include Trifolium repens; Trifolium arvense; Trifolium affine; and Trifolium occidentale. A particularly preferred Trifolium species is Trifolium repens.

Another preferred genus is Medicago. Preferred Medicago species include Medicago sativa and Medicago truncatula. A particularly preferred Medicago species is Medicago sativa, commonly known as alfalfa.

Another preferred genus is Glycine. Preferred Glycine species include Glycine max and Glycine wightii (also known as Neonotonia wightii). A particularly preferred Glycine species is Glycine max, commonly known as soy bean. A particularly preferred Glycine species is Glycine commonly known as perennial soybean.

Another preferred genus is Vigna. A particularly preferred Vigna species is Vigna unguiculata commonly known as cowpea.

Another preferred genus is Mucana. Preferred Mucana species include Mucana pruniens. A particularly preferred Mucana species is Mucana pruniens commonly known as velvetbean.

Another preferred genus is Arachis. A particularly preferred Arachis species is Arachis glabrata commonly known as perennial peanut.

Another preferred genus is Pisum. A preferred Pisum species is Pisum sativum commonly known as pea.

Another preferred genus is Lotus. Preferred Lotus species include Lotus corniculatus, Lotus pedunculatus, Lotus glabar, Lotus tenuis and Lotus uliginosus. A preferred Lotus species is Lotus corniculatus commonly known as Birdsfoot Trefoil. Another preferred Lotus species is Lotus glabar commonly known as Narrow-leaf Birdsfoot Trefoil. Another preferred Lotus species is Lotus pedunculatus commonly known as Big trefoil. Another preferred Lotus species is Lotus tenuis commonly known as Slender trefoil.

Another preferred genus is Brassica. A preferred Brassica species is Brassica oleracea, commonly known as forage kale and cabbage. A preferred Brassica genus is Camelina. A preferred Camelina species is Camelina sativa.

Other preferred species are oil seed crops including but not limited to the following genera: Brassica, Carthamus, Helianthus, Zea and Sesamum.

A preferred oil seed genera is Brassica. A preferred oil seed species is Brassica napus.

A preferred oil seed genera is Brassica. A preferred oil seed species is Brassica oleraceae.

A preferred oil seed genera is Carthamus. A preferred oil seed species is Carthamus tinctorius.

A preferred oil seed genera is Helianthus. A preferred oil seed species is Helianthus annuus.

A preferred oil seed genera is Zea. A preferred oil seed species is Zea mays.

A preferred oil seed genera is Sesamum. A preferred oil seed species is Sesamum indicum.

A preferred silage genera is Zea. A preferred silage species is Zea mays.

A preferred grain producing genera is Hordeum. A preferred grain producing species is Hordeum vulgare.

A preferred grazing genera is *Lolium*. A preferred grazing species is *Lolium perenne*.

A preferred grazing genera is *Lolium*. A preferred grazing species is *Lolium arundinaceum*.

A preferred grazing genera is *Trifolium*. A preferred grazing species is *Trifolium repens*.

A preferred grazing genera is *Hordeum*. A preferred grazing species is *Hordeum vulgare*.

Preferred plants also include forage, or animal feedstock plants. Such plants include but are not limited to the following genera: *Miscanthus, Saccharum, Panicum*.

A preferred biofuel genera is *Miscanthus*. A preferred biofuel species is *Miscanthus giganteus*.

A preferred biofuel genera is *Saccharum*. A preferred biofuel species is *Saccharum officinarum*.

A preferred biofuel genera is *Panicum*. A preferred biofuel species is *Panicum virgatum*.

Plant Parts, Propagues and Progeny

The term "plant" is intended to include a whole plant, any part of a plant, a seed, a fruit, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting progeny, comprising the polynucleotides or constructs of the invention, and/or expressing the modified DGAT1 sequences of the invention, also form an part of the present invention.

Preferably the plants, plant parts, propagules and progeny comprise a polynucleotide or construct of the invention, and/or express a modified DGAT1 sequence of the invention.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques.

A "fragment" of a polypeptide is a subsequence of the polypeptide that preferably performs a function of and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from the NCBI website on the World Wide Web at ftp://ftp.ncbi.nih.gov/blast/. The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from the world wide web at http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/.

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10-6$ more preferably less than $1\times10-9$, more preferably less than $1\times10-12$, more preferably less than $1\times10-15$, more preferably less than $1\times10-18$, more preferably less than $1\times10-21$, more preferably less than $1\times10-30$, more preferably less than $1\times10-40$, more preferably less than $1\times10-50$, more preferably less than $1\times10-60$, more preferably less than $1\times10-70$, more preferably less than $1\times10-80$, more preferably less than $1\times10-90$ and most preferably less than $1\times10-100$ when compared with any one of the specifically identified sequences.

Alternatively, variant polynucleotides of the present invention, or used in the methods of the invention, hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention, or used in the methods of the invention, also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from the NCBI website on the World Wide Web at ftp://ftp.ncbi.nih.gov/blast/ via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from the NCBI website on the World Wide Web at ftp://ftp.ncbi.nih.gov/blast/. The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http:/www.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention, or used in the methods of the invention, also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from the NCBI website on the World Wide Web at ftp://ftp.ncbi.nih.gov/blast/. The similarity of polypeptide sequences may be examined using the following unix command line parameters:

bl2seq -i peptideseq1 -j peptideseq2 -F F -p blastp

Variant polypeptide sequences preferably exhibit an E value of less than $1 \times 10-6$ more preferably less than $1 \times 10-9$, more preferably less than $1 \times 10-12$, more preferably less than $1 \times 10-15$, more preferably less than $1 \times 10-18$, more preferably less than $1 \times 10-21$, more preferably less than $1 \times 10-30$, more preferably less than $1 \times 10-40$, more preferably less than $1 \times 10-50$, more preferably less than $1 \times 10-60$, more preferably less than $1 \times 10-70$, more preferably less than $1 \times 10-80$, more preferably less than $1 \times 10-90$ and most preferably $1 \times 10-100$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:
a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence may, in some cases, identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination, mRNA stability, and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors. Introns within coding sequences can also regulate transcription and influence post-transcriptional processing (including splicing, capping and polyadenylation).

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

In certain embodiments the modified DGAT1 polynucleotides/polypeptides of the invention may be advantageously expressed under the control of selected promoter sequences as described below.

Vegetative Tissue Specific Promoters

An example of a vegetative specific promoter is found in U.S. Pat. Nos. 6,229,067; and 7,629,454; and 7,153,953; and 6,228,643.

Pollen Specific Promoters

An example of a pollen specific promoter is found in U.S. Pat. Nos. 7,141,424; and 5,545,546; and 5,412,085; and 5,086,169; and 7,667,097.

Seed Specific Promoters

An example of a seed specific promoter is found in U.S. Pat. Nos. 6,342,657; and 7,081,565; and 7,405,345; and 7,642,346; and 7,371,928. A preferred seed specific promoter is the napin promoter of Brassica napus (Josefsson et al., 1987, J Biol Chem. 262(25):12196-201; Ellerström et al., 1996, Plant Molecular Biology, Volume 32, Issue 6, pp 1019-1027).

Fruit Specific Promoters

An example of a fruit specific promoter is found in U.S. Pat. Nos. 5,536,653; and 6,127,179; and 5,608,150; and 4,943,674.

Non Photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

Tuber Specific Promoters

An example of a tuber specific promoter is found in U.S. Pat. No. 6,184,443.

Bulb Specific Promoters

An example of a bulb specific promoter is found in Smeets et al., (1997) Plant Physiol. 113:765-771.

Rhizome Preferred Promoters

An example of a rhizome preferred promoter is found Seong Jang et al., (2006) Plant Physiol. 142:1148-1159.

Endosperm Specific Promoters

An example of an endosperm specific promoter is found in U.S. Pat. No. 7,745,697.

Corm Promoters

An example of a promoter capable of driving expression in a corm is found in Schenk et al., (2001) Plant Molecular Biology, 47:399-412.

Photosynthetic Tissue Preferred Promoters

Photosynthetic tissue preferred promoters include those that are preferentially expressed in photosynthetic tissues of the plants. Photosynthetic tissues of the plant include leaves, stems, shoots and above ground parts of the plant. Photosynthetic tissue preferred promoters include light regulated promoters.

Light Regulated Promoters

Numerous light regulated promoters are known to those skilled in the art and include for example chlorophyll a/b (Cab) binding protein promoters and Rubisco Small Subunit (SSU) promoters. An example of a light regulated promoter is found in U.S. Pat. No. 5,750,385. Light regulated in this context means light inducible or light induced.

A "transgene" is a polynucleotide that is taken from one organism and introduced into a different organism by transformation. The transgene may be derived from the same species or from a different species as the species of the organism into which the transgene is introduced.

Host Cells

Host cells may be derived from, for example, bacterial, fungal, yeast, insect, mammalian, algal or plant organisms.

Host cells may also be synthetic cells. Preferred host cells are eukaryotic cells. A particularly preferred host cell is a plant cell, particularly a plant cell in a vegetative tissue of a plant.

A "transgenic plant" refers to a plant which contains new genetic material as a result of genetic manipulation or transformation. The new genetic material may be derived from a plant of the same species as the resulting transgenic plant or from a different species.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, Guide to Protein Purification).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297; Hellens et al., 2000, Plant Mol Biol 42: 819-32; Hellens et al., Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues respond to internal developmental signals or external abiotic or biotic stresses are described in the scientific literature. Exemplary promoters are described, e.g., in WO 02/00894 and WO2011/053169, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); Prunus (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), Rubus (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412), Canola (*Brassica napus* L.). (Cardoza and Stewart, 2006 Methods Mol Biol. 343:257-66), safflower (Orlikowska et al, 1995, Plant Cell Tissue and Organ Culture 40:85-91), ryegrass (Altpeter et al., 2004 Developments in Plant Breeding 11(7):255-250), rice (Christou et al., 1991 Nature Biotech. 9:957-962), maize (Wang et al., 2009 In: Handbook of Maize pp. 609-639) and *Actinidia eriantha* (Wang et al., 2006, Plant Cell Rep. 25, 5: 425-31). Transformation of other species is also contemplated by the invention. Suitable methods and protocols are available in the scientific literature.

BRIEF DESCRIPTION OF THE FIGURES

FIG. 1 shows the nucleic acid sequence and translation (SEQ ID NO: 118) of the *Arabidopsis thaliana* DGAT1 transcribed region (SEQ ID NO:81). Exon coding sequences are shown in bold face, underlined, grey blocks FIG. 2 shows the nucleic acid sequence and translation (SEQ ID NO:119) of the *Zea mays* short DGAT1 transcribed region (SEQ ID NO:82). This genomic sequence has F469 deleted and Q67 added compared to the cDNA (EU039830) and peptide (ABV91586) sequences actually used in this patent. Exon coding sequences are shown in bold face, underlined, grey blocks.

FIG. 3 shows the peptide sequence of the N-terminal cytoplasmic region of a number of plant DGAT1s including both long and short versions from the grasses as well as examples from dicotyledonous species. Left hand box represents acyl-CoA binding site (Nykiforuk et al., 2002, Biochimica et Biophysica Acta 1580:95-109). Right hand box represents first transmembrane region (McFie et al., 2010, JBC., 285:37377-37387). Left hand arrow represents boundary between exon 1 and exon 2. Right hand arrow represents boundary between exon 2 and exon 3. The sequences are AtDGAT1 (SEQ ID NO:83), BjDGAT1 (SEQ ID NO:84), BnDGAT1-AF (SEQ ID NO:85), BjDGAT1 (SEQ ID NO:86), TmajusDGAT1 (SEQ ID NO:87), EpDGAT1 (SEQ ID NO:88), VgDGAT1 (SEQ ID NO:89), NtDGAT1 (SEQ ID NO:90), PfDGAT1 (SEQ ID NO:91), ZmL (SEQ ID NO:92), SbDGAT1 (SEQ ID NO:93), OsL (SEQ ID NO:94), OsS (SEQ ID NO:95), SbDGAT1 (SEQ ID NO:96), ZmS (SEQ ID NO:97), PpDGAT1 (SEQ ID NO:98), SmDGAT1 (SEQ ID NO:99), EaDGAT1 (SEQ ID NO:100), VvDGAT1 (SEQ ID NO:101), GmDGAT1 (SEQ ID NO:102), GmDGAT1 (SEQ ID NO:103), LjDGAT1 (SEQ ID NO:104), MtDGAT1 (SEQ ID NO:105), JcDGAT1 (SEQ ID NO:106), VfDGAT1 (SEQ ID NO:107), RcDGAT1 (SEQ ID NO:108), PtDGAT1 (SEQ ID NO:109), Pt DGAT1 (SEQ ID NO:110).

EXAMPLES

Example 1: Plant DGAT1 Sequence Selection and Splice Site Prediction

The majority of nucleic acid sequences and peptide sequences for the plant type 1 DGATs can be found by accession number in public domain libraries (Table 1). For creating initial alignments we used ClustalW (Thompson et al., 1994, Nucleic Acids Res., 22, 4673-4680); these were manually edited and used to create the models to search the DGAT sequences, using the HMMER2 package (HMMER 2.3.2 (October 2003) Copyright© 1992-2003 HHMI/Washington University School of Medicine, available from the World Wide Web at http://hmmer.org). Initial matching of protein sequences against genomic DNA with splice prediction was performed with the GeneWise package (Birney et al., 2004, Genome Res. 14: 988-995). Some of the sequences retrieved appeared to have errors; in particular incorrectly predicted splice sites which would result in internal deletions that would likely result in non-functional proteins. While both dicotyledonous and monocotyledonous type 1 DGATs have 16 exons there are some differences in the position of the splicing. Exon 8 in the dicotylendonous DGAT1 gene corresponds to exons 8 and 9 in the monocotyledonous DGAT1 gene, while exon 14 in the monocotyledonous gene corresponds to exons 13 and 14 in the dicotyledonous gene. We have found that the most accurate method for determining the likely genuine coding sequence from genomic data has been to use Vector NTI Advance™ 11.0 (© 2008 Invitrogen Corporation) to translate the genome in the three forward reading frames and align these with demonstrated functional DGAT1s from dicotyledonous or monocotyledous species as appropriate (for example *A. thaliana* cDNA NM_127503, protein NP_179535 and *Z. mays* cDNA EU039830, protein ABV91586). The genomic sequence and corresponding exon/intron boundary positions for *Arabidopsis thaliana* encoding NP_179535 and *Zea mays* encoding ABV91586 that can be used as a template for determining other plant DGAT coding regions are shown in FIG. 1 and FIG. 2, respectively. An example of this template use is shown for the determination of *Z. mays* DGAT1 SEQ ID NO: 10 and SEQ ID NO: 39.

TABLE 1

| DGAT1 Species Source | DNA accession #s & BAC # | SEQ ID NO: | PROTEIN accession #s & BAC # | SEQ ID NO: |
|---|---|---|---|---|
| A. thaliana | NM_127503 | 1 | NP_179535 | 30 |
| B. juncea | AF164434 | 2 | AAY40784 | 31 |
| B. napus | AF164434_1 | 3 | AAD45536.1 | 32 |

TABLE 1-continued

| DGAT1 Species Source | DNA accession #s & BAC # | SEQ ID NO: | PROTEIN accession #s & BAC # | SEQ ID NO: |
|---|---|---|---|---|
| B. juncea | DQ016107 | 4 | AAY40785 | 33 |
| T. majus | AY084052 | 5 | AAM03340 | 34 |
| E. pitardii | FJ226588 | 6 | ACO55635 | 35 |
| V. galamensis | EF653276 | 7 | ABV21945 | 36 |
| N. tabacum | AF129003_1 | 8 | AAF19345.1 | 37 |
| P. frutescens | AF298815_1 | 9 | AAG23696.1 | 38 |
| Z. mays | From: CHORI-201 Maize B73 BAC | 10 | From: CHORI-201 Maize B73 BAC | 39 |
| S. bicolor | XM_002439374 | 11 | XP_002439419 | 40 |
| O. sativa | Os05g0196800 | 12 | NP_001054869 | 41 |
| O. sativa | From: AP003714.1 | 13 | From: AP003714.1 | 42 |
| S. bicolor | XM_002437120.1 | 14 | XP_002437165 | 43 |
| Z. mays | EU039830 | 15 | ABV91586 | 44 |
| P. patens | XM_001770877.1 | 16 | XP_001770929 | 45 |
| S. moellendorffii | XM_002964119 | 17 | XP_002964165 | 46 |
| E. alatus | AY751297 | 18 | AAV31083 | 47 |
| V. vinifera | XM_002279309 | 19 | XP_002279345 | 48 |
| G. max | AY496439 | 20 | AAS78662 | 49 |
| G. max | AB257590 | 21 | BAE93461 | 50 |
| L. japonicus | AY859489 | 22 | AAW51456 | 51 |
| M. truncatula | AC174465.2 | 23 | ABN09107 | 52 |
| J. curcas | DQ278448.1 | 24 | ABB84383 | 53 |
| V. fordii | DQ356680.1 | 25 | ABC94472 | 54 |
| V. galamensis | EF653276.1 | 26 | ABV21945 | 55 |
| R. communis | XM_002514086.1 | 27 | XP_002514132 | 56 |
| P. trichocarpa | XM_002308242.1 | 28 | XP_002308278 | 57 |
| P. trichocarpa | XM_002330474.1 | 29 | XP_002330510 | 58 |

Example 2: Modification of DGAT1 Proteins in the Region Upstream of the Acyl CoA Binding Site FIG. 3 shows alignment of a number of DGAT1 sequences from plants. The left box shows the position of the Acyl-CoA binding site.

As a starting point for their experiments the applicants used the DGAT1 sequences of SEQ ID NO: 30, 34, 39, 41, 42 and 44 as summarized in the Table 2 below. These DGAT1s were modified by replacing the sequence 13 residues upstream of the beginning of the N-terminal acyl-CoA binding region (Weselake et al. 2006) with Met-Gly-Gly-Gly-Ser (MGGGS) (Table 2, Region 1 specific modifications/truncation constructs for expression in *Saccharomyces cerevisiae*). This meant their truncated N-termini were approximately 9 residues longer than the native N-terminus of the *Selaginella moellendolffii* native DGAT1 (SEQ ID NO: 46). Furthermore this placed the N-terminal truncations 18 residues upstream of the 84 amino acid truncation performed by McFie et al., (2010, JBC., 285:37377-37387) on the mouse DGAT1 which resulted in a large increase in activity but substantial drop in both accumulation of recombinant DGAT1 and its ability to oligomerise. Thus the N-terminal truncations shown in SEQ ID NO: 59, 60, 62, 63, 64 and 65, left 32 residues of the original N-terminal putative cytoplasmic domains intact. In addition we generated a number of other truncated forms of AtDGAT1 in which repeat residues from OsL-DGAT1 were added (Table 2).

Sequences with modifications were synthesised either by GENEART AG (Germany) or GeneScript (U.S.A). Sequences were optimised for expression in *Saccharomyces cerevisiae* and flanked with appropriate restriction sites to enable the cloning into the pYES2.1 vector (Invitrogen).

TABLE 2

| Starting Sequence SEQ ID NO: | Species | N-terminal modification | Mutation # | Modified Sequence SEQ ID NO: |
|---|---|---|---|---|
| 30 | A. thaliana | MGGGS (SEQ ID NO: 113) | | 59 |
| 30 | A. thaliana | MAPPPGGGSPQQQQGGGSQ QQQGGGS (SEQ ID NO: 121) | | 60 |
| 30 | A. thaliana | Multiple individual additions within N-terminus | | 61 |
| 34 | T. majus | MGGGS (SEQ ID NO: 113) | | 62 |
| 42 | O. sativa-S | MGGGS (SEQ ID NO: 113) | | 63 |
| 41 | O. sativa-L | MGGGS (SEQ ID NO: 113) | | 64 |
| 44 | Z. mays-S | MGGGS (SEQ ID NO: 113) | | 65 |
| 39 | Z. mays-L | MGGGS (SEQ ID NO: 113) | | 66 |

Example 3: Expression of Modified DGAT1 Sequences in Cells

Expression of Constructs in *S. cerevisiae*

The parent DGAT1 constructs and modified DGAT1 constructs were placed into the galactose-inducible yeast expression vector pYES2.1/V5-His TOPO® (Invitrogen). This resulted in the addition of an inframe C-terminal V5 epitope and 6× histidine tag. The names of the modified constructs, and the number of their corresponding peptide sequences, are shown in Table 3.

The *Saccharomyces cerevisiae* quadruple mutant (H1246) in which all four neutral lipid biosynthesis genes have been disrupted (Sandager et al., 2002, The Journal of Biological Chemistry, 277:6478-6482) was transformed as per Elble (1992, BioTechniques 13, 18-20) and selected by the ability to grow in the absence of uracil. Routinely, yeast cells were grown aerobically overnight in a synthetic medium with 0.67% YNB, without uracil (SC-U) and containing 2% glucose. Cells from overnight culture were used to inoculate 200 mL of induction medium (SC-U containing 2% galactose and 1% raffinose) to an initial OD$_{600}$ of 0.4. Cells were allowed to further grow at 30° C., with shaking at 200 rpm until late stationary phase, normally 48 h. Cells were harvested by centrifugation at 1500×g for 5 min, then cell pellets were washed with distilled water and either used immediately for subsequent analysis or kept in −80° C. until required. Cell pellets for neutral lipid extraction were freeze-dried for 48 h and stored in −20° C. freezer until required.

Lipid Analysis of *S. cerevisiae*

Approximately 10 mg of freeze-dried yeast cell material was accurately weighed then disrupted using glass beads by vortexing for 1 minute. This lysate was extracted in hot methanolic HCL for fatty acid methyl ester (FAME) analysis (Browse et al., 1986, Anal. Biochem. 152, 141-145).

For FA profile analysis approximately 50 mg freeze dried yeast was placed in a 13-mm screw cap tube, and an equal volume of glass beads added before vortexing at high speed in 3× 1 min bursts. Following addition of 50 µg of 19:0 TAG internal standard, 2.4 mL of 0.17 M NaCl in MeOH was added and the mixture vortexed for 15 sec followed by the addition of then 4.8 mL of heptane and the entire contents mixed.

The solution was then incubated in 80° C. water bath for 2 h without shaking. After incubation, the solution was cooled to room temperature. After cooling, the upper phase (lipidic phase) was transferred to fresh screw-cap tube and evaporated to dryness under stream of nitrogen gas. The dried residue was then dissolved in 1 mL heptane and mixed thoroughly for TAG SPE separation using Strata Si-1 Silica column (Phenomenwx, 8B-S012-EAK).

After preconditioning with methanol and equilibrating the Silica column with heptanes the 1 mL TAG extract (including 50 µg 17:0 TAG Internal Standard was passed through the pre-equilibrated column, followed by 1.2 mL of heptane and then 2 mL of chloroform:heptane (1:9 v/v/) and the eluate collected. The total eluate collected was evaporated to dryness under the stream of N gas and the residue used for FAMEs extraction.

FAMEs of Extracted TAG

To the TAG residue above 10 µL of internal standard 15:0 FA (4 mg/mL dissolved in heptane) and 1 mL of methanolic HCl (1N) reagent containing 5% of 2,2-dimethoxypropane (as water scavenger) were added.

The tube was then flushed with N gas, then sealed immediately with Teflon-lined cap, and heated at 80° C. in a water bath for 1 h. After cooling down, 0.6 mL heptane and 1.0 mL of 0.9% (w/v) NaCl was added, the mixture vortexed then spun at 500 rpm for 1 min.

From the top heptane layer, 100 µL was collected and transferred to a flat-bottom glass insert fitted into a vial for FAMES GC/MS analysis.

Protein Extraction and Trypsin Digestion

Yeast cell pellets were washed with lysis buffer (50 mM sodium phosphate, pH 7.4, 1 mM EDTA, 5% glycerol, 1 mM PMSF) then resuspended in 500 µL lysis buffer, glass beads were added and cells disrupted by vortexing 2× at medium speed for 30 seconds. Cell debris was pelleted by centrifugation at 1000×g for 5 min, the supernatant transferred to fresh tubes and total cellular membranes pelleted by ultracentrifugation at 100,000×g for 1 h. Membrane proteins were resuspended in lysis buffer with or without detergent (1% Dodecyl maltoside) and quantified in a Qubit Fluorometer using the Qubit IT Quantitation Kit.

Trypsin was added to give a final concentration of 25 µg/mL to 50 µL of protein extract and the mixture incubated at 30° C. for 30 min. The reaction was terminated by addition of Trypsin inhibitor from *Glycine max* (Sigma-Aldrich catalogue #T6414) to a final concentration of 0.4 µg/µL. After addition of trypsin inhibitor, 4×SDS loading dye and 10× reducing agent (Invitrogen) were added, and the protein incubated at 70° C. for 10 min prior to SDS-PAGE followed by immunoblotting. The blot was probed with either Anti V5-HRP antibody (Cat #R96125, Invitrogen) at 1:2500 dilution, or anti Kar2 (y-115) antibody produced in rabbit (SC-33630, Santa Cruz Biotechnology) at 1:200 dilution. Anti Kar2 was used to detect the yeast protein Kar2, an ER luminaly-located protein (Rose et al, 1989) which serves as a control to demonstrate the presence of intact microsomes.

Example 4: Truncation of the N-Terminal Cytoplasmic Region—Region 1 of Plant DGAT1s—Enhances Lipid Production in *Saccharomyces cerevisiae*

The N-terminal cytoplasmic region can be truncated to raise the lipid yield. Table 3 shows the lipid yields of a variety of DGAT1s in which the N-terminal cytoplasmic region has been truncated. The lipid yields are presented both as grams of lipid produced per litre of (which therefore compensates for any differences in growth rate) as well as normalized as a percentage of the lipid yield of the corresponding unmodified parent DGAT1.

A comparison of A. thaliana, T. majus, O. sativa-S, O. sativa-L, Z. mays-S and Z. mays-L and their N-terminal cytoplasmic region truncated counterparts are shown in Table 3. The lipid yields are presented as grams of lipid per litre of culture at 32 and 48 hours of culture as well as a percentage of the lipid yield obtained with the corresponding native (non-truncated) DGAT1 parent isolated at the same time.

TABLE 3

| Construct Description | SEQ ID NO: | Lipid yield @ 32 hr (g FA/L) | Lipid yield as % of native parent @ 32 hr | Lipid yield @ 48 hr (g FA/L) | Lipid yield as % of native parent @ 48 hr |
|---|---|---|---|---|---|
| native A. thaliana | 67 | 0.25 | 100 | 0.25 | 100 |
| N-truncated A. thaliana | 59 | 0.36 | 147.55 | 0.37 | 148.91 |
| Native T. majus | 68 | 0.34 | 100 | 0.40 | 100 |
| N-truncated T. majus | 62 | 0.32 | 95.95 | 0.37 | 93.81 |
| Native O. sativa-S | 69 | 0.40 | 100 | 0.47 | 100 |
| Truncated O. sativa-S | 63 | 0.32 | 79.72 | 0.35 | 74.24 |
| Native O. sativa-L | 70 | 0.44 | 100 | 0.52 | 100 |
| Truncated O. sativa-L | 64 | 0.54 | 122.01 | 0.53 | 101.79 |
| Native Z. mays-S | 71 | 0.30 | 100 | 0.31 | 100 |
| Truncated Z. mays-S | 65 | 0.25 | 80.53 | 0.25 | 81.27 |
| Native Z. mays-L | 72 | 0.50 | 100 | 0.54 | 100 |
| Truncated Z. mays-L | 66 | 0.54 | 108.44 | 0.68 | 125.60 |

Example 5: Expression of Modified DGAT1 in Brassica napus

The strategy above can also be used to generate a variety of modified DGAT1 constructs for expression in the seeds of Brassica napus. The parent DGATs and their modified forms can be transferred into the Gateway®-compatible binary vector pMD107 (courtesy of Dr Mark Smith, NRC Saskatoon, SK, Canada, S7N 0W9) to place them under the control of the seed-specific napin promoter (Josefsson et al., 1987, J Biol Chem. 262(25):12196-201; Ellerström et al., 1996, Plant Molecular Biology, Volume 32, Issue 6, pp 1019-1027).

Plant Transformation

B. napus (cv. DH12075) can be transformed via Agrobacterium tumefaciens (GV3101) using the cotyledon co-cultivation method (adapted from that of Maloney et al., 1989, Plant Cell Reports Vol 8, No 4, pg 238-241). Control lines may contain an empty-vector, and when identified, null sibling lines may be subsequently used as true controls.

Approximately 200 $T_0$ transformed lines may be produced and their corresponding $T_1$ selfed seeds may be analysed for oil content by GC. Approximately 50 individual transgenic lines (including control lines) may be selected for the next generation (10 plants/line) based on their oil content, or seed weight (8 lines).

A total of approximately $T_1$ plants may be grown and screened by PCR for copy number and identification of null sibling lines. $T_2$ seeds may be analysed in triplicate for oil content by NMR.

Example 6: Expression of Modified DGAT1 in Camelina sativa

The strategy above can also be used to generate a variety of modified DGAT1 constructs for expression in the seeds of Camilina sativa and other plants Sequences with modifications were synthesised either by GENEART AG (Germany) or GeneScript (U.S.A). Sequences were optimised for expression in Brassica species and included an intron (SEQ ID NO:73) from Arabidopsis thaliana DGAT1—intron 3. Each sequence was flanked with appropriate attL recombination sites to enable the cloning Gateway® adapted vectors.

TABLE 3

| Starting seq ID # | Species | N-terminal modification | C-terminal modification | Additional information | Type of sequence | Modified SEQ ID NO |
|---|---|---|---|---|---|---|
| 39 | Z. mays-L | none | V5-His tag | + intron | NUCLEIC | 74 |
| 39 | Z. mays-L | none | V5-His tag | ORF only | NUCLEIC | 75 |
| 39 | Z. mays-L | none | V5-His tag | | PEPTIDE | 76 |
| 39 | Z. mays-L | MGGGS | V5-His tag | + intron | NUCLEIC | 77 |
| 39 | Z. mays-L | MGGGS | V5-His tag | ORF only | NUCLEIC | 78 |
| 39 | Z. mays-L | MGGGS | V5-His tag | | PEPTIDE | 79 |

The parent DGATs and their modified forms were transferred into the Gateway®-compatible binary pRSh1 Gateway adapted binary vector (Winichayakul et al., 2009, Biotechnol. Appl. Biochem. 53, 111-122) modified by replacement of the CaMV35S promoter replaced with the Brassica napus Napin promoter (SEQ ID NO:80).

Camelina sativa Transformation

C. sativa (cf. Calena) were transformed via Agrobacterium tumefaciens (GV3101) using the floral dip method (adapted from that of Clough and Bent, 1998, Plant J. 16(6):735-745). Essentially seeds were sown in potting mix in 10 cm pots in a controlled environment, approximately 6 weeks after planting the flowers were dipped for 5-14 minutes under vacuum (70-80 inch Hg) in an overnight culture of appropriated *Agrobacterium* GV3101 cells resuspended in a floral dip buffer. After vacuum-transformation, plants were kept for 24 h under low light conditions by partly covering with a black plastic sheet. Vacuum transformations can be repeated three times at approximately 10-12 days intervals, corresponding to the flowering duration. Plants were grown in potting mix in a controlled environment (16-h day length, 21-24° C., 65-70% relative humidity).

The $T_1$ seeds produced can be collected and screened for transformants by germinating and growing seedlings at 22° C. with continuous light on a half-strength MS medium (pH 5.6) selection plate containing 1% (w/v) sucrose, 300 mg/L Timentin, and 25 mg/L DL-phosphinothricin to select for herbicide resistance. T, selfed seed populations can also be screened by immuno blot for the presence of the V5 eptiope.

$T_2$ selfed seeds may be analysed for oil content by GC. Approximately 50 individual transgenic lines (including control lines) may be selected for the next generation (10 plants/line) based on their oil content, or seed weight. $T_2$ plants may be grown and screened by PCR for copy number and identification of null sibling lines. $T_2$ seeds may be analysed in triplicate for oil content by NMR or GC/MS.

---

The invention claimed is:

1. A method for producing an improved plant DGAT1, the method comprising the steps:
   a) modifying a plant DGAT1 protein by truncation of 10 or more amino acids from the N-terminal end of an N-terminal region of the protein, wherein the N-terminal region is at least 13 amino acids upstream of a conserved motif ESPLSS (Glu-Ser-Pro-Leu-Ser-Ser) (SEQ ID NO: 112) in the acyl-CoA binding site,
   b) adding a flexible peptide linker having the sequence MGGGS (SEQ ID NO: 113) to the truncated N-terminal region to produce a modified DGAT1 protein with the flexible peptide linker at the N-terminus of the modified DGAT1 protein,
   c) testing the capacity the modified DGAT1 protein to produce lipid in a cell relative to that of the unmodified DGAT1 protein, and
   d) selecting the improved DGAT1 protein on the basis of its increased capacity to produce lipid in a cell relative to that of the unmodified DGAT1 protein.

2. The method of claim 1 in which the unmodified DGAT1 protein in a) has a sequence with at least 95% identity to any one of SEQ ID NO: 30 to 58.

3. The method of claim 1 in which the unmodified DGAT1 protein in a) has a sequence with at least 99% identity to any one of SEQ ID NO: 30 to 58.

4. The method of claim 1 wherein the modification is truncation of all of the N-terminal region of the DGAT1 protein.

5. The method of claim 1 wherein when the improved DGAT1 protein is expressed in the cell, it has altered substrate specificity relative to the unmodified DGAT1.

6. The method of claim 1 wherein the improved DGAT1 protein comprises a sequence with at least 95% identity to any one of SEQ ID NO: 59, 64 and 66, and includes the flexible peptide linker.

7. The method of claim 1 wherein the improved DGAT1 protein comprises a sequence with at least 99% identity to any one of SEQ ID NO: 59, 64 and 66, and includes the flexible peptide linker.

8. An improved plant DGAT1 protein that has:
   been modified by truncation of 10 or more amino acids from the N-terminal end of an N-terminal region of a plant DGAT1 protein, wherein the N-terminal region is at least 13 amino acids upstream of a conserved motif ESPLSS (Glu-Ser-Pro-Leu-Ser-Ser) (SEQ ID NO: 112) in the acyl-CoA binding site, and to which a flexible peptide linker having the sequence MGGGS (SEQ ID NO: 113) has been added to the truncated N-terminal region, and wherein the improved DGAT1 has increased capacity to produce lipid in a cell relative to that of the unmodified DGAT1 protein, wherein the improved DGAT1 protein comprises a sequence with at least one of:

a) at least 95% identity to any one of SEQ ID NO: 59, 64 and 66, or b) at least 99% identity to any one of SEQ ID NO: 59, 64 and 66 and wherein the improved DGAT1 protein includes the flexible peptide linker.

9. A cell that expresses the improved plant DGAT1 protein of claim 8.

10. The cell of claim 9 that produces more lipid than does a control cell that does not express the improved plant DGAT1 protein.

11. The cell of claim 10 which also has an altered lipid profile relative to a control cell that does not comprise the construct.

12. The cell of claim 9 which is also transformed to express at least one of: an oleosin, steroleosin, caloleosin, polyoleosin, and an oleosin including at least one artificially introduced cysteine.

13. A plant that expresses the improved plant DGAT1 protein of claim 8.

14. The plant of claim 13 that produces more lipid, in at least one of its tissues or parts, or as a whole, than does a control plant that does not comprise the improved plant DGAT1 protein.

15. The plant of claim 13 that has an altered lipid profile, in at least one of its tissues or parts, or as a whole, relative to a control plant that does not comprise the improved plant DGAT1 protein.

16. The plant of claim 13 that is also transformed to express at least one of: an oleosin, steroleosin, caloleosin, polyoleosin, and an oleosin including at least one artificially introduced cysteine.

17. A part, propagule or progeny of the plant of claim 13, wherein the part, propagule or progeny expresses the improved DGAT1 protein.

18. The part, propagule or progeny of claim 17 that produces more lipid than does a part, propagule or progeny of a control plant that does not comprise the improved DGAT1 protein.

19. The part, propagule or progeny of claim 17 that has an altered lipid profile relative to a part, propagule or progeny of a control plant that does not comprise the improved DGAT1 protein.

20. An animal feedstock or biofuel feedstock comprising at least one cell of claim 9.

21. A biofuel feedstock or animal feedstock comprising at least one cell of claim 9.

22. A method for producing lipid, the method comprising expressing the improved DGAT1 protein in the cell of claim 9 or in a plant comprising the cell.

23. The method of claim 22 wherein expressing the improved DGAT1 protein in the cell, or plant, leads to production of the lipid in the cell or plant.

24. The method of claim 22 wherein the method includes the step of transforming the cell or plant with a polynucleotide encoding the improved DGAT1 protein.

25. The method of claim 22 which includes the step of extracting the lipid from the cell or plant.

26. A method for producing lipid, the method comprising extracting lipid from at least one of a cell of claim 9 or from a plant, plant part, propagule and progeny comprising the cell, wherein the cell, plant, plant part, propagule or progeny expresses the improved DGAT1 protein.

27. The method of claim 22 wherein the lipid is processed into at least one of:

a) a fuel,
b) an oleochemical,
c) a nutritional oil,
d) a cosmetic oil,
e) a polyunsaturated fatty acid (PUFA), and
f) a combination of any of a) to e).

* * * * *

SEQUENCE LISTING

<160> NUMBER OF SEQ ID NOS: 121

<210> SEQ ID NO 1
<211> LENGTH: 2074
<212> TYPE: DNA
<213> ORGANISM: Arabidopsis thaliana

<400> SEQUENCE: 1

```
tgaatccttt ttcctttctt cttcttcttc tcttcagaga aaactttgct tctctttcta      60
taaggaacca gacacgaatc ccattcccac cgatttctta gcttcttcct tcaatccgct     120
ctttccctct ccattagatt ctgtttcctc tttcaatttc ttctgcatgc ttctcgattc     180
tctctgacgc ctcttttctc ccgacgctgt ttcgtcaaac gcttttcgaa atggcgattt     240
tggattctgc tggcgttact acggtgacgg agaacggtgg cggagagttc gtcgatcttg     300
ataggcttcg tcgacggaaa tcgagatcgg attcttctaa cggacttctt ctctctggtt     360
ccgataataa ttctccttcg gatgatgttg gagctcccgc cgacgttagg gatcggattg     420
attccgttgt taacgatgac gctcagggaa cagccaattt ggccggagat aataacggtg     480
gtggcgataa taacggtggt ggaagaggcg gcggagaagg aagaggaaac gccgatgcta     540
cgtttacgta tcgaccgtcg gttccagctc atcggagggc gagagagagt ccacttagct     600
ccgacgcaat cttcaaacag agccatgccg gattattcaa cctctgtgta gtagttctta     660
ttgctgtaaa cagtagactc atcatcgaaa atcttatgaa gtatggttgg ttgatcagaa     720
cggatttctg gtttagttca agatcgctgc gagattggcc gcttttcatg tgttgtatat     780
ccctttcgat ctttccttg gctgccttta cggttgagaa attggtactt cagaaataca     840
tatcagaacc tgttgtcatc tttcttcata ttattatcac catgacagag gttttgtatc     900
cagtttacgt caccctaagg tgtgattctg cttttttatc aggtgtcact ttgatgctcc     960
tcacttgcat tgtgtggcta aagttggttt cttatgctca tactagctat gacataagat    1020
ccctagccaa tgcagctgat aaggccaatc ctgaagtctc ctactacgtt agcttgaaga    1080
gcttggcata tttcatggtc gctcccacat tgtgttatca gccaagttat ccacgttctg    1140
catgtatacg gaagggttgg gtggctcgtc aatttgcaaa actggtcata ttcaccggat    1200
tcatgggatt tataatagaa caatatataa atcctattgt caggaactca aagcatcctt    1260
tgaaaggcga tcttctatat gctattgaaa gagtgttgaa gctttcagtt ccaaatttat    1320
atgtgtggct ctgcatgttc tactgcttct tccacctttg gttaaacata ttggcagagc    1380
ttctctgctt cggggatcgt gaattctaca aagattggtg gaatgcaaaa agtgtgggag    1440
attactggag aatgtggaat atgcctgttc ataaatggat ggttcgacat atatacttcc    1500
cgtgcttgcg cagcaagata ccaaagacac tcgccattat cattgctttc ctagtctctg    1560
```

```
cagtctttca tgagctatgc atcgcagttc cttgtcgtct cttcaagcta tgggcttttc    1620
ttgggattat gtttcaggtg cctttggtct tcatcacaaa ctatctacag gaaaggtttg    1680
gctcaacggt ggggaacatg atcttctggt tcatcttctg cattttcgga caaccgatgt    1740
gtgtgcttct ttattaccac gacctgatga accgaaaagg atcgatgtca tgaaacaact    1800
gttcaaaaaa tgactttctt caaacatcta tggcctcgtt ggatctccgt tgatgttgtg    1860
gtggttctga tgctaaaacg acaaatagtg ttataaccat tgaagaagaa aagaaaatta    1920
gagttgttgt atctgcaaaa attttggtag agacacgcga acccgtttgg attttgttat    1980
ggtgtaaaga aatttcaatc aaaaaactgt tgtaataatt gttaccaaaa agaaatgctt    2040
ttctggaaac gaggggaaaa atagtagttt tgtt                                2074

<210> SEQ ID NO 2
<211> LENGTH: 1512
<212> TYPE: DNA
<213> ORGANISM: Brassica juncea

<400> SEQUENCE: 2
atggcgattt tggattctgg aggcgtcgct gtaccgccga cggagaacgg cgtcgcggat      60
ctcgacaggc tccaccgtcg taaatcgagt tcggattctt ccaacggact cctctccgat     120
acttccccgt cggacgatgt tggagctgcg gcggccgaaa gggatcgggt tgattccgct     180
gccgaggagg aggctcaggg aacagcgaat ttagctggcg gagatgccga aactagggaa     240
tccgccggag gcgatgtaag gtttacgtat cgaccgtcgg ttccagctca tcggaggacg     300
agggagagtc ctctcagctc cgacgctatc ttcaaacaaa gccatgcagg attgttcaac     360
ctctgtgtag ttgttcttgt tgctgttaac agtagactca tcatcgaaaa cctcatgaag     420
tatggttggt tgatcagaac tgattttggg tttagttcta catccttacg agactggccg     480
cttttcatgt gttgtctttc actttcggtc tttccttttgg ctgccttcac ggtcgagaaa    540
atggtacttc agaaattcat atctgagcct gttgccatca ttcttcatgt cattataacc     600
atgacagagg tcttgtatcc agtctacgtc acactgaggt gtgattctgc cttcttgtca     660
ggtgtcacgt tgatgctgct cacttgcatt gtgtggctga agttggtttc ttacgctcat     720
actagctacg acataagaac cctggccaat tcagctgata aggtcgatcc tgaaatctcc     780
tactatgtta gcttgaagag cttggcgtat ttcatggttg ctcccacact gtgttatcag     840
ccaagctatc cacgttctcc atgtatccgg aagggttggg tggctcgtca acttgcaaaa     900
ctggtcatat tcactggact catgggattt ataatagagc aatatataaa tcctattgtt     960
aggaactcaa agcatcctct gaaagggggac cttctatatg ctattgaaag agtgttgaag    1020
cttccagttc caaatctata tgtgtggctc tgcatgttct actgcttctt ccacctttgg    1080
ttaaacatat tggcagagct cctctgcttc ggggaccgtg aattctacaa agattggtgg    1140
aatgcaaaaa gcgttggaga ttattggaga atgtggaata tgcctgttca caaatggatg    1200
gttcgacatg tatactttcc gtgcctgcgc atcaagatac caaaagtacc cgccattatc    1260
attgctttct tagtctctgc agtctttcat gagttatgca tcgcagttcc ttgccgtctc    1320
ttcaatctat gggctttcat gggaattatg tttcaggtcc ctttggtctt tatcacaaac    1380
tttttacaag aaaggtttgg ctccatggtg ggaaacatga tctttggttc agcttcttgc    1440
attttcggac aaccgatgtg tgggcttctt tattaccatg acctgatgaa ccgcaaagga    1500
tccatgtcct ga                                                        1512
```

```
<210> SEQ ID NO 3
<211> LENGTH: 1512
<212> TYPE: DNA
<213> ORGANISM: Brassica napus

<400> SEQUENCE: 3
atggcgattt tggattctgg aggcgtcgct gtaccgccga cggagaacgg cgtcgcggat      60
ctcgacaggc tccaccgtcg taaatcgagt tcggattctt ccaacggact cctctccgat     120
acttccccgt cggacgatgt tggagctgcg gcggccgaaa gggatcgggt tgattccgct     180
gccgaggagg aggctcaggg aacagcgaat ttagctggcg agatgccga aactagggaa      240 tccgccggag gcgatgtaag gtttacgtat cgaccgtcgg ttccagctca tcggaggacg     300
agggagagtc ctctcagctc cgacgctatc ttcaaacaaa gccatgcagg attgttcaac     360
ctctgtgtag ttgttcttgt tgctgttaac agtagactca tcatcgaaaa cctcatgaag     420
tatggttggt tgatcagaac tgattttttgg tttagttcta catccttacg agactggccg    480
cttttcatgt gttgtctttc actttcggtc tttcctttgg ctgccttcac ggtcgagaaa     540
atggtacttc agaaattcat atctgagcct gttgccatca ttcttcatgt cattataacc     600
atgacagagg tcttgtatcc agtctacgtc acactgaggt gtgattctgc cttcttgtca     660
ggtgtcacgt tgatgctgct cacttgcatt gtgtggctga agttggtttc ttacgctcat     720
actagctacg acataagaac cctggccaat tcagctgata aggtcgatcc tgaaatctcc     780
tactatgtta gcttgaagag cttggcgtat ttcatggttg ctcccacact gtgttatcag     840
ccaagctatc cacgttctcc atgtatccgg aagggttggg tggctcgtca acttgcaaaa     900
ctggtcatat tcactggact catgggattt ataatagagc aatatataaa tcctattgtt     960
aggaactcaa agcatcctct gaaagggac cttctatatg ctattgaaag agtgttgaag    1020
ctttcagttc caaatctata tgtgtggctc tgcatgttct actgcttctt ccacctttgg    1080
ttaaacatat tggcagagct cctctgcttc ggggaccgtg aattctacaa agattggtgg    1140
aatgcaaaaa gcgttggaga ttattggaga atgtggaata tgcctgttca caaatggatg    1200
gttcgacatg tatactttcc gtgcctgcgc atcaagatac caaaagtacc cgccattatc    1260
attgctttct tagtctctgc agtctttcat gagttatgca tcgcagttcc ttgccgtctc    1320
ttcaatctat gggctttcat gggaattatg tttcaggtcc ctttggtctt tatcacaaac    1380 ttttttacaag aaaggtttgg ctccatggtg ggaaacatga tctttggttc agcttcttgc    1440
attttcggac aaccgatgtg tgggcttctt tattaccatg acctgatgaa ccgcaaagga    1500
tccatgtcct ga                                                        1512

<210> SEQ ID NO 4
<211> LENGTH: 1510
<212> TYPE: DNA
<213> ORGANISM: Brassica juncea

<400> SEQUENCE: 4
atggcgattt tggattctgg aactgtcacg atggcgacgg agaacggtgt cgcggatctc      60
gatatgcttc gtcgtcgtaa atcgagatcg gattcttcca acggacttct ctccgagact    120
tccccatcgg atgatgctgg agctccggcc gacgtggagat cgggttga ttcagctgct     180 caggaacag cgaatttagc tggagatacg gaaactaggg aatccggtgg aggaggagga    240
ggaggaaacg gcgaggtaag gtttacgtat cgaccgtcgg ttccagctca tcggaggacg    300
agggagagtc cactcagctc cgacgctatc ttcaaacaaa gccatgcagg attgttcaac    360
```

-continued

```
ctctgtgtag ttgttcttgt tgctgttaac agtagactca tcatcgaaaa tctcatgaag      420
tacggttggt tgatcagaac tgatttctgg tttagttcta catccctccg agattggccg      480
cttttcatgt gttgtctttc actttcaatc tttcctttgg ctgcctttac cgtcgagaaa      540
ttggtactcc agaaattcat atctgaacct gttgtcatca ttcttcatat tattatcacc      600
atgactgagg tcttgtatcc agtctacgtc accctaaggt gtgattcggc tttcttatca      660
ggtgtcacat tgatgctact cacttgcatt gtgtggctga agttggtttc ttacgctcat      720
actaattacg acataagaac cgtagctaat tcagctgata aggtcgatcc tgaagtctcc      780
tactatgtta gcttgaagag cttggcgtat ttcatggttg ctcccacatt gtgttatcag      840
ccaagctatc cacgttctcc gggtatccgg aagggttggg tggctcgtca atttgcgaaa      900
ctggtcatat tcactggact catgggtttt ataatagagc aatatataaa tcctattgtg      960
aggaactcaa agcatccttt gaaagggggat cttctatacg ctattgaaag agtgttgaag     1020
ctttcagttc caaatctata tgtgtggctc tgcatgttct actgcttctt ccacctttgg     1080
ttaaatatat tggcagagct cctttgcttc ggggatcgtg aattctacaa agattggtgg     1140
aatgcaaaaa gcgtaggaga ttattggaga atgtggaata tgcctgttca taaatggatg     1200
gttcgacatg tatactttcc atgcctgcgc ataaagatac cgaaagtacc cgccattatc     1260
attgctttct tagtctctgc agttttccat gagctgtgca ttgcagttcc ttgccgtctc     1320
tttaatttat gggctttcat aggaatcatg tttcaggtgc ctttggtctt tatcacaaac     1380
tatttacaag aaaggtttgg ctccatggtg ggaaacatga tcttctggtt cagcttctgc     1440
attttcggac aaccgatgtg tgtgcttctt tattaccatg acctcatgaa ccgcaaagga     1500
tccatgtcct                                                           1510
```

<210> SEQ ID NO 5
<211> LENGTH: 2090
<212> TYPE: DNA
<213> ORGANISM: Tropaeolum majus

<400> SEQUENCE: 5

```
acgcggggag ttttcaaaat catattatgc ttttcttca ctactgcatg aactttcttt       60
ctacttcttg caactgattt gtaatcctta cacatgtttc tagttttctc catataaaaa      120
aaatattctc tgagcttctc gattctctag agagagaagg ccaaaaaaaa atggcggtgg      180
cagagtcgtc acagaacacg acaaccatga gtggtcacgg cgactcggat ctcaacaatt      240
tccgtagaag gaaaccgagt tcctccgtga ttgaaccttc gtcgtccggt tttacatcca      300
ccaatggcgt accggcgact ggccacgtgg ctgagaatcg tgaccaggat cgggtagggg      360
ctatggagaa cgcaacagga tcggtcaact taattggaaa tggtggaggc gtggttatcg      420
ggaatgaaga gaaacaggta ggggagactg atatacgatt cacttaccgg ccttcgtttc      480
cggctcatcg gagggtgagg gagagtcctc ttagctctga tgcaatcttc aaacagagcc      540
atgcgggttt attcaacttg tgtatagtag tgctcattgc agtaaacagt aggcttatca      600
tcgaaaatct tatgaagtat ggttggttga tcgatactgg tttctggttt agctcaagat      660
cactgggtga ttggtccatc tttatgtgct gtcttacact cccaattttc ccacttgctg      720
cttttattgt tgaaaagctg gtgcagcgaa atcatatatc tgaacttgtt gctgttctcc      780
ttcatgtaat cgtttctacc gctgcagttt tatatccagt tattgtgatc ttaacgtgtg      840
attcggtgta tatgtctggt gtggtattga tgctctttgg ttgcattatg tggttgaagc      900
tggtgtcata tgcacatact agttctgata ttagaacact ggccaaatct ggctataagg      960
```

-continued

```
gggatgcgca ccccaattca accattgtga gttgctcata tgatgttagc ttgaagagtt      1020
tggcatactt catggttgct ccgacattat gttaccagcc tagctatcct cgttcgtcgt      1080
gtatccgcaa gggttgggtt gttcgtcaat ttgtcaaact aatagttttc ataggactca      1140
tggggttcat tatagaacaa tatattaatc ctatcgttcg aaattccaaa cacccattga      1200
aaggagattt tttatatgca atagaaagag ttttgaagct ttcagttcca aatctatatg      1260
tttggctttg catgttctac tctttttcc acctctggtt gaacatactg gctgagcttc      1320
ttcgctttgg tgatcgtgaa ttctacaaag attggtggaa tgcaaaaact gttgcggagt      1380
attggaaaat gtggaaatatg cctgttcata gatggatggt tcgtcatcta tattttccct     1440
gtttgaggaa tgggataccc aaggaaggtg ccattattat cgcgttctta gtttctggtg      1500
ctttccatga gctctgcatt gcagttcctt gccacgtatt caagttatgg gcctttatag      1560
gcattatgtt tcaggttccc ttggtattga ttacgaatta tctacaagaa aagttcagta      1620
attctatggg gggcaatatg atcttctggt tcatcttctg catacttggc caacctatgt      1680
gtgtccttct atattaccat gacctgataa atctaaagga aaagtgaaaa atggaagtt       1740 gcctatgctc agagtattcc tatcccaatg cacacattat atggttctgt acaatctgtg      1800 ccccttcat cctttacacg tacccatgct ggttcctgca cgatgatttg cctttgttt       1860 gtaagcaata tttggagaga gtccaattta ggaagtgact agtgtggctt atatcttgta     1920 tactacctt agtcatgggg gggttttat attactagta ccaaaagtca agttgtatat      1980
gatttacggt ttagtttctt tcatgttttt tgttttttgtg taaatatacg tttcatatat     2040
cactgttttt tcaaagtaaa atcaataata ccccatagat gttgaaactg                2090
```

<210> SEQ ID NO 6
<211> LENGTH: 1494
<212> TYPE: DNA
<213> ORGANISM: Echium pitardii

<400> SEQUENCE: 6

```
cacaaatgac aatatgggag tcgccggaga tcataagctc cgatgaagca gcagcggcgt       60
tgaggcggag aggcggcgcc aaggaggttg cggaacagag attggatagt gaagaagaga      120
agaagaagga ggaggaaaat ggaaaactga agtatactta tcgagcttcc gctccggctc      180 accgagaat caaggagagt cctcttagct ccgacgccat tttcaaacaa agtcatgcag      240
gcctcttcaa tctttgcatt gtggtgcttg ttgctgtaaa cagtcggctt atcattgaga      300
atttgatgaa gtatggttgg ctaattagct cagggttttg gttaagttca acatcattaa      360
gcgactggcc acttctaata tgttgtctca gtctgccgat attccctctg gcttcttttg      420
tggttgaaaa gttgtctcaa caggaattta tatctgagca agtggtgatc actcttcatg      480
cactcataac aacgactgtg attatgtatc cagtaattgt catcctcaga tgtgatcccg      540
ccgttctatc aggtgtgata ttgatgcttt tcacgtgtat tgtgtggttg aagctggtat      600
cttatgcaca tacaaactat gatatgcgag cactagcaaa ggactgtgat aagttacagg      660
cactatcagg ctcttcaatg gaagattgtt cttttgaagt caacttccaa gctttggtat      720
acttcatggt tgctccgaca ttatgttatc agctaaggta tccgcgtacc ccctgcattc      780
gttggggttg ggttacacgt catctcatca gttaatcat atttactgga ctgatgggat      840
tcattattga gcagtatatt aatccaattg tgaaaaattc acaacatcca ttgaagggga      900
acctgttgta tgctatagag agggtcttga agctttcagt tccaaatata tatgtctggc      960
```

```
tctgcatgtt ttattgtctc ttccatctttt ggttaaatat actagccgaa cttctgtgtt    1020
ttggggatcg tgagttctac aaagattggt ggaatgctca aacgatagag gagtattgga    1080
ggatgtggaa catgcctgta cataaatgga tggttcgtca tatatatttc ccttgcttgc    1140
ggaatgggat gcctaaggag ttggctattt tgattgcgtt cctaatatct gcaatcttcc    1200
atgagctgtg cattgctgtg ccgtgtcaca tctttaagtt ctgggctttt atcggaataa    1260
tgtttcaggt cccttggtc cttctgacaa atgttttggt aaaaagttc caaaattcaa    1320 tggttggcaa tatgatattc tggtgcttct tctgcattct tggtcaaccc atgagtctgc    1380
tgctctatta ccatgatgtc ttgaataaa aagttaatgc aaactgatac tacagatatc    1440
ttgaaaatgt catcacaaag agtgtgaagg atcgataggt ttcgctcaac agga          1494
```

<210> SEQ ID NO 7
<211> LENGTH: 1828
<212> TYPE: DNA
<213> ORGANISM: Vernonia galamensis

<400> SEQUENCE: 7

```
tctgagctca aatcaaattt ctgcgactca tacaggattc aactcaatac tttcttgatc      60
ggttctgctg ttcatttact tgtaatttct acttctgctt tgctttcatt tcaagctttt     120
ttccttaata tggcgttat tagatacgcc tcagattgga gaaataacga ccaccgccac     180
cacaactata agacggcgga ccactgtcaa gcctgatgct ggaatcggag atggattgtt    240
tgattcttcg tcgtcttcca aaaccaactc atccttcgag gatggtgaca gtttgaatgg    300
tgatttcaat gacaaattta aggaacagat cggagctggt gatgaatcca aggacgactc    360
caaggggaac ggacagaaga tagatcacgg aggagttaaa aagggacgtg aaacgactgt    420
ggtgcattat gcttatcggc cttcttctcc ggctcatcgg agaattaaag aatctccgct    480
tagctctgac gccatcttca agcagagtca tgcaggcctc tttaaccttt gcatagtggt    540
gcttgttgca gtaaatggta ggctcatcat tgagaatctg atgaagtatg gactattgat    600
caattccaac ttttggttca gttcgagatc attgagagac tggccacttc tgatgtgctg    660
cctcactcct tctgactttc cacttgctgc ctacattgtt gagaaattgg catggaaaaa    720
acgtatatcc gaccctgttg taatcacact ccatgttata ataactacaa ctgcaattct    780
ttatccggtc ttcatgattc tgaggttcga ttcagttgtt ctatcaggcg tctcgttgat    840
gctgtgtgct tgcattaatt ggttgaagtt ggtatctttt gtgcatacaa attatgacat    900
gcggtcgctt ttgaactcaa ctgataaggg agaagtggaa cccatgtctt caaatatgga    960
ttatttttat gatgtcaact tcaaaagctt ggtttatttc atggttgctc caactttgtg   1020
ttaccagata agctatcctc gcactgcatt tattcgaaag ggttgggtgt tacggcaact   1080
gatcaagcta gtaatattta cagggttcat gggattcatc attgaacaat atatcaatcc   1140
gattgtcaaa aattctcgtc atccattgaa aggagacttt ttatatgcga ttgagcgggt   1200
tttaaagctt tcagttccga atttatatgt gtggctctgt atgttctact gcttttttca   1260
cctttggtta aatatacttg ctgagcttct ttgttttggg gatcgtgaat tttataaaga   1320
ttggtggaat gcacaaacta ttgaagagta ttggaggcta tggaatatgc ctgttcataa   1380
atggattgtt aggcacccttt attttccatg cttgcgtaat gggataccta agggtgctgc   1440
catattggtt gcatttttca tgtctgccgt gttccatgag ctttgtattg ctgttccctg   1500
ccacattttc aagttttggg cttttatcgg gatcatgttt caggtcccgt tggtcctact   1560 cacaaaattac ttgcagcaca gtttcaaaa ctcgatggtg ggaaatatga tcttctggtg   1620
```

| | |
|---|---:|
| cttttttcagc attttttggtc aacccatgtg tgtattactt tactaccatg atgtcatgaa | 1680 |
| tcaaaagggg aaaagcaaat aaaaagatgt gattgtgttg ctccatttga tctcatagca | 1740 |
| tgactggact aaacaaaccc aagggacaca ttttagtcct taaaggaaaa ttttttgtagg | 1800 |
| aaaaaaaaaa aaaaaaaaaa aaaaaaaa | 1828 |

<210> SEQ ID NO 8
<211> LENGTH: 2099
<212> TYPE: DNA
<213> ORGANISM: Nicotiana tabacum

<400> SEQUENCE: 8

| | |
|---|---:|
| ggcacgagcg aaatcttacc caatcctccg ttgcttttct tttagatcct cttttttctgt | 60 |
| cattctcttt ttcccaataa caacaactca ttgcatgtga aggttgattt tgattttttgt | 120 |
| gtttattcaa actctctctt cacgatttttc ttactctttc tagaagtatc cattactttt | 180 |
| tagtctgtga ttcggcgaaa gtaagcaatg gtgatcatgg aattgccgga gagcgtcgaa | 240 |
| atgacgacga cgacgacgac ttcgggtatt gagaacctca actccgatct taatcactcg | 300 |
| gttcggagga gacgtggcag taatggtttt gaggcggcta gtgcaattaa cagttcggat | 360 |
| gcgaatatga gcgaagatag aagagatgtg tgtggcagcg gtgctggatt ggaaacggtg | 420 |
| aatgagcgga gtaaatcggt tggtgagtcc agtgatgtaa ttcgaaagga ggacgacagg | 480 |
| aatgataatg ttgcgaatgg tgaggaaagc aaatcaacgg aaacaacaac gacgccgttt | 540 |
| aaatttgctt acagggcgtc ggcaccagct caccggcgaa tcaaggagag tcctctcagc | 600 |
| tccgacgcca ttttcaaaca gagtcacgca ggcctgttca atctctgtgt ggtggtgctg | 660 |
| attgctgtta acagcaggct gattatcgag aacttgatga agtatggcct tttaattagg | 720 |
| gctggctttt ggtttagctc gaagtcgttg agggattggc cgcttctaat gtgctgtctc | 780 |
| agtctccaaa ttttgccgct cgctgctttt cttgtggaga agttggcaca gcagaggcat | 840 |
| ttgactgagc gtgcggtggt tactcttcac ataactataa caacagctgc cattttgtat | 900 |
| ccagttctgg tcattcttgg gtgtgattct gcttttctgt ttggtgtcat attgatgctg | 960 |
| gttgcttgca ttgtgtggat gaagctggtt tcttacgcac atacaaatca tgatatgaga | 1020 |
| cagctcgcaa agtctacgga caaggatgaa acttcagatg gggatttctc ttatgatgtt | 1080 |
| agcttcaaga gtttggctta cttcatggtt gcgccaacat tatgttatca gcttagctat | 1140 |
| ccccacactc catgcattcg caaaggttgg gtggcacgcc aattcatcaa gctggtaata | 1200 |
| tttacaggat tgatgggatt tatcatagaa cagtacatta acccaattgt gcaaaactca | 1260 |
| caacatcctt tgaaaggaaa cctttttatat gccatcgaga gggtattgaa gctttcggtt | 1320 |
| ccaaatttat atgtctggct ctgcatgttt tactgcttct ttcatctttg gctaaatata | 1380 |
| cttgcggaac tactatgttt tggtgatcgt gagttctaca aggattggtg gaatgccaaa | 1440 |
| acaattgatg agtactggag gatgtggaat atgcctgttc ataagtggat ggttcgtcac | 1500 |
| atttatttcc cttgcttaag aaacggaatt ccaaagggg tcgcaatact gattgctttc | 1560 |
| cttgtatctg ctgtttttcca cgagctgtgt attgctgttc catgtcgcct ttttcaagtgg | 1620 |
| tgggcattca tgggaattat gttccaggtt cctttggtca tactcacaaa cttcttacaa | 1680 |
| aacaagttcc aaagctcgat ggtgggcaat atgatgttct ggtgctttttt ctgcattctt | 1740 |
| ggtcagccaa tgtgtgtgct tctgtattac cacgatgtga tgaatagaaa aagcagtgca | 1800 |
| cgttaagctt catccaggga tgaattgttg tatgagcaag tatttttaagt tttggatccc | 1860 |

```
aagctctatt ctactgtttc tggcaaggca ttcctgctat ttccttcatc agttccaaca   1920
atattcagat gatacgaaat atctgtttgg aatgcacaac acaagccacg gccagagatg   1980
ctgatgtctc acattttatt gtgttcttca tgtcggagaa atgtaaaata ctatcttgag   2040
ataactctca tgttagtaaa tacctttttg cctctaaaaa aaaaaaaaaa aaaaaaaaa    2099

<210> SEQ ID NO 9
<211> LENGTH: 1964
<212> TYPE: DNA
<213> ORGANISM: Perilla frutescens

<400> SEQUENCE: 9
tttagaacca aactattctc cgttaagttc tgagttcgat ttctttcttt tctcaaattt     60
tccgtgcgat ggcgatcttg gactcgccgg agatcctgga cacgacgtcg tccagtgccg    120
acaacggcgc cgcacatcac accactcttc gccggagaca aagtgcgcgc tccgttccgc    180
ctcttctcga ctccgattcc aactctctgg aggcagagag cgcaatcaat gattccgaaa    240
atgttcgaaa cgacgctaat ttgatcgaaa atctccgcgg cggagccgtg aatccgaga     300 acgaaaaaca ggagagttat ggtaaggagg aggggcgaa agtgaaggag aatggagaaa    360
ctagtaatgg caacggaact gatgttatgg ccgtcaaatt cacattcagg ccggcggcgc    420
ctgctcaccg caaaaataag gagagtcctc ttagctccga cgccatcttc aaacagagcc    480
atgcaggcct cttcaacctt tgtatagtgg tgcttgttgc tgtaaatagc agactaataa    540
ttgagaattt aatgaagtat gggtggctga tcaaatcagg attttggttt agttcaacat    600
cgcttaggga ttggccactg ctaatgtgtt gtcttagtct tccagttttt gcactcgctt    660
catttcttgt cgagaagttg gtgaaactaa attatatacc tgagtgggtc gcagtctttc    720
ttcatgttac aatcacaaca gtggaaatct tgtttccagt tgttgtcatt cttaggtgtg    780
attctgctgt tctatcaggt gtcacgctaa tgctctttgc ttgcactgta tggttgaagc    840
tcgtttccta cgcacataca aactatgatt tgagagtact tgcaaaatca cttgataagt    900
gggaagctat gtccaggtac tggaacctcg actacgctta tgatgtaagc tttaagagtc    960
tggcatactt catggttgct cctacattgt gttaccagcc aagctaccct cggacagctt   1020
gcattcggaa gggttgggtg gtaaggcaac taattaagct ggtaatattc acaggactca   1080
tgggatttat tatagaacag tacataaacc cgatcgttca aaattctcaa catcctctga   1140
aaggaaacct tttatatgcc attgagaggg tcttgaagct ttctgttcca aatttatatg   1200
tgtggctctg catgttttat tgtttttttcc acctctggct aaatatactt gctgaacttc   1260
tgtgctttgg ggaccgtgag ttttataagg attggtggaa tgcgaggaca gtggaggagt   1320
actggagaat gtggaatatg cctgtccata aatggatggt tcggcatata tactgtccat   1380
gcttacaaaa tggaatacca aagatagtgg cagttttgat cgcgtttctt gtgtctgcga   1440
tttttcatga gctgtgcgtt gcagtcccct tgccaaatat tcaagttttgg gcgttctcgg   1500 gtatcatgct tcaggttcct ctcgtaatcg tgactaatta cttgcaagaa aagttcaaaa   1560
actcaatggt gggcaatatg atgttctggt gcttcttctg tatctttggt caacctatgt   1620
gtgtgttgct gtactaccac gacttgatga atcgaaaagc tagtgcaagg tagggatgtg   1680
attcatcttc tgagtagaaa tctaaagctc accagcccca acccacccga aaacaaaaa    1740 ggagcaagga tcctgattgt gagctggtag ataatttgct acaactatgt ttcttaaata   1800
gctgggagta gtttgttatc tgccttcacc taggacgacg ttatgatctg ttgtgatggg   1860 ggtaagggg catgcaaatt ttgtctattt ttcaaggaat acagaaatgg tgaaaatttg    1920
```
atgaagcata cccctcgttt actgacaaaa aaaaaaaaaa aaaa                    1964

<210> SEQ ID NO 10
<211> LENGTH: 1539
<212> TYPE: DNA
<213> ORGANISM: Zea mays

<400> SEQUENCE: 10

| | | |
|---|---|---|
| atggcggact ccgaagacgc gccgccagcc gtgcaccgcc gcccaccgcg ccccgctcgc | 60 |
| ggtgctgctg cagcccaggg cttcgcggcc gcgttgcgcc gccggctgag atccggcgct | 120 |
| gcggtggcgg cacgcgccag ctttgccgca gactccgggg acgagtctgg ccccggcgag | 180 |
| ccctcttcgt ctcgccgccg cgacaacagc gggggcgcct cgtccgccgc cggcggccgg | 240 |
| gccggggcag gggacttctc cgcgttcacc ttccgcgccg cggcgcctgt ccaccggaaa | 300 |
| gccaaggaga gccctctgag ctccgacgcc atcttcaagc agagtcatgc aggccttttc | 360 |
| aacctatgta ttgttgttct ggttgcggtg aatagcaggc tcattattga gaacctgatg | 420 |
| aagtatggct tattaataag atctggcttt tggtttaatg ctacatcatt gcgagactgg | 480 |
| ccactgctaa tgtgttgcct tagtctaccc atatttcccc ttggtgcatt tgcagtcgaa | 540 |
| aagttggcat tcaacaatct cattagtgat cctgctacta cctgttttca catccttttt | 600 |
| acaacatttg aaattgtata tccagtgctc gtgattctta agtgtgattc tgcagtttta | 660 |
| tcaggctttg tgttgatgtt tattgcctgc attgtttggc tgaagcttgt atcttttgca | 720 |
| catacaaacc atgatataag aaaactgatc acaagcggca agaaggttga taatgaactg | 780 |
| accgcggctg gcatagataa tttacaagct ccaactcttg ggagtctaac atacttcatg | 840 |
| atggctccga cactctgtta tcagccaagt tatcctcgaa caccttatgt tagaaaaggt | 900 |
| tggctggtcc gtcaagttat tctatacttg atatttactg gtctccaagg attcattatt | 960 |
| gagcaataca taaatcctat tgttgtgaac tctcaacatc cattgatggg aggattactg | 1020 |
| aatgctgtag agactgtttt gaagctctca ttaccaaatg tctacctgtg gctttgcatg | 1080 |
| ttttattgcc ttttccatct gtggttaaac atacttgctg agattcttcg atttggtgac | 1140 |
| cgagaattct acaaagactg gtggaatgca agacaattga tgagtactg gagaaaatgg | 1200 |
| aacatgcctg tgcataaatg gattgttcgt catatatatt tcccttgcat gcgaaatggt | 1260 |
| atatcaaagg aagttgctgt ttttatatcg ttctttgttt ctgctgtact tcatgagtta | 1320 |
| tgtgttgctg ttccctgcca catactcaag ttctgggctt tcttaggaat catgcttcag | 1380 |
| attcccctca tcatattgac atcatacctc aaaaataaat tcagtgacac aatggttggc | 1440 |
| aatatgatct tttggttttt tttctgcata tacgggcagc caatgtgtgt tctattgtat | 1500 |
| taccatgatg tgatgaaccg gactgagaag gcaaaataa | 1539 |

<210> SEQ ID NO 11
<211> LENGTH: 1548
<212> TYPE: DNA
<213> ORGANISM: Sorghum bicolor

<400> SEQUENCE: 11

| | | |
|---|---|---|
| atggcggaca ccgacgacgc gccgccggcc ccggccgtgc accgccgccc accgcgcccc | 60 |
| gcccgcggtg ctgccgctgc ccagggcttc gcggccaagt tgcgccgacg gctcagctcc | 120 |
| ggcgccgcgg cggcggcgcg cgccagcttc gcggcagact ccggggacga gtccggcccc | 180 |
| ggggagccct cttcgtcccg ccgccgcgac aacggcgggg acgcctcgtc cgccgccgac | 240 |

-continued

```
ggcggccggg gcggggcagg ggacttctcc gctttcacgt tccgcgccgc ggcgcctgtc    300
caccggaaag ccaaggagag cccctcagc tccgacgcta tcttcaagca gagtcatgca     360
ggccttttca acctatgtat tgttgttctg gttgcagtga atagcaggct cattattgag    420
aacctgatga agtatggctt attaataagg tctggctttt ggtttaatgc tacatcattg    480
cgagactggc cactgctaat gtgttgcctt agtctacctg tgtttcccct tggtgcattt    540
gcagttgaaa agttggcatt caacaatctc attactgatg ctgccgctac ctgttttcac    600
atctttctta caacacttga aattgtatat ccagtgcttg tgattcttaa gtgtgattct    660
gcagttttat caggctttgt gttgatgttt attgcctgca ttgttggct gaagcttgta     720
tcttttgcac atacaaacca tgatataaga aaactgatca caagcggcaa gaaggttgat    780
aatgaactga ccgtggctga catagataat ttacaagctc caactcttgg gagtctaaca    840
tacttcatga tggctccgac actctgttat cagccaagtt atcctcgaac accttatgtt    900
agaaaaggtt ggctggttcg tcaagttatt ctatacttga tatttactgg ctccaagga    960
ttcattattg agcaatacat aaatcctatt gttgtgaact ctcaacatcc attgaaggga   1020
ggattactga atgctgtaga gactgttttg aagctctcat taccaaatgt ctacctgtgg   1080
cttttgcatgt tctattgcct tttccatcta tggttaaaca tacttgctga gattcttcga   1140
tttggtgacc gtgaattcta caaagactgg tggaatgcaa aaacaattga tgagtactgg   1200
agaaaatgga acatgcctgt gcataaatgg atgcttcgtc atatatattt tccttgcata   1260
cgaaatggta tatcaaagga agttgctgct tttatagcgt tctttgtttc tgctgtattt   1320
catgagttat gtgttgctgt tccctgccac atactcaagt tctgggcttt cttaggaatc   1380
atgcttcaga ttcccctcat catactgaca tcatacctca aaataaatt caatgacaca    1440
atggttggca atatgatctt ttggttcttt ttctgcattt acgggcagcc aatgtgcgtt    1500
ctattgtatt accatgatgt gatgaaccgg actgagaaga caaaataa                1548
```

<210> SEQ ID NO 12
<211> LENGTH: 2103
<212> TYPE: DNA
<213> ORGANISM: Oryza sativa

<400> SEQUENCE: 12

```
gtcgtcccgc gtctctcctc acctctcgtc tccctcgcga cgtctcccct tctccctcca    60
cccctccaat ggtgggctcc gatggcgacg gcgacggcgg cggagggga gcacacgcgc    120
cggcggcgcc cgcgcaccac caccgccggc ccccgcgccc gcggggaggc agcggggcca    180
tcgtcgaggg cttcgcggcg gcgctccgtc gcaggatccg ctcgggggcc gcggcggccg    240
cgcgggccag cttcggggc gactccgggg acgaggccgc ctccggggag ccctcctcgt    300
cctcgtcctc gtccccgtcc cgccgccgtg gcggcgactc caacggggcg gaggcgtcct    360
ccgccgccgg gggcggtggt ggccgtggcg gcggtgggga cttctccgcg ttcacgttcc    420
gcgcggcggc gccggtgcac cgcaaggcca aggagagccc cctcagctcc gacgccatct    480
tcaagcagag tcatgcaggc cttttcaacc tatgcattgt tgttctagtt gcagtgaaca    540
gcaggcttat tatcgagaac ttaatgaagt atggcttatt aataagagct gggttttggt    600
ttaatgataa atcattgcgg gactggccac ttctaatgtg ttgtcttagt ctgcctgctt    660
tccccctggg tgcatttgca gttgaaaagt tggcatttaa caatgttatt actgatgctg    720
ttgctacctg cctccatatc ttcctttcaa caaccgaaat tgtatatcca gtgcttgtga    780
ttcttaagtg tgattctgca gttttgtctg gcttttgtt gatatttatt gcctgtattg    840
```

| | |
|---|---|
| tttggctgaa gcttgtatct tttgcacata caaaccatga tataaggcaa ctgaccatgg | 900 |
| gcggcaagaa ggttgataat gaactaagca cagttgacat ggataattta caacctccaa | 960 |
| ctttagggaa tctaatatac ttcatgatgg ctcctacact ctgttatcag ccaagctatc | 1020 |
| cccgaacttc atgtgttaga aaaggttggc tgattcgtca aattattctg tacttgatct | 1080 |
| ttactggtct tcaaggcttc attattgagc aatacataaa tccaattgtt gtgaattctc | 1140 |
| agcatccatt gaaaggagga ctcctaaatg ctgtagagac tgttttgaaa ctctcattac | 1200 |
| caaatgttta cctgtggctt tgcatgttct atgcttttt ccatctctgg ttaagtatac | 1260 |
| ttgctgagat tcttcgattt ggtgaccgtg aattctacaa agattggtgg aatgcaaaaa | 1320 |
| caattgatga gtattggaga aaatggaata tgcctgtaca taaatgggtt gttcgccata | 1380 |
| tttactttcc ttgcatgcga aatggtatat caaaggaagt tgctgtcttg atatcattcc | 1440 |
| ttgtttctgc cgtactccat gagatatgtg tcgctgttcc ctgccgcatt ctcaagttct | 1500 |
| gggcattctt aggaataatg ctacagatcc cccttatcgt attgacagca tacctcaaaa | 1560 |
| gtaaattcag agatacaatg gttggcaaca tgatatttg gttctttttc tgcatctatg | 1620 |
| ggcagccaat gtgccttctc ctgtactatc atgatgtgat gaacaggatt gagaaggcaa | 1680 |
| gataaatgcg tgttgccatc tttttcctct gtttcatttt gtaccagcag aagcacaagc | 1740 |
| aataatccac atgctagcca taaaacagca tgattcccaa cggtgtggta cagccaacct | 1800 |
| tcctgttatt ctattttctt ggctgtggtg tagatttagt ttttaacttg tggctaaccg | 1860 |
| caggaatgcc tgtagataag catctgtcat tctgtctggc gacgttctcc ttattaatgt | 1920 |
| gtagatgtag aactgtttcc gaaaactata tatcttgaat ctgttatgcc tcgacgaaca | 1980 |
| taatcctttt gttaagctta gttggtacag tctagaaagg ataagagtcg tggatgtacg | 2040 |
| atttcgtctg ccatatatca cgctcatatt ggcacaggta actttgtcgc taccttctat | 2100 |
| ctc | 2103 |

<210> SEQ ID NO 13
<211> LENGTH: 1473
<212> TYPE: DNA
<213> ORGANISM: Oryza sativa

<400> SEQUENCE: 13

| | |
|---|---|
| atggccccgc cccctcgct cgccccgat cgcggcggcg cgaacccga cgacgccctc | 60 |
| cgcctgcggg cccgcgccgc cgccgccgcc ggtgacgctc ccgctccgca gcagcagcag | 120 |
| gagcagaggc atcaggagca gcagcagcag ctgctctggt accgcgcgtc ggcgcccgcc | 180 |
| caccgccgcg tcagggagag ccccctcagc tccgacgcca tcttccgcca gagccatgca | 240 |
| ggccttctga acctatgcat tgttgtgctg gttgctgtga acagcagact tattattgag | 300 |
| aatttaatga agtatggcct actaattaga gctggatttt ggtttagtgg aacatcgctg | 360 |
| gcagattggc ctcttctcat gtgctgtctc actttaccaa ctttcccgct tgctgcactt | 420 |
| atggttgaga agttggctca agaaaaactt attagtaaac atgtggttat tcttctccat | 480 |
| atcgttatta caacatctgt ccttgtctat ccagttgttg tgattctaaa gtgtgattcg | 540 |
| gcagtattat ctggatttgt gttgatgttt cttgcaagca ttatttggtt gaagcttgtt | 600 |
| tcttttgctc atacaaatta tgatataaga atgctgtcca aaagtattga aaagggcgtg | 660 |
| acacatgaca tttctataga tccggagaac attaaatggc caacctttaa aaggctatcc | 720 |
| tacttcatgt tggccccaac actttgttac cagccaagtt atccccgaac tacatatatt | 780 |

|  |  |  |  |  | |
|---|---|---|---|---|---|
| agaaaaggtt | gggtggtccg | acaactgata | aaatgccttg | ttttttacagg | cttgatgggt | 840 |
| tttataattg | agcaatacat | aaatccaatt | gtgaagaatt | cgaagcatcc | attgaaaggg | 900 |
| aatttcttga | atgctataga | gagagtattg | aaattatcag | tgccaacatt | atatgtctgg | 960 |
| ctttgcatgt | tctactgttt | tttccatctc | tggttgaata | ttcttgctga | gctcctctgt | 1020 |
| tttggtgatc | gtgaattcta | caaggactgg | tggaatgcca | aaacagttga | agagtattgg | 1080 |
| agaatgtgga | atatgcctgt | tcacaagtgg | gtcattcgac | atatatattt | tccatgcata | 1140 |
| aggaatggtt | tttcaaaggg | tgttgctatc | ctaatctcgt | tcctggtttc | agctgcattt | 1200 |
| catgagatat | gtattattta | tttcattgtc | cttatcgatt | tgcagctatg | tgttgctgtt | 1260 |
| ccatgccaca | tttttaaatt | ctgggcattt | attgggatca | tgtttcagat | tcccctggta | 1320 |
| ttcttgacga | ataccttca | agataaaatt | aataacacaa | tggtgggcaa | catgatattt | 1380 |
| tggttcttct | tcagcatcct | ggggcaacca | atgtgtgttc | tcttatacta | ccatgatgtc | 1440 |
| atgaacaggc | aacaagccca | aacaaataga | tag |  |  | 1473 |

<210> SEQ ID NO 14
<211> LENGTH: 1590
<212> TYPE: DNA
<213> ORGANISM: Sorghum bicolor

<400> SEQUENCE: 14

|  |  |  |  |  | |
|---|---|---|---|---|---|
| atggccccgc | cccctccat | ggccgccgcc | tccgatcgcg | ccgtccccgg | cgccgacgcg | 60 |
| accgaggcgt | cctccctccg | cctccgccgc | gccccctcag | ccgacgccgg | cgaccttgcc | 120 |
| gacgattcct | caggagaccg | gcgggagaac | ggcgagccgc | aaccgccgca | ggagcagcag | 180 |
| cagcagcacg | agatgctgta | ctaccgcgcg | tcggcgcccg | cccaccgccg | cgtcaaggag | 240 |
| agccccctca | gctccgacgc | catcttccgg | cagagccatg | ctggtcttct | gaatctatgc | 300 |
| atcgttgttc | tgattgcagt | gaacagcaga | ctcattattg | agaatttaat | gaagtatggc | 360 |
| ctattgataa | gagctggatt | ttggtttagt | gcaagatcgc | tgggtgactg | gcccttcta | 420 |
| atgtgctgcc | tcactttacc | agttttccca | cttgttgccc | tcatggctga | aagctgatt | 480 |
| agaagaaagc | tcattggtga | acatgtggtt | attctactcc | atatcattat | tacaacatct | 540 |
| gtcattgtct | atccagttgt | tgtgactctt | aagtgcgact | cagcagtgct | atctggattc | 600 |
| ttgctaatgt | ttccttgcgag | catcatgtgg | atgaagcttg | tctcttatgc | acatacaaat | 660 |
| tatgatataa | gggcattgtc | caaaagtact | gaaaagggtg | ctgcatatgg | aaattatgtc | 720 |
| gatcctgaga | gtatgaaaga | tccaaccttt | aaaagtctag | tgtacttcat | gttggcccca | 780 |
| acactttgtt | accagccaac | ttatccccga | actacatgta | ttaggaaggg | ttgggtgacc | 840 |
| cgacaactta | taaagtgcct | ggttttaca | ggcttgatgg | gcttcataat | tgagcaatat | 900 |
| ataaacccaa | ttgtgaagaa | ttccaaacat | ccactgaaag | ggaatttctt | gaatgctata | 960 |
| gaaagagtct | taaactctc | agtgccaaca | ttatatgtat | ggctttgcat | gttctattgc | 1020 |
| ttttttcatt | tatggctgaa | cattctagct | gaactcctct | gtttcggtga | ccgtgaattc | 1080 |
| tacaaggact | ggtggaatgc | caaaactgtt | gaagagtact | ggaggatgtg | aacatgcct | 1140 |
| gttcataaat | ggatcatcag | acacatatat | tttccatgta | taggaaaagg | cttttccagg | 1200 |
| ggtgtagcta | ttctagtctc | gtttctggtt | tcagctgtat | ttcatgagat | atgtattgcg | 1260 |
| gtgccgtgcc | acattttcaa | attctgggca | ttttctggga | tcatgtttca | gataccgttg | 1320 |
| gtattcttga | caagatatct | ccaggctacg | ttcaagaata | taatggtggg | caacatgata | 1380 |
| ttttggttct | tcttcagtat | agtcgggcag | ccgatgtgtg | tccttttata | ctaccatgat | 1440 |

```
gtcatgaaca ggcaggccca gcaagtagat aattcggcag aaacatgtac tttaagacaa    1500
gttatcagaa gcagactgga gcgacgcagc aggaagcagc agcagcagca ggccagcagc    1560 cccccttttgc cattgttacc agctagctag                                    1590
```

<210> SEQ ID NO 15
<211> LENGTH: 1485
<212> TYPE: DNA
<213> ORGANISM: Zea mays

<400> SEQUENCE: 15

```
atggccccgc cccctccat gcctgccgcc tccgatcgcg ccggccctgg ccgcgacgcg     60
ggcgactcgt cctcccttcg cctccgccgc gcccctcag ccgacgccgg cgaccttgcc    120
ggcgattcct cgggaggctt gcgggagaac ggcgagccgc aatcgccgac gaatccgccg    180
ccgcaggagc agcagcagca cgagatgcta tactaccgcg cgtcggcgcc cgcccaccgc    240
cgcgtcaagg agagccccct cagctctgac gccatcttcc ggcagagcca tgctggtctt    300
ctgaatctat gcattgttgt tctgatcgca gtgaacagca gactcattat tgagaattta    360
atgaagtatg gcctgttgat aagagctgga ttttggttta gtgcaagatc gctgggtgac    420
tggccccttc taatgtgctg cctcactcta ccagttttcc cactagttgc actcatggct    480
gagaagctga tcacaagaaa gctcattggt gaacatgtgg ttattctact ccatatcatt    540
attacaacat ctgccattgt ctatccagtt gttgtgactc ttaagtgtga ctcagcagta    600
ctatctggat ttgtgctaat gtttcttgcg agcatcatgt ggatgaagct tgtctcttat    660
gcacatacaa attatgatat aagggtattg tccaaaagta ctgaaaaggg tgctgcatat    720
ggaaattatg tcgatcctga aatatgaaa gatccaacct ttaaaagtct agtgtacttt    780
atgttggccc caacactttg ttaccagcca acttatcctc aaactacatg tattagaaag    840
ggttgggtga cccagcaact cataaagtgc gtggttttta caggcttgat gggcttcata    900
attgagcaat atataaaccc aattgtgaag aattccaaac atccactgaa agggaatttt    960
ttgaatgcta tagaaagagt cttaaaactc tcagtgccaa cattatatgt atggctttgc   1020
atgttctatt gctttttttca tttatggctg aacattgtag ctgaactcct ctgtttcggt   1080
gaccgtgaat tctataagga ctggtggaat gccaaaactg ttgaagagta ctggaggatg   1140
tggaacatgc ctgttcataa gtggatcatc agacacatat attttccatg tataaggaaa   1200
ggcttttcca ggggtgtagc tattctaatc tcgtttctgg tttcagctgt atttcatgag   1260
atatgtattg cggtgccttg ccacattttc aaattctggg catttctgg gatcatgttt    1320 cagataccct tggtattctt gacaagatat ctccatgcta cgttcaagca tgtaatggtg   1380
ggcaacatga tattttggtt cttcttcagt atagtcggac agccgatgtg tgtccttcta   1440
tactaccatg acgtcatgaa caggcaggcc caggcaagta gatag                   1485
```

<210> SEQ ID NO 16
<211> LENGTH: 1912
<212> TYPE: DNA
<213> ORGANISM: Physcomitrella patens

<400> SEQUENCE: 16

```
atgcctgtga agagtagcaa tctggcgggg gagagggctg ccaccagcca tattaatgcc     60
aacacgaaat tcgacctgcg ggggtgtacg cctgcgcatc gcgttaggag ggaaagcccg    120
cttagttcag acgcaatttt tcatcagagt catgctgggt tgttcaatct ctgtattgtt    180
```

```
gttttgatag ctgttaacag ccggcttatt attgagaact taatgaagta tggactactc      240
attagaactg gtttctggtt tagctccaag tctgcacgcg attggccact cttgatgtgc      300
ggtttgagtt taccgacttt tcccctttgca gcgttactag tggaaaaact atgctggaaa    360
aatgaaaacg ggaaatggtt gattttcgta ctacacctca taatcagcac tgtagggata     420
ctgtatcctg gatatgttat acacagggtg caatccgcac tgctgcctgg tcttgtattg     480
atactcattg cagtgactgg gtggatgaag cttatatctt acgctcatgt caacaaggac     540
atgcgagaac ttttgagagc caaagaaaag ctacctgagg caccacagta cgcagataaa     600
atagaggttc cggaccacct tacgatccaa aatattgctt atttcatgct cgcgcccaca     660
ctttgctacc agttgagcta ccctcgttcg gacacaattc gaaaaagttg ggtgttacgg     720
caagccggga aattggttgt gttcttgggt ttagggggat tcatcattga gcagtacata     780
aatcccactg tgaagaattc acagcacccg ctcagggggca actatcttca agcactggag    840
agggttttaa agctttcgtt gccagttctt tatgttttggc tgtgcttgtt ctactgttta    900
tttcatcttt ggttgaatat tgtggcgagc tacttcgctt tggggacag ggaattttat      960 aaggactggt ggaatgctca aacagttgaa gagtattggc gaatgtggaa catgcctgtg     1020
cacaagtgga tggtgcggca tatttatttt ccctccattc gagctggctt atcaaagaaa     1080
gcagcagtac tactggtgtt tgcaatttca gctttgtttc atgaggttat cattggtgtt     1140
ccgtgtcata tgcttcgatg ctgggctttt cttggtatca tgatgcaggt tccgttggtg     1200
tacttgacaa acgtgataaa agagcggtac catagctcta tggttggaaa tatggtattt     1260
tggttcttct tttgcattgt cgggcaaccc atgtgcttgc ttctctacta ccacgacgtt     1320
ttcaacaact ttcccagtac ctgaactgag atcacccatt cgtgcagttg ttaatcttgt     1380
gaatagcact cctcatctgt accttgttat ggcttccact tctcgagaat cgactaaacc     1440
gcaactcata tgtttgtcaa taacgattca ttcgtaggcg ggttggtgtg agattacaag    1500
agaggaaact ttcgtcgtaa gccagcagtg tagatacagt ccaggtagga gtgtaacggg    1560
cacttgcttc aagggcagat ccttgtcaac gcaagctttt gttggagctt gttggagctt    1620
gtttcgcact tagtattctt ttctagctgt agttttaggt gacgttagtc tattcttggt    1680
cccatcatcc atcctgtaag atgctgggcg tgctcacgtg cagaagctgc ctcgaatcct    1740
acgttacaat ttcatgttgg ataccgcgtg gatgtccgct tcagaatctg cgtcatgatg    1800
atgcacacca ttttttctta ttggaaactg aacagagggt agtgatacgt aagaacattt    1860
tgggaaccgt gcctgaaaat cgtcggagca ataatgatg tggttttgca gc              1912

<210> SEQ ID NO 17
<211> LENGTH: 1278
<212> TYPE: DNA
<213> ORGANISM: Selaginella moellendorffii

<400> SEQUENCE: 17
atgcggccct cgctcccggc gcaccggcgg agcaaggaga gcccgctcag ctccgacgcc       60
atcttcacgc agagccacgc cggcctcttc aacctctgca tcgtcgtgct ggtggcggtg      120
aacagccggc tcatcatcga gaatctcatg aagtatggcc tcctcatcca ggccgaggtc      180
ctcttcagct ccaagtcgct caaggactgg ccgctcctca tgtgtggcct ctcgctgctg      240
atcttccccc tcgccgccta tgtcatcgag aagatcaagg cccgccgccc cgccaccgcc     300
gtggcgccgc tccacttgat caacctcgcc gccgcgctgc tctacccgat ctacgtgatc     360
gagatgttcc agtcggatct cctctcgggg ctggttctca tgctcatcgc cgtcaccggc    420
```

```
tggctcaagc tcgtctccta cgcgcacacc aacgccgaca tccgcgcggt gaagaaggac    480
ggtggcaaga tcgagctccc cgccgaggcg ccggcgatcg actacccgga caacatctcg    540
ctcaagaaca tcgcctactt catggcagcg ccgacgctgt gctaccagct gagctacccg    600
cgctcgccgc ggattagaac cgggtgggtg ctccggcagc tgggcaagtg gatcgtcttc    660
aacggattca tgggcttcat catcgggcag tacatgaatc cgatcatccg gaactcgacg    720
cacccgctca aggggaacta cctctacgcg atcgagcgcg tgctcaagct gtccatcccc    780
acgctctacg tctggctcgg cttcttctac tgcttcttcc acctgtggct caacatcgtg    840
gcggagatcc tgtgcttcgg cgaccgcgag ttctacaagg actggtggaa cgccaagtcg    900
gtggacgagt actggcggct gtggaacatg cccgtccacc gctggctcgt ccgccacgtc    960
tacttcccgt gcctccggct gggcctccac aagcagttcg ccattttggt ggtgttcgtc   1020
atctccggga tctttcacga gatttgcatc gcggtgccgt gccacatgct gcggggctgg   1080
gcgtttctgg ggatcatgtt ccaggtgccg ctggttctgg tgaccaacgt cctccagcgc   1140
aagttccaga gctccatggt cggcaacatg atcttctggt tcttcttttg catcgtcggg   1200
cagccgatgt gcgtgctgct ctactatcac gacgttgtca acaggcagca gctccagcta   1260
gctgggcggt ccaaataa                                                 1278

<210> SEQ ID NO 18
<211> LENGTH: 1524
<212> TYPE: DNA
<213> ORGANISM: Euonymus alatus

<400> SEQUENCE: 18
atggctgcta acttgaacga agcctcggat cttaattttt cgcttcggag gagaactggt     60
ggcatctcaa gtacgactgt gcctgattct agttccgaga caagttcgtc ggaggcggac    120
tatttggacg gaggcaaagg tgccgcggac gtcaaagatc gtggggatgg tgcggtggag    180
tttcagaatt cgatgaagaa cgtggagagg attgagaaac atgagagccg agtaggattg    240
gattcgagat tcacgtatag gccatcggtc ccggctcatc gcacaataaa ggagagcccg    300
cttagctcgg acgcaatatt caaacagagt cacgcaggtc tcttcaatct ctgtatagta    360
gttctggttg ctgtgaacag caggctgatc attgaaaatc taatgaagta tggatggtta    420
ataaggagtg ggttttggtt cagctcaaga tcattgagag actggcccct ttttatgtgt    480
tgtctcacac taccagtatt ccctcttgct gcttttctgt ttgagaagtt ggctcaaaaa    540
aatttaatat ctgaacctgt tgttgttttg cttcatatag taaacactac agctgccgtt    600 ttatacctg ttttggtgat tctaaggtgt gattctgcct ttatgtctgg ggttacgttg    660
atgctctttg cttgtattgt gtggttaaag ttggtatctt atgctcatac caactatgat    720
atgagagccc tcaccaagtc tgttgaaaag ggggacacgc cgttgagctc tcagaacatg    780
gattactcgt tgatgtcaa tatcaagagt ttggcatatt ttatgttgc tcccacatta    840 tgttaccaga ttagctatcc tcgtaccccca tatgttcgca agggttgggt ggttcgtcaa    900
tttgtcaagt taataatatt tactggactt atgggattta taattgaaca atatatcaat    960
cctattgtcc agaattcaca acacccttgg aaaggaaact ttttgtatgc cattgagaga   1020
gttttgaagc tttcagtccc aaacctttat gtttggctct gcatgttcta ctgccttttt   1080
catctctggt taaacactac tgctgaactt cttttgtttg tgatcgtga gttctacaag   1140 gattggtgga acgctaaaac tgttgaggag tactggagaa tgtggaacat gcctgttcat   1200
```

```
aagtggatgg ttcgtcatat ctacttccca tgcttgagga acgggatacc caagggtgtt    1260
gcttttgtca tttccttctt agtttctgcc gtcttccatg agctatgcat tgctgttccc    1320
tgccacatct tcaagttatg ggctttcttt ggaataatgc ttcaggttcc cttggtgttg    1380
atcacaagtt atctgcaaaa taagttcaga agctcaatgg tgggaaatat gatgttttgg    1440
ttctctttct gcattttgg tcaacctatg tgcttacttc tatattacca tgatttgatg     1500
aatcgcaatg ggaagatgga gtag                                           1524
```

<210> SEQ ID NO 19
<211> LENGTH: 1557
<212> TYPE: DNA
<213> ORGANISM: Vitis vinifera

<400> SEQUENCE: 19

```
atggcgatct gcaactcgcc tgtcagtgtg accacgtcgt catcaagctc tcacgccgat     60
tcagatctcg acttttccat tcggaagagg ttcggcggga aggggaaggc cgtggcggat    120
tcgtcgctgg agacggagac ggaggcggcg gcggcggcg tgctcgaagc agagaagtcg     180
gtgggcgagg tggggagtgg cggtgatcga ggggaatcgg ggagtcaggt ggtgaggaat    240
ggggagaacg gagtggctga ggttgccgcg aaattcgcgt accggccgtg tgcgccggct    300
caccggaaag tgaaggaaag tcctctcagt tctgacgcca ttttcagaca gagtcatgcg    360
ggtctcttca acctctgtat agtagtgctt gtagctgtaa acagccggct tatcattgag    420
aatcttatga agtatggttg gttaatcagg gctggttttt ggtttagttc aaaatcattg    480
agagattggc cactctttat gtgctgttta accctcccaa tctttccact tgctgctttt    540
gtggttgaaa agttggctca acaaaagtat atctctgagc aggttgttgt ctctcttcac    600
atcataatta ctacagctgc agttttgttt ccagttttgg tgattctaag gtgtgattca    660
gctgttctct ctggtgtcac actaatgctc tttgcttgca ttgtgtggtt aaaattggta    720
tcttttgcac atacaaatta tgacatgaga gcagttgcca agttaattga taaggggat     780 gacttgtcca cttcattgaa tatggattac ccttatgatg tcaacttcaa gagtttggca    840
tacttcatgg ttgcccccac gctatgttac cagccaagct atcctcgcag cacatgcatt    900
cggaagggtt gggtctttcg ccaatttgtc aagttggcaa tatttacagg tgttatggga    960
tttataatag aacagtatat taatccaatt gttcagaatt ctcagcaccc tttgaagggg   1020 aattttttt atgcattgga gaggattttg aagctttctg ttccaaattt atatgtgtgg    1080
ctctgcatgt tctactgctt tttccacctc tggttaaata tacttgctga gcttcttcgt    1140
tttggggacc gtgagttcta taagattgg tggaatgcaa aacagttga ggagtattgg      1200 agaatgtgga atatgcctgt tcataaatgg atggttcgcc atctctattt tccatgtcta    1260
cggaatggga tatctaaggg agtttctgtg gtgattgcct ttgccatatc tgccatattc    1320
catgagctat gcattgctgt accttgtcac atgtttaagc tttggctttt cattggaatt    1380
atgttccagg ttcccttggt tttggtcaca aattacttgc aaaataagtt cagaaattct    1440
atggtgggaa atatgatctt ctggctgttt ttcagcattc ttggtcagcc aatgtgtgtg    1500
cttctatatt accatgactt gatgaatcga aaagagacaa ctgaatcaag cctctga       1557
```

<210> SEQ ID NO 20
<211> LENGTH: 1880
<212> TYPE: DNA
<213> ORGANISM: Glycine max
<220> FEATURE:
<221> NAME/KEY: misc_feature
<222> LOCATION: (1798)..(1798)
<223> OTHER INFORMATION: n is a, c, g, or t

<400> SEQUENCE: 20

```
gaagagaaga ctgagttagt aaacacgctc gctcggtctt cttttccaat ggcgatttcc      60
gatgagcctg aaactgtagc cactgctctc aaccactctt ccctgcgccg ccgtcccacc     120
gccgctggcc tcttcaattc gcccgagacg accaccgaca gttccggtga tgacttggcc     180
aaggattccg gttccgacga ctccatcagc agcgacgccg ccaattcgca accgcaacaa     240
aaacaagaca ctgatttctc cgtcctcaaa ttcgcctacc gtccttccgt ccccgctcat     300
cgcaaagtga aggaaagtcc gctcagctcc gacaccattt tccgtcagag tcacgcgggc     360
ctcttcaacc tctgtatagt agtccttgtt gctgtgaata gccgactcat cattgagaat     420
ttaatgaagt atggttggtt gatcaaatct ggcttttggt ttagctcaaa gtcattgaga     480
gactggcccc tcttcatgtg ttgtctttct cttgtggtat ttccttttgc tgcatttata     540
gtggagaagt tggcacagca gaagtgtata cccgaaccag ttgttgttgt acttcatata     600
atcattacct cagcttcact tttctatcca gttttagtaa ttctcaggtg tgattctgct     660
tttctatcag gtgttacgtt aatgctattt gcttgtgttg tatggttaaa attggtgtct     720
tatgcacata caaactatga tatgagagca cttaccaaat cagttgaaaa gggagaagct     780
ctgcccgata ctctgaacat ggactatcct tacaatgtaa gcttcaagag cttagcatat     840
ttcctggttg cccctacatt atgttaccag ccaagctatc ctcgcacacc ttatattcga     900
aagggttggc tgtttcgcca acttgtcaag ctgataatat ttacaggagt tatgggattt     960
ataatagaac aatacattaa tcccattgta caaaattcac agcatcctct caagggaaac    1020
cttctttacg ccatcgagag agttctgaag ctttctgttc caaatttata tgtgtggctc    1080
tgcatgttct attgcttttt ccacctttgg ttaaatatat tggcagagct tcttcgattt    1140
ggtgatcgtg aattctacca ggattggtgg aatgccaaaa ctgttgaaga ttattggagg    1200
atgtggaata tgcctgttca caaatggatg atccgccacc tatattttcc atgtttaagg    1260
cacggtatac caaaggccgt tgctctttta attgccttcc tggtttctgc tttattccat    1320
gagctgtgca tcgctgttcc ttgccacata ttcaagttgt gggctttcgg tggaattatg    1380
tttcaggttc ctttggtctt catcactaat tatctgcaaa ataaattcag aaactcgatg    1440
gttggaaata tgattttttg gttcatattc agtattcttg gtcaacctat gtgcgtactg    1500
ctatattacc atgacttaat gaataggaaa ggcaaacttg actgaaggtg cacgtggata    1560
agcttttctg tttttggagt gtataattga tgtcgatatg ttgatcaata ttggtttcca    1620
cgagtacttt catctaccat ggcagtggct gctctgaagg atttccacct gatataccag    1680
gtcgcgaggc taattcatct tgatctatgt acttaatcaa ctctcctctg gcaattgtat    1740
cgatatatgc aattttgaga gccatacact ggcattgata actgccaagg aacagtgnta    1800
gctgttttc tgttaaatgt taattagtag agagctagat gtaaataaat ttatgctcaa    1860
aaaaaaaaaa aaaaaaaaa                                                 1880
```

<210> SEQ ID NO 21
<211> LENGTH: 1960
<212> TYPE: DNA
<213> ORGANISM: Glycine max

<400> SEQUENCE: 21

```
acgcgggggg agaagagaag actgagttag aaaacacgct cggtcttctt ctccaatggc      60
```

```
gatttccgat gagcctgaaa gtgtagccac tgctctcaac cactcttccc tgcgccgccg      120
tccctccgcc acctccaccg ccggcctctt caattcgcct gagacaacca ccgacagttc      180
cggtgatgac ttggccaagg attctggttc cgacgactcc atcaacagcg acgacgccgc      240
cgtcaattcc caacagcaaa acgaaaaaca agacactgat ttctccgtcc tcaaattcgc      300
ctaccgtcct tccgtccccg ctcaccgcaa agtgaaggaa agtccgctca gctccgacac      360
tattttccgt cagagtcacg cgggcctctt caacctttgt atagtagtcc ttgttgctgt      420
gaatagccga ctcatcattg agaatttaat gaagtatggt tggttgatca aatctggctt      480
ttggtttagc tcaaagtcat tgagagactg gccccttttc atgtgttgtc tttctcttgt      540
ggtatttcct ttcgctgcct ttatagtgga gaagttggca caacggaagt gtatacccga      600
accagttgtt gttgtacttc atataatcat tacctcaact tcgcttttct atccagtttt      660
agttattctc aggtgtgatt ctgcttttgt atcaggtgtc acgttaatgc tgttttcttg      720
tgttgtatgg ttaaaattgg tgtcttatgc acatacaaac tatgatatga gagcacttac      780
caaattagtt gaaaagggag aagcactgct cgatactctg aacatggact atccttacaa      840
cgtaagcttc aagagcttgg catatttcct ggttgcccct acattatgtt accagccaag      900
ctatcctcgc acaccttata ttcgaaaggg ttggttgttt cgccaacttg tcaagctgat      960
aatatttaca ggagttatgg gatttataat agaacaatat attaatccca tagtacaaaa     1020
ttcacagcat cctctcaagg gaaaccttct ttacgccacc gagagagttc tgaagctttc     1080
tgttccaaat ttatatgtgt ggctctgcat gttctattgc ttttttccacc tttggttaaa     1140 tatcctggca gagcttcttc gatttggtga tcgtgaattc tacaaggatt ggtggaatgc     1200
caaaactgtc gaagattatt ggaggatgtg gaatatgcct gttcacaaat ggatgatccg     1260
ccacctatat tatccatgtt taaggcacgg tctcccaaag gctgctgctc ttttaattgc     1320
cttcctggtt tctgctttat tccatgagct gtgcattgct gttccttgcc acatattcaa     1380
gttgtgggct ttcggtggaa ttatgtttca ggttcctttg gtcttgatca ctaattatct     1440
gcaaaataaa ttcagaaact caatggttgg aaatatgatt ttttggttca tattcagtat     1500
ccttggtcaa cctatgtgtg tactgctata ctaccatgac ttgatgaata ggaaaggcaa     1560
acttgactga agctacggcc attacatttt aaaggtgcac atggatgagc ttttcagttt     1620
tcagattgta aaattgatgt ggatatgttg gtcaatattg ttttctacga atgctttcat     1680
ctaccatggc attggctgct ctgaaggaat tccacgggat atgccagttc acgaggctaa     1740
ttcattatct tgatctatgt acttaccaac tctcctctgg caattgtatc aaaatatgca     1800
attttgagag ccatacactg gcattgataa ctgccaagga acactctaac tgttttctgt     1860
tagctgttaa ttagtagagg gctagatgta aatggtttat gctcaatata tttatttcct     1920
cctagtcttc aagttccaaa aaaaaaaaaa aaaaaaaaa                             1960
```

<210> SEQ ID NO 22
<211> LENGTH: 1536
<212> TYPE: DNA
<213> ORGANISM: Lotus japonicus

<400> SEQUENCE: 22

```
atggcgattt ccgaagactc tgaatctcta ttcgccgccg ccgccgcttc ctccgtcatc       60
caaagcggct cttccgtacg ccgcaggccc agcgctatct ccgccgtcgc gacagtcgaa      120
gacgagagtt cgagtgaaga gccggtgccg gtgagggatt ctggttccga cgtcgacgac      180
tccgtaagca gcgagcaaca cgtctccccc gccaccgcca atcgagagaa gaatcaggtg      240
```

```
catgacatct cagccaccaa attcgcctac cgtccttccg cccccgctca tcgcagagtc      300
aaggagagcc ccctcagctc cgacaacatt ttccgtcatc atgcgggtct cttcaacctt      360
tgtatagttg tgcttgttgc agtgaatagc agacttatca ttgagaattt gatgaagtat      420
ggttggttga ttaggactgg cttttggttt agttcaaaat cattgaggga ttggccactc      480
ttcatgtgtt gtctcagtct tgcaatattt ccttttgccg cctttgtagt cgagaagttg      540
gtgcaacaga agtgtatttc tgaaccagtt gttgttcttc atatattcat ttcaacagct      600
gcagttgtct atccagtttt agtaatcctc aggactgatt ctgcttttcc atcaggcgtc      660
acattaatgt tatttgcttg cattgtatgg ctaaaactgg tgtcttatgc acatacgaac      720
tatgatatga gagaacttac caaatcaatt gaaaagggag aagcacttcc caatactctg      780
aatatggact attcttatga tgtgagcttc aagagcttgg catactttat gattgctcct      840
acattatgtt accagccaag atatcctcgc agtccttcta tccggaaagg ttgggtgctt      900
cgtcaacttg tcaagctgat aatatttaca ggagtaatgg gatttataat agaacaatat      960
attaatccta tagttcaaaa ttcacagcat cctttgaagg aaacctact atatgccatt     1020 gaaagagttc tgaagctgtc tgttccaaac ttatatgtgt ggctctgcat gttctactgc     1080 ttttccacc tttggttaaa tattctcgca gagcttctta gatttggtga tcgcgagttc     1140
tacaaggatt ggtggaatgc caaaactttt gaagagtatt ggaggatgtg gaatatgcct     1200
gttcacaaat ggatgatccg acacctatat tttccatgtt taagaaatgg tatacccaag     1260
ggtgttgcta ttttaattgc cttcctggtt tctgcattgt tccatgagct gtgcattgct     1320
gttccttgcc acattttcaa gttgtgggct tttggtggaa ttatgtttca ggttcctttg     1380
atcttgataa caaattatct gcaaaataag ttcagaaact caatggttgg aaacatgatt     1440
ttttggttca tattcagtat tcttggtcaa ccaatggccg tactgctata ctaccacgat     1500
ttgatgaatc ggaaaagcaa acttgaccaa agctag                               1536
```

<210> SEQ ID NO 23
<211> LENGTH: 1620
<212> TYPE: DNA
<213> ORGANISM: Medicago truncatula

<400> SEQUENCE: 23

```
atggcaattt ccgatacacc ggaaaccact gcaaccgcca cagccaccgt aacaaccatc       60
gaaaccgaca cagatctcaa acgctcttca ctccgacgac gaccgagcgc cacatcaacc      120
gccggtggtc tcttcgacgc ggaaagtgca gctgcagatg ccgttcgaga ttcaggctcc      180
gatgattcgt tgaacggtaa gatcaacaac aagaagagg ttaaagatcg aaaaacggat       240
catgcagaag gaattgttga cgatgatgat gataatgcgg ttaagaagaa tggtggtaat      300
gacgtcatca atgatcgtga aaatgttgct gtcgatttca aattcactta tcgtccttca      360
gttcccgctc accggagaag caaagaaagt cctcttagct ccgcaatat ttttagacag       420 agtcatgcag gactgttcaa tctctgtatt gtggtgcttg ttgcagtgaa tagtaggctt      480
attattgaaa atctgatgaa gtatggatgg ttgattcgat ctggcttttg gtttagttca      540
aaatcgctta gagattggcc cctcttcatg tgttgtctta gtcttgcaat atttccactt      600
gctgcctttg tagtcgaaaa gttggcccaa caaaaacgta tttctgaacc agttattgtt      660
ctccttcata ttgtaattac aactgttata tcttatggat ccatggcctt gctgtgcagg      720
tgcgattctg ctttttttatc tggttccacg ttaatgctat tgacttgcat agtgtggtta      780
```

```
aaattggtgt catatgcaca tacaacctat gatatgagag cgcttgctgt ttcaaatgaa        840
aagggagaaa caatgcccga tactttcaat atggaggagt acccacacaa tgtgagcttc        900
cagagtttag catacttcat ggttgctcct acattatgct accagccaag ctatcctcgc        960
acaccttcgg ttcgaaaggg ttgggtctgt cgacaacttc tcaagctggt catatttaca       1020
ggagttatgg gatttataat agaacaatat atgaatccta ttgtccagaa ttcacaacat       1080
ccattgaagg gaaaccttct atatgccatt gagagagttc tgaagctttc tgttccaaat       1140
gtttatgtgt ggctgtgcat gttctattgc ttttttccatc tttggttaaa tatacttgcg      1200
gagcttctcc ggtttggtga tcgtgagttc tacaaagatt ggtggaatgc ccaaacggtt       1260
gaagagtatt ggaggatgtg gaatatgcct gtgcacaaat ggatggttcg tcacgtgtat       1320
tttccctgca taaggtttgg tatacccaag ggtgctgctg ctttgactgc tttcctggtt       1380
tctgctgtgt tccatgagtt atgcattgct gttccttgcc gcatgttcaa gttgtgggct       1440
tttattggaa ttatgttcca ggttcctttg gtcttgatca ccaattacct gaaaaataaa       1500
tacagaaact caatggttgg aaatatgatt ttttggttca tattttgtat tcttggtcaa       1560
cctatgtgtg tactactata ctatcatgac ttgatgaata ggaaaggtga aattgactga       1620
```

<210> SEQ ID NO 24
<211> LENGTH: 1566
<212> TYPE: DNA
<213> ORGANISM: Jatropha curcas

<400> SEQUENCE: 24

```
atgacgattt tggagaccac tactagcgga ggtgatggtg ttgctgagtc gtcttccgat         60
cttaacgtat cgcttcgacg gagacggaaa ggcaccagct cggatggagc tttgccggaa        120
ttgacttcga atattgttga attggaatct gaaagcggtg gccaggtgat gatggatcca        180
ggtatggtga cggaaccgga gacagagaaa attaatggaa agattgcgg cggtgacaag         240 gataagattg acaatcgcga gatcgtgggg aggtcggata ttaaattcac gtaccggcca        300
tcggtgccgg ctcatcgagc gctcagggag agtccgctta gctctgatgc tatatttaaa       360
caaagtcatg caggtctgtt caacctctgt atagtagtgc ttgttgctgt taacagcagg        420
cttatcattg aaaatctaat gaagtatggt tggttaatta aaacgggggt ttggtttagt       480
tcaagatcgt tgagagattg gccccttctt atgtgctgtc ttaccctccc tatattctct       540
cttgccgcct atctagttga gaagttggca tatcgaaaat atatatctgc acctattgtt       600
atttctcttc atatgctcat taccacaaca gcagttttgt acccagtttc tgtgattctc       660
agttgtgggt ctgctgttct gtctggtgtt gcattgatgc tctttgcttg tatcgtgtgg        720
ttgaaattag tatcttatgc acatacaaac atgacacatga gagccattgc caactcagct       780
gacaagggag atgcactatc cgatacttca ggtgcagatt cttcacgtga tgttagcttc       840
aagagtttgg tctacttcat ggttgctcct acgctatgtt accagccaag ttatcctcga       900
acagattcag ttagaaaggg ttgggtggtt cgtcaatttg tcaagttaat aatatttaca       960
ggattcatgg gatttatcat agaacaatat atcaatccta ttgtccagaa ttcacaacac       1020
cccttaaagg gggatctatt tatatgccatt gaaaggggttt tgaagctctc agttccaaac     1080
ttatatgtgt ggctctgcat gttctactgc ttttttcatc tatggttaaa tatacttgct       1140
gagctccttc ggtttggtga cagagagttc tataaagatt ggtggaatgc aaggacagtt       1200
gaggagtact ggagaatgtg gaatatgcct gttcataagt ggatggttcg ccatatctac       1260
tttccatgct tgcggcataa aataccaagg ggggtagcct tgttaattgc tttcttcgtt       1320
```

```
tcagctgtat tcatgagtt gtgcattgct gttccttgcc acatgttcaa gctctgggct    1380
tttattggaa ttatgtttca gattccattg gtcgggatca ctaattacct ccagaacaag    1440
ttcagaagct ccatggtggg aaatatgatc ttttggttca ttttctgcat tcttggtcaa    1500
cccatgtgtg tgctattgta ttatcatgac ctaatgaatc ggaaaggcaa tgctgaatta    1560
agatga                                                               1566
```

<210> SEQ ID NO 25
<211> LENGTH: 2084
<212> TYPE: DNA
<213> ORGANISM: Vernicia fordii

<400> SEQUENCE: 25

```
tctctctctc tttgctttac gtgtacatcg accaccacca cagccatctt gcgactgttc      60
aattatccta taagtaccac cgcattcatc accgccaatc cttaactcta atttgctata     120
ctaaacactt gctttatatg cgcttttcta tttactcttc actgtaattt cttattggta     180
ttcaaagtgt tttcaatgac aatccctgaa cgccggata attccacgga tgctaccacc      240
agtggcggtg ctgagtcctc ttccgatctt aacctttctc ttcgacggag gaggactgct     300
tcaaactccg atggagctgt cgcggaattg gcttccaaga ttgatgagtt ggaatctgat     360 gccgaggag gccaggtgat taaggatccg ggagcagaaa tggattcggg gactttgaaa     420
agtaatggaa aagattgcgg aaccgttaag gataggattg aaaatcgtga aatcgtgga      480 ggatcggatg ttaaattcac gtatcggccg tcggtgccgg ctcaccgggc gctcaaggag     540
agtccgctta gctctgataa tatatttaaa caaagtcatg caggtctctt caatctctgt     600
atagtagtgc ttgtagcggt taacagtcgg cttatcattg aaaacataat gaagtatggt     660
tggttaatta agactgggtt tggtttagt tcaagatcgt tgagagactg gccacttctt     720
atgtgctgtc ttaccctccc aatatttct cttgctgcct atctagttga aagttggcc      780 tgtcggaagt atatatctgc acccactgtt gttttcttc atattctttt ctcctcaaca     840
gcagttttat accctgtttc tgtgattctc agttgtgaat ctgctgttt gtccggtgtc     900 gcattgatgc tctttgcttg tatcgtgtgg ttgaaattgg tatcttatgc acatacaaac     960
tttgatatga gagcaattgc taactcagtt gataagggag atgcgctatc caatgcttcg    1020
agtgcagagt cctctcatga tgttagcttc aagagtttgg tttatttcat ggttgctccc    1080
acattgtgtt accagccaag ttatcctcga actgcatcca ttcgaaaggg ttgggtggtt    1140
cgtcaatttg ttaagttaat aatatttaca ggattcatgg gattatcat agaacaatat    1200 atcaatccta tcgttcagaa ttcacaacat cctttaaaag gggatctctt atatgccatt    1260
gagagggttt tgaagctctc agttccgaat ttatatgtct ggctttgcat gttctactgc    1320
ttttttcacc tatggttaaa tatacttgct gagctccttc gctttggtga tagagagttc    1380
tataaagatt ggtggaatgc aaggacagtt gaggagtatt ggagaatgtg aatatgcctt    1440
gttcataagt ggatggttcg ccatatctac tttccatgct gcggcataa aataccaagg    1500 ggggtggcct tattaattac ttctcttcgtt tcagcagtat ttcatgagtt gtgcattgct    1560
gttccttgcc acatattcaa gctctgggct tttattggaa taatgtttca gattcctttg    1620
gtcgggatca caaattacct tcaaaacaag ttcagaagct caatggtggg aacatgatc     1680 ttctggttca ttttctgcat tcttggtcaa ccatgtgct tgctgttgta ttaccatgac     1740
ctaatgaatc gaaaagggac taccgaatca agatgacact aactcatcgt gtggtagact    1800
```

```
ctatatatat acatagactt accagagatg ggttgcttcc aacatattgt gcacaagagg    1860
caattgttgt tctcatcaga agagtgggtt aattaattaa ttaatgtaca agcaattttg    1920
aaagtataat cactggcagg gactagtgcc cgactgtagt actgagatta tagaggtatt    1980
atcaatcgtt agtggaaaat tgtaaatgta taaagttcaa tctttgtatt gtttcttttc    2040
taatatcata ttttttttta ttgctcatca aaaaaaaaaa aaaa                    2084
```

<210> SEQ ID NO 26
<211> LENGTH: 1828
<212> TYPE: DNA
<213> ORGANISM: Vernonia galamensis

<400> SEQUENCE: 26

```
tctgagctca aatcaaattt ctgcgactca tacaggattc aactcaatac tttcttgatc      60
ggttctgctg ttcatttact tgtaatttct acttctgctt tgctttcatt tcaagctttt     120
ttccttaata atggcgttat tagatacgcc tcagattgga gaaataacga ccaccgccac     180
cacaactata agacggcgga ccactgtcaa gcctgatgct ggaatcggag atggattgtt     240
tgattcttcg tcgtcttcca aaaccaactc atccttcgag gatggtgaca gtttgaatgg     300
tgatttcaat gacaaattta aggaacagat cggagctggt gatgaatcca aggacgactc     360 caagggaac ggacagaaga tagatcacgg aggagttaaa aagggacgtg aaacgactgt      420
ggtgcattat gcttatcggc cttcttctcc ggctcatcgg agaattaaag aatctccgct     480
tagctctgac gccatcttca agcagagtca tgcaggcctc tttaaccttt gcatagtggt     540
gcttgttgca gtaaatggta ggctcatcat tgagaatctg atgaagtatg gactattgat     600
caattccaac ttttggttca gttcgagatc attgagagac tggccacttc tgatgtgctg     660
cctcactcct tctgactttc cacttgctgc ctacattgtt gagaaattgg catggaaaaa     720
acgtatatcc gaccctgttg taatcacact ccatgttata ataactacaa ctgcaattct     780
ttatccggtc ttcatgattc tgaggttcga ttcagttgtt ctatcaggcg tctcgttgat     840
gctgtgtgct tgcattaatt ggttgaagtt ggtatctttt gtgcatacaa attatgacat     900
gcggtcgctt ttgaactcaa ctgataaggg agaagtggaa cccatgtctt caaatatgga     960 ttattttttat gatgtcaact tcaaaagctt ggtttatttc atggttgctc caactttgtg    1020
ttaccagata agctatcctc gcactgcatt tattcgaaag ggttgggtgt acggcaact     1080 gatcaagcta gtaatattta cagggttcat gggattcatc attgaacaat atatcaatcc    1140
gattgtcaaa aattctcgtc atccattgaa aggagacttt ttatatgcga ttgagcgggt    1200
tttaaagctt tcagttccga atttatatgt gtggctctgt atgttctact gctttttttca   1260 cctttggtta aatatacttg ctgagcttct tgtttttggg gatcgtgaat tttataaaga    1320
ttggtggaat gcacaaacta tgaagagta ttggaggcta tggaatatgc ctgttcataa     1380
atggattgtt aggcaccttt atttttccatg cttgcgtaat gggatacct aagggtgctgc     1440 catattggtt gcatttttca tgtctgccgt gttccatgag ctttgtattg ctgttccctg     1500 ccacatttc aagttttggg cttttatcgg gatcatgttt caggtcccgt tggtcctact     1560
cacaaattac ttgcagcaca agtttcaaaa ctcgatggtg ggaaatatga tcttctggtg     1620 cttttttcagc attttttggtc aacccatgtg tgtattactt tactaccatg atgtcatgaa    1680
tcaaaggggg aaaagcaaat aaaaagatgt gattgtgttg ctccatttga tctcatagca    1740
tgactggact aaacaaaccc aagggacaca ttttagtcct taaggaaaaa ttttttgtagg    1800 aaaaaaaaaa aaaaaaaaaa aaaaaaaa                                        1828
```

<210> SEQ ID NO 27
<211> LENGTH: 2020
<212> TYPE: DNA
<213> ORGANISM: Ricinus communis

<400> SEQUENCE: 27

```
cttcttcttc tgctgctgtt cctctctcct ccaccgccac gctcacctct ctttgcatga     60
cataatacta ttgttcttat tatcattttc actctttaaa tacaaacatc aattattcct    120
tttctatcaa acacatgtat tctattctct cgtcgtctag attctcatct tcattgaatc    180
ctccttctta gcgtgtcttt gtccacttct tttgggcacc gacgttttta atctccatga    240
cgattctcga aacgccagaa actcttggcg tcatctcctc ctccgccact tccgatctca    300
acctctctct ccgacgtaga cggacctcaa atgactccga tggtgcactt gctgatttgg    360
cttcgaagtt tgatgatgat gacgacgtaa gatcggaaga ttctgctgaa aatattatcg    420
aagatcctgt agcagcggtt actgaattgg cgacagcaaa gagtaacgga aaagactgtg    480
ttgccaatag taataaggat aaaattgata gccatggagg atcatcggat tttaaacttg    540
catataggcc ttcggttcca gctcaccggt cacttaagga gagtccgctt agctctgatt    600
taatatttaa acaaagtcat gcaggtctgt ttaacctttg tatagtagtg ctcgtagctg    660
ttaacagcag gctcatcatt gagaatttaa tgaagtatgg ctggttaatt aagacgggct    720
tttggtttag ttcaagatca ttgagagatt ggccgctttt tatgtgctgt ctttctctcc    780
cagtattccc ccttgctgcc tatctagttg agaaggccgc atatcgaaaa tatatatctc    840
cgcctattgt tattttcctt catgtgatca tcacctcagc agctgttttg tacccagctt    900
ctgtaattct cagttgtgaa tctgcttttt tatctggtgt cacattgatg gaacttgctt    960
gtatggtatg gttgaaattg gtatcctatg cacatacaaa ctatgatatg agagcgatcg   1020
ctgacaccat tcataaggaa gatgcatcca attcttctag tacagagtat tgtcatgatg   1080
tgagctttaa gactttggcg tacttcatgg tcgcacccac attatgttac cagccaagtt   1140
atcctcgcac agcatttatt agaaagggct gggtgttccg tcaatttgtc aaactaataa   1200
tttttacagg attcatggga tttatcatag aacaatacat caatcctatc gtccagaatt   1260
ctcaacaccc tttaaaaggg gatctcttat atgccattga gagggttctg aagctctcag   1320
ttccgaattt atatgtgtgg ctctgcttgt tctactgctt ttttcacctg tggttgaata   1380
tagttgctga gctccttcgc ttcggtgacc gggagttcta caaagattgg tggaatgcaa   1440
aaactgttga ggagtactgg aggatgtgga atatgcctgt tcacaagtgg atggttcgcc   1500
atatctactt cccatgccta cgtcgtaaaa taccaagggg ggtagcaata gttattgctt   1560
tcttcgtttc agctgtattt catgagttgt gcattgctgt tccttgccac atgttcaaac   1620
tttgggcttt ttttggaata atgtttcaga ttcctttagt tgtgatcact aattattttc   1680
aaaggaagtt cagaagctca atggtgggaa atatgatctt ctggttcttt ttctgcattc   1740
tcggccaacc tatgtgtgta ctgttgtatt accatgacct aatgaatcgc gatgggaact   1800
gaaccatggg ctcagtccag atatgggtac accttccaag atgttatttt cgtgagtgaa   1860
gactgcacca cagtgttgtt cttgttacac aatccccatt gacagagtag gttaatcgtc   1920
agtttcagga gataagacac aattttgaaa gtacagcaga ggctgctatt aatgtatcat   1980
gttgagtttc tgttatgtta tgttattctt ttttaatctc                          2020
```

<210> SEQ ID NO 28

```
<211> LENGTH: 1444
<212> TYPE: DNA
<213> ORGANISM: Populus trichocarpa

<400> SEQUENCE: 28
aaatcatggc ggcgttagag tctccggaga atcatatacg acgtcggatc ttaacttctc    60
cgttcgacgg aggtctacta ctgtcacgga ttcgccttcg acggagatga tggaatcgga   120
ggatttgaaa agtaatggta agaatgcga aaggttacg aatgagaatc gatcggatat    180
taaattcaat tatcggcctt caatgcctgc tcatcgtggt gttagagaga gtcctcttag   240
ttctgatgct attttaaaac aaagtcatgc aggtctcttc aatctctgta tagttgtgct   300
tgtggctata aacagcaggc ttatcattga aaatataatc aagtatggtt ggttaattaa   360
cggtggattt tggtttagtt caaaatcatt aagagactgg ccctgtttta tgtgctgtct   420
tagccttcca gcattccctt cgcggcccta tcttgttgag aagttggcat atcaaaatta   480
tttacctcaa cttgttgttg ttttccttca tacaatcatc accacaggat cactttttata   540
tccagttttta gtaattctca ggtgtgattc tgcttttcta tctggtgtca cgttgatgct   600
cttttcttgc attgtgtggc taaaattggt atcttatgct catacaaact ctgatttgag   660
agcaattgcc aagtcaatag ataggaaga tgtcccatcc atttctcctt atgtgggtaa    720
tccttatgat acttacttta agagtttggt ctacttcatg gtggctccca cattatgtta   780
ccagtcaagc tatcctcgca ctgaatctgt tcgaaaggga tgggtggttc aacaatttgt   840
caagttaata tatttactg gattcatggg atttatcata gaacaatata tcaatcctat   900
tgttaagaat tcacagcacc cttttaaagg aaatctcttg tatgccattg agagggtctt   960
gaagctctca gttcctaatt tatatgtatg gctttgcatg ttctactgct ttttccacct  1020
gtggttaaat atacttgccg agctcctttg ctttggtgat cgggagttct acaaggattg  1080
gtggaatgca agaactgttg aagaatattg gagaatgtgg aatatgccag ttcataagtg  1140
gatggttcgc catatctatt ttccatgcct acgaataaaa ataccgaagg ggttagctat  1200
acttattgcc ttcttagttt cagctgtatt tcacgagctg tgcattgctg ttccctgcca  1260
cgtgttcaag ctctgggcat ttattggaat tatgttacag gttcccttag tggtgatcac  1320
aaaatttctc caaaataagt tcagaagctc catggtggga aacatgatct tctggttgtt  1380
tttcagcatt cttggtcaac caatgtgtgt gcttctgtat taccatgact tgatgaatcg  1440
gaag                                                               1444

<210> SEQ ID NO 29
<211> LENGTH: 1816
<212> TYPE: DNA
<213> ORGANISM: Populus trichocarpa

<400> SEQUENCE: 29 aacatatttta aatcatggcg gagtcagagt caccggagaa tcgtatagcg gcaatggaaa    60
gtacatcttc ctcgacgtca gatctcaact tctctattcg acgaggtct acagtcatgg    120
actcggcttc gacggaaatg atgggatcgg agggtttgaa agtagtggt aaagcatgcg   180
ataaggttaa gattgagaag caatcagata tgaaattcaa ttatcggcca tcaatgcccg   240
ctcatagtgg tgttagagag agtcctctta gttctgatgc tatttttaaa caaagtcatg   300
caggtctctt caatctctgt atagtagtgc ttgtggctgt aaacagcagg cttatcattg   360
aaaatttaat caagtacggc tggttaatca attcaggatt tggtttagt tcaaaatcat   420
taagagactg gcccctgttt atgtgctgtc ttagtcttcc agcattccct ctcgcggcct   480
```

```
atctcgttga agttggca tatcgaaatt gtatatctga acttgttgtt gttttccttc     540
ataatcat caccacagca tcactttgt atccagtttt agtaattctc aggtgtgatt      600
ctgctttact atctggtggc acattgatgc tctttgcttg cattgtgtgg ttgaaattgg   660
tatcttttgc acatacaagc tctgatatga gcaattgc caagtcaatt gataaggaaa    720
ataccccatc catttcttcg aaagcagata attcttatga tgctaacttt aagagtttgg  780
tctacttcat ggtggctccc acattatgtt accagtcaag ctatcctcgt tctgcatctg  840
ttcgaaaggg ttgggtggtt cgacaatttg tcaagttaat aatatttact ggattcatgg  900
gatttatcat agaacaatat atcaatccta ttgttcagaa ctcgcagcac cctttgaaag  960
gaaatctctt gtatgccatt gagagggtct tgaagctctc agttcctaat ttatatgttt 1020
ggctctgcat gttctactgc ttttccact tgtggttaaa tatacttgcc gagctccttc  1080
gctttggtga tcgggagttc tacaaggatt ggtggaatgc aagaactgtt gaagagtact 1140
ggagaatgtg aatatgcca gttcataagt ggatggttcg ccatatctat tttccatgtt  1200
tacggaataa aataccaaag tgggcagcct tacttattgc cttctttgtc tcagctgtat  1260
ttcatgagtt gtgtattgct gttccttgcc acatgttcaa gctctgggca tttattggaa 1320
ttatgtttca ggttccctta gtggtgatca caaaattcct tcaaaataag ttcaaaagct 1380
caatggtggg caatatgatc ttctggttat ttttcagcat tcttggtcaa cctatgtgtg 1440
tgcttctata ttaccatgac ttgatgaatc ggaaagggaa aactgaacga agatgacaaa 1500
tgcggtatgg tagagatcgt caagatgaac aaaatgcacg ttatgatag tagagcaggc  1560
attaggtgtg cctttctta tgtattctgc aggagaaatt gactcgatt tgttgagtcg   1620
agagatggtc tcttcaggac ttttattttt atgtatctca attgacgtgc aagcaatttt 1680
ggaagtacaa gcactggcaa ttaaaatgcc aatgcaacag tggatctgtt gtgttggtta 1740
atcatttcca gaaatttgta aatgtttctt gttccgtctt ttgcttcaaa ggaaataaaa 1800
aaagaagaaa atttct                                                  1816

<210> SEQ ID NO 30
<211> LENGTH: 520
<212> TYPE: PRT
<213> ORGANISM: Arabidopsis thaliana

<400> SEQUENCE: 30

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asp Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125
```

```
Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
                195                 200                 205

Val Ile Phe Leu His Ile Ile Ile Thr Met Thr Glu Val Leu Tyr Pro
210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
                260                 265                 270

Asn Pro Glu Val Ser Tyr Tyr Val Ser Leu Lys Ser Leu Ala Tyr Phe
                275                 280                 285

Met Val Ala Pro Thr Leu Cys Tyr Gln Pro Ser Tyr Pro Arg Ser Ala
290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
                370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
                435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
                500                 505                 510

Met Asn Arg Lys Gly Ser Met Ser
                515                 520

<210> SEQ ID NO 31
<211> LENGTH: 503
<212> TYPE: PRT
```

<213> ORGANISM: Brassica juncea

<400> SEQUENCE: 31

```
Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Arg Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Leu Val Ala
        115                 120                 125

Val Asn Ser Arg Pro Ile Ile Glu Asn Leu Met Lys Tyr Gly Trp Leu
130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Leu Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
        275                 280                 285

Ile Arg Lys Gly Trp Val Ala Arg Gln Phe Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400
```

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
        435                 440                 445

Ile Met Phe Gln Val Pro Leu Val Phe Ile Thr Asn Phe Leu Gln Glu
    450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
                485                 490                 495

Asn Arg Lys Gly Ser Met Ser
            500

<210> SEQ ID NO 32
<211> LENGTH: 503
<212> TYPE: PRT
<213> ORGANISM: Brassica napus

<400> SEQUENCE: 32

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Leu Val Ala
        115                 120                 125

Val Asn Ser Arg Leu Ile Ile Glu Asn Leu Met Lys Tyr Gly Trp Leu
    130                 135                 140

Ile Arg Thr Asp Phe Trp Phe Ser Ser Thr Ser Leu Arg Asp Trp Pro
145                 150                 155                 160

Leu Phe Met Cys Cys Leu Ser Leu Ser Val Phe Pro Leu Ala Ala Phe
                165                 170                 175

Thr Val Glu Lys Met Val Leu Gln Lys Phe Ile Ser Glu Pro Val Ala
            180                 185                 190

Ile Ile Leu His Val Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Ser Tyr Asp Ile Arg Thr Leu Ala Asn Ser Ala Asp Lys Val Asp
                245                 250                 255

Pro Glu Ile Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Cys
            275                 280                 285

Ile Arg Lys Gly Trp Val Ala Arg Gln Leu Ala Lys Leu Val Ile Phe
290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
            325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
            355                 360                 365

Cys Phe Gly Asp Arg Glu Phe Tyr Lys Asp Trp Trp Asn Ala Lys Ser
            370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Met Gly
            435                 440                 445

Ile Met Phe Gln Val Pro Leu Val Phe Ile Thr Asn Phe Leu Gln Glu
            450                 455                 460

Arg Phe Gly Ser Met Val Gly Asn Met Ile Phe Gly Ser Ala Ser Cys
465                 470                 475                 480

Ile Phe Gly Gln Pro Met Cys Gly Leu Leu Tyr Tyr His Asp Leu Met
                485                 490                 495

Asn Arg Lys Gly Ser Met Ser
            500

<210> SEQ ID NO 33
<211> LENGTH: 503
<212> TYPE: PRT
<213> ORGANISM: Brassica juncea

<400> SEQUENCE: 33

Met Ala Ile Leu Asp Ser Gly Thr Val Thr Met Ala Thr Glu Asn Gly
1               5                   10                  15

Val Ala Asp Leu Asp Met Leu Arg Arg Arg Lys Ser Arg Ser Asp Ser
                20                  25                  30

Ser Asn Gly Leu Leu Ser Glu Thr Ser Pro Ser Asp Asp Ala Gly Ala
            35                  40                  45

Pro Ala Asp Val Glu Asp Arg Val Asp Ser Ala Ala Gln Gly Thr Ala
50                  55                  60

Asn Leu Ala Gly Asp Thr Glu Arg Glu Ser Gly Gly Gly Gly
65                  70                  75                  80

Gly Gly Asn Gly Glu Val Arg Phe Thr Tyr Arg Pro Ser Val Pro Ala
                85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Leu Val Ala
            115                 120                 125

Val Asn Ser Arg Leu Ile Ile Glu Asn Leu Met Lys Tyr Gly Trp Leu

```
        130                 135                 140
Ile Arg Thr Asp Phe Trp Phe Ser Ser Thr Ser Leu Arg Asp Trp Pro
145                 150                 155                 160

Leu Phe Met Cys Cys Leu Ser Leu Ser Ile Phe Pro Leu Ala Ala Phe
                165                 170                 175

Thr Val Glu Lys Leu Val Leu Gln Lys Phe Ile Ser Glu Pro Val Val
            180                 185                 190

Ile Ile Leu His Ile Ile Ile Thr Met Thr Glu Val Leu Tyr Pro Val
        195                 200                 205

Tyr Val Thr Leu Arg Cys Asp Ser Ala Phe Leu Ser Gly Val Thr Leu
    210                 215                 220

Met Leu Leu Thr Cys Ile Val Trp Leu Lys Leu Val Ser Tyr Ala His
225                 230                 235                 240

Thr Asn Tyr Asp Ile Arg Thr Val Ala Asn Ser Ala Asp Lys Val Asp
                245                 250                 255

Pro Glu Val Ser Tyr Tyr Val Ser Leu Lys Ser Leu Ala Tyr Phe Met
            260                 265                 270

Val Ala Pro Thr Leu Cys Tyr Gln Pro Ser Tyr Pro Arg Ser Pro Gly
        275                 280                 285

Ile Arg Lys Gly Trp Val Ala Arg Gln Phe Ala Lys Leu Val Ile Phe
    290                 295                 300

Thr Gly Leu Met Gly Phe Ile Ile Glu Gln Tyr Ile Asn Pro Ile Val
305                 310                 315                 320

Arg Asn Ser Lys His Pro Leu Lys Gly Asp Leu Leu Tyr Ala Ile Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Cys Phe Gly Asp Arg Glu Phe Tyr Lys Asp Trp Trp Asn Ala Lys Ser
    370                 375                 380

Val Gly Asp Tyr Trp Arg Met Trp Asn Met Pro Val His Lys Trp Met
385                 390                 395                 400

Val Arg His Val Tyr Phe Pro Cys Leu Arg Ile Lys Ile Pro Lys Val
                405                 410                 415

Pro Ala Ile Ile Ile Ala Phe Leu Val Ser Ala Val Phe His Glu Leu
            420                 425                 430

Cys Ile Ala Val Pro Cys Arg Leu Phe Asn Leu Trp Ala Phe Ile Gly
        435                 440                 445

Ile Met Phe Gln Val Pro Leu Val Phe Ile Thr Asn Tyr Leu Gln Glu
    450                 455                 460

Arg Phe Gly Ser Met Val Gly Asn Met Ile Phe Trp Phe Ser Phe Cys
465                 470                 475                 480

Ile Phe Gly Gln Pro Met Cys Val Leu Leu Tyr Tyr His Asp Leu Met
                485                 490                 495

Asn Arg Lys Gly Ser Met Ser
            500

<210> SEQ ID NO 34
<211> LENGTH: 518
<212> TYPE: PRT
<213> ORGANISM: Tropaeolum majus

<400> SEQUENCE: 34
```

```
Met Ala Val Ala Glu Ser Ser Gln Asn Thr Thr Met Ser Gly His
1               5                   10                  15

Gly Asp Ser Asp Leu Asn Asn Phe Arg Arg Lys Pro Ser Ser Ser
            20                  25                  30

Val Ile Glu Pro Ser Ser Ser Gly Phe Thr Ser Thr Asn Gly Val Pro
        35                  40                  45

Ala Thr Gly His Val Ala Glu Asn Arg Asp Gln Asp Arg Val Gly Ala
    50                  55                  60

Met Glu Asn Ala Thr Gly Ser Val Asn Leu Ile Gly Asn Gly Gly Gly
65                  70                  75                  80

Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
            115                 120                 125

Asn Leu Cys Ile Val Val Leu Ile Ala Val Asn Ser Arg Leu Ile Ile
        130                 135                 140

Glu Asn Leu Met Lys Tyr Gly Trp Leu Ile Asp Thr Gly Phe Trp Phe
145                 150                 155                 160

Ser Ser Arg Ser Leu Gly Asp Trp Ser Ile Phe Met Cys Cys Leu Thr
                165                 170                 175

Leu Pro Ile Phe Pro Leu Ala Ala Phe Ile Val Glu Lys Leu Val Gln
            180                 185                 190

Arg Asn His Ile Ser Glu Leu Val Ala Val Leu Leu His Val Ile Val
            195                 200                 205

Ser Thr Ala Ala Val Leu Tyr Pro Val Ile Val Ile Leu Thr Cys Asp
    210                 215                 220

Ser Val Tyr Met Ser Gly Val Val Leu Met Leu Phe Gly Cys Ile Met
225                 230                 235                 240

Trp Leu Lys Leu Val Ser Tyr Ala His Thr Ser Ser Asp Ile Arg Thr
                245                 250                 255

Leu Ala Lys Ser Gly Tyr Lys Gly Asp Ala His Pro Asn Ser Thr Ile
                260                 265                 270

Val Ser Cys Ser Tyr Asp Val Ser Leu Lys Ser Leu Ala Tyr Phe Met
            275                 280                 285

Val Ala Pro Thr Leu Cys Tyr Gln Pro Ser Tyr Pro Arg Ser Ser Cys
            290                 295                 300

Ile Arg Lys Gly Trp Val Val Arg Gln Phe Val Lys Leu Ile Val Phe
305                 310                 315                 320

Ile Gly Leu Met Gly Phe Ile Ile Glu Gln Tyr Ile Asn Pro Ile Val
                325                 330                 335

Arg Asn Ser Lys His Pro Leu Lys Gly Asp Phe Leu Tyr Ala Ile Glu
                340                 345                 350

Arg Val Leu Lys Leu Ser Val Pro Asn Leu Tyr Val Trp Leu Cys Met
            355                 360                 365

Phe Tyr Ser Phe Phe His Leu Trp Leu Asn Ile Leu Ala Glu Leu Leu
    370                 375                 380

Arg Phe Gly Asp Arg Glu Phe Tyr Lys Asp Trp Trp Asn Ala Lys Thr
385                 390                 395                 400

Val Ala Glu Tyr Trp Lys Met Trp Asn Met Pro Val His Arg Trp Met
                405                 410                 415

Val Arg His Leu Tyr Phe Pro Cys Leu Arg Asn Gly Ile Pro Lys Glu
```

```
                 420                 425                 430
Gly Ala Ile Ile Ile Ala Phe Leu Val Ser Gly Ala Phe His Glu Leu
            435                 440                 445

Cys Ile Ala Val Pro Cys His Val Phe Lys Leu Trp Ala Phe Ile Gly
        450                 455                 460

Ile Met Phe Gln Val Pro Leu Val Leu Ile Thr Asn Tyr Leu Gln Glu
465                 470                 475                 480

Lys Phe Ser Asn Ser Met Val Gly Asn Met Ile Phe Trp Phe Ile Phe
                485                 490                 495

Cys Ile Leu Gly Gln Pro Met Cys Val Leu Tyr Tyr His Asp Leu
            500                 505                 510

Ile Asn Leu Lys Glu Lys
            515

<210> SEQ ID NO 35
<211> LENGTH: 473
<212> TYPE: PRT
<213> ORGANISM: Echium pitardii

<400> SEQUENCE: 35

Met Thr Ile Trp Glu Ser Pro Glu Ile Ile Ser Ser Asp Glu Ala Ala
1               5                  10                  15

Ala Ala Leu Arg Arg Arg Gly Gly Ala Lys Glu Val Ala Glu Gln Arg
            20                  25                  30

Leu Asp Ser Glu Glu Glu Lys Lys Glu Glu Glu Asn Gly Lys Leu
        35                  40                  45

Lys Tyr Thr Tyr Arg Ala Ser Ala Pro Ala His Arg Arg Ile Lys Glu
50                  55                  60

Ser Pro Leu Ser Ser Asp Ala Ile Phe Lys Gln Ser His Ala Gly Leu
65                  70                  75                  80

Phe Asn Leu Cys Ile Val Val Leu Val Ala Val Asn Ser Arg Leu Ile
                85                  90                  95

Ile Glu Asn Leu Met Lys Tyr Gly Trp Leu Ile Ser Ser Gly Phe Trp
            100                 105                 110

Leu Ser Ser Thr Ser Leu Ser Asp Trp Pro Leu Leu Ile Cys Cys Leu
        115                 120                 125

Ser Leu Pro Ile Phe Pro Leu Ala Ser Phe Val Val Glu Lys Leu Ser
130                 135                 140

Gln Gln Glu Phe Ile Ser Glu Gln Val Val Ile Thr Leu His Ala Leu
145                 150                 155                 160

Ile Thr Thr Thr Val Ile Met Tyr Pro Val Ile Val Leu Arg Cys
                165                 170                 175

Asp Pro Ala Val Leu Ser Gly Val Ile Leu Met Leu Phe Thr Cys Ile
            180                 185                 190

Val Trp Leu Lys Leu Val Ser Tyr Ala His Thr Asn Tyr Asp Met Arg
        195                 200                 205

Ala Leu Ala Lys Asp Cys Asp Lys Leu Gln Ala Leu Ser Gly Ser Ser
210                 215                 220

Met Glu Asp Cys Ser Phe Glu Val Asn Phe Gln Ala Leu Val Tyr Phe
225                 230                 235                 240

Met Val Ala Pro Thr Leu Cys Tyr Gln Leu Arg Tyr Pro Arg Thr Pro
                245                 250                 255

Cys Ile Arg Trp Gly Trp Val Thr Arg His Leu Ile Lys Leu Ile Ile
            260                 265                 270
```

```
Phe Thr Gly Leu Met Gly Phe Ile Ile Glu Gln Tyr Ile Asn Pro Ile
            275                 280                 285

Val Lys Asn Ser Gln His Pro Leu Lys Gly Asn Leu Leu Tyr Ala Ile
290                 295                 300

Glu Arg Val Leu Lys Leu Ser Val Pro Asn Ile Tyr Val Trp Leu Cys
305                 310                 315                 320

Met Phe Tyr Cys Phe Phe His Leu Trp Leu Asn Ile Leu Ala Glu Leu
                325                 330                 335

Leu Cys Phe Gly Asp Arg Glu Phe Tyr Lys Asp Trp Trp Asn Ala Gln
                340                 345                 350

Thr Ile Glu Glu Tyr Trp Arg Met Trp Asn Met Pro Val His Lys Trp
            355                 360                 365

Met Val Arg His Ile Tyr Phe Pro Cys Leu Arg Asn Gly Met Pro Lys
370                 375                 380

Glu Leu Ala Ile Leu Ile Ala Phe Leu Ile Ser Ala Ile Phe His Glu
385                 390                 395                 400

Leu Cys Ile Ala Val Pro Cys His Ile Phe Lys Phe Trp Ala Phe Ile
                405                 410                 415

Gly Ile Met Phe Gln Val Pro Leu Val Leu Thr Asn Val Leu Val
                420                 425                 430

Lys Lys Phe Gln Asn Ser Met Val Gly Asn Met Ile Phe Trp Cys Phe
            435                 440                 445

Phe Cys Ile Leu Gly Gln Pro Met Ser Leu Leu Leu Tyr Tyr His Asp
                450                 455                 460

Val Leu Asn Arg Lys Val Asn Ala Asn
465                 470

<210> SEQ ID NO 36
<211> LENGTH: 523
<212> TYPE: PRT
<213> ORGANISM: Vernonia galamensis

<400> SEQUENCE: 36

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
                20                  25                  30

Gly Asp Gly Leu Phe Asp Ser Ser Ser Ser Lys Thr Asn Ser Ser
            35                  40                  45

Phe Glu Asp Gly Asp Ser Leu Asn Gly Asp Phe Asn Asp Lys Phe Lys
        50                  55                  60

Glu Gln Ile Gly Ala Gly Asp Glu Ser Lys Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
                100                 105                 110

Lys Glu Ser Pro Leu Ser Ser Asp Ala Ile Phe Lys Gln Ser His Ala
            115                 120                 125

Gly Leu Phe Asn Leu Cys Ile Val Val Leu Val Ala Val Asn Gly Arg
        130                 135                 140

Leu Ile Ile Glu Asn Leu Met Lys Tyr Gly Leu Leu Ile Asn Ser Asn
145                 150                 155                 160

Phe Trp Phe Ser Ser Arg Ser Leu Arg Asp Trp Pro Leu Leu Met Cys
                165                 170                 175
```

Cys Leu Thr Pro Ser Asp Phe Pro Leu Ala Ala Tyr Ile Val Glu Lys
                180                 185                 190

Leu Ala Trp Lys Lys Arg Ile Ser Asp Pro Val Val Ile Thr Leu His
            195                 200                 205

Val Ile Ile Thr Thr Thr Ala Ile Leu Tyr Pro Val Phe Met Ile Leu
210                 215                 220

Arg Phe Asp Ser Val Val Leu Ser Gly Val Ser Leu Met Leu Cys Ala
225                 230                 235                 240

Cys Ile Asn Trp Leu Lys Leu Val Ser Phe Val His Thr Asn Tyr Asp
                245                 250                 255

Met Arg Ser Leu Leu Asn Ser Thr Asp Lys Gly Glu Val Glu Pro Met
            260                 265                 270

Ser Ser Asn Met Asp Tyr Phe Tyr Asp Val Asn Phe Lys Ser Leu Val
        275                 280                 285

Tyr Phe Met Val Ala Pro Thr Leu Cys Tyr Gln Ile Ser Tyr Pro Arg
290                 295                 300

Thr Ala Phe Ile Arg Lys Gly Trp Val Leu Arg Gln Leu Ile Lys Leu
305                 310                 315                 320

Val Ile Phe Thr Gly Phe Met Gly Phe Ile Ile Glu Gln Tyr Ile Asn
                325                 330                 335

Pro Ile Val Lys Asn Ser Arg His Pro Leu Lys Gly Asp Phe Leu Tyr
            340                 345                 350

Ala Ile Glu Arg Val Leu Lys Leu Ser Val Pro Asn Leu Tyr Val Trp
        355                 360                 365

Leu Cys Met Phe Tyr Cys Phe Phe His Leu Trp Leu Asn Ile Leu Ala
370                 375                 380

Glu Leu Leu Cys Phe Gly Asp Arg Glu Phe Tyr Lys Asp Trp Trp Asn
385                 390                 395                 400

Ala Gln Thr Ile Glu Glu Tyr Trp Arg Leu Trp Asn Met Pro Val His
                405                 410                 415

Lys Trp Ile Val Arg His Leu Tyr Phe Pro Cys Leu Arg Asn Gly Ile
            420                 425                 430

Pro Lys Gly Ala Ala Ile Leu Val Ala Phe Phe Met Ser Ala Val Phe
        435                 440                 445

His Glu Leu Cys Ile Ala Val Pro Cys His Ile Phe Lys Phe Trp Ala
450                 455                 460

Phe Ile Gly Ile Met Phe Gln Val Pro Leu Val Leu Leu Thr Asn Tyr
465                 470                 475                 480

Leu Gln His Lys Phe Gln Asn Ser Met Val Gly Asn Met Ile Phe Trp
                485                 490                 495

Cys Phe Phe Ser Ile Phe Gly Gln Pro Met Cys Val Leu Leu Tyr Tyr
            500                 505                 510

His Asp Val Met Asn Gln Lys Gly Lys Ser Lys
        515                 520

<210> SEQ ID NO 37
<211> LENGTH: 532
<212> TYPE: PRT
<213> ORGANISM: Nicotiana tabacum

<400> SEQUENCE: 37

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val

```
                20                  25                  30
Arg Arg Arg Arg Gly Ser Asn Gly Phe Glu Ala Ala Ser Ala Ile Asn
            35                  40                  45

Ser Ser Asp Ala Asn Met Ser Glu Asp Arg Arg Asp Val Cys Gly Ser
 50                  55                  60

Gly Ala Gly Leu Glu Thr Val Asn Glu Arg Ser Lys Ser Val Gly Glu
 65                  70                  75                  80

Ser Ser Asp Val Ile Arg Lys Glu Asp Arg Asn Asp Asn Val Ala
            85                  90                  95

Asn Gly Glu Glu Ser Lys Ser Thr Glu Thr Thr Thr Pro Phe Lys
            100                 105                 110

Phe Ala Tyr Arg Ala Ser Ala Pro Ala His Arg Arg Ile Lys Glu Ser
            115                 120                 125

Pro Leu Ser Ser Asp Ala Ile Phe Lys Gln Ser His Ala Gly Leu Phe
            130                 135                 140

Asn Leu Cys Val Val Val Leu Ile Ala Val Asn Ser Arg Leu Ile Ile
145                 150                 155                 160

Glu Asn Leu Met Lys Tyr Gly Leu Leu Ile Arg Ala Gly Phe Trp Phe
            165                 170                 175

Ser Ser Lys Ser Leu Arg Asp Trp Pro Leu Leu Met Cys Cys Leu Ser
            180                 185                 190

Leu Gln Ile Leu Pro Leu Ala Ala Phe Leu Val Glu Lys Leu Ala Gln
            195                 200                 205

Gln Arg His Leu Thr Glu Arg Ala Val Val Thr Leu His Ile Thr Ile
            210                 215                 220

Thr Thr Ala Ala Ile Leu Tyr Pro Val Leu Val Ile Leu Gly Cys Asp
225                 230                 235                 240

Ser Ala Phe Leu Phe Gly Val Ile Leu Met Leu Val Ala Cys Ile Val
            245                 250                 255

Trp Met Lys Leu Val Ser Tyr Ala His Thr Asn His Asp Met Arg Gln
            260                 265                 270

Leu Ala Lys Ser Thr Asp Lys Asp Glu Thr Ser Asp Gly Asp Phe Ser
            275                 280                 285

Tyr Asp Val Ser Phe Lys Ser Leu Ala Tyr Phe Met Val Ala Pro Thr
            290                 295                 300

Leu Cys Tyr Gln Leu Ser Tyr Pro His Thr Pro Cys Ile Arg Lys Gly
305                 310                 315                 320

Trp Val Ala Arg Gln Phe Ile Lys Leu Val Phe Thr Gly Leu Met
            325                 330                 335

Gly Phe Ile Ile Glu Gln Tyr Ile Asn Pro Ile Val Gln Asn Ser Gln
            340                 345                 350

His Pro Leu Lys Gly Asn Leu Leu Tyr Ala Ile Glu Arg Val Leu Lys
            355                 360                 365

Leu Ser Val Pro Asn Leu Tyr Val Trp Leu Cys Met Phe Tyr Cys Phe
            370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Ile Asp Glu Tyr
            405                 410                 415

Trp Arg Met Trp Asn Met Pro Val His Lys Trp Met Val Arg His Ile
            420                 425                 430

Tyr Phe Pro Cys Leu Arg Asn Gly Ile Pro Lys Gly Val Ala Ile Leu
            435                 440                 445
```

```
Ile Ala Phe Leu Val Ser Ala Val Phe His Glu Leu Cys Ile Ala Val
    450                 455                 460

Pro Cys Arg Leu Phe Lys Trp Trp Ala Phe Met Gly Ile Met Phe Gln
465                 470                 475                 480

Val Pro Leu Val Ile Leu Thr Asn Phe Leu Gln Asn Lys Phe Gln Ser
                485                 490                 495

Ser Met Val Gly Asn Met Met Phe Trp Cys Phe Phe Cys Ile Leu Gly
            500                 505                 510

Gln Pro Met Cys Val Leu Leu Tyr Tyr His Asp Val Met Asn Arg Lys
        515                 520                 525

Ser Ser Ala Arg
    530

<210> SEQ ID NO 38
<211> LENGTH: 534
<212> TYPE: PRT
<213> ORGANISM: Perilla frutescens

<400> SEQUENCE: 38

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Gln Ser
                20                  25                  30

Ala Arg Ser Val Pro Pro Leu Leu Asp Ser Asp Ser Asn Ser Leu Glu
            35                  40                  45

Ala Glu Ser Ala Ile Asn Asp Ser Glu Asn Val Arg Asn Asp Ala Asn
        50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
        115                 120                 125

Ser Ser Asp Ala Ile Phe Lys Gln Ser His Ala Gly Leu Phe Asn Leu
    130                 135                 140

Cys Ile Val Val Leu Val Ala Val Asn Ser Arg Leu Ile Ile Glu Asn
145                 150                 155                 160

Leu Met Lys Tyr Gly Trp Leu Ile Lys Ser Gly Phe Trp Phe Ser Ser
                165                 170                 175

Thr Ser Leu Arg Asp Trp Pro Leu Leu Met Cys Cys Leu Ser Leu Pro
            180                 185                 190

Val Phe Ala Leu Ala Ser Phe Leu Val Glu Lys Leu Val Lys Leu Asn
        195                 200                 205

Tyr Ile Pro Glu Trp Val Ala Val Phe Leu His Val Thr Ile Thr Thr
    210                 215                 220

Val Glu Ile Leu Phe Pro Val Val Ile Leu Arg Cys Asp Ser Ala
225                 230                 235                 240

Val Leu Ser Gly Val Thr Leu Met Leu Phe Ala Cys Thr Val Trp Leu
                245                 250                 255

Lys Leu Val Ser Tyr Ala His Thr Asn Tyr Asp Leu Arg Val Leu Ala
            260                 265                 270

Lys Ser Leu Asp Lys Trp Glu Ala Met Ser Arg Tyr Trp Asn Leu Asp
```

```
              275                 280                 285
Tyr Ala Tyr Asp Val Ser Phe Lys Ser Leu Ala Tyr Phe Met Val Ala
    290                 295                 300
Pro Thr Leu Cys Tyr Gln Pro Ser Tyr Pro Arg Thr Ala Cys Ile Arg
305                 310                 315                 320
Lys Gly Trp Val Val Arg Gln Leu Ile Lys Leu Val Ile Phe Thr Gly
                325                 330                 335
Leu Met Gly Phe Ile Ile Glu Gln Tyr Ile Asn Pro Ile Val Gln Asn
            340                 345                 350
Ser Gln His Pro Leu Lys Gly Asn Leu Leu Tyr Ala Ile Glu Arg Val
        355                 360                 365
Leu Lys Leu Ser Val Pro Asn Leu Tyr Val Trp Leu Cys Met Phe Tyr
    370                 375                 380
Cys Phe Phe His Leu Trp Leu Asn Ile Leu Ala Glu Leu Leu Cys Phe
385                 390                 395                 400
Gly Asp Arg Glu Phe Tyr Lys Asp Trp Trp Asn Ala Arg Thr Val Glu
                405                 410                 415
Glu Tyr Trp Arg Met Trp Asn Met Pro Val His Lys Trp Met Val Arg
            420                 425                 430
His Ile Tyr Cys Pro Cys Leu Gln Asn Gly Ile Pro Lys Ile Val Ala
        435                 440                 445
Val Leu Ile Ala Phe Leu Val Ser Ala Ile Phe His Glu Leu Cys Val
    450                 455                 460
Ala Val Pro Cys Gln Ile Phe Lys Phe Trp Ala Phe Ser Gly Ile Met
465                 470                 475                 480
Leu Gln Val Pro Leu Val Ile Val Thr Asn Tyr Leu Gln Glu Lys Phe
                485                 490                 495
Lys Asn Ser Met Val Gly Asn Met Met Phe Trp Cys Phe Phe Cys Ile
            500                 505                 510
Phe Gly Gln Pro Met Cys Val Leu Leu Tyr Tyr His Asp Leu Met Asn
        515                 520                 525
Arg Lys Ala Ser Ala Arg
    530

<210> SEQ ID NO 39
<211> LENGTH: 512
<212> TYPE: PRT
<213> ORGANISM: Zea mays

<400> SEQUENCE: 39

Met Ala Asp Ser Glu Asp Ala Pro Pro Val His Arg Arg Pro Pro
1               5                   10                  15
Arg Pro Ala Arg Gly Ala Ala Ala Gln Gly Phe Ala Ala Leu
            20                  25                  30
Arg Arg Arg Leu Arg Ser Gly Ala Ala Val Ala Ala Arg Ala Ser Phe
        35                  40                  45
Ala Ala Asp Ser Gly Asp Glu Ser Gly Pro Gly Glu Pro Ser Ser Ser
    50                  55                  60
Arg Arg Arg Asp Asn Ser Gly Gly Ala Ser Ser Ala Ala Gly Gly Arg
65                  70                  75                  80
Ala Gly Ala Gly Asp Phe Ser Ala Phe Thr Phe Arg Ala Ala Ala Pro
                85                  90                  95
Val His Arg Lys Ala Lys Glu Ser Pro Leu Ser Ser Asp Ala Ile Phe
            100                 105                 110
```

-continued

```
Lys Gln Ser His Ala Gly Leu Phe Asn Leu Cys Ile Val Val Leu Val
            115                 120                 125
Ala Val Asn Ser Arg Leu Ile Ile Glu Asn Leu Met Lys Tyr Gly Leu
        130                 135                 140
Leu Ile Arg Ser Gly Phe Trp Phe Asn Ala Thr Ser Leu Arg Asp Trp
145                 150                 155                 160
Pro Leu Leu Met Cys Cys Leu Ser Leu Pro Ile Phe Pro Leu Gly Ala
                165                 170                 175
Phe Ala Val Glu Lys Leu Ala Phe Asn Asn Leu Ile Ser Asp Pro Ala
            180                 185                 190
Thr Thr Cys Phe His Ile Leu Phe Thr Thr Phe Glu Ile Val Tyr Pro
        195                 200                 205
Val Leu Val Ile Leu Lys Cys Asp Ser Ala Val Leu Ser Gly Phe Val
    210                 215                 220
Leu Met Phe Ile Ala Cys Ile Val Trp Leu Lys Leu Val Ser Phe Ala
225                 230                 235                 240
His Thr Asn His Asp Ile Arg Lys Leu Ile Thr Ser Gly Lys Lys Val
                245                 250                 255
Asp Asn Glu Leu Thr Ala Ala Gly Ile Asp Asn Leu Gln Ala Pro Thr
            260                 265                 270
Leu Gly Ser Leu Thr Tyr Phe Met Met Ala Pro Thr Leu Cys Tyr Gln
        275                 280                 285
Pro Ser Tyr Pro Arg Thr Pro Tyr Val Arg Lys Gly Trp Leu Val Arg
    290                 295                 300
Gln Val Ile Leu Tyr Leu Ile Phe Thr Gly Leu Gln Gly Phe Ile Ile
305                 310                 315                 320
Glu Gln Tyr Ile Asn Pro Ile Val Val Asn Ser Gln His Pro Leu Met
                325                 330                 335
Gly Gly Leu Leu Asn Ala Val Glu Thr Val Leu Lys Leu Ser Leu Pro
            340                 345                 350
Asn Val Tyr Leu Trp Leu Cys Met Phe Tyr Cys Leu Phe His Leu Trp
        355                 360                 365
Leu Asn Ile Leu Ala Glu Ile Leu Arg Phe Gly Asp Arg Glu Phe Tyr
    370                 375                 380
Lys Asp Trp Trp Asn Ala Lys Thr Ile Asp Glu Tyr Trp Arg Lys Trp
385                 390                 395                 400
Asn Met Pro Val His Lys Trp Ile Val Arg His Ile Tyr Phe Pro Cys
                405                 410                 415
Met Arg Asn Gly Ile Ser Lys Gly Val Ala Val Phe Ile Ser Phe Phe
            420                 425                 430
Val Ser Ala Val Leu His Glu Leu Cys Val Ala Val Pro Cys His Ile
        435                 440                 445
Leu Lys Phe Trp Ala Phe Leu Gly Ile Met Leu Gln Ile Pro Leu Ile
    450                 455                 460
Ile Leu Thr Ser Tyr Leu Lys Asn Lys Phe Ser Asp Thr Met Val Gly
465                 470                 475                 480
Asn Met Ile Phe Trp Phe Phe Phe Cys Ile Tyr Gly Gln Pro Met Cys
                485                 490                 495
Val Leu Leu Tyr Tyr His Asp Val Met Asn Arg Thr Glu Lys Ala Lys
            500                 505                 510

<210> SEQ ID NO 40
<211> LENGTH: 515
<212> TYPE: PRT
```

<213> ORGANISM: Sorghum bicolor

<400> SEQUENCE: 40

```
Met Ala Asp Thr Asp Ala Pro Pro Pro Ala Val His Arg Arg
1               5                   10                  15

Pro Pro Arg Pro Ala Arg Gly Ala Ala Ala Gln Gly Phe Ala Ala
                20                  25                  30

Lys Leu Arg Arg Arg Leu Ser Ser Gly Ala Ala Ala Ala Arg Ala
                35                  40                  45

Ser Phe Ala Ala Asp Ser Gly Asp Glu Ser Gly Pro Gly Glu Pro Ser
    50                  55                  60

Ser Ser Arg Arg Arg Asp Asn Gly Gly Asp Ala Ser Ala Ala Asp
65              70                  75                  80

Gly Gly Arg Gly Gly Ala Gly Asp Phe Ser Ala Phe Thr Phe Arg Ala
                85                  90                  95

Ala Ala Pro Val His Arg Lys Ala Lys Glu Ser Pro Leu Ser Ser Asp
            100                 105                 110

Ala Ile Phe Lys Gln Ser His Ala Gly Leu Phe Asn Leu Cys Ile Val
        115                 120                 125

Val Leu Val Ala Val Asn Ser Arg Leu Ile Ile Glu Asn Leu Met Lys
130                 135                 140

Tyr Gly Leu Leu Ile Arg Ser Gly Phe Trp Phe Asn Ala Thr Ser Leu
145                 150                 155                 160

Arg Asp Trp Pro Leu Leu Met Cys Cys Leu Ser Leu Pro Val Phe Pro
                165                 170                 175

Leu Gly Ala Phe Ala Val Glu Lys Leu Ala Phe Asn Asn Leu Ile Thr
            180                 185                 190

Asp Ala Ala Ala Thr Cys Phe His Ile Phe Leu Thr Thr Leu Glu Ile
        195                 200                 205

Val Tyr Pro Val Leu Val Ile Leu Lys Cys Asp Ser Ala Val Leu Ser
210                 215                 220

Gly Phe Val Leu Met Phe Ile Ala Cys Ile Val Trp Leu Lys Leu Val
225                 230                 235                 240

Ser Phe Ala His Thr Asn His Asp Ile Arg Lys Leu Ile Thr Ser Gly
                245                 250                 255

Lys Lys Val Asp Asn Glu Leu Thr Val Ala Asp Ile Asp Asn Leu Gln
            260                 265                 270

Ala Pro Thr Leu Gly Ser Leu Thr Tyr Phe Met Met Ala Pro Thr Leu
        275                 280                 285

Cys Tyr Gln Pro Ser Tyr Pro Arg Thr Pro Tyr Val Arg Lys Gly Trp
290                 295                 300

Leu Val Arg Gln Val Ile Leu Tyr Leu Ile Phe Thr Gly Leu Gln Gly
305                 310                 315                 320

Phe Ile Ile Glu Gln Tyr Ile Asn Pro Ile Val Val Asn Ser Gln His
                325                 330                 335

Pro Leu Lys Gly Gly Leu Leu Asn Ala Val Glu Thr Val Leu Lys Leu
            340                 345                 350

Ser Leu Pro Asn Val Tyr Leu Trp Leu Cys Met Phe Tyr Cys Leu Phe
        355                 360                 365

His Leu Trp Leu Asn Ile Leu Ala Glu Ile Leu Arg Phe Gly Asp Arg
370                 375                 380

Glu Phe Tyr Lys Asp Trp Trp Asn Ala Lys Thr Ile Asp Glu Tyr Trp
385                 390                 395                 400
```

```
Arg Lys Trp Asn Met Pro Val His Lys Trp Met Leu Arg His Ile Tyr
                405                 410                 415

Phe Pro Cys Ile Arg Asn Gly Ile Ser Lys Glu Val Ala Ala Phe Ile
            420                 425                 430

Ala Phe Phe Val Ser Ala Val Phe His Glu Leu Cys Val Ala Val Pro
        435                 440                 445

Cys His Ile Leu Lys Phe Trp Ala Phe Leu Gly Ile Met Leu Gln Ile
    450                 455                 460

Pro Leu Ile Ile Leu Thr Ser Tyr Leu Lys Asn Lys Phe Asn Asp Thr
465                 470                 475                 480

Met Val Gly Asn Met Ile Phe Trp Phe Phe Cys Ile Tyr Gly Gln
                485                 490                 495

Pro Met Cys Val Leu Leu Tyr Tyr His Asp Val Met Asn Arg Thr Glu
                500                 505                 510

Lys Thr Lys
        515

<210> SEQ ID NO 41
<211> LENGTH: 538
<212> TYPE: PRT
<213> ORGANISM: Oryza sativa

<400> SEQUENCE: 41

Met Val Gly Ser Asp Gly Asp Gly Asp Gly Gly Gly Gly Glu Ala His
1               5                   10                  15

Ala Pro Ala Ala Pro Ala His His Arg Arg Pro Arg Pro Arg
            20                  25                  30

Gly Gly Ser Gly Ala Ile Val Glu Gly Phe Ala Ala Leu Arg Arg
        35                  40                  45

Arg Ile Arg Ser Gly Ala Ala Ala Ala Arg Ala Ser Phe Gly Gly
    50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Leu Leu Ile Arg Ala Gly Phe
                165                 170                 175

Trp Phe Asn Asp Lys Ser Leu Arg Asp Trp Pro Leu Leu Met Cys Cys
            180                 185                 190

Leu Ser Leu Pro Ala Phe Pro Leu Gly Ala Phe Ala Val Glu Lys Leu
        195                 200                 205

Ala Phe Asn Asn Val Ile Thr Asp Ala Val Ala Thr Cys Leu His Ile
    210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
                245                 250                 255
```

```
Ile Val Trp Leu Lys Leu Val Ser Phe Ala His Thr Asn His Asp Ile
            260                 265                 270

Arg Gln Leu Thr Met Gly Gly Lys Val Asp Asn Glu Leu Ser Thr
        275                 280                 285

Val Asp Met Asp Asn Leu Gln Pro Pro Thr Leu Gly Asn Leu Ile Tyr
290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
                325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Lys Gly Gly Leu Leu Asn Ala
        355                 360                 365

Val Glu Thr Val Leu Lys Leu Ser Leu Pro Asn Val Tyr Leu Trp Leu
370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
                405                 410                 415

Lys Thr Ile Asp Glu Tyr Trp Arg Lys Trp Asn Met Pro Val His Lys
            420                 425                 430

Trp Val Arg His Ile Tyr Phe Pro Cys Met Arg Asn Gly Ile Ser
        435                 440                 445

Lys Glu Val Ala Val Leu Ile Ser Phe Leu Val Ser Ala Val Leu His
    450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
                485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
        515                 520                 525

Asp Val Met Asn Arg Ile Glu Lys Ala Arg
    530                 535

<210> SEQ ID NO 42
<211> LENGTH: 477
<212> TYPE: PRT
<213> ORGANISM: Oryza sativa

<400> SEQUENCE: 42

Met Ala Pro Pro Pro Ser Leu Ala Pro Asp Arg Gly Gly Gly Glu Pro
1               5                   10                  15

Asp Asp Ala Leu Arg Leu Arg Ala Arg Ala Ala Ala Ala Gly Asp
            20                  25                  30

Ala Pro Ala Pro Gln Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
```

```
                85                  90                  95
Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
            115                 120                 125

Cys Leu Thr Leu Pro Thr Phe Pro Leu Ala Ala Leu Met Val Glu Lys
            130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Ile Leu
                165                 170                 175

Lys Cys Asp Ser Ala Val Leu Ser Gly Phe Val Leu Met Phe Leu Ala
                180                 185                 190

Ser Ile Ile Trp Leu Lys Leu Val Ser Phe Ala His Thr Asn Tyr Asp
                195                 200                 205

Ile Arg Met Leu Ser Lys Ser Ile Glu Lys Gly Val Thr His Asp Ile
            210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
                260                 265                 270

Leu Val Phe Thr Gly Leu Met Gly Phe Ile Ile Glu Gln Tyr Ile Asn
                275                 280                 285

Pro Ile Val Lys Asn Ser Lys His Pro Leu Lys Gly Asn Phe Leu Asn
290                 295                 300

Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
            355                 360                 365

Lys Trp Val Ile Arg His Ile Tyr Phe Pro Cys Ile Arg Asn Gly Phe
            370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
            420                 425                 430

Leu Gln Asp Lys Phe Asn Asn Thr Met Val Gly Asn Met Ile Phe Trp
            435                 440                 445

Phe Phe Phe Ser Ile Leu Gly Gln Pro Met Cys Val Leu Leu Tyr Tyr
            450                 455                 460

His Asp Val Met Asn Arg Gln Gln Ala Gln Thr Asn Arg
465                 470                 475

<210> SEQ ID NO 43
<211> LENGTH: 529
<212> TYPE: PRT
<213> ORGANISM: Sorghum bicolor
```

<400> SEQUENCE: 43

```
Met Ala Pro Pro Pro Ser Met Ala Ala Ser Asp Arg Ala Val Pro
1               5                   10                  15

Gly Ala Asp Ala Thr Glu Ala Ser Ser Leu Arg Leu Arg Arg Ala Pro
            20                  25                  30

Ser Ala Asp Ala Gly Asp Leu Ala Asp Asp Ser Ser Gly Asp Arg Arg
        35                  40                  45

Glu Asn Gly Glu Pro Gln Pro Gln Glu Gln Gln Gln His Glu
    50                  55                  60

Met Leu Tyr Tyr Arg Ala Ser Ala Pro Ala His Arg Arg Val Lys Glu
65              70                  75                  80

Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
            100                 105                 110

Ile Glu Asn Leu Met Lys Tyr Gly Leu Leu Ile Arg Ala Gly Phe Trp
        115                 120                 125

Phe Ser Ala Arg Ser Leu Gly Asp Trp Pro Leu Leu Met Cys Cys Leu
130                 135                 140

Thr Leu Pro Val Phe Pro Leu Val Ala Leu Met Ala Glu Lys Leu Ile
145                 150                 155                 160

Arg Arg Lys Leu Ile Gly Glu His Val Val Ile Leu His Ile Ile
            165                 170                 175

Ile Thr Thr Ser Val Ile Val Tyr Pro Val Val Val Thr Leu Lys Cys
            180                 185                 190

Asp Ser Ala Val Leu Ser Gly Phe Leu Leu Met Phe Leu Ala Ser Ile
            195                 200                 205

Met Trp Met Lys Leu Val Ser Tyr Ala His Thr Asn Tyr Asp Ile Arg
    210                 215                 220

Ala Leu Ser Lys Ser Thr Glu Lys Gly Ala Ala Tyr Gly Asn Tyr Val
225                 230                 235                 240

Asp Pro Glu Ser Met Lys Asp Pro Thr Phe Lys Ser Leu Val Tyr Phe
                245                 250                 255

Met Leu Ala Pro Thr Leu Cys Tyr Gln Pro Thr Tyr Pro Arg Thr Thr
            260                 265                 270

Cys Ile Arg Lys Gly Trp Val Thr Arg Gln Leu Ile Lys Cys Leu Val
            275                 280                 285

Phe Thr Gly Leu Met Gly Phe Ile Ile Glu Gln Tyr Ile Asn Pro Ile
    290                 295                 300

Val Lys Asn Ser Lys His Pro Leu Lys Gly Asn Phe Leu Asn Ala Ile
305                 310                 315                 320

Glu Arg Val Leu Lys Leu Ser Val Pro Thr Leu Tyr Val Trp Leu Cys
            325                 330                 335

Met Phe Tyr Cys Phe Phe His Leu Trp Leu Asn Ile Leu Ala Glu Leu
            340                 345                 350

Leu Cys Phe Gly Asp Arg Glu Phe Tyr Lys Asp Trp Asn Ala Lys
    355                 360                 365

Thr Val Glu Glu Tyr Trp Arg Met Trp Asn Met Pro His Lys Trp
    370                 375                 380

Ile Ile Arg His Ile Tyr Phe Pro Cys Ile Arg Lys Gly Phe Ser Arg
385                 390                 395                 400

Gly Val Ala Ile Leu Val Ser Phe Leu Val Ser Ala Val Phe His Glu
```

```
                405                 410                 415
Ile Cys Ile Ala Val Pro Cys His Ile Phe Lys Phe Trp Ala Phe Ser
                420                 425                 430

Gly Ile Met Phe Gln Ile Pro Leu Val Phe Leu Thr Arg Tyr Leu Gln
            435                 440                 445

Ala Thr Phe Lys Asn Ile Met Val Gly Asn Met Ile Phe Trp Phe Phe
450                 455                 460

Phe Ser Ile Val Gly Gln Pro Met Cys Val Leu Leu Tyr Tyr His Asp
465                 470                 475                 480

Val Met Asn Arg Gln Ala Gln Gln Val Asp Asn Ser Ala Glu Thr Cys
                485                 490                 495

Thr Leu Arg Gln Val Ile Arg Ser Arg Leu Glu Arg Ser Arg Lys
                500                 505                 510

Gln Gln Gln Gln Gln Ala Ser Ser Pro Pro Leu Pro Leu Leu Pro Ala
                515                 520                 525

Ser

<210> SEQ ID NO 44
<211> LENGTH: 494
<212> TYPE: PRT
<213> ORGANISM: Zea mays

<400> SEQUENCE: 44

Met Ala Pro Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
            20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Gln Glu Gln
50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
            115                 120                 125

Ala Gly Phe Trp Phe Ser Ala Arg Ser Leu Gly Asp Trp Pro Leu Leu
        130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
        210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
```

```
            245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
            275                 280                 285

Lys Cys Val Val Phe Thr Gly Leu Met Gly Phe Ile Ile Glu Gln Tyr
            290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
                340                 345                 350

Val Ala Glu Leu Leu Cys Phe Gly Asp Arg Glu Phe Tyr Lys Asp Trp
                355                 360                 365

Trp Asn Ala Lys Thr Val Glu Glu Tyr Trp Arg Met Trp Asn Met Pro
            370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
                435                 440                 445

Arg Tyr Leu His Ala Thr Phe Lys His Val Met Val Gly Asn Met Ile
            450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 45
<211> LENGTH: 447
<212> TYPE: PRT
<213> ORGANISM: Physcomitrella patens

<400> SEQUENCE: 45

Met Pro Val Lys Ser Ser Asn Leu Ala Gly Glu Arg Ala Ala Thr Ser
1               5                   10                  15

His Ile Asn Ala Asn Thr Lys Phe Asp Leu Arg Gly Cys Thr Pro Ala
                20                  25                  30

His Arg Val Arg Arg Glu Ser Pro Leu Ser Ser Asp Ala Ile Phe His
            35                  40                  45

Gln Ser His Ala Gly Leu Phe Asn Leu Cys Ile Val Val Leu Ile Ala
        50                  55                  60

Val Asn Ser Arg Leu Ile Ile Glu Asn Leu Met Lys Tyr Gly Leu Leu
65                  70                  75                  80

Ile Arg Thr Gly Phe Trp Phe Ser Ser Lys Ser Ala Arg Asp Trp Pro
                85                  90                  95

Leu Leu Met Cys Gly Leu Ser Leu Pro Thr Phe Pro Phe Ala Ala Leu
            100                 105                 110

Leu Val Glu Lys Leu Cys Trp Lys Asn Glu Asn Gly Lys Trp Leu Ile
        115                 120                 125
```

```
Phe Val Leu His Leu Ile Ile Ser Thr Val Gly Ile Leu Tyr Pro Gly
            130                 135                 140

Tyr Val Ile His Arg Val Gln Ser Ala Leu Leu Pro Gly Leu Val Leu
145                 150                 155                 160

Ile Leu Ile Ala Val Thr Gly Trp Met Lys Leu Ile Ser Tyr Ala His
                165                 170                 175

Val Asn Lys Asp Met Arg Glu Leu Leu Arg Ala Lys Glu Lys Leu Pro
            180                 185                 190

Glu Ala Pro Gln Tyr Ala Asp Lys Ile Glu Val Pro Asp His Leu Thr
            195                 200                 205

Ile Gln Asn Ile Ala Tyr Phe Met Leu Ala Pro Thr Leu Cys Tyr Gln
210                 215                 220

Leu Ser Tyr Pro Arg Ser Asp Thr Ile Arg Lys Ser Trp Val Leu Arg
225                 230                 235                 240

Gln Ala Gly Lys Leu Val Val Phe Leu Gly Leu Gly Phe Ile Ile
                245                 250                 255

Glu Gln Tyr Ile Asn Pro Thr Val Lys Asn Ser Gln His Pro Leu Arg
                260                 265                 270

Gly Asn Tyr Leu Gln Ala Leu Glu Arg Val Leu Lys Leu Ser Leu Pro
            275                 280                 285

Val Leu Tyr Val Trp Leu Cys Leu Phe Tyr Cys Leu Phe His Leu Trp
290                 295                 300

Leu Asn Ile Val Ala Glu Leu Leu Arg Phe Gly Asp Arg Glu Phe Tyr
305                 310                 315                 320

Lys Asp Trp Trp Asn Ala Gln Thr Val Glu Glu Tyr Trp Arg Met Trp
                325                 330                 335

Asn Met Pro Val His Lys Trp Met Val Arg His Ile Tyr Phe Pro Ser
            340                 345                 350

Ile Arg Ala Gly Leu Ser Lys Lys Ala Ala Val Leu Leu Val Phe Ala
            355                 360                 365

Ile Ser Ala Leu Phe His Glu Val Ile Ile Gly Val Pro Cys His Met
            370                 375                 380

Leu Arg Cys Trp Ala Phe Leu Gly Ile Met Met Gln Val Pro Leu Val
385                 390                 395                 400

Tyr Leu Thr Asn Val Ile Lys Glu Arg Tyr His Ser Ser Met Val Gly
                405                 410                 415

Asn Met Val Phe Trp Phe Phe Cys Ile Val Gly Gln Pro Met Cys
            420                 425                 430

Leu Leu Leu Tyr Tyr His Asp Val Phe Asn Asn Phe Pro Ser Thr
            435                 440                 445

<210> SEQ ID NO 46
<211> LENGTH: 425
<212> TYPE: PRT
<213> ORGANISM: Selaginella moellendorffii

<400> SEQUENCE: 46

Met Arg Pro Ser Leu Pro Ala His Arg Arg Ser Lys Glu Ser Pro Leu
1               5                   10                  15

Ser Ser Asp Ala Ile Phe Thr Gln Ser His Ala Gly Leu Phe Asn Leu
            20                  25                  30

Cys Ile Val Val Leu Val Ala Val Asn Ser Arg Leu Ile Ile Glu Asn
            35                  40                  45

Leu Met Lys Tyr Gly Leu Leu Ile Gln Ala Glu Val Leu Phe Ser Ser
50                  55                  60
```

Lys Ser Leu Lys Asp Trp Pro Leu Leu Met Cys Gly Leu Ser Leu Leu
65                  70                  75                  80

Ile Phe Pro Leu Ala Ala Tyr Val Ile Glu Lys Ile Lys Ala Arg Arg
                85                  90                  95

Pro Ala Thr Ala Val Ala Pro Leu His Leu Ile Asn Leu Ala Ala Ala
            100                 105                 110

Leu Leu Tyr Pro Ile Tyr Val Ile Glu Met Phe Gln Ser Asp Leu Leu
            115                 120                 125

Ser Gly Leu Val Leu Met Leu Ile Ala Val Thr Gly Trp Leu Lys Leu
        130                 135                 140

Val Ser Tyr Ala His Thr Asn Ala Asp Ile Arg Ala Val Lys Lys Asp
145                 150                 155                 160

Gly Gly Lys Ile Glu Leu Pro Ala Glu Ala Pro Ala Ile Asp Tyr Pro
                165                 170                 175

Asp Asn Ile Ser Leu Lys Asn Ile Ala Tyr Phe Met Ala Ala Pro Thr
            180                 185                 190

Leu Cys Tyr Gln Leu Ser Tyr Pro Arg Ser Pro Arg Ile Arg Thr Gly
        195                 200                 205

Trp Val Leu Arg Gln Leu Gly Lys Trp Ile Val Phe Asn Gly Phe Met
210                 215                 220

Gly Phe Ile Ile Gly Gln Tyr Met Asn Pro Ile Ile Arg Asn Ser Thr
225                 230                 235                 240

His Pro Leu Lys Gly Asn Tyr Leu Tyr Ala Ile Glu Arg Val Leu Lys
                245                 250                 255

Leu Ser Ile Pro Thr Leu Tyr Val Trp Leu Gly Phe Phe Tyr Cys Phe
            260                 265                 270

Phe His Leu Trp Leu Asn Ile Val Ala Glu Ile Leu Cys Phe Gly Asp
        275                 280                 285

Arg Glu Phe Tyr Lys Asp Trp Trp Asn Ala Lys Ser Val Asp Glu Tyr
    290                 295                 300

Trp Arg Leu Trp Asn Met Pro Val His Arg Trp Leu Val Arg His Val
305                 310                 315                 320

Tyr Phe Pro Cys Leu Arg Leu Gly Leu His Lys Gln Phe Ala Ile Leu
                325                 330                 335

Val Val Phe Val Ile Ser Gly Ile Phe His Glu Ile Cys Ile Ala Val
            340                 345                 350

Pro Cys His Met Leu Arg Gly Trp Ala Phe Leu Gly Ile Met Phe Gln
        355                 360                 365

Val Pro Leu Val Leu Val Thr Asn Val Leu Gln Arg Lys Phe Gln Ser
    370                 375                 380

Ser Met Val Gly Asn Met Ile Phe Trp Phe Phe Phe Cys Ile Val Gly
385                 390                 395                 400

Gln Pro Met Cys Val Leu Leu Tyr Tyr His Asp Val Val Asn Arg Gln
                405                 410                 415

Gln Leu Gln Leu Ala Gly Arg Ser Lys
            420                 425

<210> SEQ ID NO 47
<211> LENGTH: 507
<212> TYPE: PRT
<213> ORGANISM: Euonymus alatus

<400> SEQUENCE: 47

Met Ala Ala Asn Leu Asn Glu Ala Ser Asp Leu Asn Phe Ser Leu Arg

```
  1               5                   10                  15
Arg Arg Thr Gly Gly Ile Ser Ser Thr Thr Val Pro Asp Ser Ser Ser
                20                  25                  30

Glu Thr Ser Ser Ser Glu Ala Asp Tyr Leu Asp Gly Lys Gly Ala
                35                  40                  45

Ala Asp Val Lys Asp Arg Gly Asp Gly Ala Val Glu Phe Gln Asn Ser
 50                  55                  60

Met Lys Asn Val Glu Arg Ile Glu Lys His Glu Ser Arg Val Gly Leu
 65                  70                  75                  80

Asp Ser Arg Phe Thr Tyr Arg Pro Ser Val Pro Ala His Arg Thr Ile
                85                  90                  95

Lys Glu Ser Pro Leu Ser Ser Asp Ala Ile Phe Lys Gln Ser His Ala
                100                 105                 110

Gly Leu Phe Asn Leu Cys Ile Val Val Leu Val Ala Val Asn Ser Arg
                115                 120                 125

Leu Ile Ile Glu Asn Leu Met Lys Tyr Gly Trp Leu Ile Arg Ser Gly
130                 135                 140

Phe Trp Phe Ser Ser Arg Ser Leu Arg Asp Trp Pro Leu Phe Met Cys
145                 150                 155                 160

Cys Leu Thr Leu Pro Val Phe Pro Leu Ala Ala Phe Leu Phe Glu Lys
                165                 170                 175

Leu Ala Gln Lys Asn Leu Ile Ser Glu Pro Val Val Leu Leu His
                180                 185                 190

Ile Val Asn Thr Thr Ala Ala Val Leu Tyr Pro Val Leu Val Ile Leu
                195                 200                 205

Arg Cys Asp Ser Ala Phe Met Ser Gly Val Thr Leu Met Leu Phe Ala
                210                 215                 220

Cys Ile Val Trp Leu Lys Leu Val Ser Tyr Ala His Thr Asn Tyr Asp
225                 230                 235                 240

Met Arg Ala Leu Thr Lys Ser Val Glu Lys Gly Asp Thr Pro Leu Ser
                245                 250                 255

Ser Gln Asn Met Asp Tyr Ser Phe Asp Val Asn Ile Lys Ser Leu Ala
                260                 265                 270

Tyr Phe Met Val Ala Pro Thr Leu Cys Tyr Gln Ile Ser Tyr Pro Arg
                275                 280                 285

Thr Pro Tyr Val Arg Lys Gly Trp Val Val Arg Gln Phe Val Lys Leu
                290                 295                 300

Ile Ile Phe Thr Gly Leu Met Gly Phe Ile Ile Glu Gln Tyr Ile Asn
305                 310                 315                 320

Pro Ile Val Gln Asn Ser Gln His Pro Leu Lys Gly Asn Phe Leu Tyr
                325                 330                 335

Ala Ile Glu Arg Val Leu Lys Leu Ser Val Pro Asn Leu Tyr Val Trp
                340                 345                 350

Leu Cys Met Phe Tyr Cys Leu Phe His Leu Trp Leu Asn Ile Leu Ala
                355                 360                 365

Glu Leu Leu Cys Phe Gly Asp Arg Glu Phe Tyr Lys Asp Trp Trp Asn
                370                 375                 380

Ala Lys Thr Val Glu Glu Tyr Trp Arg Met Trp Asn Met Pro Val His
385                 390                 395                 400

Lys Trp Met Val Arg His Ile Tyr Phe Pro Cys Leu Arg Asn Gly Ile
                405                 410                 415

Pro Lys Gly Val Ala Phe Val Ile Ser Phe Leu Val Ser Ala Val Phe
                420                 425                 430
```

His Glu Leu Cys Ile Ala Val Pro Cys His Ile Phe Lys Leu Trp Ala
            435                 440                 445

Phe Phe Gly Ile Met Leu Gln Val Pro Leu Val Leu Ile Thr Ser Tyr
450                 455                 460

Leu Gln Asn Lys Phe Arg Ser Ser Met Val Gly Asn Met Met Phe Trp
465                 470                 475                 480

Phe Ser Phe Cys Ile Phe Gly Gln Pro Met Cys Leu Leu Leu Tyr Tyr
            485                 490                 495

His Asp Leu Met Asn Arg Asn Gly Lys Met Glu
            500                 505

<210> SEQ ID NO 48
<211> LENGTH: 518
<212> TYPE: PRT
<213> ORGANISM: Vitis vinifera

<400> SEQUENCE: 48

Met Ala Ile Cys Asn Ser Pro Val Ser Val Thr Thr Ser Ser Ser Ser
1               5                   10                  15

Ser His Ala Asp Ser Asp Leu Asp Phe Ser Ile Arg Lys Arg Phe Gly
            20                  25                  30

Gly Lys Gly Lys Ala Val Ala Asp Ser Ser Leu Glu Thr Glu Thr Glu
        35                  40                  45

Ala Ala Ala Ala Val Leu Glu Ala Glu Lys Ser Val Gly Glu Val
    50                  55                  60

Gly Ser Gly Gly Asp Arg Gly Glu Ser Gly Ser Gln Val Val Arg Asn
65                  70                  75                  80

Gly Glu Asn Gly Val Ala Glu Val Ala Ala Lys Phe Ala Tyr Arg Pro
                85                  90                  95

Cys Ala Pro Ala His Arg Lys Val Lys Glu Ser Pro Leu Ser Ser Asp
            100                 105                 110

Ala Ile Phe Arg Gln Ser His Ala Gly Leu Phe Asn Leu Cys Ile Val
        115                 120                 125

Val Leu Val Ala Val Asn Ser Arg Leu Ile Ile Glu Asn Leu Met Lys
130                 135                 140

Tyr Gly Trp Leu Ile Arg Ala Gly Phe Trp Phe Ser Ser Lys Ser Leu
145                 150                 155                 160

Arg Asp Trp Pro Leu Phe Met Cys Cys Leu Thr Leu Pro Ile Phe Pro
                165                 170                 175

Leu Ala Ala Phe Val Val Glu Lys Leu Ala Gln Gln Lys Tyr Ile Ser
            180                 185                 190

Glu Gln Val Val Val Ser Leu His Ile Ile Ile Thr Thr Ala Ala Val
        195                 200                 205

Leu Phe Pro Val Leu Val Ile Leu Arg Cys Asp Ser Ala Val Leu Ser
210                 215                 220

Gly Val Thr Leu Met Leu Phe Ala Cys Ile Val Trp Leu Lys Leu Val
225                 230                 235                 240

Ser Phe Ala His Thr Asn Tyr Asp Met Arg Ala Val Ala Lys Leu Ile
                245                 250                 255

Asp Lys Gly Asp Asp Leu Ser Thr Ser Leu Asn Met Asp Tyr Pro Tyr
            260                 265                 270

Asp Val Asn Phe Lys Ser Leu Ala Tyr Phe Met Val Ala Pro Thr Leu
        275                 280                 285

Cys Tyr Gln Pro Ser Tyr Pro Arg Ser Thr Cys Ile Arg Lys Gly Trp

```
        290                 295                 300
Val Phe Arg Gln Phe Val Lys Leu Ala Ile Phe Thr Gly Val Met Gly
305                 310                 315                 320

Phe Ile Ile Glu Gln Tyr Ile Asn Pro Ile Val Gln Asn Ser Gln His
                325                 330                 335

Pro Leu Lys Gly Asn Phe Phe Tyr Ala Leu Glu Arg Ile Leu Lys Leu
            340                 345                 350

Ser Val Pro Asn Leu Tyr Val Trp Leu Cys Met Phe Tyr Cys Phe Phe
        355                 360                 365

His Leu Trp Leu Asn Ile Leu Ala Glu Leu Leu Arg Phe Gly Asp Arg
    370                 375                 380

Glu Phe Tyr Lys Asp Trp Trp Asn Ala Lys Thr Val Glu Glu Tyr Trp
385                 390                 395                 400

Arg Met Trp Asn Met Pro Val His Lys Trp Met Val Arg His Leu Tyr
                405                 410                 415

Phe Pro Cys Leu Arg Asn Gly Ile Ser Lys Gly Val Ser Val Val Ile
            420                 425                 430

Ala Phe Ala Ile Ser Ala Ile Phe His Glu Leu Cys Ile Ala Val Pro
        435                 440                 445

Cys His Met Phe Lys Leu Trp Ala Phe Ile Gly Ile Met Phe Gln Val
    450                 455                 460

Pro Leu Val Leu Val Thr Asn Tyr Leu Gln Asn Lys Phe Arg Asn Ser
465                 470                 475                 480

Met Val Gly Asn Met Ile Phe Trp Leu Phe Phe Ser Ile Leu Gly Gln
                485                 490                 495

Pro Met Cys Val Leu Leu Tyr Tyr His Asp Leu Met Asn Arg Lys Glu
            500                 505                 510

Thr Thr Glu Ser Ser Leu
            515

<210> SEQ ID NO 49
<211> LENGTH: 498
<212> TYPE: PRT
<213> ORGANISM: Glycine max

<400> SEQUENCE: 49

Met Ala Ile Ser Asp Glu Pro Glu Thr Val Ala Thr Ala Leu Asn His
1               5                   10                  15

Ser Ser Leu Arg Arg Pro Thr Ala Ala Gly Leu Phe Asn Ser Pro
            20                  25                  30

Glu Thr Thr Thr Asp Ser Ser Gly Asp Asp Leu Ala Lys Asp Ser Gly
                35                  40                  45

Ser Asp Asp Ser Ile Ser Ser Asp Ala Ala Asn Ser Gln Pro Gln Gln
        50                  55                  60

Lys Gln Asp Thr Asp Phe Ser Val Leu Lys Phe Ala Tyr Arg Pro Ser
65                  70                  75                  80

Val Pro Ala His Arg Lys Val Lys Glu Ser Pro Leu Ser Ser Asp Thr
                85                  90                  95

Ile Phe Arg Gln Ser His Ala Gly Leu Phe Asn Leu Cys Ile Val Val
            100                 105                 110

Leu Val Ala Val Asn Ser Arg Leu Ile Ile Glu Asn Leu Met Lys Tyr
        115                 120                 125

Gly Trp Leu Ile Lys Ser Gly Phe Trp Phe Ser Ser Lys Ser Leu Arg
    130                 135                 140
```

```
Asp Trp Pro Leu Phe Met Cys Cys Leu Ser Leu Val Val Phe Pro Phe
145                 150                 155                 160

Ala Ala Phe Ile Val Glu Lys Leu Ala Gln Gln Lys Cys Ile Pro Glu
            165                 170                 175

Pro Val Val Val Leu His Ile Ile Ile Thr Ser Ala Ser Leu Phe
        180                 185                 190

Tyr Pro Val Leu Val Ile Leu Arg Cys Asp Ser Ala Phe Leu Ser Gly
        195                 200                 205

Val Thr Leu Met Leu Phe Ala Cys Val Val Trp Leu Lys Leu Val Ser
210                 215                 220

Tyr Ala His Thr Asn Tyr Asp Met Arg Ala Leu Thr Lys Ser Val Glu
225                 230                 235                 240

Lys Gly Glu Ala Leu Pro Asp Thr Leu Asn Met Asp Tyr Pro Tyr Asn
            245                 250                 255

Val Ser Phe Lys Ser Leu Ala Tyr Phe Leu Val Ala Pro Thr Leu Cys
            260                 265                 270

Tyr Gln Pro Ser Tyr Pro Arg Thr Pro Tyr Ile Arg Lys Gly Trp Leu
            275                 280                 285

Phe Arg Gln Leu Val Lys Leu Ile Ile Phe Thr Gly Val Met Gly Phe
290                 295                 300

Ile Ile Glu Gln Tyr Ile Asn Pro Ile Val Gln Asn Ser Gln His Pro
305                 310                 315                 320

Leu Lys Gly Asn Leu Leu Tyr Ala Ile Glu Arg Val Leu Lys Leu Ser
            325                 330                 335

Val Pro Asn Leu Tyr Val Trp Leu Cys Met Phe Tyr Cys Phe Phe His
            340                 345                 350

Leu Trp Leu Asn Ile Leu Ala Glu Leu Leu Arg Phe Gly Asp Arg Glu
            355                 360                 365

Phe Tyr Gln Asp Trp Trp Asn Ala Lys Thr Val Glu Asp Tyr Trp Arg
            370                 375                 380

Met Trp Asn Met Pro Val His Lys Trp Met Ile Arg His Leu Tyr Phe
385                 390                 395                 400

Pro Cys Leu Arg His Gly Ile Pro Lys Ala Val Ala Leu Leu Ile Ala
            405                 410                 415

Phe Leu Val Ser Ala Leu Phe His Glu Leu Cys Ile Ala Val Pro Cys
            420                 425                 430

His Ile Phe Lys Leu Trp Ala Phe Gly Gly Ile Met Phe Gln Val Pro
            435                 440                 445

Leu Val Phe Ile Thr Asn Tyr Leu Gln Asn Lys Phe Arg Asn Ser Met
            450                 455                 460

Val Gly Asn Met Ile Phe Trp Phe Ile Phe Ser Ile Leu Gly Gln Pro
465                 470                 475                 480

Met Cys Val Leu Leu Tyr Tyr His Asp Leu Met Asn Arg Lys Gly Lys
                485                 490                 495

Leu Asp

<210> SEQ ID NO 50
<211> LENGTH: 504
<212> TYPE: PRT
<213> ORGANISM: Glycine max

<400> SEQUENCE: 50

Met Ala Ile Ser Asp Glu Pro Glu Ser Val Ala Thr Ala Leu Asn His
1               5                   10                  15
```

Ser Ser Leu Arg Arg Pro Ser Ala Thr Ser Thr Ala Gly Leu Phe
            20                  25                  30

Asn Ser Pro Glu Thr Thr Thr Asp Ser Ser Gly Asp Asp Leu Ala Lys
        35                  40                  45

Asp Ser Gly Ser Asp Asp Ser Ile Asn Ser Asp Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
            100                 105                 110

Asn Leu Cys Ile Val Val Leu Val Ala Val Asn Ser Arg Leu Ile Ile
        115                 120                 125

Glu Asn Leu Met Lys Tyr Gly Trp Leu Ile Lys Ser Gly Phe Trp Phe
    130                 135                 140

Ser Ser Lys Ser Leu Arg Asp Trp Pro Leu Phe Met Cys Cys Leu Ser
145                 150                 155                 160

Leu Val Val Phe Pro Phe Ala Ala Phe Ile Val Glu Lys Leu Ala Gln
                165                 170                 175

Arg Lys Cys Ile Pro Glu Pro Val Val Val Leu His Ile Ile Ile
            180                 185                 190

Thr Ser Thr Ser Leu Phe Tyr Pro Val Leu Val Ile Leu Arg Cys Asp
        195                 200                 205

Ser Ala Phe Val Ser Gly Val Thr Leu Met Leu Phe Ser Cys Val Val
    210                 215                 220

Trp Leu Lys Leu Val Ser Tyr Ala His Thr Asn Tyr Asp Met Arg Ala
225                 230                 235                 240

Leu Thr Lys Leu Val Glu Lys Gly Glu Ala Leu Leu Asp Thr Leu Asn
                245                 250                 255

Met Asp Tyr Pro Tyr Asn Val Ser Phe Lys Ser Leu Ala Tyr Phe Leu
            260                 265                 270

Val Ala Pro Thr Leu Cys Tyr Gln Pro Ser Tyr Pro Arg Thr Pro Tyr
        275                 280                 285

Ile Arg Lys Gly Trp Leu Phe Arg Gln Leu Val Lys Leu Ile Ile Phe
    290                 295                 300

Thr Gly Val Met Gly Phe Ile Ile Glu Gln Tyr Ile Asn Pro Ile Val
305                 310                 315                 320

Gln Asn Ser Gln His Pro Leu Lys Gly Asn Leu Leu Tyr Ala Thr Glu
                325                 330                 335

Arg Val Leu Lys Leu Ser Val Pro Asn Leu Tyr Val Trp Leu Cys Met
            340                 345                 350

Phe Tyr Cys Phe Phe His Leu Trp Leu Asn Ile Leu Ala Glu Leu Leu
        355                 360                 365

Arg Phe Gly Asp Arg Glu Phe Tyr Lys Asp Trp Asn Ala Lys Thr
    370                 375                 380

Val Glu Asp Tyr Trp Arg Met Trp Asn Met Pro Val His Lys Trp Met
385                 390                 395                 400

Ile Arg His Leu Tyr Tyr Pro Cys Leu Arg His Gly Leu Pro Lys Ala
                405                 410                 415

Ala Ala Leu Leu Ile Ala Phe Leu Val Ser Ala Leu Phe His Glu Leu
            420                 425                 430

Cys Ile Ala Val Pro Cys His Ile Phe Lys Leu Trp Ala Phe Gly Gly

-continued

```
            435                 440                 445
Ile Met Phe Gln Val Pro Leu Val Leu Ile Thr Asn Tyr Leu Gln Asn
        450                 455                 460

Lys Phe Arg Asn Ser Met Val Gly Asn Met Ile Phe Trp Phe Ile Phe
465                 470                 475                 480

Ser Ile Leu Gly Gln Pro Met Cys Val Leu Leu Tyr Tyr His Asp Leu
                485                 490                 495

Met Asn Arg Lys Gly Lys Leu Asp
                500

<210> SEQ ID NO 51
<211> LENGTH: 511
<212> TYPE: PRT
<213> ORGANISM: Lotus japonicus

<400> SEQUENCE: 51

Met Ala Ile Ser Glu Asp Ser Glu Ser Leu Phe Ala Ala Ala Ala Ala
1               5                   10                  15

Ser Ser Val Ile Gln Ser Gly Ser Ser Val Arg Arg Pro Ser Ala
                20                  25                  30

Ile Ser Ala Val Ala Thr Val Glu Asp Glu Ser Ser Glu Glu Pro
            35                  40                  45

Val Pro Val Arg Asp Ser Gly Ser Asp Val Asp Ser Val Ser Ser
50                  55                  60

Glu Gln His Val Ser Pro Ala Thr Ala Asn Arg Glu Lys Asn Gln Val
65                  70                  75                  80

His Asp Ile Ser Ala Thr Lys Phe Ala Tyr Arg Pro Ser Ala Pro Ala
                85                  90                  95

His Arg Arg Val Lys Glu Ser Pro Leu Ser Ser Asp Asn Ile Phe Arg
            100                 105                 110

His His Ala Gly Leu Phe Asn Leu Cys Ile Val Val Leu Val Ala Val
        115                 120                 125

Asn Ser Arg Leu Ile Ile Glu Asn Leu Met Lys Tyr Gly Trp Leu Ile
130                 135                 140

Arg Thr Gly Phe Trp Phe Ser Ser Lys Ser Leu Arg Asp Trp Pro Leu
145                 150                 155                 160

Phe Met Cys Cys Leu Ser Leu Ala Ile Phe Pro Phe Ala Ala Phe Val
                165                 170                 175

Val Glu Lys Leu Val Gln Gln Lys Cys Ile Ser Glu Pro Val Val Val
            180                 185                 190

Leu His Ile Phe Ile Ser Thr Ala Val Val Tyr Pro Val Leu Val
        195                 200                 205

Ile Leu Arg Thr Asp Ser Ala Phe Pro Ser Gly Val Thr Leu Met Leu
    210                 215                 220

Phe Ala Cys Ile Val Trp Leu Lys Leu Val Ser Tyr Ala His Thr Asn
225                 230                 235                 240

Tyr Asp Met Arg Glu Leu Thr Lys Ser Ile Glu Lys Gly Glu Ala Leu
                245                 250                 255

Pro Asn Thr Leu Asn Met Asp Tyr Ser Tyr Asp Val Ser Phe Lys Ser
            260                 265                 270

Leu Ala Tyr Phe Met Ile Ala Pro Thr Leu Cys Tyr Gln Pro Arg Tyr
        275                 280                 285

Pro Arg Ser Pro Ser Ile Arg Lys Gly Trp Val Leu Arg Gln Leu Val
    290                 295                 300
```

```
Lys Leu Ile Ile Phe Thr Gly Val Met Gly Phe Ile Glu Gln Tyr
305                 310                 315                 320

Ile Asn Pro Ile Val Gln Asn Ser Gln His Pro Leu Lys Gly Asn Leu
            325                 330                 335

Leu Tyr Ala Ile Glu Arg Val Leu Lys Leu Ser Val Pro Asn Leu Tyr
            340                 345                 350

Val Trp Leu Cys Met Phe Tyr Cys Phe Phe His Leu Trp Leu Asn Ile
            355                 360                 365

Leu Ala Glu Leu Leu Arg Phe Gly Asp Arg Gly Phe Tyr Lys Asp Trp
370                 375                 380

Trp Asn Ala Lys Thr Phe Glu Glu Tyr Trp Arg Met Trp Asn Met Pro
385                 390                 395                 400

Val His Lys Trp Met Ile Arg His Leu Tyr Phe Pro Cys Leu Arg Asn
            405                 410                 415

Gly Ile Pro Lys Gly Val Ala Ile Leu Ile Ala Phe Leu Val Ser Ala
            420                 425                 430

Leu Phe His Glu Leu Cys Ile Ala Val Pro Cys His Ile Phe Lys Leu
            435                 440                 445

Trp Ala Phe Gly Gly Ile Met Phe Gln Val Pro Leu Ile Leu Ile Thr
450                 455                 460

Asn Tyr Leu Gln Asn Lys Phe Arg Asn Ser Met Val Gly Asn Met Ile
465                 470                 475                 480

Phe Trp Phe Ile Phe Ser Ile Leu Gly Gln Pro Met Ala Val Leu Leu
                485                 490                 495

Tyr Tyr His Asp Leu Met Asn Arg Lys Ser Lys Leu Asp Gln Ser
            500                 505                 510

<210> SEQ ID NO 52
<211> LENGTH: 539
<212> TYPE: PRT
<213> ORGANISM: Medicago truncatula

<400> SEQUENCE: 52

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
                20                  25                  30

Arg Arg Pro Ser Ala Thr Ser Thr Ala Gly Gly Leu Phe Asp Ala Glu
            35                  40                  45

Ser Ala Ala Ala Asp Ala Val Arg Asp Ser Gly Ser Asp Asp Ser Leu
50                  55                  60

Asn Gly Lys Ile Asn Asn Glu Glu Val Lys Asp Arg Lys Thr Asp
65                  70                  75                  80

His Ala Glu Gly Ile Val Asp Asp Asp Asp Asn Ala Val Lys Lys
                85                  90                  95

Asn Gly Gly Asn Asp Val Ile Asn Asp Arg Glu Asn Val Ala Val Asp
            100                 105                 110

Phe Lys Phe Thr Tyr Arg Pro Ser Val Pro Ala His Arg Arg Ser Lys
            115                 120                 125

Glu Ser Pro Leu Ser Ser Gly Asn Ile Phe Arg Gln Ser His Ala Gly
130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Trp Leu Ile Arg Ser Gly Phe
                165                 170                 175
```

Trp Phe Ser Ser Lys Ser Leu Arg Asp Trp Pro Leu Phe Met Cys Cys
            180                 185                 190

Leu Ser Leu Ala Ile Phe Pro Leu Ala Ala Phe Val Glu Lys Leu
        195                 200                 205

Ala Gln Gln Lys Arg Ile Ser Glu Pro Val Ile Val Leu Leu His Ile
    210                 215                 220

Val Ile Thr Thr Val Ala Ile Ile Tyr Pro Val Leu Val Ile Leu Trp
225                 230                 235                 240

Cys Asp Ser Ala Phe Leu Ser Gly Ser Thr Leu Met Leu Leu Thr Cys
                245                 250                 255

Ile Val Trp Leu Lys Leu Val Ser Tyr Ala His Thr Thr Tyr Asp Met
            260                 265                 270

Arg Ala Leu Ala Val Ser Asn Glu Lys Gly Glu Thr Met Pro Asp Thr
        275                 280                 285

Phe Asn Met Glu Glu Tyr Pro His Asn Val Ser Phe Gln Ser Leu Ala
    290                 295                 300

Tyr Phe Met Val Ala Pro Thr Leu Cys Tyr Gln Pro Ser Tyr Pro Arg
305                 310                 315                 320

Thr Pro Ser Val Arg Lys Gly Trp Val Cys Arg Gln Leu Leu Lys Leu
                325                 330                 335

Val Ile Phe Thr Gly Val Met Gly Phe Ile Ile Glu Gln Tyr Met Asn
            340                 345                 350

Pro Ile Val Gln Asn Ser Gln His Pro Leu Lys Gly Asn Leu Leu Tyr
        355                 360                 365

Ala Ile Glu Arg Val Leu Lys Leu Ser Val Pro Asn Val Tyr Val Trp
    370                 375                 380

Leu Cys Met Phe Tyr Cys Phe His Leu Trp Leu Asn Ile Leu Ala
385                 390                 395                 400

Glu Leu Leu Arg Phe Gly Asp Arg Glu Phe Tyr Lys Asp Trp Trp Asn
                405                 410                 415

Ala Gln Thr Val Glu Glu Tyr Trp Arg Met Trp Asn Met Pro Val His
            420                 425                 430

Lys Trp Met Val Arg His Val Tyr Phe Pro Cys Ile Arg Phe Gly Ile
        435                 440                 445

Pro Lys Gly Ala Ala Ala Leu Thr Ala Phe Leu Val Ser Ala Val Phe
    450                 455                 460

His Glu Leu Cys Ile Ala Val Pro Cys Arg Met Phe Lys Leu Trp Ala
465                 470                 475                 480

Phe Ile Gly Ile Met Phe Gln Val Pro Leu Val Leu Ile Thr Asn Tyr
                485                 490                 495

Leu Lys Asn Lys Tyr Arg Asn Ser Met Val Gly Asn Met Ile Phe Trp
            500                 505                 510

Phe Ile Phe Cys Ile Leu Gly Gln Pro Met Cys Val Leu Leu Tyr Tyr
        515                 520                 525

His Asp Leu Met Asn Arg Lys Gly Glu Ile Asp
    530                 535

<210> SEQ ID NO 53
<211> LENGTH: 539
<212> TYPE: PRT
<213> ORGANISM: Jatropha curcas

<400> SEQUENCE: 53

Met Ala Ile Ser Asp Thr Pro Glu Thr Thr Ala Thr Ala Thr Ala Thr

```
1               5                   10                  15
Val Thr Thr Ile Glu Thr Asp Thr Asp Leu Lys Arg Ser Ser Leu Arg
                20                  25                  30

Arg Arg Pro Ser Ala Thr Ser Thr Ala Gly Gly Leu Phe Asp Ala Glu
        35                  40                  45

Ser Ala Ala Asp Ala Val Arg Asp Ser Gly Ser Asp Ser Leu
    50                  55                  60

Asn Gly Lys Ile Asn Asn Glu Glu Val Lys Asp Arg Lys Thr Asp
65                  70                  75                  80

His Ala Glu Gly Ile Val Asp Asp Asp Asn Ala Val Lys Lys
                85                  90                  95

Asn Gly Gly Asn Asp Val Ile Asn Asp Arg Glu Asn Val Ala Val Asp
                100                 105                 110

Phe Lys Phe Thr Tyr Arg Pro Ser Val Pro Ala His Arg Arg Ser Lys
        115                 120                 125

Glu Ser Pro Leu Ser Ser Gly Asn Ile Phe Arg Gln Ser His Ala Gly
        130                 135                 140

Leu Phe Asn Leu Cys Ile Val Val Leu Val Ala Val Asn Ser Arg Leu
145                 150                 155                 160

Ile Ile Glu Asn Leu Met Lys Tyr Gly Trp Leu Ile Arg Ser Gly Phe
                165                 170                 175

Trp Phe Ser Ser Lys Ser Leu Arg Asp Trp Pro Leu Phe Met Cys Cys
                180                 185                 190

Leu Ser Leu Ala Ile Phe Pro Leu Ala Ala Phe Val Val Glu Lys Leu
        195                 200                 205

Ala Gln Gln Lys Arg Ile Ser Glu Pro Val Ile Val Leu Leu His Ile
        210                 215                 220

Val Ile Thr Thr Val Ala Ile Ile Tyr Pro Val Leu Val Ile Leu Trp
225                 230                 235                 240

Cys Asp Ser Ala Phe Leu Ser Gly Ser Thr Leu Met Leu Leu Thr Cys
                245                 250                 255

Ile Val Trp Leu Lys Leu Val Ser Tyr Ala His Thr Thr Tyr Asp Met
                260                 265                 270

Arg Ala Leu Ala Val Ser Asn Glu Lys Gly Glu Thr Met Pro Asp Thr
        275                 280                 285

Phe Asn Met Glu Glu Tyr Pro His Asn Val Ser Phe Gln Ser Leu Ala
        290                 295                 300

Tyr Phe Met Val Ala Pro Thr Leu Cys Tyr Gln Pro Ser Tyr Pro Arg
305                 310                 315                 320

Thr Pro Ser Val Arg Lys Gly Trp Val Cys Arg Gln Leu Leu Lys Leu
                325                 330                 335

Val Ile Phe Thr Gly Val Met Gly Phe Ile Ile Glu Gln Tyr Met Asn
                340                 345                 350

Pro Ile Val Gln Asn Ser Gln His Pro Leu Lys Gly Asn Leu Leu Tyr
        355                 360                 365

Ala Ile Glu Arg Val Leu Lys Leu Ser Val Pro Asn Val Tyr Val Trp
        370                 375                 380

Leu Cys Met Phe Tyr Cys Phe Phe His Leu Trp Leu Asn Ile Leu Ala
385                 390                 395                 400

Glu Leu Leu Arg Phe Gly Asp Arg Glu Phe Tyr Lys Asp Trp Trp Asn
                405                 410                 415

Ala Gln Thr Val Glu Glu Tyr Trp Arg Met Trp Asn Met Pro Val His
        420                 425                 430
```

```
Lys Trp Met Val Arg His Val Tyr Phe Pro Cys Ile Arg Phe Gly Ile
            435                 440                 445

Pro Lys Gly Ala Ala Ala Leu Thr Ala Phe Leu Val Ser Ala Val Phe
        450                 455                 460

His Glu Leu Cys Ile Ala Val Pro Cys Arg Met Phe Lys Leu Trp Ala
465                 470                 475                 480

Phe Ile Gly Ile Met Phe Gln Val Pro Leu Val Leu Ile Thr Asn Tyr
                485                 490                 495

Leu Lys Asn Lys Tyr Arg Asn Ser Met Val Gly Asn Met Ile Phe Trp
            500                 505                 510

Phe Ile Phe Cys Ile Leu Gly Gln Pro Met Cys Val Leu Leu Tyr Tyr
        515                 520                 525

His Asp Leu Met Asn Arg Lys Gly Glu Ile Asp
    530                 535

<210> SEQ ID NO 54
<211> LENGTH: 521
<212> TYPE: PRT
<213> ORGANISM: Vernicia fordii

<400> SEQUENCE: 54

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
    50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125

Leu Cys Ile Val Val Leu Val Ala Val Asn Ser Arg Leu Ile Ile Glu
130                 135                 140

Asn Leu Met Lys Tyr Gly Trp Leu Ile Lys Thr Gly Phe Trp Phe Ser
145                 150                 155                 160

Ser Arg Ser Leu Arg Asp Trp Pro Leu Leu Met Cys Cys Leu Thr Leu
            165                 170                 175

Pro Ile Phe Ser Leu Ala Ala Tyr Leu Val Glu Lys Leu Ala Tyr Arg
        180                 185                 190

Lys Tyr Ile Ser Ala Pro Ile Val Ile Phe His Met Leu Ile Thr
            195                 200                 205

Thr Thr Ala Val Leu Tyr Pro Val Ser Val Ile Leu Ser Cys Gly Ser
    210                 215                 220

Ala Val Leu Ser Gly Val Ala Leu Met Leu Phe Ala Cys Ile Val Trp
225                 230                 235                 240

Leu Lys Leu Val Ser Tyr Ala His Thr Asn Tyr Asp Met Arg Ala Ile
                245                 250                 255

Ala Asn Ser Ala Asp Lys Gly Asp Ala Leu Ser Asp Thr Ser Gly Ala
```

```
                260                 265                 270
Asp Ser Ser Arg Asp Val Ser Phe Lys Ser Leu Val Tyr Phe Met Val
            275                 280                 285
Ala Pro Thr Leu Cys Tyr Gln Pro Ser Tyr Pro Arg Thr Asp Ser Val
            290                 295                 300
Arg Lys Gly Trp Val Val Arg Gln Phe Val Lys Leu Ile Ile Phe Thr
305                 310                 315                 320
Gly Phe Met Gly Phe Ile Ile Glu Gln Tyr Ile Asn Pro Ile Val Gln
                325                 330                 335
Asn Ser Gln His Pro Leu Lys Gly Asp Leu Leu Tyr Ala Ile Glu Arg
            340                 345                 350
Val Leu Lys Leu Ser Val Pro Asn Leu Tyr Val Trp Leu Cys Met Phe
            355                 360                 365
Tyr Cys Phe Phe His Leu Trp Leu Asn Ile Leu Ala Glu Leu Leu Arg
            370                 375                 380
Phe Gly Asp Arg Glu Phe Tyr Lys Asp Trp Trp Asn Ala Arg Thr Val
385                 390                 395                 400
Glu Glu Tyr Trp Arg Met Trp Asn Met Pro Val His Lys Trp Met Val
                405                 410                 415
Arg His Ile Tyr Phe Pro Cys Leu Arg His Lys Ile Pro Arg Gly Val
            420                 425                 430
Ala Leu Leu Ile Ala Phe Phe Val Ser Ala Val Phe His Glu Leu Cys
            435                 440                 445
Ile Ala Val Pro Cys His Met Phe Lys Leu Trp Ala Phe Ile Gly Ile
            450                 455                 460
Met Phe Gln Ile Pro Leu Val Gly Ile Thr Asn Tyr Leu Gln Asn Lys
465                 470                 475                 480
Phe Arg Ser Ser Met Val Gly Asn Met Ile Phe Trp Phe Ile Phe Cys
                485                 490                 495
Ile Leu Gly Gln Pro Met Cys Val Leu Leu Tyr Tyr His Asp Leu Met
            500                 505                 510
Asn Arg Lys Gly Asn Ala Glu Leu Arg
            515                 520

<210> SEQ ID NO 55
<211> LENGTH: 526
<212> TYPE: PRT
<213> ORGANISM: Vernonia galamensis

<400> SEQUENCE: 55

Met Thr Ile Pro Glu Thr Pro Asp Asn Ser Thr Asp Ala Thr Thr Ser
1               5                   10                  15
Gly Gly Ala Glu Ser Ser Ser Asp Leu Asn Leu Ser Leu Arg Arg Arg
            20                  25                  30
Arg Thr Ala Ser Asn Ser Asp Gly Ala Val Ala Glu Leu Ala Ser Lys
            35                  40                  45
Ile Asp Glu Leu Glu Ser Asp Ala Gly Gly Gln Val Ile Lys Asp
            50                  55                  60
Pro Gly Ala Glu Met Asp Ser Gly Thr Leu Lys Ser Asn Gly Lys Asp
65                  70                  75                  80
Cys Gly Thr Val Lys Asp Arg Ile Glu Asn Arg Glu Asn Arg Gly Gly
                85                  90                  95
Ser Asp Val Lys Phe Thr Tyr Arg Pro Ser Val Pro Ala His Arg Ala
            100                 105                 110
```

-continued

```
Leu Lys Glu Ser Pro Leu Ser Ser Asp Asn Ile Phe Lys Gln Ser His
            115                 120                 125
Ala Gly Leu Phe Asn Leu Cys Ile Val Leu Val Ala Val Asn Ser
        130                 135                 140
Arg Leu Ile Ile Glu Asn Ile Met Lys Tyr Gly Trp Leu Ile Lys Thr
145                 150                 155                 160
Gly Phe Trp Phe Ser Ser Arg Ser Leu Arg Asp Trp Pro Leu Leu Met
                165                 170                 175
Cys Cys Leu Thr Leu Pro Ile Phe Ser Leu Ala Ala Tyr Leu Val Glu
                180                 185                 190
Lys Leu Ala Cys Arg Lys Tyr Ile Ser Ala Pro Thr Val Val Phe Leu
            195                 200                 205
His Ile Leu Phe Ser Ser Thr Ala Val Leu Tyr Pro Val Ser Val Ile
        210                 215                 220
Leu Ser Cys Glu Ser Ala Val Leu Ser Gly Val Ala Leu Met Leu Phe
225                 230                 235                 240
Ala Cys Ile Val Trp Leu Lys Leu Val Ser Tyr Ala His Thr Asn Phe
                245                 250                 255
Asp Met Arg Ala Ile Ala Asn Ser Val Asp Lys Gly Asp Ala Leu Ser
                260                 265                 270
Asn Ala Ser Ser Ala Glu Ser Ser His Asp Val Ser Phe Lys Ser Leu
            275                 280                 285
Val Tyr Phe Met Val Ala Pro Thr Leu Cys Tyr Gln Pro Ser Tyr Pro
        290                 295                 300
Arg Thr Ala Ser Ile Arg Lys Gly Trp Val Val Arg Gln Phe Val Lys
305                 310                 315                 320
Leu Ile Ile Phe Thr Gly Phe Met Gly Phe Ile Ile Glu Gln Tyr Ile
                325                 330                 335
Asn Pro Ile Val Gln Asn Ser Gln His Pro Leu Lys Gly Asp Leu Leu
                340                 345                 350
Tyr Ala Ile Glu Arg Val Leu Lys Leu Ser Val Pro Asn Leu Tyr Val
            355                 360                 365
Trp Leu Cys Met Phe Tyr Cys Phe Phe His Leu Trp Leu Asn Ile Leu
        370                 375                 380
Ala Glu Leu Leu Arg Phe Gly Asp Arg Glu Phe Tyr Lys Asp Trp Trp
385                 390                 395                 400
Asn Ala Arg Thr Val Glu Glu Tyr Trp Arg Met Trp Asn Met Pro Val
                405                 410                 415
His Lys Trp Met Val Arg His Ile Tyr Phe Pro Cys Leu Arg His Lys
                420                 425                 430
Ile Pro Arg Gly Val Ala Leu Leu Ile Thr Phe Phe Val Ser Ala Val
            435                 440                 445
Phe His Glu Leu Cys Ile Ala Val Pro Cys His Ile Phe Lys Leu Trp
        450                 455                 460
Ala Phe Ile Gly Ile Met Phe Gln Ile Pro Leu Val Gly Ile Thr Asn
465                 470                 475                 480
Tyr Leu Gln Asn Lys Phe Arg Ser Ser Met Val Gly Asn Met Ile Phe
                485                 490                 495
Trp Phe Ile Phe Cys Ile Leu Gly Gln Pro Met Cys Leu Leu Leu Tyr
                500                 505                 510
Tyr His Asp Leu Met Asn Arg Lys Gly Thr Thr Glu Ser Arg
            515                 520                 525
```

<210> SEQ ID NO 56
<211> LENGTH: 523
<212> TYPE: PRT
<213> ORGANISM: Ricinus communis

<400> SEQUENCE: 56

```
Met Ala Leu Leu Asp Thr Pro Gln Ile Gly Glu Ile Thr Thr Thr Ala
1               5                   10                  15

Thr Thr Thr Ile Arg Arg Thr Thr Val Lys Pro Asp Ala Gly Ile
            20                  25                  30

Gly Asp Gly Leu Phe Asp Ser Ser Ser Ser Lys Thr Asn Ser Ser
        35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
        115                 120                 125

Gly Leu Phe Asn Leu Cys Ile Val Val Leu Val Ala Val Asn Gly Arg
    130                 135                 140

Leu Ile Ile Glu Asn Leu Met Lys Tyr Gly Leu Leu Ile Asn Ser Asn
145                 150                 155                 160

Phe Trp Phe Ser Ser Arg Ser Leu Arg Asp Trp Pro Leu Leu Met Cys
                165                 170                 175

Cys Leu Thr Pro Ser Asp Phe Pro Leu Ala Ala Tyr Ile Val Glu Lys
            180                 185                 190

Leu Ala Trp Lys Lys Arg Ile Ser Asp Pro Val Val Ile Thr Leu His
        195                 200                 205

Val Ile Ile Thr Thr Thr Ala Ile Leu Tyr Pro Val Phe Met Ile Leu
    210                 215                 220

Arg Phe Asp Ser Val Val Leu Ser Gly Val Ser Leu Met Leu Cys Ala
225                 230                 235                 240

Cys Ile Asn Trp Leu Lys Leu Val Ser Phe Val His Thr Asn Tyr Asp
                245                 250                 255

Met Arg Ser Leu Leu Asn Ser Thr Asp Lys Gly Glu Val Glu Pro Met
            260                 265                 270

Ser Ser Asn Met Asp Tyr Phe Tyr Asp Val Asn Phe Lys Ser Leu Val
        275                 280                 285

Tyr Phe Met Val Ala Pro Thr Leu Cys Tyr Gln Ile Ser Tyr Pro Arg
    290                 295                 300

Thr Ala Phe Ile Arg Lys Gly Trp Val Leu Arg Gln Leu Ile Lys Leu
305                 310                 315                 320

Val Ile Phe Thr Gly Phe Met Gly Phe Ile Ile Glu Gln Tyr Ile Asn
                325                 330                 335

Pro Ile Val Lys Asn Ser Arg His Pro Leu Lys Gly Asp Phe Leu Tyr
            340                 345                 350

Ala Ile Glu Arg Val Leu Lys Leu Ser Val Pro Asn Leu Tyr Val Trp
        355                 360                 365

Leu Cys Met Phe Tyr Cys Phe Phe His Leu Trp Leu Asn Ile Leu Ala
    370                 375                 380
```

```
Glu Leu Leu Cys Phe Gly Asp Arg Glu Phe Tyr Lys Asp Trp Trp Asn
385                 390                 395                 400

Ala Gln Thr Ile Glu Glu Tyr Trp Arg Leu Trp Asn Met Pro Val His
        405                 410                 415

Lys Trp Ile Val Arg His Leu Tyr Phe Pro Cys Leu Arg Asn Gly Ile
            420                 425                 430

Pro Lys Gly Ala Ala Ile Leu Val Ala Phe Phe Met Ser Ala Val Phe
        435                 440                 445

His Glu Leu Cys Ile Ala Val Pro Cys His Ile Phe Lys Phe Trp Ala
    450                 455                 460

Phe Ile Gly Ile Met Phe Gln Val Pro Leu Val Leu Thr Asn Tyr
465                 470                 475                 480

Leu Gln His Lys Phe Gln Asn Ser Met Val Gly Asn Met Ile Phe Trp
            485                 490                 495

Cys Phe Phe Ser Ile Phe Gly Gln Pro Met Cys Val Leu Leu Tyr Tyr
                500                 505                 510

His Asp Val Met Asn Gln Lys Gly Lys Ser Lys
        515                 520

<210> SEQ ID NO 57
<211> LENGTH: 521
<212> TYPE: PRT
<213> ORGANISM: Populus trichocarpa

<400> SEQUENCE: 57

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Thr Ser Asn
            20                  25                  30

Asp Ser Asp Gly Ala Leu Ala Asp Leu Ala Ser Lys Phe Asp Asp Asp
        35                  40                  45

Asp Asp Val Arg Ser Glu Asp Ser Ala Glu Asn Ile Ile Glu Asp Pro
    50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
            180                 185                 190

Lys Ala Ala Tyr Arg Lys Tyr Ile Ser Pro Ile Val Ile Phe Leu
        195                 200                 205

His Val Ile Ile Thr Ser Ala Ala Val Leu Tyr Pro Ala Ser Val Ile
    210                 215                 220

Leu Ser Cys Glu Ser Ala Phe Leu Ser Gly Val Thr Leu Met Glu Leu
225                 230                 235                 240
```

```
Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
            260                 265                 270

Ser Ser Ser Thr Glu Tyr Cys His Asp Val Ser Phe Lys Thr Leu Ala
        275                 280                 285

Tyr Phe Met Val Ala Pro Thr Leu Cys Tyr Gln Pro Ser Tyr Pro Arg
    290                 295                 300

Thr Ala Phe Ile Arg Lys Gly Trp Val Phe Arg Gln Phe Val Lys Leu
305                 310                 315                 320

Ile Ile Phe Thr Gly Phe Met Gly Phe Ile Glu Gln Tyr Ile Asn
                325                 330                 335

Pro Ile Val Gln Asn Ser Gln His Pro Leu Lys Gly Asp Leu Leu Tyr
                340                 345                 350

Ala Ile Glu Arg Val Leu Lys Leu Ser Val Pro Asn Leu Tyr Val Trp
                355                 360                 365

Leu Cys Leu Phe Tyr Cys Phe Phe His Leu Trp Leu Asn Ile Val Ala
            370                 375                 380

Glu Leu Leu Arg Phe Gly Asp Arg Glu Phe Tyr Lys Asp Trp Trp Asn
385                 390                 395                 400

Ala Lys Thr Val Glu Glu Tyr Trp Arg Met Trp Asn Met Pro Val His
                405                 410                 415

Lys Trp Met Val Arg His Ile Tyr Phe Pro Cys Leu Arg Arg Lys Ile
                420                 425                 430

Pro Arg Gly Val Ala Ile Val Ala Phe Phe Val Ser Ala Val Phe
                435                 440                 445

His Glu Leu Cys Ile Ala Val Pro Cys His Met Phe Lys Leu Trp Ala
    450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
                485                 490                 495

Phe Phe Phe Cys Ile Leu Gly Gln Pro Met Cys Val Leu Leu Tyr Tyr
            500                 505                 510

His Asp Leu Met Asn Arg Asp Gly Asn
    515                 520

<210> SEQ ID NO 58
<211> LENGTH: 493
<212> TYPE: PRT
<213> ORGANISM: Populus trichocarpa

<400> SEQUENCE: 58

Met Ala Glu Ser Glu Ser Pro Glu Asn Arg Ile Ala Ala Met Glu Ser
1                   5                   10                  15

Thr Ser Ser Ser Thr Ser Asp Leu Asn Phe Ser Ile Arg Arg Ser
                20                  25                  30

Thr Val Met Asp Ser Ala Ser Thr Glu Met Met Gly Ser Glu Gly Leu
            35                  40                  45

Lys Ser Ser Gly Lys Ala Cys Asp Lys Val Lys Ile Glu Lys Gln Ser
        50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
```

```
                85                  90                  95
Gly Leu Phe Asn Leu Cys Ile Val Val Leu Ala Val Asn Ser Arg
            100                 105                 110

Leu Ile Ile Glu Asn Leu Ile Lys Tyr Gly Trp Leu Ile Asn Ser Gly
            115                 120                 125

Phe Trp Phe Ser Ser Lys Ser Leu Arg Asp Trp Pro Leu Phe Met Cys
130                 135                 140

Cys Leu Ser Leu Pro Ala Phe Pro Leu Ala Tyr Leu Val Glu Lys
145                 150                 155                 160

Leu Ala Tyr Arg Asn Cys Ile Ser Glu Leu Val Val Phe Leu His
            165                 170                 175

Ile Ile Ile Thr Thr Ala Ser Leu Leu Tyr Pro Val Leu Val Ile Leu
            180                 185                 190

Arg Cys Asp Ser Ala Leu Leu Ser Gly Gly Thr Leu Met Leu Phe Ala
            195                 200                 205

Cys Ile Val Trp Leu Lys Leu Val Ser Phe Ala His Thr Ser Ser Asp
        210                 215                 220

Met Arg Ala Ile Ala Lys Ser Ile Asp Lys Glu Asn Thr Pro Ser Ile
225                 230                 235                 240

Ser Ser Lys Ala Asp Asn Ser Tyr Asp Ala Asn Phe Lys Ser Leu Val
                245                 250                 255

Tyr Phe Met Val Ala Pro Thr Leu Cys Tyr Gln Ser Ser Tyr Pro Arg
            260                 265                 270

Ser Ala Ser Val Arg Lys Gly Trp Val Val Arg Gln Phe Val Lys Leu
            275                 280                 285

Ile Ile Phe Thr Gly Phe Met Gly Phe Ile Ile Glu Gln Tyr Ile Asn
        290                 295                 300

Pro Ile Val Gln Asn Ser Gln His Pro Leu Lys Gly Asn Leu Leu Tyr
305                 310                 315                 320

Ala Ile Glu Arg Val Leu Lys Leu Ser Val Pro Asn Leu Tyr Val Trp
            325                 330                 335

Leu Cys Met Phe Tyr Cys Phe Phe His Leu Trp Leu Asn Ile Leu Ala
            340                 345                 350

Glu Leu Leu Arg Phe Gly Asp Arg Glu Phe Tyr Lys Asp Trp Trp Asn
            355                 360                 365

Ala Arg Thr Val Glu Glu Tyr Trp Arg Met Trp Asn Met Pro Val His
            370                 375                 380

Lys Trp Met Val Arg His Ile Tyr Phe Pro Cys Leu Arg Asn Lys Ile
385                 390                 395                 400

Pro Lys Trp Ala Ala Leu Leu Ile Ala Phe Phe Val Ser Ala Val Phe
                405                 410                 415

His Glu Leu Cys Ile Ala Val Pro Cys His Met Phe Lys Leu Trp Ala
            420                 425                 430

Phe Ile Gly Ile Met Phe Gln Val Pro Leu Val Val Ile Thr Lys Phe
            435                 440                 445

Leu Gln Asn Lys Phe Lys Ser Ser Met Val Gly Asn Met Ile Phe Trp
            450                 455                 460

Leu Phe Phe Ser Ile Leu Gly Gln Pro Met Cys Val Leu Leu Tyr Tyr
465                 470                 475                 480

His Asp Leu Met Asn Arg Lys Gly Lys Thr Glu Arg Arg
            485                 490

<210> SEQ ID NO 59
```

<211> LENGTH: 457
<212> TYPE: PRT
<213> ORGANISM: Artificial Sequence
<220> FEATURE:
<223> OTHER INFORMATION: A. thaliana

<400> SEQUENCE: 59

| | | | | | | | | | | | | | | |
|---|---|---|---|---|---|---|---|---|---|---|---|---|---|---|
| Met | Gly | Gly | Gly | Ser | Ala | Thr | Phe | Thr | Tyr | Arg | Pro | Ser | Val | Pro | Ala |
| 1 | | | | 5 | | | | | 10 | | | | | 15 | |
| His | Arg | Arg | Ala | Arg | Glu | Ser | Pro | Leu | Ser | Ser | Asp | Ala | Ile | Phe | Lys |
| | | | 20 | | | | | 25 | | | | | 30 | | |
| Gln | Ser | His | Ala | Gly | Leu | Phe | Asn | Leu | Cys | Val | Val | Val | Leu | Ile | Ala |
| | | | 35 | | | | | 40 | | | | | 45 | | |
| Val | Asn | Ser | Arg | Leu | Ile | Ile | Glu | Asn | Leu | Met | Lys | Tyr | Gly | Trp | Leu |
| | 50 | | | | | 55 | | | | | 60 | | | | |
| Ile | Arg | Thr | Asp | Phe | Trp | Phe | Ser | Ser | Arg | Ser | Leu | Arg | Asp | Trp | Pro |
| 65 | | | | | 70 | | | | | 75 | | | | | 80 |
| Leu | Phe | Met | Cys | Cys | Ile | Ser | Leu | Ser | Ile | Phe | Pro | Leu | Ala | Ala | Phe |
| | | | | 85 | | | | | 90 | | | | | 95 | |
| Thr | Val | Glu | Lys | Leu | Val | Leu | Gln | Lys | Tyr | Ile | Ser | Glu | Pro | Val | Val |
| | | | | 100 | | | | | 105 | | | | | 110 | |
| Ile | Phe | Leu | His | Ile | Ile | Ile | Thr | Met | Thr | Glu | Val | Leu | Tyr | Pro | Val |
| | | | | 115 | | | | | 120 | | | | | 125 | |
| Tyr | Val | Thr | Leu | Arg | Cys | Asp | Ser | Ala | Phe | Leu | Ser | Gly | Val | Thr | Leu |
| | | 130 | | | | | 135 | | | | | 140 | | | |
| Met | Leu | Leu | Thr | Cys | Ile | Val | Trp | Leu | Lys | Leu | Val | Ser | Tyr | Ala | His |
| 145 | | | | | 150 | | | | | 155 | | | | | 160 |
| Thr | Ser | Tyr | Asp | Ile | Arg | Ser | Leu | Ala | Asn | Ala | Ala | Asp | Lys | Ala | Asn |
| | | | | 165 | | | | | 170 | | | | | 175 | |
| Pro | Glu | Val | Ser | Tyr | Tyr | Val | Ser | Leu | Lys | Ser | Leu | Ala | Tyr | Phe | Met |
| | | | | 180 | | | | | 185 | | | | | 190 | |
| Val | Ala | Pro | Thr | Leu | Cys | Tyr | Gln | Pro | Ser | Tyr | Pro | Arg | Ser | Ala | Cys |
| | | | | 195 | | | | | 200 | | | | | 205 | |
| Ile | Arg | Lys | Gly | Trp | Val | Ala | Arg | Gln | Phe | Ala | Lys | Leu | Val | Ile | Phe |
| | | 210 | | | | | 215 | | | | | 220 | | | |
| Thr | Gly | Phe | Met | Gly | Phe | Ile | Ile | Glu | Gln | Tyr | Ile | Asn | Pro | Ile | Val |
| 225 | | | | | 230 | | | | | 235 | | | | | 240 |
| Arg | Asn | Ser | Lys | His | Pro | Leu | Lys | Gly | Asp | Leu | Leu | Tyr | Ala | Ile | Glu |
| | | | | 245 | | | | | 250 | | | | | 255 | |
| Arg | Val | Leu | Lys | Leu | Ser | Val | Pro | Asn | Leu | Tyr | Val | Trp | Leu | Cys | Met |
| | | | | 260 | | | | | 265 | | | | | 270 | |
| Phe | Tyr | Cys | Phe | Phe | His | Leu | Trp | Leu | Asn | Ile | Leu | Ala | Glu | Leu | Leu |
| | | | | 275 | | | | | 280 | | | | | 285 | |
| Cys | Phe | Gly | Asp | Arg | Glu | Phe | Tyr | Lys | Asp | Trp | Asn | Ala | Lys | Ser |
| | | 290 | | | | | 295 | | | | | 300 | | | |
| Val | Gly | Asp | Tyr | Trp | Arg | Met | Trp | Asn | Met | Pro | Val | His | Lys | Trp | Met |
| 305 | | | | | 310 | | | | | 315 | | | | | 320 |
| Val | Arg | His | Ile | Tyr | Phe | Pro | Cys | Leu | Arg | Ser | Lys | Ile | Pro | Lys | Thr |
| | | | | 325 | | | | | 330 | | | | | 335 | |
| Leu | Ala | Ile | Ile | Ile | Ala | Phe | Leu | Val | Ser | Ala | Val | Phe | His | Glu | Leu |
| | | | | 340 | | | | | 345 | | | | | 350 | |
| Cys | Ile | Ala | Val | Pro | Cys | Arg | Leu | Phe | Lys | Leu | Trp | Ala | Phe | Leu | Gly |
| | | | | 355 | | | | | 360 | | | | | 365 | |
| Ile | Met | Phe | Gln | Val | Pro | Leu | Val | Phe | Ile | Thr | Asn | Tyr | Leu | Gln | Glu |
| | | | | 370 | | | | | 375 | | | | | 380 | |

```
Arg Phe Gly Ser Thr Val Gly Asn Met Ile Phe Trp Phe Ile Phe Cys
385                 390                 395                 400

Ile Phe Gly Gln Pro Met Cys Val Leu Leu Tyr Tyr His Asp Leu Met
            405                 410                 415

Asn Arg Lys Gly Ser Met Ser Ala Lys Gly Glu Leu Arg Gly His Pro
        420                 425                 430

Phe Glu Gly Lys Pro Ile Pro Asn Pro Leu Leu Gly Leu Asp Ser Thr
    435                 440                 445

Arg Thr Gly His His His His His His
    450                 455

<210> SEQ ID NO 60
<211> LENGTH: 478
<212> TYPE: PRT
<213> ORGANISM: Artificial Sequence
<220> FEATURE:
<223> OTHER INFORMATION: A. thaliana

<400> SEQUENCE: 60

Met Ala Pro Pro Gly Gly Ser Pro Gln Gln Gln Gln Gly Gly
1               5                   10                  15

Gly Ser Gln Gln Gln Gly Gly Gly Ser Ala Thr Phe Thr Tyr Arg
            20                  25                  30

Pro Ser Val Pro Ala His Arg Ala Arg Glu Ser Pro Leu Ser Ser
        35                  40                  45

Asp Ala Ile Phe Lys Gln Ser His Ala Gly Leu Phe Asn Leu Cys Val
    50                  55                  60

Val Val Leu Ile Ala Val Asn Ser Arg Leu Ile Ile Glu Asn Leu Met
65                  70                  75                  80

Lys Tyr Gly Trp Leu Ile Arg Thr Asp Phe Trp Phe Ser Ser Arg Ser
                85                  90                  95

Leu Arg Asp Trp Pro Leu Phe Met Cys Cys Ile Ser Leu Ser Ile Phe
            100                 105                 110

Pro Leu Ala Ala Phe Thr Val Glu Lys Leu Val Leu Gln Lys Tyr Ile
        115                 120                 125

Ser Glu Pro Val Val Ile Phe Leu His Ile Ile Ile Thr Met Thr Glu
    130                 135                 140

Val Leu Tyr Pro Val Tyr Val Thr Leu Arg Cys Asp Ser Ala Phe Leu
145                 150                 155                 160

Ser Gly Val Thr Leu Met Leu Leu Thr Cys Ile Val Trp Leu Lys Leu
                165                 170                 175

Val Ser Tyr Ala His Thr Ser Tyr Asp Ile Arg Ser Leu Ala Asn Ala
            180                 185                 190

Ala Asp Lys Ala Asn Pro Glu Val Ser Tyr Tyr Val Ser Leu Lys Ser
        195                 200                 205

Leu Ala Tyr Phe Met Val Ala Pro Thr Leu Cys Tyr Gln Pro Ser Tyr
    210                 215                 220

Pro Arg Ser Ala Cys Ile Arg Lys Gly Trp Val Ala Arg Gln Phe Ala
225                 230                 235                 240

Lys Leu Val Ile Phe Thr Gly Phe Met Gly Phe Ile Ile Glu Gln Tyr
                245                 250                 255

Ile Asn Pro Ile Val Arg Asn Ser Lys His Pro Leu Lys Gly Asp Leu
            260                 265                 270

Leu Tyr Ala Ile Glu Arg Val Leu Lys Leu Ser Val Pro Asn Leu Tyr
        275                 280                 285
```

```
Val Trp Leu Cys Met Phe Tyr Cys Phe Phe His Leu Trp Leu Asn Ile
    290                 295                 300

Leu Ala Glu Leu Leu Cys Phe Gly Asp Arg Glu Phe Tyr Lys Asp Trp
305                 310                 315                 320

Trp Asn Ala Lys Ser Val Gly Asp Tyr Trp Arg Met Trp Asn Met Pro
                325                 330                 335

Val His Lys Trp Met Val Arg His Ile Tyr Phe Pro Cys Leu Arg Ser
                340                 345                 350

Lys Ile Pro Lys Thr Leu Ala Ile Ile Ala Phe Leu Val Ser Ala
                355                 360                 365

Val Phe His Glu Leu Cys Ile Ala Val Pro Cys Arg Leu Phe Lys Leu
    370                 375                 380

Trp Ala Phe Leu Gly Ile Met Phe Gln Val Pro Leu Val Phe Ile Thr
385                 390                 395                 400

Asn Tyr Leu Gln Glu Arg Phe Gly Ser Thr Val Gly Asn Met Ile Phe
                405                 410                 415

Trp Phe Ile Phe Cys Ile Phe Gly Gln Pro Met Cys Val Leu Leu Tyr
                420                 425                 430

Tyr His Asp Leu Met Asn Arg Lys Gly Ser Met Ser Ala Lys Gly Glu
                435                 440                 445

Leu Arg Gly His Pro Phe Glu Gly Lys Pro Ile Pro Asn Pro Leu Leu
450                 455                 460

Gly Leu Asp Ser Thr Arg Thr Gly His His His His His
465                 470                 475

<210> SEQ ID NO 61
<211> LENGTH: 567
<212> TYPE: PRT
<213> ORGANISM: Artificial Sequence
<220> FEATURE:
<223> OTHER INFORMATION: A. thaliana

<400> SEQUENCE: 61

Met Ala Pro Pro Ala Ile Leu Asp Ser Ala Gly Val Thr Thr Val
1               5                   10                  15

Thr Glu Asn Gly Gly Gly Glu Phe Val Asp Leu Asp Arg Leu Arg Arg
                20                  25                  30

Arg Lys Ser Arg Ser Asp Ser Ser Asn Gly Leu Leu Leu Ser Gly Ser
            35                  40                  45

Asp Asn Asn Ser Pro Ser Asp Asp Val Gly Ala Pro Ala Pro Gln Gln
        50                  55                  60

Gln Gln Asp Val Arg Asp Arg Ile Gln Gln Gln Asp Ser Val Val
65                  70                  75                  80

Asn Asp Asp Ala Gln Gly Thr Ala Asn Leu Ala Gly Asp Asn Asn Gly
                85                  90                  95

Gly Gly Asp Asn Asn Gly Gly Arg Gly Gly Glu Gly Arg Gly
            100                 105                 110

Asn Ala Asp Ala Thr Phe Thr Tyr Arg Pro Ser Val Pro Ala His Arg
        115                 120                 125

Arg Ala Arg Glu Ser Pro Leu Ser Ser Asp Ala Ile Phe Lys Gln Ser
    130                 135                 140

His Ala Gly Leu Phe Asn Leu Cys Val Val Leu Ile Ala Val Asn
145                 150                 155                 160

Ser Arg Leu Ile Ile Glu Asn Leu Met Lys Tyr Gly Trp Leu Ile Arg
                165                 170                 175
```

```
Thr Asp Phe Trp Phe Ser Ser Arg Ser Leu Arg Asp Trp Pro Leu Phe
            180                 185                 190

Met Cys Cys Ile Ser Leu Ser Ile Phe Pro Leu Ala Ala Phe Thr Val
            195                 200             205

Glu Lys Leu Val Leu Gln Lys Tyr Ile Ser Glu Pro Val Val Ile Phe
210                 215                 220

Leu His Ile Ile Ile Thr Met Thr Glu Val Leu Tyr Pro Val Tyr Val
225                 230                 235                 240

Thr Leu Arg Cys Asp Ser Ala Phe Leu Ser Gly Val Thr Leu Met Leu
                245                 250                 255

Leu Thr Cys Ile Val Trp Leu Lys Leu Val Ser Tyr Ala His Thr Ser
            260                 265                 270

Tyr Asp Ile Arg Ser Leu Ala Asn Ala Ala Asp Lys Ala Asn Pro Glu
            275                 280                 285

Val Ser Tyr Tyr Val Ser Leu Lys Ser Leu Ala Tyr Phe Met Val Ala
    290                 295                 300

Pro Thr Leu Cys Tyr Gln Pro Ser Tyr Pro Arg Ser Ala Cys Ile Arg
305                 310                 315                 320

Lys Gly Trp Val Ala Arg Gln Phe Ala Lys Leu Val Ile Phe Thr Gly
                325                 330                 335

Phe Met Gly Phe Ile Ile Glu Gln Tyr Ile Asn Pro Ile Val Arg Asn
                340                 345                 350

Ser Lys His Pro Leu Lys Gly Asp Leu Leu Tyr Ala Ile Glu Arg Val
            355                 360                 365

Leu Lys Leu Ser Val Pro Asn Leu Tyr Val Trp Leu Cys Met Phe Tyr
370                 375                 380

Cys Phe Phe His Leu Trp Leu Asn Ile Leu Ala Glu Leu Leu Cys Phe
385                 390                 395                 400

Gly Asp Arg Glu Phe Tyr Lys Asp Trp Trp Asn Ala Lys Ser Val Gly
                405                 410                 415

Asp Tyr Trp Arg Met Trp Asn Met Pro Val His Lys Trp Met Val Arg
                420                 425                 430

His Ile Tyr Phe Pro Cys Leu Arg Ser Lys Ile Pro Lys Thr Leu Ala
            435                 440                 445

Ile Ile Ile Ala Phe Leu Val Ser Ala Val Phe His Glu Leu Cys Ile
450                 455                 460

Ala Val Pro Cys Arg Leu Phe Lys Leu Trp Ala Phe Leu Gly Ile Met
465                 470                 475                 480

Phe Gln Val Pro Leu Val Phe Ile Thr Asn Tyr Leu Gln Glu Arg Phe
                485                 490                 495

Gly Ser Thr Val Gly Asn Met Ile Phe Trp Phe Ile Phe Cys Ile Phe
            500                 505                 510

Gly Gln Pro Met Cys Val Leu Leu Tyr Tyr His Asp Leu Met Asn Arg
            515                 520                 525

Lys Gly Ser Met Ser Ala Lys Gly Glu Leu Arg Gly His Pro Phe Glu
            530                 535                 540

Gly Lys Pro Ile Pro Asn Pro Leu Leu Gly Leu Asp Ser Thr Arg Thr
545                 550                 555                 560

Gly His His His His His
                565

<210> SEQ ID NO 62
<211> LENGTH: 463
```

<212> TYPE: PRT
<213> ORGANISM: Artificial Sequence
<220> FEATURE:
<223> OTHER INFORMATION: T. majus

<400> SEQUENCE: 62

Met Gly Gly Gly Ser Ile Arg Phe Thr Tyr Arg Pro Ser Phe Pro Ala
1               5                   10                  15

His Arg Arg Val Arg Glu Ser Pro Leu Ser Ser Asp Ala Ile Phe Lys
            20                  25                  30

Gln Ser His Ala Gly Leu Phe Asn Leu Cys Ile Val Val Leu Ile Ala
        35                  40                  45

Val Asn Ser Arg Leu Ile Ile Glu Asn Leu Met Lys Tyr Gly Trp Leu
    50                  55                  60

Ile Asp Thr Gly Phe Trp Phe Ser Ser Arg Ser Leu Gly Asp Trp Ser
65                  70                  75                  80

Ile Phe Met Cys Cys Leu Thr Leu Pro Ile Phe Pro Leu Ala Ala Phe
                85                  90                  95

Ile Val Glu Lys Leu Val Gln Arg Asn His Ile Ser Glu Leu Val Ala
            100                 105                 110

Val Leu Leu His Val Ile Val Ser Thr Ala Ala Val Leu Tyr Pro Val
        115                 120                 125

Ile Val Ile Leu Thr Cys Asp Ser Val Tyr Met Ser Gly Val Val Leu
130                 135                 140

Met Leu Phe Gly Cys Ile Met Trp Leu Lys Leu Val Ser Tyr Ala His
145                 150                 155                 160

Thr Ser Ser Asp Ile Arg Thr Leu Ala Lys Ser Gly Tyr Lys Gly Asp
                165                 170                 175

Ala His Pro Asn Ser Thr Ile Val Ser Cys Ser Tyr Asp Val Ser Leu
            180                 185                 190

Lys Ser Leu Ala Tyr Phe Met Val Ala Pro Thr Leu Cys Tyr Gln Pro
        195                 200                 205

Ser Tyr Pro Arg Ser Ser Cys Ile Arg Lys Gly Trp Val Val Arg Gln
    210                 215                 220

Phe Val Lys Leu Ile Val Phe Ile Gly Leu Met Gly Phe Ile Ile Glu
225                 230                 235                 240

Gln Tyr Ile Asn Pro Ile Val Arg Asn Ser Lys His Pro Leu Lys Gly
                245                 250                 255

Asp Phe Leu Tyr Ala Ile Glu Arg Val Leu Lys Leu Ser Val Pro Asn
            260                 265                 270

Leu Tyr Val Trp Leu Cys Met Phe Tyr Ser Phe Phe His Leu Trp Leu
        275                 280                 285

Asn Ile Leu Ala Glu Leu Leu Arg Phe Gly Asp Arg Glu Phe Tyr Lys
    290                 295                 300

Asp Trp Trp Asn Ala Lys Thr Val Ala Glu Tyr Trp Lys Met Trp Asn
305                 310                 315                 320

Met Pro Val His Arg Trp Met Val Arg His Leu Tyr Phe Pro Cys Leu
                325                 330                 335

Arg Asn Gly Ile Pro Lys Glu Gly Ala Ile Ile Ala Phe Leu Val
            340                 345                 350

Ser Gly Ala Phe His Glu Leu Cys Ile Ala Val Pro Cys His Val Phe
        355                 360                 365

Lys Leu Trp Ala Phe Ile Gly Ile Met Phe Gln Val Pro Leu Val Leu
    370                 375                 380

```
Ile Thr Asn Tyr Leu Gln Glu Lys Phe Ser Asn Ser Met Val Gly Asn
385                 390                 395                 400

Met Ile Phe Trp Phe Ile Phe Cys Ile Leu Gly Gln Pro Met Cys Val
            405                 410                 415

Leu Leu Tyr Tyr His Asp Leu Ile Asn Leu Lys Glu Lys Ala Lys Gly
            420                 425                 430

Glu Leu Arg Gly His Pro Phe Glu Gly Lys Pro Ile Pro Asn Pro Leu
            435                 440                 445

Leu Gly Leu Asp Ser Thr Arg Thr Gly His His His His His His
    450                 455                 460
```

<210> SEQ ID NO 63
<211> LENGTH: 467
<212> TYPE: PRT
<213> ORGANISM: Artificial Sequence
<220> FEATURE:
<223> OTHER INFORMATION: O. sativa-S

<400> SEQUENCE: 63

```
Met Gly Gly Gly Ser Gln Leu Leu Trp Tyr Arg Ala Ser Ala Pro Ala
1               5                   10                  15

His Arg Arg Val Arg Glu Ser Pro Leu Ser Ser Asp Ala Ile Phe Arg
            20                  25                  30

Gln Ser His Ala Gly Leu Leu Asn Leu Cys Ile Val Val Leu Val Ala
        35                  40                  45

Val Asn Ser Arg Leu Ile Ile Glu Asn Leu Met Lys Tyr Gly Leu Leu
    50                  55                  60

Ile Arg Ala Gly Phe Trp Phe Ser Gly Thr Ser Leu Ala Asp Trp Pro
65                  70                  75                  80

Leu Leu Met Cys Cys Leu Thr Leu Pro Thr Phe Pro Leu Ala Ala Leu
                85                  90                  95

Met Val Glu Lys Leu Ala Gln Arg Lys Leu Ile Ser Lys His Val Val
            100                 105                 110

Ile Leu Leu His Ile Val Ile Thr Thr Ser Val Leu Val Tyr Pro Val
            115                 120                 125

Val Val Ile Leu Lys Cys Asp Ser Ala Val Leu Ser Gly Phe Val Leu
    130                 135                 140

Met Phe Leu Ala Ser Ile Ile Trp Leu Lys Leu Val Ser Phe Ala His
145                 150                 155                 160

Thr Asn Tyr Asp Ile Arg Met Leu Ser Lys Ser Ile Glu Lys Gly Val
                165                 170                 175

Thr His Asp Ile Ser Ile Asp Pro Glu Asn Ile Lys Trp Pro Thr Phe
            180                 185                 190

Lys Arg Leu Ser Tyr Phe Met Leu Ala Pro Thr Leu Cys Tyr Gln Pro
            195                 200                 205

Ser Tyr Pro Arg Thr Thr Tyr Ile Arg Lys Gly Trp Val Val Arg Gln
    210                 215                 220

Leu Ile Lys Cys Leu Val Phe Thr Gly Leu Met Gly Phe Ile Ile Glu
225                 230                 235                 240

Gln Tyr Ile Asn Pro Ile Val Lys Asn Ser Lys His Pro Leu Lys Gly
                245                 250                 255

Asn Phe Leu Asn Ala Ile Glu Arg Val Leu Lys Leu Ser Val Pro Thr
            260                 265                 270

Leu Tyr Val Trp Leu Cys Met Phe Tyr Cys Phe Phe His Leu Trp Leu
            275                 280                 285
```

```
Asn Ile Leu Ala Glu Leu Leu Cys Phe Gly Asp Arg Glu Phe Tyr Lys
    290                 295                 300
Asp Trp Trp Asn Ala Lys Thr Val Glu Glu Tyr Trp Arg Met Trp Asn
305                 310                 315                 320
Met Pro Val His Lys Trp Val Ile Arg His Ile Tyr Phe Pro Cys Ile
                325                 330                 335
Arg Asn Gly Phe Ser Lys Gly Val Ala Ile Leu Ile Ser Phe Leu Val
                340                 345                 350
Ser Ala Ala Phe His Glu Leu Cys Val Ala Val Pro Cys His Ile Phe
                355                 360                 365
Lys Phe Trp Ala Phe Ile Gly Ile Met Phe Gln Ile Pro Leu Val Phe
    370                 375                 380
Leu Thr Lys Tyr Leu Gln Asp Lys Phe Asn Asn Thr Met Val Gly Asn
385                 390                 395                 400
Met Ile Phe Trp Phe Phe Ser Ile Leu Gly Gln Pro Met Cys Val
                405                 410                 415
Leu Leu Tyr Tyr His Asp Val Met Asn Arg Gln Gln Ala Gln Thr Asn
                420                 425                 430
Arg Ala Lys Gly Glu Leu Arg Gly His Pro Phe Glu Gly Lys Pro Ile
                435                 440                 445
Pro Asn Pro Leu Leu Gly Leu Asp Ser Thr Arg Thr Gly His His His
    450                 455                 460
His His His
465

<210> SEQ ID NO 64
<211> LENGTH: 465
<212> TYPE: PRT
<213> ORGANISM: Artificial Sequence
<220> FEATURE:
<223> OTHER INFORMATION: O. sativa-L

<400> SEQUENCE: 64

Met Gly Gly Gly Ser Ser Ala Phe Thr Phe Arg Ala Ala Ala Pro Val
1               5                   10                  15
His Arg Lys Ala Lys Glu Ser Pro Leu Ser Ser Asp Ala Ile Phe Lys
                20                  25                  30
Gln Ser His Ala Gly Leu Phe Asn Leu Cys Ile Val Val Leu Val Ala
                35                  40                  45
Val Asn Ser Arg Leu Ile Ile Glu Asn Leu Met Lys Tyr Gly Leu Leu
    50                  55                  60
Ile Arg Ala Gly Phe Trp Phe Asn Asp Lys Ser Leu Arg Asp Trp Pro
65                  70                  75                  80
Leu Leu Met Cys Cys Leu Ser Leu Pro Ala Phe Pro Leu Gly Ala Phe
                85                  90                  95
Ala Val Glu Lys Leu Ala Phe Asn Asn Val Ile Thr Asp Ala Val Ala
                100                 105                 110
Thr Cys Leu His Ile Phe Leu Ser Thr Thr Glu Ile Val Tyr Pro Val
                115                 120                 125
Leu Val Ile Leu Lys Cys Asp Ser Ala Val Leu Ser Gly Phe Leu Leu
    130                 135                 140
Ile Phe Ile Ala Cys Ile Val Trp Leu Lys Leu Val Ser Phe Ala His
145                 150                 155                 160
Thr Asn His Asp Ile Arg Gln Leu Thr Met Gly Gly Lys Lys Val Asp
                165                 170                 175
```

```
Asn Glu Leu Ser Thr Val Asp Met Asp Asn Leu Gln Pro Pro Thr Leu
            180                 185                 190

Gly Asn Leu Ile Tyr Phe Met Met Ala Pro Thr Leu Cys Tyr Gln Pro
            195                 200                 205

Ser Tyr Pro Arg Thr Ser Cys Val Arg Lys Gly Trp Leu Ile Arg Gln
            210                 215                 220

Ile Ile Leu Tyr Leu Ile Phe Thr Gly Leu Gln Gly Phe Ile Ile Glu
225                 230                 235                 240

Gln Tyr Ile Asn Pro Ile Val Val Asn Ser Gln His Pro Leu Lys Gly
            245                 250                 255

Gly Leu Leu Asn Ala Val Glu Thr Val Leu Lys Leu Ser Leu Pro Asn
            260                 265                 270

Val Tyr Leu Trp Leu Cys Met Phe Tyr Ala Phe Phe His Leu Trp Leu
            275                 280                 285

Ser Ile Leu Ala Glu Ile Leu Arg Phe Gly Asp Arg Glu Phe Tyr Lys
            290                 295                 300

Asp Trp Trp Asn Ala Lys Thr Ile Asp Glu Tyr Trp Arg Lys Trp Asn
305                 310                 315                 320

Met Pro Val His Lys Trp Val Arg His Ile Tyr Phe Pro Cys Met
            325                 330                 335

Arg Asn Gly Ile Ser Lys Glu Val Ala Val Leu Ile Ser Phe Leu Val
            340                 345                 350

Ser Ala Val Leu His Glu Ile Cys Val Ala Val Pro Cys Arg Ile Leu
            355                 360                 365

Lys Phe Trp Ala Phe Leu Gly Ile Met Leu Gln Ile Pro Leu Ile Val
            370                 375                 380

Leu Thr Ala Tyr Leu Lys Ser Lys Phe Arg Asp Thr Met Val Gly Asn
385                 390                 395                 400

Met Ile Phe Trp Phe Phe Cys Ile Tyr Gly Gln Pro Met Cys Leu
            405                 410                 415

Leu Leu Tyr Tyr His Asp Val Met Asn Arg Ile Glu Lys Ala Arg Ala
            420                 425                 430

Lys Gly Glu Leu Arg Gly His Pro Phe Glu Gly Lys Pro Ile Pro Asn
            435                 440                 445

Pro Leu Leu Gly Leu Asp Ser Thr Arg Thr Gly His His His His
    450                 455                 460

His
465

<210> SEQ ID NO 65
<211> LENGTH: 466
<212> TYPE: PRT
<213> ORGANISM: Artificial Sequence
<220> FEATURE:
<223> OTHER INFORMATION: Z. mays-S

<400> SEQUENCE: 65

Met Gly Gly Gly Ser Glu Met Leu Tyr Tyr Arg Ala Ser Ala Pro Ala
1               5                   10                  15

His Arg Arg Val Lys Glu Ser Pro Leu Ser Ser Asp Ala Ile Phe Arg
            20                  25                  30

Gln Ser His Ala Gly Leu Leu Asn Leu Cys Ile Val Val Leu Ile Ala
            35                  40                  45

Val Asn Ser Arg Leu Ile Ile Glu Asn Leu Met Lys Tyr Gly Leu Leu
        50                  55                  60
```

```
Ile Arg Ala Gly Phe Trp Phe Ser Ala Arg Ser Leu Gly Asp Trp Pro
 65                  70                  75                  80

Leu Leu Met Cys Cys Leu Thr Leu Pro Val Phe Pro Leu Val Ala Leu
                 85                  90                  95

Met Ala Glu Lys Leu Ile Thr Arg Lys Leu Ile Gly Glu His Val Val
            100                 105                 110

Ile Leu Leu His Ile Ile Ile Thr Thr Ser Ala Ile Val Tyr Pro Val
            115                 120                 125

Val Val Thr Leu Lys Cys Asp Ser Ala Val Leu Ser Gly Phe Val Leu
            130                 135                 140

Met Phe Leu Ala Ser Ile Met Trp Met Lys Leu Val Ser Tyr Ala His
145                 150                 155                 160

Thr Asn Tyr Asp Ile Arg Val Leu Ser Lys Ser Thr Glu Lys Gly Ala
                165                 170                 175

Ala Tyr Gly Asn Tyr Val Asp Pro Glu Asn Met Lys Asp Pro Thr Phe
                180                 185                 190

Lys Ser Leu Val Tyr Phe Met Leu Ala Pro Thr Leu Cys Tyr Gln Pro
            195                 200                 205

Thr Tyr Pro Gln Thr Thr Cys Ile Arg Lys Gly Trp Val Thr Gln Gln
210                 215                 220

Leu Ile Lys Cys Val Val Phe Thr Gly Leu Met Gly Phe Ile Ile Glu
225                 230                 235                 240

Gln Tyr Ile Asn Pro Ile Val Lys Asn Ser Lys His Pro Leu Lys Gly
                245                 250                 255

Asn Phe Leu Asn Ala Ile Glu Arg Val Leu Lys Leu Ser Val Pro Thr
            260                 265                 270

Leu Tyr Val Trp Leu Cys Met Phe Tyr Cys Phe Phe His Leu Trp Leu
            275                 280                 285

Asn Ile Val Ala Glu Leu Leu Cys Phe Gly Asp Arg Glu Phe Tyr Lys
290                 295                 300

Asp Trp Trp Asn Ala Lys Thr Val Glu Glu Tyr Trp Arg Met Trp Asn
305                 310                 315                 320

Met Pro Val His Lys Trp Ile Ile Arg His Ile Tyr Phe Pro Cys Ile
                325                 330                 335

Arg Lys Gly Phe Ser Arg Gly Val Ala Ile Leu Ile Ser Phe Leu Val
            340                 345                 350

Ser Ala Val Phe His Glu Ile Cys Ile Ala Val Pro Cys His Ile Phe
            355                 360                 365

Lys Phe Trp Ala Phe Ser Gly Ile Met Phe Gln Ile Pro Leu Val Phe
            370                 375                 380

Leu Thr Arg Tyr Leu His Ala Thr Phe Lys His Val Met Val Gly Asn
385                 390                 395                 400

Met Ile Phe Trp Phe Phe Ser Ile Val Gly Gln Pro Met Cys Val
                405                 410                 415

Leu Leu Tyr Tyr His Asp Val Met Asn Arg Gln Ala Gln Ala Ser Arg
            420                 425                 430

Ala Lys Gly Glu Leu Arg Gly His Pro Phe Glu Gly Lys Pro Ile Pro
            435                 440                 445

Asn Pro Leu Leu Gly Leu Asp Ser Thr Arg Thr Gly His His His
            450                 455                 460

His His
465
```

```
<210> SEQ ID NO 66
<211> LENGTH: 465
<212> TYPE: PRT
<213> ORGANISM: Artificial Sequence
<220> FEATURE:
<223> OTHER INFORMATION: Z. mays-L

<400> SEQUENCE: 66

Met Gly Gly Gly Ser Ser Ala Phe Thr Phe Arg Ala Ala Ala Pro Val
1               5                   10                  15

His Arg Lys Ala Lys Glu Ser Pro Leu Ser Ser Asp Ala Ile Phe Lys
            20                  25                  30

Gln Ser His Ala Gly Leu Phe Asn Leu Cys Ile Val Val Leu Val Ala
        35                  40                  45

Val Asn Ser Arg Leu Ile Ile Glu Asn Leu Met Lys Tyr Gly Leu Leu
    50                  55                  60

Ile Arg Ser Gly Phe Trp Phe Asn Ala Thr Ser Leu Arg Asp Trp Pro
65                  70                  75                  80

Leu Leu Met Cys Cys Leu Ser Leu Pro Ile Phe Pro Leu Gly Ala Phe
                85                  90                  95

Ala Val Glu Lys Leu Ala Phe Asn Asn Leu Ile Ser Asp Pro Ala Thr
            100                 105                 110

Thr Cys Phe His Ile Leu Phe Thr Thr Phe Glu Ile Val Tyr Pro Val
        115                 120                 125

Leu Val Ile Leu Lys Cys Asp Ser Ala Val Leu Ser Gly Phe Val Leu
    130                 135                 140

Met Phe Ile Ala Cys Ile Val Trp Leu Lys Leu Val Ser Phe Ala His
145                 150                 155                 160

Thr Asn His Asp Ile Arg Lys Leu Ile Thr Ser Gly Lys Lys Val Asp
                165                 170                 175

Asn Glu Leu Thr Ala Ala Gly Ile Asp Asn Leu Gln Ala Pro Thr Leu
            180                 185                 190

Gly Ser Leu Thr Tyr Phe Met Met Ala Pro Thr Leu Cys Tyr Gln Pro
        195                 200                 205

Ser Tyr Pro Arg Thr Pro Tyr Val Arg Lys Gly Trp Leu Val Arg Gln
    210                 215                 220

Val Ile Leu Tyr Leu Ile Phe Thr Gly Leu Gln Gly Phe Ile Ile Glu
225                 230                 235                 240

Gln Tyr Ile Asn Pro Ile Val Val Asn Ser Gln His Pro Leu Met Gly
                245                 250                 255

Gly Leu Leu Asn Ala Val Glu Thr Val Leu Lys Leu Ser Leu Pro Asn
            260                 265                 270

Val Tyr Leu Trp Leu Cys Met Phe Tyr Cys Leu Phe His Leu Trp Leu
        275                 280                 285

Asn Ile Leu Ala Glu Ile Leu Arg Phe Gly Asp Arg Glu Phe Tyr Lys
    290                 295                 300

Asp Trp Trp Asn Ala Lys Thr Ile Asp Glu Tyr Trp Arg Lys Trp Asn
305                 310                 315                 320

Met Pro Val His Lys Trp Ile Val Arg His Ile Tyr Phe Pro Cys Met
                325                 330                 335

Arg Asn Gly Ile Ser Lys Glu Val Ala Val Phe Ile Ser Phe Phe Val
            340                 345                 350

Ser Ala Val Leu His Glu Leu Cys Val Ala Val Pro Cys His Ile Leu
        355                 360                 365

Lys Phe Trp Ala Phe Leu Gly Ile Met Leu Gln Ile Pro Leu Ile Ile
```

```
                    370                 375                 380
Leu Thr Ser Tyr Leu Lys Asn Lys Phe Ser Asp Thr Met Val Gly Asn
385                 390                 395                 400

Met Ile Phe Trp Phe Phe Cys Ile Tyr Gly Gln Pro Met Cys Val
                405                 410                 415

Leu Leu Tyr Tyr His Asp Val Met Asn Arg Thr Glu Lys Ala Lys Ala
                420                 425                 430

Lys Gly Glu Leu Arg Gly His Pro Phe Glu Lys Pro Ile Pro Asn
                435                 440                 445

Pro Leu Leu Gly Leu Asp Ser Thr Arg Thr Gly His His His His
                450                 455                 460

His
465

<210> SEQ ID NO 67
<211> LENGTH: 554
<212> TYPE: PRT
<213> ORGANISM: Artificial Sequence
<220> FEATURE:
<223> OTHER INFORMATION: A. thaliana

<400> SEQUENCE: 67

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
                20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
        50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
            130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
                180                 185                 190

Phe Thr Val Glu Lys Leu Val Leu Gln Lys Tyr Ile Ser Glu Pro Val
                195                 200                 205

Val Ile Phe Leu His Ile Ile Ile Thr Met Thr Glu Val Leu Tyr Pro
            210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255

His Thr Ser Tyr Asp Ile Arg Ser Leu Ala Asn Ala Ala Asp Lys Ala
```

```
            260                 265                 270
Asn Pro Glu Val Ser Tyr Tyr Val Ser Leu Lys Ser Leu Ala Tyr Phe
        275                 280                 285

Met Val Ala Pro Thr Leu Cys Tyr Gln Pro Ser Tyr Pro Arg Ser Ala
        290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                    325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
            370                 375                 380

Leu Cys Phe Gly Asp Arg Glu Phe Tyr Lys Asp Trp Trp Asn Ala Lys
385                 390                 395                 400

Ser Val Gly Asp Tyr Trp Arg Met Trp Asn Met Pro Val His Lys Trp
                    405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
                435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                    485                 490                 495

Cys Ile Phe Gly Gln Pro Met Cys Val Leu Leu Tyr Tyr His Asp Leu
                500                 505                 510

Met Asn Arg Lys Gly Ser Met Ser Ala Lys Gly Glu Leu Arg Gly His
                515                 520                 525

Pro Phe Glu Gly Lys Pro Ile Pro Asn Pro Leu Leu Gly Leu Asp Ser
        530                 535                 540

Thr Arg Thr Gly His His His His His His
545                 550

<210> SEQ ID NO 68
<211> LENGTH: 552
<212> TYPE: PRT
<213> ORGANISM: Artificial Sequence
<220> FEATURE:
<223> OTHER INFORMATION: T. majus

<400> SEQUENCE: 68

Met Ala Val Ala Glu Ser Ser Gln Asn Thr Thr Thr Met Ser Gly His
1               5                   10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
                35                  40                  45

Ala Thr Gly His Val Ala Glu Asn Arg Asp Gln Asp Arg Val Gly Ala
            50                  55                  60

Met Glu Asn Ala Thr Gly Ser Val Asn Leu Ile Gly Asn Gly Gly Gly
```

```
                65                  70                  75                  80
        Val Val Ile Gly Asn Glu Glu Lys Gln Val Gly Glu Thr Asp Ile Arg
                            85                  90                  95

Phe Thr Tyr Arg Pro Ser Phe Pro Ala His Arg Arg Val Arg Glu Ser
                           100                 105                 110

Pro Leu Ser Ser Asp Ala Ile Phe Lys Gln Ser His Ala Gly Leu Phe
                           115                 120                 125

Asn Leu Cys Ile Val Val Leu Ile Ala Val Asn Ser Arg Leu Ile Ile
                           130                 135                 140

Glu Asn Leu Met Lys Tyr Gly Trp Leu Ile Asp Thr Gly Phe Trp Phe
        145                 150                 155                 160

Ser Ser Arg Ser Leu Gly Asp Trp Ser Ile Phe Met Cys Cys Leu Thr
                           165                 170                 175

Leu Pro Ile Phe Pro Leu Ala Ala Phe Ile Val Glu Lys Leu Val Gln
                           180                 185                 190

Arg Asn His Ile Ser Glu Leu Val Ala Val Leu Leu His Val Ile Val
                           195                 200                 205

Ser Thr Ala Ala Val Leu Tyr Pro Val Ile Val Ile Leu Thr Cys Asp
                           210                 215                 220

Ser Val Tyr Met Ser Gly Val Val Leu Met Leu Phe Gly Cys Ile Met
        225                 230                 235                 240

Trp Leu Lys Leu Val Ser Tyr Ala His Thr Ser Ser Asp Ile Arg Thr
                           245                 250                 255

Leu Ala Lys Ser Gly Tyr Lys Gly Asp Ala His Pro Asn Ser Thr Ile
                           260                 265                 270

Val Ser Cys Ser Tyr Asp Val Ser Leu Lys Ser Leu Ala Tyr Phe Met
                           275                 280                 285

Val Ala Pro Thr Leu Cys Tyr Gln Pro Ser Tyr Pro Arg Ser Ser Cys
                           290                 295                 300

Ile Arg Lys Gly Trp Val Val Arg Gln Phe Val Lys Leu Ile Val Phe
        305                 310                 315                 320

Ile Gly Leu Met Gly Phe Ile Ile Glu Gln Tyr Ile Asn Pro Ile Val
                           325                 330                 335

Arg Asn Ser Lys His Pro Leu Lys Gly Asp Phe Leu Tyr Ala Ile Glu
                           340                 345                 350

Arg Val Leu Lys Leu Ser Val Pro Asn Leu Tyr Val Trp Leu Cys Met
                           355                 360                 365

Phe Tyr Ser Phe Phe His Leu Trp Leu Asn Ile Leu Ala Glu Leu Leu
                           370                 375                 380

Arg Phe Gly Asp Arg Glu Phe Tyr Lys Asp Trp Trp Asn Ala Lys Thr
        385                 390                 395                 400

Val Ala Glu Tyr Trp Lys Met Trp Asn Met Pro Val His Arg Trp Met
                           405                 410                 415

Val Arg His Leu Tyr Phe Pro Cys Leu Arg Asn Gly Ile Pro Lys Glu
                           420                 425                 430

Gly Ala Ile Ile Ile Ala Phe Leu Val Ser Gly Ala Phe His Glu Leu
                           435                 440                 445

Cys Ile Ala Val Pro Cys His Val Phe Lys Leu Trp Ala Phe Ile Gly
                           450                 455                 460

Ile Met Phe Gln Val Pro Leu Val Leu Ile Thr Asn Tyr Leu Gln Glu
        465                 470                 475                 480

Lys Phe Ser Asn Ser Met Val Gly Asn Met Ile Phe Trp Phe Ile Phe
                           485                 490                 495
```

-continued

```
Cys Ile Leu Gly Gln Pro Met Cys Val Leu Tyr Tyr His Asp Leu
            500                 505                 510

Ile Asn Leu Lys Glu Lys Ala Lys Gly Glu Leu Arg Gly His Pro Phe
        515                 520                 525

Glu Gly Lys Pro Ile Pro Asn Pro Leu Leu Gly Leu Asp Ser Thr Arg
    530                 535                 540

Thr Gly His His His His His His
545                 550

<210> SEQ ID NO 69
<211> LENGTH: 511
<212> TYPE: PRT
<213> ORGANISM: Artificial Sequence
<220> FEATURE:
<223> OTHER INFORMATION: O. sativa-S

<400> SEQUENCE: 69

Met Ala Pro Pro Pro Ser Leu Ala Pro Asp Arg Gly Gly Glu Pro
1               5                   10                  15

Asp Asp Ala Leu Arg Leu Arg Ala Arg Ala Ala Ala Ala Gly Asp
            20                  25                  30

Ala Pro Ala Pro Gln Gln Gln Glu Gln Arg His Gln Glu Gln Gln
        35                  40                  45

Gln Gln Leu Leu Trp Tyr Arg Ala Ser Ala Pro Ala His Arg Arg Val
    50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Leu Val Ala Val Asn Ser Arg
                85                  90                  95

Leu Ile Ile Glu Asn Leu Met Lys Tyr Gly Leu Leu Ile Arg Ala Gly
            100                 105                 110

Phe Trp Phe Ser Gly Thr Ser Leu Ala Asp Trp Pro Leu Leu Met Cys
        115                 120                 125

Cys Leu Thr Leu Pro Thr Phe Pro Leu Ala Ala Leu Met Val Glu Lys
130                 135                 140

Leu Ala Gln Arg Lys Leu Ile Ser Lys His Val Val Ile Leu Leu His
145                 150                 155                 160

Ile Val Ile Thr Thr Ser Val Leu Val Tyr Pro Val Val Ile Leu
                165                 170                 175

Lys Cys Asp Ser Ala Val Leu Ser Gly Phe Val Leu Met Phe Leu Ala
            180                 185                 190

Ser Ile Ile Trp Leu Lys Leu Val Ser Phe Ala His Thr Asn Tyr Asp
        195                 200                 205

Ile Arg Met Leu Ser Lys Ser Ile Glu Lys Gly Val Thr His Asp Ile
    210                 215                 220

Ser Ile Asp Pro Glu Asn Ile Lys Trp Pro Thr Phe Lys Arg Leu Ser
225                 230                 235                 240

Tyr Phe Met Leu Ala Pro Thr Leu Cys Tyr Gln Pro Ser Tyr Pro Arg
                245                 250                 255

Thr Thr Tyr Ile Arg Lys Gly Trp Val Val Arg Gln Leu Ile Lys Cys
            260                 265                 270

Leu Val Phe Thr Gly Leu Met Gly Phe Ile Ile Glu Gln Tyr Ile Asn
        275                 280                 285

Pro Ile Val Lys Asn Ser Lys His Pro Leu Lys Gly Asn Phe Leu Asn
    290                 295                 300
```

```
Ala Ile Glu Arg Val Leu Lys Leu Ser Val Pro Thr Leu Tyr Val Trp
305                 310                 315                 320

Leu Cys Met Phe Tyr Cys Phe Phe His Leu Trp Leu Asn Ile Leu Ala
                325                 330                 335

Glu Leu Leu Cys Phe Gly Asp Arg Glu Phe Tyr Lys Asp Trp Trp Asn
            340                 345                 350

Ala Lys Thr Val Glu Glu Tyr Trp Arg Met Trp Asn Met Pro Val His
        355                 360                 365

Lys Trp Val Ile Arg His Ile Tyr Phe Pro Cys Ile Arg Asn Gly Phe
    370                 375                 380

Ser Lys Gly Val Ala Ile Leu Ile Ser Phe Leu Val Ser Ala Ala Phe
385                 390                 395                 400

His Glu Leu Cys Val Ala Val Pro Cys His Ile Phe Lys Phe Trp Ala
                405                 410                 415

Phe Ile Gly Ile Met Phe Gln Ile Pro Leu Val Phe Leu Thr Lys Tyr
            420                 425                 430

Leu Gln Asp Lys Phe Asn Asn Thr Met Val Gly Asn Met Ile Phe Trp
        435                 440                 445

Phe Phe Phe Ser Ile Leu Gly Gln Pro Met Cys Val Leu Leu Tyr Tyr
    450                 455                 460

His Asp Val Met Asn Arg Gln Gln Ala Gln Thr Asn Arg Ala Lys Gly
465                 470                 475                 480

Glu Leu Arg Gly His Pro Phe Glu Gly Lys Pro Ile Pro Asn Pro Leu
                485                 490                 495

Leu Gly Leu Asp Ser Thr Arg Thr Gly His His His His His
            500                 505                 510

<210> SEQ ID NO 70
<211> LENGTH: 572
<212> TYPE: PRT
<213> ORGANISM: Artificial Sequence
<220> FEATURE:
<223> OTHER INFORMATION: O. sativa-L

<400> SEQUENCE: 70

Met Val Gly Ser Asp Gly Asp Gly Asp Gly Gly Gly Gly Glu Ala His
1               5                   10                  15

Ala Pro Ala Ala Pro Ala His His Arg Arg Pro Pro Arg Pro Arg
                20                  25                  30

Gly Gly Ser Gly Ala Ile Val Glu Gly Phe Ala Ala Ala Leu Arg Arg
            35                  40                  45

Arg Ile Arg Ser Gly Ala Ala Ala Ala Arg Ala Ser Phe Gly Gly
    50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160
```

```
Ile Ile Glu Asn Leu Met Lys Tyr Gly Leu Ile Arg Ala Gly Phe
            165                 170                 175

Trp Phe Asn Asp Lys Ser Leu Arg Asp Trp Pro Leu Leu Met Cys Cys
            180                 185                 190

Leu Ser Leu Pro Ala Phe Pro Leu Gly Ala Phe Ala Val Glu Lys Leu
            195                 200                 205

Ala Phe Asn Asn Val Ile Thr Asp Ala Val Ala Thr Cys Leu His Ile
210                 215                 220

Phe Leu Ser Thr Thr Glu Ile Val Tyr Pro Val Leu Val Ile Leu Lys
225                 230                 235                 240

Cys Asp Ser Ala Val Leu Ser Gly Phe Leu Leu Ile Phe Ile Ala Cys
            245                 250                 255

Ile Val Trp Leu Lys Leu Val Ser Phe Ala His Thr Asn His Asp Ile
            260                 265                 270

Arg Gln Leu Thr Met Gly Gly Lys Val Asp Asn Glu Leu Ser Thr
            275                 280                 285

Val Asp Met Asp Asn Leu Gln Pro Pro Thr Leu Gly Asn Leu Ile Tyr
290                 295                 300

Phe Met Met Ala Pro Thr Leu Cys Tyr Gln Pro Ser Tyr Pro Arg Thr
305                 310                 315                 320

Ser Cys Val Arg Lys Gly Trp Leu Ile Arg Gln Ile Ile Leu Tyr Leu
            325                 330                 335

Ile Phe Thr Gly Leu Gln Gly Phe Ile Ile Glu Gln Tyr Ile Asn Pro
            340                 345                 350

Ile Val Val Asn Ser Gln His Pro Leu Lys Gly Gly Leu Leu Asn Ala
            355                 360                 365

Val Glu Thr Val Leu Lys Leu Ser Leu Pro Asn Val Tyr Leu Trp Leu
370                 375                 380

Cys Met Phe Tyr Ala Phe Phe His Leu Trp Leu Ser Ile Leu Ala Glu
385                 390                 395                 400

Ile Leu Arg Phe Gly Asp Arg Glu Phe Tyr Lys Asp Trp Trp Asn Ala
            405                 410                 415

Lys Thr Ile Asp Glu Tyr Trp Arg Lys Trp Asn Met Pro Val His Lys
            420                 425                 430

Trp Val Val Arg His Ile Tyr Phe Pro Cys Met Arg Asn Gly Ile Ser
            435                 440                 445

Lys Glu Val Ala Val Leu Ile Ser Phe Leu Val Ser Ala Val Leu His
    450                 455                 460

Glu Ile Cys Val Ala Val Pro Cys Arg Ile Leu Lys Phe Trp Ala Phe
465                 470                 475                 480

Leu Gly Ile Met Leu Gln Ile Pro Leu Ile Val Leu Thr Ala Tyr Leu
            485                 490                 495

Lys Ser Lys Phe Arg Asp Thr Met Val Gly Asn Met Ile Phe Trp Phe
            500                 505                 510

Phe Phe Cys Ile Tyr Gly Gln Pro Met Cys Leu Leu Leu Tyr Tyr His
            515                 520                 525

Asp Val Met Asn Arg Ile Glu Lys Ala Arg Ala Lys Gly Glu Leu Arg
530                 535                 540

Gly His Pro Phe Glu Gly Lys Pro Ile Pro Asn Pro Leu Leu Gly Leu
545                 550                 555                 560

Asp Ser Thr Arg Thr Gly His His His His His
            565                 570
```

```
<210> SEQ ID NO 71
<211> LENGTH: 528
<212> TYPE: PRT
<213> ORGANISM: Artificial Sequence
<220> FEATURE:
<223> OTHER INFORMATION: Z. mays-S

<400> SEQUENCE: 71

Met Ala Pro Pro Ser Met Pro Ala Ser Asp Arg Ala Gly Pro
1               5                   10                  15

Gly Arg Asp Ala Gly Asp Ser Ser Leu Arg Leu Arg Arg Ala Pro
                20                  25                  30

Ser Ala Asp Ala Gly Asp Leu Ala Gly Asp Ser Ser Gly Gly Leu Arg
            35                  40                  45

Glu Asn Gly Glu Pro Gln Ser Pro Thr Asn Pro Pro Gln Glu Gln
        50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys Tyr Gly Leu Leu Ile Arg
        115                 120                 125

Ala Gly Phe Trp Phe Ser Ala Arg Ser Leu Gly Asp Trp Pro Leu Leu
    130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
            180                 185                 190

Thr Leu Lys Cys Asp Ser Ala Val Leu Ser Gly Phe Val Leu Met Phe
        195                 200                 205

Leu Ala Ser Ile Met Trp Met Lys Leu Val Ser Tyr Ala His Thr Asn
    210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
            260                 265                 270

Pro Gln Thr Thr Cys Ile Arg Lys Gly Trp Val Thr Gln Gln Leu Ile
        275                 280                 285

Lys Cys Val Val Phe Thr Gly Leu Met Gly Phe Ile Ile Glu Gln Tyr
    290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
            340                 345                 350

Val Ala Glu Leu Leu Cys Phe Gly Asp Arg Glu Phe Tyr Lys Asp Trp
        355                 360                 365
```

```
Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
                405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
                435                 440                 445

Arg Tyr Leu His Ala Thr Phe Lys His Val Met Val Gly Asn Met Ile
    450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg Ala Lys
                485                 490                 495

Gly Glu Leu Arg Gly His Pro Phe Glu Gly Lys Pro Ile Pro Asn Pro
                500                 505                 510

Leu Leu Gly Leu Asp Ser Thr Arg Thr Gly His His His His His His
                515                 520                 525

<210> SEQ ID NO 72
<211> LENGTH: 546
<212> TYPE: PRT
<213> ORGANISM: Artificial Sequence
<220> FEATURE:
<223> OTHER INFORMATION: Z. mays-L

<400> SEQUENCE: 72

Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
                20                  25                  30

Arg Arg Arg Leu Arg Ser Gly Ala Ala Val Ala Ala Arg Ala Ser Phe
            35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
                100                 105                 110

Lys Gln Ser His Ala Gly Leu Phe Asn Leu Cys Ile Val Val Leu Val
            115                 120                 125

Ala Val Asn Ser Arg Leu Ile Ile Glu Asn Leu Met Lys Tyr Gly Leu
    130                 135                 140

Leu Ile Arg Ser Gly Phe Trp Phe Asn Ala Thr Ser Leu Arg Asp Trp
145                 150                 155                 160

Pro Leu Leu Met Cys Cys Leu Ser Leu Pro Ile Phe Pro Leu Gly Ala
                165                 170                 175

Phe Ala Val Glu Lys Leu Ala Phe Asn Asn Leu Ile Ser Asp Pro Ala
                180                 185                 190

Thr Thr Cys Phe His Ile Leu Phe Thr Thr Phe Glu Ile Val Tyr Pro
            195                 200                 205
```

Val Leu Val Ile Leu Lys Cys Asp Ser Ala Val Leu Ser Gly Phe Val
    210                 215                 220
Leu Met Phe Ile Ala Cys Ile Val Trp Leu Lys Leu Val Ser Phe Ala
225                 230                 235                 240
His Thr Asn His Asp Ile Arg Lys Leu Ile Thr Ser Gly Lys Lys Val
                245                 250                 255
Asp Asn Glu Leu Thr Ala Ala Gly Ile Asp Asn Leu Gln Ala Pro Thr
            260                 265                 270
Leu Gly Ser Leu Thr Tyr Phe Met Met Ala Pro Thr Leu Cys Tyr Gln
        275                 280                 285
Pro Ser Tyr Pro Arg Thr Pro Tyr Val Arg Lys Gly Trp Leu Val Arg
    290                 295                 300
Gln Val Ile Leu Tyr Leu Ile Phe Thr Gly Leu Gln Gly Phe Ile Ile
305                 310                 315                 320
Glu Gln Tyr Ile Asn Pro Ile Val Asn Ser Gln His Pro Leu Met
                325                 330                 335
Gly Gly Leu Leu Asn Ala Val Glu Thr Val Leu Lys Leu Ser Leu Pro
            340                 345                 350
Asn Val Tyr Leu Trp Leu Cys Met Phe Tyr Cys Leu Phe His Leu Trp
        355                 360                 365
Leu Asn Ile Leu Ala Glu Ile Leu Arg Phe Gly Asp Arg Glu Phe Tyr
    370                 375                 380
Lys Asp Trp Trp Asn Ala Lys Thr Ile Asp Glu Tyr Trp Arg Lys Trp
385                 390                 395                 400
Asn Met Pro Val His Lys Trp Ile Val Arg His Ile Tyr Phe Pro Cys
                405                 410                 415
Met Arg Asn Gly Ile Ser Lys Glu Val Ala Val Phe Ile Ser Phe Phe
            420                 425                 430
Val Ser Ala Val Leu His Glu Leu Cys Val Ala Val Pro Cys His Ile
        435                 440                 445
Leu Lys Phe Trp Ala Phe Leu Gly Ile Met Leu Gln Ile Pro Leu Ile
    450                 455                 460
Ile Leu Thr Ser Tyr Leu Lys Asn Lys Phe Ser Asp Thr Met Val Gly
465                 470                 475                 480
Asn Met Ile Phe Trp Phe Phe Phe Cys Ile Tyr Gly Gln Pro Met Cys
                485                 490                 495
Val Leu Leu Tyr Tyr His Asp Val Met Asn Arg Thr Glu Lys Ala Lys
            500                 505                 510
Ala Lys Gly Glu Leu Arg Gly His Pro Phe Glu Gly Lys Pro Ile Pro
        515                 520                 525
Asn Pro Leu Leu Gly Leu Asp Ser Thr Arg Thr Gly His His His
    530                 535                 540
His His
545

<210> SEQ ID NO 73
<211> LENGTH: 102
<212> TYPE: DNA
<213> ORGANISM: Arabidopsis thaliana

<400> SEQUENCE: 73
gtaaaagaag atgttttta tttccagcaa tgttacattg ttatacgtat aatgatgagt    60
ttagtgatca agttcctctt tgattcttct ttcttgttgc ag                      102

<210> SEQ ID NO 74
<211> LENGTH: 1743
<212> TYPE: DNA
<213> ORGANISM: Artificial Sequence
<220> FEATURE:
<223> OTHER INFORMATION: Brassica optimised

<400> SEQUENCE: 74

```
atggctgatt ctgaggatgc tcctcctgct gttcatagaa ggcctccaag acctgctaga      60
ggtgctgctg ctgctgtaaa agaagatgtt ttttatttcc agcaatgtta cattgttata     120
cgtataatga tgagtttagt gatcaagttc ctctttgatt cttctttctt gttgcagcaa     180
ggattcgctc tgctcttag aagaaggctt agaagcggag ctgctgttgc tgctagagct      240
tctttcgctg ctgattctgg tgatgagtct ggacctggtg agccttcttc atctaggcgt     300
agagataact ctggtggagc ttcttctgct gctggtggta gagctggtgc tggtgatttc     360
tctgctttca ccttcagagc tgctgctcct gttcacagaa aggctaaaga atctccactc     420
tcgagtgatg ctatcttcaa gcagtctcac gctggacttt tcaacctctg catcgttgtt     480
cttgttgctg tgaacagcag actcatcatc gagaacctca tgaagtacgg acttctcatc     540
agatctggat tctggttcaa cgctaccctc ttagagatt ggcctcttct tatgtgctgt      600
ctctctcttc caatcttccc tcttggtgct ttcgctgttg agaagcttgc tttcaacaac     660
ctcatctctg atcctgctac tacttgcttc cacatccttt tcactacctt cgagatcgtt     720
taccctgttc tcgttatcct taaatgcgat tctgctgttc tttctggatt cgtgctcatg     780
ttcattgctt gcatcgtttg gcttaagctc gtttctttcg ctcacactaa ccacgatatc     840
agaaagctca tcacctctgg aaagaaggtt gacaacgagc ttactgctgc tggaatcgat     900
aaccttcagg ctcctactct tggatctctc acctacttca tgatggctcc taccctttgt     960
taccaacctt cttaccctag aaccccttac gttagaaagg gatggcttgt tagacaggtt    1020
atcctctacc ttatcttcac tggacttcag ggattcatca tcgagcagta catcaaccct    1080
atcgttgtta actctcagca tcctcttatg ggaggacttc ttaacgctgt tgagactgtg    1140
cttaagcttt ctctccctaa cgtttacctt tggctctgta tgttctactg cctttttccac   1200
ctttggctta acatccttgc tgagatcctt agattcggag acagagagtt ctacaaggat    1260
tggtggaacg ctaagactat cgatgagtac tggcgtaagt ggaacatgcc tgttcataag    1320
tggatcgtga ggcatatcta cttcccttgc atgagaaacg aatctctaa agaggttgcc     1380
gttttcatct ctttcttcgt gtctgctgtt ctccatgagc tttgtgttgc tgttccttgc    1440
cacatcctta agttctgggc tttccttgga atcatgcttc agatccctct tatcatcctt    1500
accagctacc tcaagaacaa gttctctgat accatggtgg aaacatgat tttctggttc     1560
ttttctgca tctacggaca acctatgtgt gttcttctct actaccacga tgttatgaac     1620
agaaccgaga aggccaaggc taagggtgag cttagaggtc atcctttcga gggtaagcct    1680
atccctaacc ctcttctcgg tctcgattct actagaactg gtcatcatca tcaccatcac    1740
tga                                                                  1743
```

<210> SEQ ID NO 75
<211> LENGTH: 1641
<212> TYPE: DNA
<213> ORGANISM: Artificial Sequence
<220> FEATURE:
<223> OTHER INFORMATION: Brassica optimised

<400> SEQUENCE: 75

```
atggctgatt ctgaggatgc tcctcctgct gttcatagaa ggcctccaag acctgctaga    60
ggtgctgctg ctgctcaagg attcgctgct gctcttagaa gaaggcttag aagcggagct   120
gctgttgctg ctagagcttc tttcgctgct gattctggtg atgagtctgg acctggtgag   180
ccttcttcat ctaggcgtag agataactct ggtggagctt cttctgctgc tggtggtaga   240
gctggtgctg gtgatttctc tgctttcacc ttcagagctg ctgctcctgt tcacagaaag   300
gctaaagaat ctccactctc gagtgatgct atcttcaagc agtctcacgc tggactttc   360
aacctctgca tcgttgttct tgttgctgtg aacagcagac tcatcatcga aacctcatg   420
aagtacggac ttctcatcag atctggattc tggttcaacg ctacctctct tagagattgg   480
cctcttctta tgtgctgtct ctctcttcca atcttccctc ttggtgcttt cgctgttgag   540
aagcttgctt tcaacaacct catctctgat cctgctacta cttgcttcca catccttttc   600
actaccttcg agatcgttta ccctgttctc gttatcctta aatgcgattc tgctgttctt   660
tctggattcg tgctcatgtt cattgcttgc atcgtttggc ttaagctcgt ttctttcgct   720
cacactaacc acgatatcag aaagctcatc acctctggaa agaaggttga caacgagctt   780
actgctgctg aatcgataa ccttcaggct cctactcttg gatctctcac ctacttcatg   840
atggctccta cctttgtta ccaaccttct taccctagaa ccccttacgt tagaaaggga   900
tggcttgtta gacaggttat cctctacctt atcttcactg gacttcaggg attcatcatc   960
gagcagtaca tcaaccctat cgttgttaac tctcagcatc ctcttatggg aggacttctt  1020
aacgctgttg agactgtgct taagcttct ctccctaacg tttaccttgg ctctgtatg  1080
ttctactgcc ttttccacct ttggcttaac atccttgctg agatcctag attcggagac  1140
agagagttct acaaggattg gtggaacgct aagactatcg atgagtactg gcgtaagtgg  1200
aacatgcctt tcataagtg gatcgtgagg catatctact tcccttgcat gagaaacgga  1260
atctctaaag aggttgccgt tttcatctct ttcttcgtgt ctgctgttct ccatgagctt  1320
tgtgttgctg ttccttgcca catccttaag ttctgggctt ccttggaat catgcttcag  1380
atccctctta tcatccttac cagctacctc aagaacaagt tctctgatac catggtggga  1440
aacatgatt tctggttctt tttctgcatc tacggacaac ctatgtgtgt tcttctctac  1500
taccacgatg ttatgaacag aaccgagaag gccaaggcta agggtgagct tagaggtcat  1560
cctttcgagg gtaagcctat ccctaacct cttctcggtc tcgattctac tagaactggt  1620
catcatcatc accatcactg a                                             1641
```

<210> SEQ ID NO 76
<211> LENGTH: 546
<212> TYPE: PRT
<213> ORGANISM: Artificial Sequence
<220> FEATURE:
<223> OTHER INFORMATION: Brassica optimised

<400> SEQUENCE: 76

```
Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Leu
            20                  25                  30

Arg Arg Arg Leu Arg Ser Gly Ala Ala Val Ala Ala Arg Ala Ser Phe
        35                  40                  45

Ala Ala Asp Ser Gly Asp Glu Ser Gly Pro Gly Glu Pro Ser Ser Ser
    50                  55                  60

Arg Arg Arg Asp Asn Ser Gly Gly Ala Ser Ser Ala Ala Gly Gly Arg
```

```
            65                  70                  75                  80
Ala Gly Ala Gly Asp Phe Ser Ala Phe Thr Phe Arg Ala Ala Pro
                    85                  90                  95
Val His Arg Lys Ala Lys Glu Ser Pro Leu Ser Ser Asp Ala Ile Phe
                    100                 105                 110
Lys Gln Ser His Ala Gly Leu Phe Asn Leu Cys Ile Val Val Leu Val
                    115                 120                 125
Ala Val Asn Ser Arg Leu Ile Ile Glu Asn Leu Met Lys Tyr Gly Leu
                    130                 135                 140
Leu Ile Arg Ser Gly Phe Trp Phe Asn Ala Thr Ser Leu Arg Asp Trp
145                 150                 155                 160
Pro Leu Leu Met Cys Cys Leu Ser Leu Pro Ile Phe Pro Leu Gly Ala
                    165                 170                 175
Phe Ala Val Glu Lys Leu Ala Phe Asn Asn Leu Ile Ser Asp Pro Ala
                    180                 185                 190
Thr Thr Cys Phe His Ile Leu Phe Thr Thr Phe Glu Ile Val Tyr Pro
                    195                 200                 205
Val Leu Val Ile Leu Lys Cys Asp Ser Ala Val Leu Ser Gly Phe Val
                    210                 215                 220
Leu Met Phe Ile Ala Cys Ile Val Trp Leu Lys Leu Val Ser Phe Ala
225                 230                 235                 240
His Thr Asn His Asp Ile Arg Lys Leu Ile Thr Ser Gly Lys Lys Val
                    245                 250                 255
Asp Asn Glu Leu Thr Ala Ala Gly Ile Asp Asn Leu Gln Ala Pro Thr
                    260                 265                 270
Leu Gly Ser Leu Thr Tyr Phe Met Met Ala Pro Thr Leu Cys Tyr Gln
                    275                 280                 285
Pro Ser Tyr Pro Arg Thr Pro Tyr Val Arg Lys Gly Trp Leu Val Arg
                    290                 295                 300
Gln Val Ile Leu Tyr Leu Ile Phe Thr Gly Leu Gln Gly Phe Ile Ile
305                 310                 315                 320
Glu Gln Tyr Ile Asn Pro Ile Val Val Asn Ser Gln His Pro Leu Met
                    325                 330                 335
Gly Gly Leu Leu Asn Ala Val Glu Thr Val Leu Lys Leu Ser Leu Pro
                    340                 345                 350
Asn Val Tyr Leu Trp Leu Cys Met Phe Tyr Cys Leu Phe His Leu Trp
                    355                 360                 365
Leu Asn Ile Leu Ala Glu Ile Leu Arg Phe Gly Asp Arg Glu Phe Tyr
370                 375                 380
Lys Asp Trp Trp Asn Ala Lys Thr Ile Asp Glu Tyr Trp Arg Lys Trp
385                 390                 395                 400
Asn Met Pro Val His Lys Trp Ile Val Arg His Ile Tyr Phe Pro Cys
                    405                 410                 415
Met Arg Asn Gly Ile Ser Lys Glu Val Ala Val Phe Ile Ser Phe Phe
                    420                 425                 430
Val Ser Ala Val Leu His Glu Leu Cys Val Ala Val Pro Cys His Ile
                    435                 440                 445
Leu Lys Phe Trp Ala Phe Leu Gly Ile Met Leu Gln Ile Pro Leu Ile
                    450                 455                 460
Ile Leu Thr Ser Tyr Leu Lys Asn Lys Phe Ser Asp Thr Met Val Gly
465                 470                 475                 480
Asn Met Ile Phe Trp Phe Phe Cys Ile Tyr Gly Gln Pro Met Cys
                    485                 490                 495
```

Val Leu Leu Tyr Tyr His Asp Val Met Asn Arg Thr Glu Lys Ala Lys
            500                 505                 510

Ala Lys Gly Glu Leu Arg Gly His Pro Phe Glu Gly Lys Pro Ile Pro
        515                 520                 525

Asn Pro Leu Leu Gly Leu Asp Ser Thr Arg Thr Gly His His His
        530                 535                 540

His His
545

<210> SEQ ID NO 77
<211> LENGTH: 1500
<212> TYPE: DNA
<213> ORGANISM: Artificial Sequence
<220> FEATURE:
<223> OTHER INFORMATION: Brassica optimised

<400> SEQUENCE: 77

| | | | | |
|---|---|---|---|---|
| atgggtggtg gttcttctgc tttcaccttc agagctgctg ctcctgttca tagaaaggct | | | | 60 |
| aaagaatctc cacgtaaaag aagatgtttt ttatttccag caatgttaca ttgttatacg | | | | 120 |
| tataatgatg agtttagtga tcaagttcct ctttgattct tctttcttgt tgcagtctcg | | | | 180 |
| agtgatgcta tcttcaagca gtctcacgct ggacttttca acctctgcat cgttgttctt | | | | 240 |
| gttgctgtga acagcagact catcatcgag aacctcatga gtacggact tctcatcaga | | | | 300 |
| tctggattct ggttcaacgc tacctctctt agagattggc ctcttcttat gtgctgtctc | | | | 360 |
| tctcttccaa tcttccctct tggtgctttc gctgttgaga gcttgctttc aacaacctc | | | | 420 |
| atctctgatc ctgctactac ttgcttccac atccttttca ctaccttcga gatcgtttac | | | | 480 |
| cctgttctcg ttatccttaa atgcgattct gctgttcttt ctggattcgt gctcatgttc | | | | 540 |
| attgcttgca tcgtttggct taagctcgtt tctttcgctc acactaacca cgatatcaga | | | | 600 |
| aagctcatca cctctggaaa gaaggttgac aacgagctta ctgctgctgg aatcgataac | | | | 660 |
| cttcaggctc ctactcttgg atctctcacc tacttcatga tggctcctac cctttgttac | | | | 720 |
| caaccttctt accctagaac cccttacgtt agaaagggat ggcttgttag acaggttatc | | | | 780 |
| ctctacctta tcttcactgg acttcaggga ttcatcatcg agcagtacat caaccctatc | | | | 840 |
| gttgttaact ctcagcatcc tcttatggga ggacttctta acgctgttga gactgtgctt | | | | 900 |
| aagctttctc tccctaacgt ttaccttggg ctctgtatgt tctactgcct tttccacctt | | | | 960 |
| tggcttaaca tccttgctga gatccttaga ttcggagaca gagagttcta caaggattgg | | | | 1020 |
| tggaacgcta agactatcga tgagtactgg cgtaagtgga acatgcctgt tcataagtgg | | | | 1080 |
| atcgtgaggc atatctactt cccttgcatg agaaacggaa tctctaaaga ggttgccgtt | | | | 1140 |
| ttcatctctt tcttcgtgtc tgctgttctc catgagcttt gtgttgctgt tccttgccac | | | | 1200 |
| atccttaagt tctgggcttt ccttggaatc atgcttcaga tccctcttat catccttacc | | | | 1260 |
| agctacctca gaacaagtt ctctgatacc atggtgggaa acatgatttt ctggttcttt | | | | 1320 |
| ttctgcatct acggacaacc tatgtgtgtt cttctctact accacgatgt tatgaacaga | | | | 1380 |
| accgagaagg ccaaggctaa gggtgagctt agaggtcatc ctttcgaggg taagcctatc | | | | 1440 |
| cctaaccctc ttctcggtct cgattctact agaactggtc atcatcatca ccatcactga | | | | 1500 |

<210> SEQ ID NO 78
<211> LENGTH: 1398
<212> TYPE: DNA
<213> ORGANISM: Artificial Sequence
<220> FEATURE:

<223> OTHER INFORMATION: Brassica optimised

<400> SEQUENCE: 78

```
atgggtggtg gttcttctgc tttcaccttc agagctgctg ctcctgttca tagaaaggct      60
aaagaatctc cactctcgag tgatgctatc ttcaagcagt ctcacgctgg acttttcaac     120
ctctgcatcg ttgttcttgt tgctgtgaac agcagactca tcatcgagaa cctcatgaag     180
tacggacttc tcatcagatc tggattctgg ttcaacgcta cctctcttag agattggcct     240
cttcttatgt gctgtctctc tcttccaatc ttccctcttg gtgctttcgc tgttgagaag     300
cttgctttca caacctcat ctctgatcct gctactactt gcttccacat cctttcact      360
accttcgaga tcgtttaccc tgttctcgtt atccttaaat gcgattctgc tgttctttct     420
ggattcgtgc tcatgttcat tgcttgcatc gtttggctta agctcgtttc tttcgctcac     480
actaaccacg atatcagaaa gctcatcacc tctggaaaga aggttgacaa cgagcttact     540
gctgctggaa tcgataacct tcaggctcct actcttggat ctctcaccta cttcatgatg     600
gctcctaccc tttgttacca accttcttac cctagaaccc cttacgttag aaagggatgg     660
cttgttagac aggttatcct ctaccttatc ttcactggac ttcagggatt catcatcgag     720
cagtacatca accctatcgt tgttaactct cagcatcctc ttatgggagg acttcttaac     780
gctgttgaga ctgtgcttaa gctttctctc cctaacgttt acctttggct ctgtatgttc     840
tactgccttt tccaccttg gcttaacatc cttgctgaga tccttagatt cggagacaga     900
gagttctaca aggattggtg gaacgctaag actatcgatg agtactggcg taagtggaac     960
atgcctgttc ataagtggat cgtgaggcat atctacttcc cttgcatgag aaacggaatc    1020
tctaaagagg ttgccgtttt catctctttc ttcgtgtctg ctgttctcca tgagctttgt    1080
gttgctgttc cttgccacat ccttaagttc tgggctttcc ttggaatcat gcttcagatc    1140
cctcttatca tccttaccag ctacctcaag aacaagttct ctgataccat ggtgggaaac    1200
atgattttct ggttcttttt ctgcatctac ggacaaccta tgtgtgttct tctctactac    1260
cacgatgtta tgaacagaac cgagaaggcc aaggctaagg gtgagcttag aggtcatcct    1320
ttcgagggta agcctatccc taaccctctt ctcggtctcg attctactag aactggtcat    1380
catcatcacc atcactga                                                  1398
```

<210> SEQ ID NO 79
<211> LENGTH: 465
<212> TYPE: PRT
<213> ORGANISM: Artificial Sequence
<220> FEATURE:
<223> OTHER INFORMATION: Brassica optimised

<400> SEQUENCE: 79

```
Met Gly Gly Gly Ser Ser Ala Phe Thr Phe Arg Ala Ala Ala Pro Val
  1               5                  10                  15

His Arg Lys Ala Lys Glu Ser Pro Leu Ser Ser Asp Ala Ile Phe Lys
             20                  25                  30

Gln Ser His Ala Gly Leu Phe Asn Leu Cys Ile Val Val Leu Val Ala
         35                  40                  45

Val Asn Ser Arg Leu Ile Ile Glu Asn Leu Met Lys Tyr Gly Leu Leu
     50                  55                  60

Ile Arg Ser Gly Phe Trp Phe Asn Ala Thr Ser Leu Arg Asp Trp Pro
 65                  70                  75                  80

Leu Leu Met Cys Cys Leu Ser Leu Pro Ile Phe Pro Leu Gly Ala Phe
                 85                  90                  95
```

Ala Val Glu Lys Leu Ala Phe Asn Asn Leu Ile Ser Asp Pro Ala Thr
            100                 105                 110

Thr Cys Phe His Ile Leu Phe Thr Thr Phe Glu Ile Val Tyr Pro Val
            115                 120                 125

Leu Val Ile Leu Lys Cys Asp Ser Ala Val Leu Ser Gly Phe Val Leu
        130                 135                 140

Met Phe Ile Ala Cys Ile Val Trp Leu Lys Leu Val Ser Phe Ala His
145                 150                 155                 160

Thr Asn His Asp Ile Arg Lys Leu Ile Thr Ser Gly Lys Lys Val Asp
                165                 170                 175

Asn Glu Leu Thr Ala Ala Gly Ile Asp Asn Leu Gln Ala Pro Thr Leu
            180                 185                 190

Gly Ser Leu Thr Tyr Phe Met Met Ala Pro Thr Leu Cys Tyr Gln Pro
        195                 200                 205

Ser Tyr Pro Arg Thr Pro Tyr Val Arg Lys Gly Trp Leu Val Arg Gln
    210                 215                 220

Val Ile Leu Tyr Leu Ile Phe Thr Gly Leu Gln Gly Phe Ile Ile Glu
225                 230                 235                 240

Gln Tyr Ile Asn Pro Ile Val Val Asn Ser Gln His Pro Leu Met Gly
                245                 250                 255

Gly Leu Leu Asn Ala Val Glu Thr Val Leu Lys Leu Ser Leu Pro Asn
            260                 265                 270

Val Tyr Leu Trp Leu Cys Met Phe Tyr Cys Leu Phe His Leu Trp Leu
        275                 280                 285

Asn Ile Leu Ala Glu Ile Leu Arg Phe Gly Asp Arg Glu Phe Tyr Lys
    290                 295                 300

Asp Trp Trp Asn Ala Lys Thr Ile Asp Glu Tyr Trp Arg Lys Trp Asn
305                 310                 315                 320

Met Pro Val His Lys Trp Ile Val Arg His Ile Tyr Phe Pro Cys Met
                325                 330                 335

Arg Asn Gly Ile Ser Lys Glu Val Ala Val Phe Ile Ser Phe Phe Val
            340                 345                 350

Ser Ala Val Leu His Glu Leu Cys Val Ala Val Pro Cys His Ile Leu
        355                 360                 365

Lys Phe Trp Ala Phe Leu Gly Ile Met Leu Gln Ile Pro Leu Ile Ile
    370                 375                 380

Leu Thr Ser Tyr Leu Lys Asn Lys Phe Ser Asp Thr Met Val Gly Asn
385                 390                 395                 400

Met Ile Phe Trp Phe Phe Cys Ile Tyr Gly Gln Pro Met Cys Val
                405                 410                 415

Leu Leu Tyr Tyr His Asp Val Met Asn Arg Thr Glu Lys Ala Lys Ala
            420                 425                 430

Lys Gly Glu Leu Arg Gly His Pro Phe Glu Gly Lys Pro Ile Pro Asn
        435                 440                 445

Pro Leu Leu Gly Leu Asp Ser Thr Arg Thr Gly His His His His His
    450                 455                 460

His
465

<210> SEQ ID NO 80
<211> LENGTH: 1148
<212> TYPE: DNA
<213> ORGANISM: Brassica napus -continued

```
<400> SEQUENCE: 80
tttcttcatc ggtgattgat tcctttaaag acttatgttt cttatcttgc ttctgaggca       60
agtattcagt taccagttac cacttatatt ctggactttc tgactgcatc ctcatttttc     120
caacatttta aatttcacta ttggctgaat gcttcttctt tgaggaagaa acaattcaga     180
tggcagaaat gtatcaacca atgcatatat acaaatgtac ctcttgttct caaaacatct     240
atcggatggt tccatttgct tgtcatcca attagtgact actttatatt attcactcct     300
ctttattact atttttcatgc gaggttgcca tgtacattat atttgtaagg attgacgcta     360
ttgagcgttt ttcttcaatt ttctttattt tagacatggg tatgaaatgt gtgttagagt     420
tgggttgaat gagatatacg ttcaagtgaa gtggcatacc gttctcgagt aaggatgacc     480
tacccattct tgagacaaat gttacatttt agtatcagag taaatgtgt acctataact       540 caaattcgat tgacatgtat ccattcaaca taaaattaaa ccagcctgca cctgcatcca     600
catttcaagt attttcaaac cgttcggctc ctatccaccg ggtgtaacaa gacggattcc     660
gaatttggaa gattttgact caaattccca atttatattg accgtgacta aatcaacttt     720
aacttctata attctgatta agctcccaat ttatattccc aacggcacta cctccaaaat     780
ttatagactc tcatcccctt taaaccaac ttagtaaacg tttttttttt taattttatg      840
aagttaagtt tttaccttgt ttttaaaaag aatcgttcat aagatgccat gccagaacat     900
tagctacacg ttacacatag catgcagccg cggagaattt tttttcttcg ccacttgtca     960
ctcccttcaa acacctaaga gcttctctct cacagcacac acatacaatc acatgcgtgc    1020
atgcattatt acacgtgatc gccatgcaaa tctcctttat agcctataaa ttaactcatc    1080
cgcttcactc tttactcaaa ccaaaactca tcaatacaaa caagattaaa aacatacacg    1140
gactctag                                                              1148

<210> SEQ ID NO 81
<211> LENGTH: 3531
<212> TYPE: DNA
<213> ORGANISM: Arabidopsis thaliana

<400> SEQUENCE: 81
tgaatccttt ttcctttctt cttcttcttc tcttcagaga aaactttgct tctctttcta      60
taaggaacca gacacgaatc ccattcccac cgatttctta gcttcttcct tcaatccgct     120
ctttccctct ccattagatt ctgtttcctc tttcaatttc ttctgcatgc ttctcgattc     180
tctctgacgc ctcttttctc ccgacgctgt ttcgtcaaac gcttttcgaa atggcgattt     240
tggattctgc tggcgttact acggtgacgg agaacggtgg cggagagttc gtcgatcttg     300
ataggcttcg tcgacggaaa tcgagatcgg attcttctaa cggacttctt ctctctggtt     360
ccgataataa ttctccttcg gatgatgttg gagctcccgc cgacgttagg gatcggattg     420
attccgttgt taacgatgac gctcagggaa cagccaattt ggccggagat aataacggtg     480
gtggcgataa taacggtggt ggaagaggcg gcggagaagg aagaggaaac gccgatgcta     540
cgtttacgta tcgaccgtcg gttccagctc atcgagggc gagagagagt ccacttagct      600
ccgacgcaat cttcaaacag gtttaaaatc tcagaaatct tcgaatttgg tgtttgcttg     660
ttgttttata tggaattgag tttggtgatt gttttgcatt gcagagccat gccggattat     720
tcaacctctg tgtagtagtt cttattgctg taaacagtag actcatcatc gaaaatctta     780
tgaaggtttg ctgttacttg tttctccttt taggaattga attgcttgaa aatttatcag     840
agacgaataa ctttgttgtt gctatcattc atgtagtatg gttggttgat cagaacggat     900
```

| | |
|---|---|
| ttctggttta gttcaagatc gctgcgagat tggccgcttt tcatgtgttg gtaaaagaag | 960 |
| atgtttttta tttccagcaa tgttacattg ttatacgtat aatgatgagt ttagtgatca | 1020 |
| agttcctctt tgattcttct ttcttgttgc agtatatccc tttcgatctt tcctttggct | 1080 |
| gcctttacgg ttgagaaatt ggtacttcag aaatacatat cagaacctgt gagtaattac | 1140 |
| tattctccag ccattactgt aattttatt gaagacaagt ttgtatcatg aagaacttac | 1200 |
| aagttctgtt ttgaaaatgc tcaaggttgt catctttctt catattatta tcaccatgac | 1260 |
| agaggttttg tatccagttt acgtcaccct aaggtgatac tgttttttctg gtctcagttt | 1320 |
| gtgatactgt ttttaagttt agttgtctga cccggtgatc ttgaaaatgg acaggtgtga | 1380 |
| ttctgctttt ttatcaggtg tcactttgat gctcctcact tgcattgtgt ggctaaagtt | 1440 |
| ggtttcttat gctcatacta gctatgacat aagatcccta gccaatgcag ctgataaggt | 1500 |
| aaaatacgaa aaagaagcgt atgtattagt cacttgcact gtgttactgt tttaaccaaa | 1560 |
| cactgttatg aactttaggc caatcctgaa gtctcctact acgttagctt gaagagcttg | 1620 |
| gcatatttca tggtcgctcc cacattgtgt tatcaggtaa ctgcaaagtg catcaaccat | 1680 |
| tcttatactt gcaagagttt cttgtctaaa cctcggatct ttgcttttcc ccagccaagt | 1740 |
| tatccacgtt ctgcatgtat acggaagggt tgggtggctc gtcaatttgc aaaactggtc | 1800 |
| atattcaccg gattcatggg atttataata gaacaagtac gttttcacat cttgctttat | 1860 |
| tagttttcct tggtgaaaat catcatccct gcgttgtcac cacttgactt catgttcttt | 1920 |
| tgttacattt tggcagtata taaatcctat tgtcaggaac tcaaagcatc ctttgaaagg | 1980 |
| cgatcttcta tatgctattg aaagagtgtt gaagctttca gttccaaatt tatatgtgtg | 2040 |
| gctctgcatg ttctactgct tcttccacct tggtatgct gtgatcccat ctctttcaaa | 2100 |
| ataatttgca aattcgaaaa accgaaaaag gctaaatctc atacgaattt gatattttta | 2160 |
| gtttcttaga gtcggtgatg taatttcagt tactgaacgc aaatctcttg tccaaaggtt | 2220 |
| aaacatattg gcagagcttc tctgcttcgg ggatcgtgaa ttctacaaag attggtggaa | 2280 |
| tgcaaaaagt gtgggagatg tgagctattt tactcaaaag aaaacttatg attttttaatg | 2340 |
| ttgtcgttgt ttttgggtca tctaactaac caaattcatg tattcactgt cttcctttat | 2400 |
| cagtactgga gaatgtggaa tatggtatgg ttctcttcct aaacatcacc ttcttttgta | 2460 |
| cacaaaatag aagaagagag ctaattaaga tcttgttttc cttgacagcc tgttcataaa | 2520 |
| tggatggttc gacatatata cttcccgtgc ttgcgcagca agataccaaa ggtgagtgag | 2580 |
| atataccg atatgcaatt gtcgagattt gtttctgtga tataaattta accctccaca | 2640 |
| cacttgtttt tcagacactc gccattatca ttgctttcct agtctctgca gtctttcatg | 2700 |
| aggtatacat actttctaca ttgccctgtc tctagacgca tgaacacacg ctagtgaaag | 2760 |
| aaatgctaat attcaaagca ttgttttttac ttaacgatct tgtgttacaa atttccttttt | 2820 |
| gacagctatg catcgcagtt ccttgtcgtc tcttcaagct atgggctttt cttgggatta | 2880 |
| tgtttcaggt taaaaaatta ctaaactgct gcagtcgatt tttactaaac tctaatctca | 2940 |
| tattctgacc aaccaatttg tttgagtagg tgcctttggt cttcatcaca aactatctac | 3000 |
| aggaaaggtt tggctcaacg gtatgctctc aaacccgag aaaatagaac gaataactct | 3060 |
| ttctttcata gcctagccat ttaaatcgca atgctgaaac ttaataataa aggtgatctg | 3120 |
| ttttggaatg ggatcatatt attaggtggg gaacatgatc ttctggttca tcttctgcat | 3180 |
| tttcggacaa ccgatgtgtg tgcttctttta ttaccacgac ctgatgaacc gaaaaggatc | 3240 |

| | |
|---|---:|
| gatgtcatga acaactgtt caaaaaatga cttctcttcaa acatctatgg cctcgttgga | 3300 |
| tctccgttga tgttgtggtg gttctgatgc taaaacgaca aatagtgtta taaccattga | 3360 |
| agaagaaaag aaaattagag ttgttgtatc tgcaaaaatt ttggtagaga cacgcgaacc | 3420 |
| cgtttggatt ttgttatggt gtaaagaaat ttcaatcaaa aaactgttgt aataattgtt | 3480 |
| accaaaaaga aatgcttttc tggaaacgag gggaaaaata gtagttttgt t | 3531 |

<210> SEQ ID NO 82
<211> LENGTH: 6346
<212> TYPE: DNA
<213> ORGANISM: Zea mays

<400> SEQUENCE: 82

| | |
|---|---:|
| atggccccgc cccctccat gcctgccgcc tccgatcgcg ccggccctgg ccgcgacgcg | 60 |
| ggcgactcgt cctcccttcg cctccgccgc gcccctcag ccgacgccgg cgaccttgcc | 120 |
| ggcgattcct cggtaggctt gcgggagaac ggcgagccgc aaccgccgac gaatccgccg | 180 |
| ccgcaggagc agcagcagca gcacgagatg ctatactacc gcgcgtcggc gcccgcccac | 240 |
| cgccgcgtca aggagagccc cctcagctct gacgccatct ccggcaggt gaggagacgc | 300 |
| gaattttagg ctcgctgttt gtaagcgatt gtttgatccc cgcgcttgtg cttcgatcca | 360 |
| cgccagttgc aaaatcctgc aaattgtttg ttgcttccag tcaactctgc ctctgttttt | 420 |
| ttttggttgg tgtgtgtgtg tgtgtgtgtg ttcaaatcac actttgtgct atcggtagct | 480 |
| taacactgcc ggttgccatc tcgcgcgcac ggatgtttta ttgtgggcct tgggcttcgg | 540 |
| aattgtggat agattgtgcg cgtgtactcg aatgggcaca attcgtttcg tgggggcat | 600 |
| atgctgctgc gattgaggtc ggtgtttact tgttttggga tcagggggac cagtgccggt | 660 |
| gcgcgggtgc cagatgcatg ccacgcagaa tttggcatcg gccggctgaa gcagcaaaca | 720 |
| acgagcgtaa ccgttaccac tggaggagct ttggcttgtc gaaacggatg actggatgag | 780 |
| cgaatgaatc attgaattca ttgttggcgg tactcactat agtgatgtgg acagttgttg | 840 |
| ggacagcacc tgcagtgccc ccagtattat taatgctgac ttttctaact acaatgcgtg | 900 |
| ttacattgtt tgtacacctt ggcttttcctg cttggggcat tgcttcttgt tgaggaccat | 960 |
| ataactgtgc acctacatag aactgtattg gaccacttgt aagttttaac tggttagccc | 1020 |
| tccattttt aataggtata ttattagaca attttttattg tcattgacat tatttttgtt | 1080 |
| tgctactctc ggagcccttt tcccagtgta atcttaatag ggctcaaatc acagcagaaa | 1140 |
| cacgtgagac gtaattttct agtgatactt ttattagact ttgttgtttc tgcacatact | 1200 |
| ctaaatctgt tttgaaggta ggagtgctta tttggatgat aaataatcct gggattacac | 1260 |
| agtggacaac gctttgataa ttgagtccat gctaacttga ttataatata tcagtattcc | 1320 |
| atatatcatt ttatcttgta cttcaactga gatcatcctt attttttgca aaccgtattt | 1380 |
| attggttgct ctggagaatt gaagtctga aactaagcac ttctcctgat tgcagagcca | 1440 |
| tgctggtctt ctgaatctat gcattgttgt tctgatcgca gtgaacagca gactcattat | 1500 |
| tgagaattta atgaaggttt attactttct ttctttttc attttcctca ccttcattta | 1560 |
| cagatccctc aatccatctc cttctgaaat acatctggtc ttcttcctgc gcatttgtct | 1620 |
| agtgtaaatc tgacacattc tgtgttttat ttaaattggc tggtgcagta tggcctgttg | 1680 |
| ataagagctg gattttggtt tagtgcaaga tcgctgggtg actggcccct tctaatgtgc | 1740 |
| tggtagaaat tgttgtcatt tttaattcag atggtttca aataagaact gtggagtaat | 1800 |
| caatctgtca atttcagcct cactctacca gttttcccac tagttgcact catggctgag | 1860 |

```
aagctgatca caagaaagct cattggtgaa catgtaagtt tgactcacaa gattgcgtag    1920
tattttgtag agaagttctc ttttgttatt tcttaggtat aagtgttgag gattgaatta    1980
gatgtaaaac tagacagtcc tctattctgc atcttccagg tgccatttat cgtttatgac    2040
ttctatacac ctcttgcagg tggttattct actccatatc attattacaa catctgccat    2100
tgtctatcca gttgttgtga ctcttaagta agcatttctt tctgctttgc agtttgtttg    2160
gatgcatctt attttgacat tcgttgagct ctagtatttc atggtatgga atacattcaa    2220
ttaatcttgt tcgtaatttg ctgtacttca tggtatggtg ccaactaca ttattgtgcc     2280 ccaaacattt agtctttccc ttcaagatac gtactatact atgcaaattg ggtggataaa    2340
aaggtagcta cataacactt ttatttaatt gtatctggtg actccacact ataatacaaa    2400
gaaacgcaac tctccagcat attcaagaaa aaaatgtatc tggtgataaa aatctattgc    2460
aaatgttcat ttatctctag tagaagaaat ccttactatc ttactctgtc ttgatctgtt    2520
cactgactgc atcaataggg aagatttgt tagtccatca atattgatac acattttatt    2580
atgcagatat tttgtttctt tcatgtagct tctagcttgt aaccccttc ctaacatgaa     2640 gctgatcttt ccattgtaca agaaaaattg gatatatttg ttcacatgct tggaaattga    2700
ataaacaaac tgtagtattt ctgatgttga tgtgcaagta gtagactttg gttgagtcaa    2760
ttgttatctc tcaaaagag ccattaggag caagttacct tttcattgat tatattttct      2820
gtgagactgc aagagttaag aatgttgtat ggttgatgcc ttatgctgtt agtttaagt     2880 ttgttataat tgccaagaaa tgttacttga aaagatattg tcccatgcat caattatgga    2940
ttatcagttc agtcatattc cgaaaaattt caggtgtgac tcagcagtac tatctggatt    3000
tgtgctaatg tttcttgcga gcatcatgtg gatgaagctt gtctcttatg cacatacaaa    3060
ttatgatata agggtattgt ccaaaagtac tgagaaggta atgcattgac atgttaatct    3120
gaatcagttc aaatattttg ttaacatgtt gcccatttct caaaattgat ttgttgacgt    3180
tcaaactttt cttaaaactc cttttggtgg ccaaatttt ctgaagctag aatatctccc      3240
acttgtttaa acttcttttc cagtttcatt tcatgaatgt cttatatcta gtttcaattt    3300
ttgcatagga tgaaatgtgg tgccaatcaa tatacgttac catcaagaga gtaaaaaat     3360 tgttcttaac ttctcataca gtgttttgt tacatgggct gatcatatat actctcatgt      3420
gttagcttaa ctgttagtgt atacctctat tgtaatgggc cttggtccac ctaaccctgt    3480
tatatcaatg cattcccaac cctaattagg gttagggttt ccctcattct aacttcaggc    3540
aacggtagca tatgattata tcccttcatt ttcatttttc atgcaaataa ccactattgc    3600
tatattctta ttttagggt gctgcatatg gaattatgt cgatcctgag aatatgaaag       3660
atccaacctt taaagtcta gtgtacttca tgttggcccc aacactttgt taccaggtac     3720
tattattgga ccaatgcccc gttttgttt taatgtcta cactctgctt ttcttcatcg       3780
cgtctatcta gttatgccag tgacaacatg aatttcctga tgtcactttg gcatgttatg    3840
cagccaactt atcctcaaac tacatgtatt agaaagggtt gggtgaccca gcaactcata    3900
aagtgcgtgg ttttacagg cttgatgggc ttcataattg agcaagtgag cctcctatat     3960
tccttaagta acttgtattt atacataact ttggattaaa ttaccaattt ttcttctatt    4020
ttgcagtata taaacccaat tgtgaagaat ccaaacatc cactgaaagg gaatttttg       4080 aatgctatag aaagagtctt aaaactctca gtgccaacat tatatgtatg gctttgcatg    4140
ttctattgct ttttcatttt atggttagta tcttgcttca gttcaacagt accttaaatt    4200
```

```
tgtgcggcag tgattggttt atataacagg ttaattgggt tttgacctgc atgggacttt    4260
gatttccatt ttccatggca ttcttgtttg ctcttttggt tggtttcagg ctgaacattg    4320
tagctgaact cctctgtttc ggtgaccgtg aattctataa ggactggtgg aatgccaaaa    4380
ctgttgaaga ggtgagatgc ctgttaaaat tgagttcgtt tcttttgaag tgagaacttt    4440
aaataggact gacatcaatt atattctcat gtacttaaat gtgatggtat tttgggctt     4500
tacctcagta ctggaggatg tggaacatgg taatctttt gttacttcta tattcagatt     4560
ctatacccct ttatttagtt gagactttgt tacttaacta aggacagttg tgatggtagt    4620
ggtactcttc tatttagtta agacttcctt aacttctgtc actgagcttg agatatttgt    4680
ctaataatat ctttcaaata actgacaatt agtctatttt ttgtcagcct gttcataagt    4740
ggatcatcag acacatatat tttccatgta taaggaaagg cttttccagg taattgctt     4800
ctatatgtgt acaaaactct acatttgttc tttgcttttg aattctccaa atgcagttta    4860
gtttggaaca tcgatgcaat atagaattca caatatacaa atgatgttct ttagaaaatg    4920
gggaagcaga gctggacaga gtgttagcac tcaattgtca atttgtcata ataataatga    4980
atacaactga acaagtggct gaaactgttg tgagaaaatc agaacactag tggtcaatat    5040
tatttgcata gtaaatcaat ttggtaatgt aaattaagat atgaagttct tacttcttat    5100
ataaagattt actatgcttg aattttatag tggctgaaac tttactgttc ttggataaag    5160
attttaaata aaaacaaagg atatctagac ttggcaacaa aatgctgcct tctgctgact    5220
ggcaaaagta aattagacaa tgtgaataca tggacataca taaaattttg ttggtccttt    5280
cattttttgca gaactgacat gatttttcact gcctacttct caaattcgta ttgtatctac    5340
actgcagggt gtagctattc taatctcgtt tctggtttca gctgtattcc atgaggtact    5400
ttaagttctt cagaagcctt tttcatgatc ggttcaattt ctgttttttcc taagacatgc    5460
tattgttcga attccactca gcacattact aacaatacgt ttgaccttac gtaccaatat    5520
atcatcacca catctctttt tacattgtga attcacagat atgtattgcg gtgccgtgcc    5580
acattttcaa attctgggca ttttctggga tcatgtttca ggtatagaaa taacactaat    5640
atataactac tacctccatt ccgaattata agtcttctg gcttggcttt tctagttaca     5700
ttatactagg tatatatcta gattataata gttatatatc tagacattgt gtatatctag    5760
atgcatacca aatgttacct atctagaaaa taggatcatg gtttcaggta tagaagtagt    5820
aataatataa taactactac ctccatttcg aactgtaagt cattatgact tggcttttat    5880
agataatgct aagagttata tatctggaca ttatctagat gcgtagctac gaatctagga    5940
aaactagaac gacttgtaat tatccctgcc ttttctttttg agtccatcag tgtctattct    6000
cttacgtttt gattccatca ttacatccat aagaacaata ctacatcttg gatacaatgt    6060
accttccact gttttcacat aggctgacac tggttgatgt ctgactcaca gataccgttg    6120
gtattcttga caagatatct ccatgctacg ttcaagcatg taatggtacg ctgtgtcaat    6180
tatgtccttt ttttcccatt acctcttgcc actacctaac catcatcttc ttatttggca    6240
ggtgggcaac atgatatttt ggttcttcag tatagtcgga cagccgatgt gtgtccttct    6300
atactaccat gacgtcatga acaggcaggc ccaggcaagt agatag                    6346
```

<210> SEQ ID NO 83
<211> LENGTH: 157
<212> TYPE: PRT
<213> ORGANISM: Arabidopsis thaliana

<400> SEQUENCE: 83

```
Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
            20                  25                  30

Ser Asp Ser Ser Asn Gly Leu Leu Leu Ser Gly Ser Asn Asn Ser
        35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
            115                 120                 125

Lys Gln Ser His Ala Gly Leu Phe Asn Leu Cys Val Val Val Leu Ile
            130                 135                 140

Ala Val Asn Ser Arg Leu Ile Ile Glu Asn Leu Asn Lys
145                 150                 155

<210> SEQ ID NO 84
<211> LENGTH: 140
<212> TYPE: PRT
<213> ORGANISM: Brassica juncea

<400> SEQUENCE: 84

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Arg Ser Asp
            20                  25                  30

Ser Ser Asn Gly Leu Leu Ser Asp Thr Ser Pro Ser Asp Val Gly
        35                  40                  45

Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
65                  70                  75                  80

Ser Ala Gly Gly Asp Val Arg Phe Thr Tyr Arg Pro Ser Val Pro Ala
                85                  90                  95

His Arg Arg Thr Arg Glu Ser Pro Leu Ser Ser Asp Ala Ile Phe Lys
            100                 105                 110

Gln Ser His Ala Gly Leu Phe Asn Leu Cys Val Val Val Leu Val Ala
            115                 120                 125

Val Asn Ser Arg Pro Ile Ile Glu Asn Leu Met Lys
130                 135                 140

<210> SEQ ID NO 85
<211> LENGTH: 140
<212> TYPE: PRT
<213> ORGANISM: Brassica napus

<400> SEQUENCE: 85

Met Ala Ile Leu Asp Ser Gly Gly Val Ala Val Pro Pro Thr Glu Asn
1               5                   10                  15

Gly Val Ala Asp Leu Asp Arg Leu His Arg Arg Lys Ser Ser Asp
            20                  25                  30
```

Ser Ser Asn Gly Leu Leu Ser Asp Thr Ser Pro Ser Asp Val Gly
        35                  40                  45

Ala Ala Ala Glu Arg Asp Arg Val Asp Ser Ala Glu Glu Glu
 50                  55                  60

Ala Gln Gly Thr Ala Asn Leu Ala Gly Gly Asp Ala Glu Thr Arg Glu
 65                  70                  75                  80

Ser Ala Gly Gly Asp Val Arg Phe Thr Tyr Arg Pro Ser Val Pro Ala
                 85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Val Leu Val Ala
                115                 120                 125

Val Asn Ser Arg Leu Ile Ile Glu Asn Leu Met Lys
            130                 135                 140

<210> SEQ ID NO 86
<211> LENGTH: 140
<212> TYPE: PRT
<213> ORGANISM: Brassica juncea

<400> SEQUENCE: 86

Met Ala Ile Leu Asp Ser Gly Thr Val Thr Met Ala Thr Glu Asn Gly
 1               5                  10                  15

Val Ala Asp Leu Asp Met Leu Arg Arg Arg Lys Ser Arg Ser Asp Ser
                20                  25                  30

Ser Asn Gly Leu Leu Ser Glu Thr Ser Pro Ser Asp Asp Ala Gly Ala
            35                  40                  45

Pro Ala Asp Val Glu Asp Arg Val Asp Ser Ala Ala Gln Gly Thr Ala
 50                  55                  60

Asn Leu Ala Gly Asp Thr Glu Thr Arg Glu Ser Gly Gly Gly Gly Gly
 65                  70                  75                  80

Gly Gly Asn Gly Glu Val Arg Phe Thr Tyr Arg Pro Ser Val Pro Ala
                 85                  90                  95

His Arg Arg Thr Arg Glu Ser Pro Leu Ser Ser Asp Ala Ile Phe Lys
                100                 105                 110

Gln Ser His Ala Gly Leu Phe Asn Leu Cys Val Val Val Leu Val Ala
                115                 120                 125

Val Asn Ser Arg Leu Ile Ile Glu Asn Leu Met Lys
            130                 135                 140

<210> SEQ ID NO 87
<211> LENGTH: 149
<212> TYPE: PRT
<213> ORGANISM: Tropaeolum majus

<400> SEQUENCE: 87

Met Ala Val Ala Glu Ser Ser Gln Asn Thr Thr Thr Met Ser Gly His
 1               5                  10                  15

Gly Asp Ser Asp Leu Asn Asn Phe Arg Arg Arg Lys Pro Ser Ser Ser
                20                  25                  30

Val Ile Glu Pro Ser Ser Ser Gly Phe Thr Ser Thr Asn Gly Val Pro
            35                  40                  45

Ala Thr Gly His Val Ala Glu Asn Arg Asp Gln Asp Arg Val Gly Ala
 50                  55                  60

Met Glu Asn Ala Thr Gly Ser Val Asn Leu Ile Gly Asn Gly Gly Gly
 65                  70                  75                  80

```
Val Val Ile Gly Asn Glu Glu Lys Gln Val Gly Glu Thr Asp Ile Arg
                85                  90                  95

Phe Thr Tyr Arg Pro Ser Phe Pro Ala His Arg Arg Val Arg Glu Ser
            100                 105                 110

Pro Leu Ser Ser Asp Ala Ile Phe Lys Gln Ser His Ala Gly Leu Phe
        115                 120                 125

Asn Leu Cys Ile Val Val Leu Ile Ala Val Asn Ser Arg Leu Ile Ile
    130                 135                 140

Glu Asn Leu Asn Lys
145

<210> SEQ ID NO 88
<211> LENGTH: 103
<212> TYPE: PRT
<213> ORGANISM: Echium pitardii

<400> SEQUENCE: 88

Met Thr Ile Trp Glu Ser Pro Glu Ile Ile Ser Ser Asp Glu Ala Ala
1               5                   10                  15

Ala Ala Leu Arg Arg Arg Gly Gly Ala Lys Glu Val Ala Glu Gln Arg
            20                  25                  30

Leu Asp Ser Glu Glu Glu Lys Lys Lys Glu Glu Glu Asn Gly Lys Leu
        35                  40                  45

Lys Tyr Thr Tyr Arg Ala Ser Ala Pro Ala His Arg Arg Ile Lys Glu
    50                  55                  60

Ser Pro Leu Ser Ser Asp Ala Ile Phe Lys Gln Ser His Ala Gly Leu
65                  70                  75                  80

Phe Asn Leu Cys Ile Val Val Leu Val Ala Val Asn Ser Arg Leu Ile
                85                  90                  95

Ile Glu Asn Leu Pro Met Lys
            100

<210> SEQ ID NO 89
<211> LENGTH: 152
<212> TYPE: PRT
<213> ORGANISM: Vernonia galamensis

<400> SEQUENCE: 89

Met Ala Leu Leu Asp Thr Pro Gln Ile Gly Glu Ile Thr Thr Thr Ala
1               5                   10                  15

Thr Thr Thr Ile Arg Arg Arg Thr Thr Val Lys Pro Asp Ala Gly Ile
            20                  25                  30

Gly Asp Gly Leu Phe Asp Ser Ser Ser Ser Ser Lys Thr Asn Ser Ser
        35                  40                  45

Phe Glu Asp Gly Asp Ser Leu Asn Gly Asp Phe Asn Asp Lys Phe Lys
    50                  55                  60

Glu Gln Ile Gly Ala Gly Asp Glu Ser Lys Asp Asp Ser Lys Gly Asn
65                  70                  75                  80

Gly Gln Lys Ile Asp His Gly Gly Val Lys Lys Gly Arg Glu Thr Thr
                85                  90                  95

Val Val His Tyr Ala Tyr Arg Pro Ser Ser Pro Ala His Arg Arg Ile
            100                 105                 110

Lys Glu Ser Pro Leu Ser Ser Asp Ala Ile Phe Lys Gln Ser His Ala
        115                 120                 125

Gly Leu Phe Asn Leu Cys Ile Val Val Leu Val Ala Val Asn Gly Arg
    130                 135                 140
```

```
Leu Ile Ile Glu Asn Leu Asn Lys
145                 150

<210> SEQ ID NO 90
<211> LENGTH: 165
<212> TYPE: PRT
<213> ORGANISM: Nicotiana tabacum

<400> SEQUENCE: 90

Met Val Ile Met Glu Leu Pro Glu Ser Val Glu Met Thr Thr Thr Thr
1               5                   10                  15

Thr Thr Ser Gly Ile Glu Asn Leu Asn Ser Asp Leu Asn His Ser Val
            20                  25                  30

Arg Arg Arg Arg Cys Ser Asn Gly Phe Glu Ala Ala Ser Ala Ile Asn
        35                  40                  45

Ser Ser Asp Ala Asn Met Ser Glu Asp Arg Arg Asp Val Cys Gly Ser
    50                  55                  60

Gly Ala Gly Leu Glu Thr Val Asn Glu Arg Ser Lys Ser Val Gly Glu
65                  70                  75                  80

Ser Ser Asp Val Ile Arg Lys Glu Asp Arg Asn Asp Asn Val Ala
                85                  90                  95

Asn Gly Glu Glu Ser Lys Ser Thr Glu Thr Thr Thr Pro Phe Lys
            100                 105                 110

Phe Ala Tyr Arg Ala Ser Ala Pro Ala His Arg Arg Ile Lys Glu Ser
            115                 120                 125

Pro Leu Ser Ser Asp Ala Ile Phe Lys Gln Ser His Ala Gly Leu Phe
130                 135                 140

Asn Leu Cys Val Val Val Leu Ile Ala Val Asn Ser Arg Leu Ile Ile
145                 150                 155                 160

Glu Asn Leu Asn Lys
            165

<210> SEQ ID NO 91
<211> LENGTH: 163
<212> TYPE: PRT
<213> ORGANISM: Perilla frutescens

<400> SEQUENCE: 91

Met Ala Ile Leu Asp Ser Pro Glu Ile Leu Asp Thr Thr Ser Ser Ser
1               5                   10                  15

Ala Asp Asn Gly Ala Ala His His Thr Thr Leu Arg Arg Arg Arg Ser
            20                  25                  30

Ala Arg Ser Val Pro Pro Leu Leu Asp Ser Asp Ser Asn Ser Leu Glu
        35                  40                  45

Ala Glu Ser Ala Ile Asn Asp Ser Glu Asn Val Arg Asn Asp Ala Asn
    50                  55                  60

Leu Ile Glu Asn Leu Arg Gly Gly Ala Val Glu Ser Glu Asn Glu Lys
65                  70                  75                  80

Gln Glu Ser Tyr Gly Lys Glu Glu Gly Ala Lys Val Lys Glu Asn Gly
                85                  90                  95

Glu Thr Ser Asn Gly Asn Gly Thr Asp Val Met Ala Val Lys Phe Thr
            100                 105                 110

Phe Arg Pro Ala Ala Pro Ala His Arg Lys Asn Lys Glu Ser Pro Leu
            115                 120                 125

Ser Ser Asp Ala Ile Phe Lys Gln Ser His Ala Gly Leu Phe Asn Leu
130                 135                 140
```

```
Cys Ile Val Val Leu Val Ala Val Asn Ser Arg Leu Ile Ile Glu Asn
145                 150                 155                 160

Leu Asn Lys
```

<210> SEQ ID NO 92
<211> LENGTH: 141
<212> TYPE: PRT
<213> ORGANISM: Zea mays

<400> SEQUENCE: 92

```
Met Ala Asp Ser Glu Asp Ala Pro Pro Ala Val His Arg Arg Pro Pro
1               5                   10                  15

Arg Pro Ala Arg Gly Ala Ala Ala Gln Gly Phe Ala Ala Ala Ala Leu
                20                  25                  30

Arg Arg Arg Leu Arg Ser Gly Ala Ala Val Ala Ala Arg Ala Ser Phe
            35                  40                  45

Ala Ala Asp Ser Gly Asp Glu Ser Gly Pro Gly Glu Pro Ser Ser Ser
        50                  55                  60

Arg Arg Arg Asp Asn Ser Gly Gly Ala Ser Ser Ala Ala Gly Gly Arg
65                  70                  75                  80

Ala Gly Ala Gly Asp Phe Ser Ala Phe Thr Phe Arg Ala Ala Ala Pro
                85                  90                  95

Val His Arg Lys Ala Lys Glu Ser Pro Leu Ser Ser Asp Ala Ile Phe
            100                 105                 110

Lys Gln Ser His Ala Gly Leu Phe Asn Leu Cys Ile Val Val Leu Val
        115                 120                 125

Ala Val Asn Ser Arg Leu Ile Ile Glu Asn Leu Met Lys
    130                 135                 140
```

<210> SEQ ID NO 93
<211> LENGTH: 141
<212> TYPE: PRT
<213> ORGANISM: Sorghum bicolor

<400> SEQUENCE: 93

```
Met Ala Asp Thr Asp Asp Ala Pro Pro Ala Pro Ala Val His Arg Arg
1               5                   10                  15

Pro Pro Arg Pro Ala Arg Gly Ala Ala Ala Ala Gln Ala Ala Glu Leu
                20                  25                  30

Arg Arg Arg Leu Ser Ser Gly Ala Ala Ala Ala Arg Ala Ser Phe
            35                  40                  45

Ala Ala Asp Ser Gly Asp Glu Ser Gly Pro Gly Glu Pro Ser Ser Ser
        50                  55                  60

Arg Arg Arg Asp Asn Gly Gly Asp Ala Ser Ser Ala Ala Asp Gly Gly
65                  70                  75                  80

Arg Gly Gly Ala Gly Asp Phe Ser Ala Phe Ile Phe Arg Ala Ala Ala
                85                  90                  95

Pro Val His Phe Glu Ala Lys Glu Ser Pro Leu Ser Ser Asp Ala Ile
            100                 105                 110

Phe Glu Gln Ser His Ala Leu Glu Asn Leu Cys Ile Val Val Leu Val
        115                 120                 125

Ala Val Asn Ser Pro Leu Ile Ile Glu Asn Leu Asn Lys
    130                 135                 140
```

<210> SEQ ID NO 94
<211> LENGTH: 167

```
<212> TYPE: PRT
<213> ORGANISM: Oryza sativa

<400> SEQUENCE: 94

Met Val Gly Ser Asp Gly Asp Gly Gly Gly Glu Ala His
1               5                   10                  15

Ala Pro Ala Ala Pro Ala His His Arg Arg Pro Pro Pro Arg
                20                  25                  30

Gly Gly Ser Gly Ala Thr Val Glu Gly Phe Ala Ala Leu Arg Arg
            35                  40                  45

Pro Ile Arg Ser Gly Ala Ala Ala Ala Arg Ala Ser Phe Gly Gly
        50                  55                  60

Asp Ser Gly Asp Glu Ala Ala Ser Gly Glu Pro Ser Ser Ser Ser
65                  70                  75                  80

Ser Ser Pro Ser Arg Arg Arg Gly Gly Asp Ser Asn Gly Ala Glu Ala
                85                  90                  95

Ser Ser Ala Ala Gly Gly Gly Gly Arg Gly Gly Gly Asp Phe
            100                 105                 110

Ser Ala Phe Thr Phe Arg Ala Ala Ala Pro Val His Arg Lys Ala Lys
        115                 120                 125

Glu Ser Pro Leu Ser Ser Asp Ala Ile Phe Lys Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Asn Lys
                165

<210> SEQ ID NO 95
<211> LENGTH: 104
<212> TYPE: PRT
<213> ORGANISM: Oryza sativa

<400> SEQUENCE: 95

Met Ala Pro Pro Pro Ser Leu Ala Pro Asp Arg Gly Gly Gly Glu Pro
1               5                   10                  15

Asp Asp Ala Leu Arg Leu Arg Ala Ala Ala Ala Ala Ala Gly Asp
                20                  25                  30

Ala Pro Ala Pro Gln Gln Gln Gln Glu Gln Arg His Gln Glu Gln Gln
            35                  40                  45

Gln Gln Leu Leu Trp Tyr Arg Ala Ser Ala Pro Ala His Arg Arg Val
        50                  55                  60

Arg Glu Ser Pro Leu Ser Ser Asp Ala Ile Phe Arg Gln Ser His Ala
65                  70                  75                  80

Gly Leu Leu Asn Leu Cys Ile Val Val Leu Val Ala Val Asn Ser Arg
                85                  90                  95

Leu Ile Ile Glu Asn Leu Met Lys
                100

<210> SEQ ID NO 96
<211> LENGTH: 118
<212> TYPE: PRT
<213> ORGANISM: Sorghum bicolor

<400> SEQUENCE: 96

Met Ala Pro Pro Pro Ser Met Ala Ala Ala Ser Asp Arg Ala Val Pro
1               5                   10                  15

Gly Ala Asp Ala Thr Glu Ala Ser Ser Leu Arg Leu Arg Arg Ala Pro
```

```
            20                  25                  30

Ser Ala Asp Ala Gly Asp Leu Ala Asp Ser Ser Gly Asp Arg Arg
        35                  40                  45

Glu Asn Gly Glu Pro Gln Pro Pro Gln Glu Gln Gln Gln His Glu
    50                  55                  60

Met Leu Tyr Tyr Arg Ala Ser Ala Pro Ala His Arg Arg Val Lys Glu
65                  70                  75                  80

Ser Pro Leu Ser Ser Asp Ala Ile Phe Arg Gln Ser His Ala Gly Leu
                85                  90                  95

Leu Asn Leu Cys Ile Val Val Leu Ile Ala Val Asn Ser Arg Leu Ile
            100                 105                 110

Ile Glu Asn Leu Met Lys
            115
```

<210> SEQ ID NO 97
<211> LENGTH: 122
<212> TYPE: PRT
<213> ORGANISM: Zea mays

<400> SEQUENCE: 97

```
Met Ala Pro Pro Pro Ser Met Pro Ala Ala Ser Asp Arg Ala Gly Pro
1               5                   10                  15

Gly Arg Asp Ala Gly Asp Ser Ser Ser Leu Arg Leu Arg Arg Ala Pro
            20                  25                  30

Ser Ala Asp Ala Gly Asp Leu Ala Gly Asp Ser Ser Gly Gly Leu Arg
        35                  40                  45

Glu Asn Gly Glu Pro Gln Ser Pro Thr Asn Pro Pro Gln Glu Gln
    50                  55                  60

Gln Gln His Glu Met Leu Tyr Tyr Arg Ala Ser Ala Pro Ala His Arg
65                  70                  75                  80

Arg Val Lys Glu Ser Pro Leu Ser Ser Asp Ala Ile Phe Arg Gln Ser
                85                  90                  95

His Ala Gly Leu Leu Asn Leu Cys Ile Val Val Leu Ile Ala Val Asn
            100                 105                 110

Ser Arg Leu Ile Ile Glu Asn Leu Met Lys
            115                 120
```

<210> SEQ ID NO 98
<211> LENGTH: 76
<212> TYPE: PRT
<213> ORGANISM: Physcomitrella patens

<400> SEQUENCE: 98

```
Met Pro Val Lys Ser Ser Asn Leu Ala Gly Glu Arg Ala Ala Thr Ser
1               5                   10                  15

His Ile Asn Ala Asn Thr Lys Phe Asp Leu Arg Gly Cys Thr Pro Ala
            20                  25                  30

His Arg Val Arg Arg Glu Ser Pro Leu Ser Ser Asp Ala Ile Phe His
        35                  40                  45

Gln Ser His Ala Gly Leu Phe Asn Leu Cys Ile Val Val Leu Ile Ala
    50                  55                  60

Val Asn Ser Arg Leu Ile Ile Glu Asn Leu Met Lys
65                  70                  75
```

<210> SEQ ID NO 99
<211> LENGTH: 51
<212> TYPE: PRT

<213> ORGANISM: Selaginella moellendorffii

<400> SEQUENCE: 99

Met Arg Pro Ser Leu Pro Ala His Arg Arg Ser Lys Glu Ser Pro Leu
1               5                   10                  15

Ser Ser Asp Ala Ile Phe Thr Gln Ser His Ala Gly Leu Phe Asn Leu
            20                  25                  30

Cys Ile Val Val Leu Val Ala Val Asn Ser Arg Leu Ile Ile Glu Asn
        35                  40                  45

Leu Met Lys
    50

<210> SEQ ID NO 100
<211> LENGTH: 136
<212> TYPE: PRT
<213> ORGANISM: Euonymus alatus

<400> SEQUENCE: 100

Met Ala Ala Asn Leu Asn Glu Ala Ser Asp Leu Asn Phe Ser Leu Arg
1               5                   10                  15

Arg Arg Thr Gly Gly Ile Ser Ser Thr Thr Val Pro Asp Ser Ser Ser
            20                  25                  30

Glu Thr Ser Ser Ser Glu Ala Asp Phe Leu Asp Gly Gly Lys Gly Ala
        35                  40                  45

Ala Asp Val Lys Asp Arg Gly Asp Gly Ala Val Glu Phe Gln Asn Ser
    50                  55                  60

Met Lys Asn Val Glu Arg Ile Glu Lys His Glu Ser Arg Val Gly Leu
65                  70                  75                  80

Asp Ser Arg Phe Thr Tyr Arg Pro Ser Val Pro Ala His Arg Thr Ile
                85                  90                  95

Lys Glu Ser Pro Leu Ser Ser Asp Ala Ile Phe Lys Gln Ser His Ala
            100                 105                 110

Gly Leu Phe Asn Leu Cys Ile Val Val Leu Val Ala Val Asn Ser Arg
        115                 120                 125

Leu Ile Ile Glu Asn Leu Asn Lys
    130                 135

<210> SEQ ID NO 101
<211> LENGTH: 146
<212> TYPE: PRT
<213> ORGANISM: Vitis vinifera

<400> SEQUENCE: 101

Met Ala Ile Cys Asn Ser Phe Pro Ser Val Thr Thr Ser Ser Ser Ser
1               5                   10                  15

Ser His Ala Asp Ser Asp Leu Asp Phe Ser Ile Arg Lys Arg Phe Gly
            20                  25                  30

Gly Lys Gly Lys Ala Val Ala Asp Ser Ser Leu Glu Thr Glu Thr Glu
        35                  40                  45

Ala Ala Ala Ala Ala Val Leu Glu Ala Glu Lys Ser Val Gly Glu Val
    50                  55                  60

Gly Ser Gly Gly Asp Arg Gly Ser Gly Ser Gln Val Arg Asn
65                  70                  75                  80

Gly Glu Asn Gly Val Ala Glu Val Ala Ala Lys Phe Ala Tyr Arg Pro
                85                  90                  95

Cys Ala Pro Ala His Arg Lys Val Lys Glu Ser Pro Leu Ser Ser Asp
            100                 105                 110

```
Ala Ile Phe Arg Gln Ser His Ala Cys Gly Leu Phe Asn Leu Cys Ile
        115                 120                 125

Val Val Leu Val Ala Val Asn Ser Arg Leu Ile Ile Glu Asn Leu Asn
130                 135                 140

Asn Lys
145

<210> SEQ ID NO 102
<211> LENGTH: 128
<212> TYPE: PRT
<213> ORGANISM: Glycine max

<400> SEQUENCE: 102

Met Ala Ile Ser Asp Glu Pro Glu Thr Val Ala Thr Ala Leu Asn His
1               5                   10                  15

Ser Ser Leu Arg Arg Pro Thr Ala Ala Gly Leu Phe Asn Ser Pro
            20                  25                  30

Glu Thr Thr Thr Asp Ser Ser Gly Asp Leu Ala Lys Asp Ser Gly
                35                  40                  45

Ser Asp Asp Ser Ile Ser Ser Asp Ala Ala Asn Ser Gln Pro Gln Gln
50                  55                  60

Lys Lys Gln Asp Thr Asp Phe Ser Val Leu Lys Phe Ala Tyr Arg Pro
65                  70                  75                  80

Ser Val Pro Ala His Arg Glu Val Glu Ser Pro Leu Ser Ser Asp
                85                  90                  95

Thr Ile Phe Arg Gln Ser His Ala Gly Leu Phe Asn Leu Cys Ile Val
            100                 105                 110

Val Leu Val Ala Val Asn Ser Arg Leu Ile Ile Glu Asn Leu Met Lys
        115                 120                 125

<210> SEQ ID NO 103
<211> LENGTH: 133
<212> TYPE: PRT
<213> ORGANISM: Glycine max

<400> SEQUENCE: 103

Met Ala Ile Ser Asp Glu Pro Glu Ser Val Ala Thr Ala Leu Asn His
1               5                   10                  15

Ser Ser Leu Arg Arg Pro Ser Ala Thr Ser Thr Ala Gly Leu Phe
            20                  25                  30

Asn Ser Pro Glu Thr Thr Thr Asp Ser Ser Gly Asp Leu Ala Lys
        35                  40                  45

Asp Ser Gly Ser Asp Asp Ser Ile Asn Ser Asp Ala Ala Val Asn
    50                  55                  60

Ser Gln Gln Gln Asn Glu Lys Gln Asp Thr Asp Phe Ser Val Leu Lys
65                  70                  75                  80

Phe Ala Tyr Arg Pro Ser Val Pro Ala His Arg Lys Val Lys Glu Ser
                85                  90                  95

Pro Leu Ser Ser Asp Thr Ile Phe Arg Gln Ser His Ala Gly Leu Phe
                100                 105                 110

Asn Leu Cys Ile Val Val Leu Val Ala Val Asn Ser Arg Leu Ile Ile
            115                 120                 125

Glu Asn Leu Met Lys
        130

<210> SEQ ID NO 104
```

<211> LENGTH: 139
<212> TYPE: PRT
<213> ORGANISM: Lotus japonicus

<400> SEQUENCE: 104

Met Ala Ile Ser Glu Asp Ser Glu Ser Leu Phe Ala Ala Ala Ala
1               5                   10                  15

Ser Ser Val Ile Gln Ser Gly Ser Ser Val Arg Arg Pro Ser Ala
            20                  25                  30

Ile Ser Ala Val Ala Thr Val Glu Asp Glu Ser Ser Glu Glu Pro
            35                  40                  45

Val Pro Val Arg Asp Ser Gly Ser Asp Val Asp Ser Val Ser Ser
50                  55                  60

Glu Gln His Val Ser Pro Ala Thr Ala Asn Arg Glu Lys Asn Gln Val
65                  70                  75                  80

His Asp Ile Ser Ala Thr Lys Phe Ala Tyr Arg Pro Ser Ala Pro Ala
                85                  90                  95

His Arg Arg Val Lys Glu Ser Pro Leu Ser Ser Asp Asn Ile Phe Arg
            100                 105                 110

His His Ala Gly Leu Phe Asn Leu Cys Ile Val Val Leu Val Ala Val
            115                 120                 125

Asn Ser Arg Leu Ile Ile Glu Asn Leu Asn Lys
        130                 135

<210> SEQ ID NO 105
<211> LENGTH: 167
<212> TYPE: PRT
<213> ORGANISM: Medicago truncatula

<400> SEQUENCE: 105

Met Ala Ile Ser Asp Thr Pro Glu Thr Thr Ala Thr Ala Thr Ala Thr
1               5                   10                  15

Val Thr Thr Ile Glu Thr Asp Thr Asp Leu Lys Arg Ser Ser Leu Arg
            20                  25                  30

Arg Arg Pro Ser Ala Thr Ser Thr Ala Gly Gly Leu Phe Asp Ala Glu
        35                  40                  45

Ser Ala Ala Ala Asp Ala Val Arg Asp Ser Gly Ser Asp Asp Ser Leu
50                  55                  60

Asn Gly Lys Ile Asn Asn Glu Glu Glu Val Lys Asp Arg Lys Thr Asp
65                  70                  75                  80

His Ala Glu Gly Ile Val Asp Asp Asp Asp Asn Ala Val Lys Lys
                85                  90                  95

Asn Gly Gly Asn Asp Val Ile Asn Asp Arg Glu Asn Val Ala Val Asp
            100                 105                 110

Phe Lys Phe Thr Tyr Arg Pro Ser Val Pro Ala His Arg Arg Ser Lys
        115                 120                 125

Glu Ser Pro Leu Ser Ser Gly Asn Ile Phe Arg Gln Ser His Ala Gly
    130                 135                 140

Leu Phe Asn Leu Cys Ile Val Val Leu Val Ala Val Asn Ser Arg Leu
145                 150                 155                 160

Ile Ile Glu Asn Leu Asn Lys
            165

<210> SEQ ID NO 106
<211> LENGTH: 148
<212> TYPE: PRT
<213> ORGANISM: Jatropha curcas

<400> SEQUENCE: 106

Met Thr Ile Leu Glu Thr Thr Thr Ser Gly Gly Asp Gly Val Ala Glu
1               5                   10                  15

Ser Ser Ser Asp Leu Asn Val Ser Leu Arg Arg Arg Lys Gly Thr
            20                  25                  30

Ser Ser Asp Gly Ala Leu Pro Glu Leu Thr Ser Asn Ile Val Glu Leu
        35                  40                  45

Glu Ser Glu Ser Gly Gly Gln Val Met Met Asp Pro Gly Met Val Thr
50                  55                  60

Glu Pro Glu Thr Glu Lys Ile Asn Gly Lys Asp Cys Gly Gly Asp Lys
65                  70                  75                  80

Asp Lys Ile Asp Asn Arg Glu Asn Arg Gly Arg Ser Asp Ile Lys Phe
                85                  90                  95

Thr Tyr Arg Pro Ser Val Pro Ala His Arg Ala Leu Arg Glu Ser Pro
            100                 105                 110

Leu Ser Ser Asp Ala Ile Phe Lys Gln Ser His Ala Gly Leu Phe Asn
        115                 120                 125

Leu Cys Ile Val Val Leu Val Ala Val Asn Ser Arg Leu Ile Ile Glu
130                 135                 140

Asn Leu Asn Lys
145

<210> SEQ ID NO 107
<211> LENGTH: 153
<212> TYPE: PRT
<213> ORGANISM: Vernicia fordii

<400> SEQUENCE: 107

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
        35                  40                  45

Ile Asp Glu Leu Glu Ser Asp Ala Gly Gly Gln Val Ile Lys Asp
50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
            100                 105                 110

Leu Lys Glu Ser Pro Leu Ser Ser Asp Asn Ile Phe Lys Gln Ser His
        115                 120                 125

Ala Gly Leu Phe Asn Leu Cys Ile Val Val Leu Val Ala Val Asn Ser
130                 135                 140

Arg Leu Ile Ile Glu Asn Ile Asn Lys
145                 150

<210> SEQ ID NO 108
<211> LENGTH: 153
<212> TYPE: PRT
<213> ORGANISM: Vernonia galamensis

<400> SEQUENCE: 108

Met Thr Ile Leu Glu Thr Pro Glu Thr Leu Gly Val Ile Ser Ser Ser
1               5                   10                  15

Ala Thr Ser Asp Leu Asn Leu Ser Leu Arg Arg Arg Arg Thr Ser Asn
            20                  25                  30

Asp Ser Asp Gly Ala Leu Ala Asp Leu Ala Ser Lys Phe Asp Asp Asp
            35                  40                  45

Asp Asp Val Arg Ser Glu Asp Ser Ala Glu Asn Ile Ile Glu Asp Pro
50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
            115                 120                 125

Ala Gly Leu Phe Asn Leu Cys Ile Val Val Leu Val Ala Val Asn Ser
            130                 135                 140

Arg Leu Ile Ile Glu Asn Leu Asn Lys
145                 150

<210> SEQ ID NO 109
<211> LENGTH: 79
<212> TYPE: PRT
<213> ORGANISM: Ricinus communis

<400> SEQUENCE: 109

Met Met Glu Ser Glu Asp Leu Lys Ser Asn Gly Lys Glu Cys Asp Lys
1               5                   10                  15

Val Thr Asn Glu Asn Arg Ser Asp Ile Lys Phe Asn Tyr Arg Pro Ser
            20                  25                  30

Met Pro Ala His Arg Gly Val Arg Glu Ser Pro Leu Ser Ser Asp Ala
            35                  40                  45

Ile Phe Lys Gln Ser His Ala Gly Leu Phe Asn Leu Cys Ile Val Val
50                  55                  60

Leu Val Ala Ile Asn Ser Arg Leu Ile Ile Glu Asn Ile Ile Lys
65                  70                  75

<210> SEQ ID NO 110
<211> LENGTH: 120
<212> TYPE: PRT
<213> ORGANISM: Populus trichocarpa

<400> SEQUENCE: 110

Met Ala Glu Ser Glu Ser Pro Glu Asn Arg Ile Ala Ala Met Glu Ser
1               5                   10                  15

Thr Ser Ser Ser Thr Ser Asp Leu Asn Phe Ser Ile Arg Arg Arg Ser
            20                  25                  30

Thr Val Met Asp Ser Ala Ser Thr Glu Met Met Gly Ser Glu Gly Leu
            35                  40                  45

Lys Ser Ser Gly Lys Ala Cys Asp Lys Val Lys Ile Glu Lys Gln Ser
            50                  55                  60

Asp Met Lys Phe Asn Tyr Arg Pro Ser Met Pro Ala His Ser Gly Val
65                  70                  75                  80

Arg Glu Ser Pro Leu Ser Ser Asp Ala Ile Phe Lys Gln Ser His Ala
            85                  90                  95

Gly Leu Phe Asn Leu Cys Ile Val Val Leu Val Ala Val Asn Ser Arg
            100                 105                 110

Leu Ile Ile Glu Asn Leu Ile Lys
        115                 120

<210> SEQ ID NO 111
<211> LENGTH: 11
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 111

Xaa Leu Xaa Lys Xaa Xaa Ser Xaa Xaa Xaa Val
1               5                   10

<210> SEQ ID NO 112
<211> LENGTH: 6
<212> TYPE: PRT
<213> ORGANISM: Artificial Sequence
<220> FEATURE:
<223> OTHER INFORMATION: Construct

<400> SEQUENCE: 112

Glu Ser Pro Leu Ser Ser
1               5

<210> SEQ ID NO 113
<211> LENGTH: 5
<212> TYPE: PRT
<213> ORGANISM: Artificial Sequence
<220> FEATURE:
<223> OTHER INFORMATION: Construct

<400> SEQUENCE: 113

Met Gly Gly Gly Ser
1               5

<210> SEQ ID NO 114
<211> LENGTH: 18
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(16)

<223> OTHER INFORMATION: Xaa can be any naturally occurring amino acid

<400> SEQUENCE: 114

Xaa Xaa Xaa Glu Ser Pro Leu Ser Ser Xaa Xaa Ile Phe Xaa Xaa Xaa
1               5                   10                  15

His Ala

<210> SEQ ID NO 115
<211> LENGTH: 18
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 115

Xaa Xaa Xaa Glu Ser Pro Leu Ser Ser Xaa Xaa Ile Phe Xaa Xaa Ser
1               5                   10                  15

His Ala

<210> SEQ ID NO 116
<211> LENGTH: 18
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (1)..(1)
<223> OTHER INFORMATION: Xaa is Arg, Lys, Val, Thr, Ala, Ser or Gly
<220> FEATURE:
<221> NAME/KEY: misc_feature
<222> LOCATION: (2)..(2)
<223> OTHER INFORMATION: Xaa is Ala, Thr, Val, Ile, Asn, Arg, Ser or Leu
<220> FEATURE:
<221> NAME/KEY: misc_feature
<222> LOCATION: (3)..(3)
<223> OTHER INFORMATION: Xaa is Arg or Lys
<220> FEATURE:
<221> NAME/KEY: misc_feature
<222> LOCATION: (10)..(10)
<223> OTHER INFORMATION: Xaa is Asp or Gly
<220> FEATURE:
<221> NAME/KEY: misc_feature
<222> LOCATION: (11)..(11)
<223> OTHER INFORMATION: Xaa is Ala, Thr, Asn or Leu
<220> FEATURE:
<221> NAME/KEY: misc_feature
<222> LOCATION: (14)..(14)
<223> OTHER INFORMATION: Xaa is Lys or Arg
<220> FEATURE:
<221> NAME/KEY: misc_feature
<222> LOCATION: (15)..(15)
<223> OTHER INFORMATION: Xaa is Gln or His
<220> FEATURE:
<221> NAME/KEY: misc_feature
<222> LOCATION: (16)..(16)
<223> OTHER INFORMATION: Xaa is Ser or absent

<400> SEQUENCE: 116

Xaa Xaa Xaa Glu Ser Pro Leu Ser Ser Xaa Xaa Ile Phe Xaa Xaa Xaa

```
<210> SEQ ID NO 117
<211> LENGTH: 18
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (1)..(1)
<223> OTHER INFORMATION: Xaa is Arg, Lys, Val, Thr, Ala, Ser or Gly
<220> FEATURE:
<221> NAME/KEY: misc_feature
<222> LOCATION: (2)..(2)
<223> OTHER INFORMATION: Xaa is Ala, Thr, Val, Ile, Asn, Arg, Ser or Leu
<220> FEATURE:
<221> NAME/KEY: misc_feature
<222> LOCATION: (3)..(3)
<223> OTHER INFORMATION: Xaa is Arg or Lys
<220> FEATURE:
<221> NAME/KEY: misc_feature
<222> LOCATION: (10)..(10)
<223> OTHER INFORMATION: Xaa is Asp or Gly
<220> FEATURE:
<221> NAME/KEY: misc_feature
<222> LOCATION: (11)..(11)
<223> OTHER INFORMATION: Xaa is Ala, Thr, Asn or Leu
<220> FEATURE:
<221> NAME/KEY: misc_feature
<222> LOCATION: (14)..(14)
<223> OTHER INFORMATION: Xaa is Lys or Arg
<220> FEATURE:
<221> NAME/KEY: misc_feature
<222> LOCATION: (15)..(15)
<223> OTHER INFORMATION: Xaa is Gln or His

<400> SEQUENCE: 117
```

Xaa Xaa Xaa Glu Ser Pro Leu Ser Ser Xaa Xaa Ile Phe Xaa Xaa Ser
1               5                   10                  15

His Ala

```
<210> SEQ ID NO 118
<211> LENGTH: 521
<212> TYPE: PRT
<213> ORGANISM: Artificial Sequence
<220> FEATURE:
<223> OTHER INFORMATION: Construct

<400> SEQUENCE: 118
```

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
                20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
        50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Arg Gly Gly Gly Glu
                85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe

```
            115                 120                 125
Lys Gln Gln Ser His Ala Gly Leu Phe Asn Leu Cys Val Val Leu
    130                 135                 140

Ile Ala Val Asn Ser Arg Leu Ile Ile Glu Asn Leu Met Lys Tyr Gly
145                 150                 155                 160

Trp Leu Ile Arg Thr Asp Phe Trp Phe Ser Arg Ser Leu Arg Asp
                165                 170                 175

Trp Pro Leu Phe Met Cys Trp Ile Ser Leu Ser Ile Phe Pro Leu Ala
                180                 185                 190

Ala Phe Thr Val Glu Lys Leu Val Leu Gln Lys Tyr Ile Ser Glu Pro
        195                 200                 205

Val Val Ile Phe Leu His Ile Ile Ile Thr Met Thr Glu Val Leu Tyr
    210                 215                 220

Pro Val Tyr Val Thr Leu Arg Cys Asp Ser Ala Phe Leu Ser Gly Val
225                 230                 235                 240

Thr Leu Met Leu Leu Thr Cys Ile Val Trp Leu Lys Leu Val Ser Tyr
                245                 250                 255

Ala His Thr Ser Tyr Asp Ile Arg Ser Leu Ala Asn Ala Ala Asp Lys
                260                 265                 270

Ala Asn Pro Glu Val Ser Tyr Val Ser Leu Lys Ser Leu Ala Tyr
        275                 280                 285

Phe Met Val Ala Pro Thr Leu Cys Tyr Gln Pro Ser Tyr Pro Arg Ser
    290                 295                 300

Ala Cys Ile Arg Lys Gly Trp Val Ala Arg Gln Phe Ala Lys Leu Val
305                 310                 315                 320

Ile Phe Thr Gly Phe Met Gly Phe Ile Ile Glu Gln Tyr Ile Asn Pro
                325                 330                 335

Ile Val Arg Asn Ser Lys His Pro Leu Lys Gly Asp Leu Leu Tyr Ala
                340                 345                 350

Ile Glu Arg Val Leu Lys Leu Ser Val Pro Asn Leu Tyr Val Trp Leu
                355                 360                 365

Cys Met Phe Tyr Cys Phe Phe His Leu Trp Leu Asn Ile Leu Ala Glu
                370                 375                 380

Leu Leu Cys Phe Gly Asp Arg Glu Phe Tyr Lys Asp Trp Trp Asn Ala
385                 390                 395                 400

Lys Ser Val Gly Asp Tyr Trp Arg Met Trp Asn Met Pro Val His Lys
                405                 410                 415

Trp Met Val Arg His Ile Tyr Phe Pro Cys Leu Arg Ser Lys Ile Pro
                420                 425                 430

Lys Thr Leu Ala Ile Ile Ile Ala Phe Leu Val Ser Ala Val Phe His
            435                 440                 445

Glu Leu Cys Ile Ala Val Pro Cys Arg Leu Phe Lys Leu Trp Ala Phe
    450                 455                 460

Leu Gly Ile Met Phe Gln Val Pro Leu Val Phe Ile Thr Asn Tyr Leu
465                 470                 475                 480

Gln Glu Arg Phe Gly Ser Thr Val Gly Asn Met Ile Phe Trp Phe Ile
                485                 490                 495

Phe Cys Ile Phe Gly Gln Pro Met Cys Val Leu Leu Tyr Tyr His Asp
                500                 505                 510

Leu Met Asn Arg Lys Gly Ser Met Ser
                515                 520

<210> SEQ ID NO 119
```

<211> LENGTH: 493
<212> TYPE: PRT
<213> ORGANISM: Artificial Sequence
<220> FEATURE:
<223> OTHER INFORMATION: Construct

<400> SEQUENCE: 119

Met Ala Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
                20                  25                  30

Ser Ala Asp Ala Gly Asp Leu Ala Gly Asp Ser Ser Val Gly Leu Arg
                35                  40                  45

Glu Asn Gly Glu Pro Gln Pro Pro Thr Asn Pro Pro Gln Glu Gln
    50                  55                  60

Gln Gln Gln His Glu Met Leu Tyr Tyr Arg Ala Ser Pro Ala His
65                  70                  75                  80

Arg Arg Val Lys Glu Ser Pro Leu Ser Ser Asp Ala Ile Phe Arg Gln
                85                  90                  95

Ser His Ala Gly Leu Leu Asn Leu Cys Ile Val Val Leu Ile Ala Val
                100                 105                 110

Asn Ser Arg Leu Ile Ile Glu Asn Leu Met Lys Tyr Gly Leu Leu Ile
                115                 120                 125

Arg Ala Gly Phe Trp Phe Ser Ala Arg Ser Leu Gly Asp Trp Pro Leu
    130                 135                 140

Leu Met Cys Trp Leu Thr Leu Pro Val Phe Pro Leu Val Ala Leu Met
145                 150                 155                 160

Ala Glu Lys Leu Ile Thr Arg Lys Leu Ile Gly Glu His Val Val Ile
                165                 170                 175

Leu Leu His Ile Ile Ile Thr Thr Ser Ala Ile Val Tyr Pro Val Val
                180                 185                 190

Val Thr Leu Lys Cys Asp Ser Ala Val Leu Ser Gly Phe Val Leu Met
                195                 200                 205

Phe Leu Ala Ser Ile Met Trp Met Lys Leu Val Ser Tyr Ala His Thr
    210                 215                 220

Asn Tyr Asp Ile Arg Val Leu Ser Lys Ser Thr Glu Lys Gly Ala Ala
225                 230                 235                 240

Tyr Gly Asn Tyr Val Asp Pro Glu Asn Met Lys Asp Pro Thr Phe Lys
                245                 250                 255

Ser Leu Val Tyr Phe Met Leu Ala Pro Thr Leu Cys Tyr Gln Pro Thr
                260                 265                 270

Tyr Pro Gln Thr Thr Cys Ile Arg Lys Gly Trp Val Thr Gln Gln Leu
    275                 280                 285

Ile Lys Cys Val Val Phe Thr Gly Leu Met Gly Phe Ile Ile Glu Gln
    290                 295                 300

Tyr Ile Asn Pro Ile Val Lys Asn Ser Lys His Pro Leu Lys Gly Asn
305                 310                 315                 320

Phe Leu Asn Ala Ile Glu Arg Val Leu Lys Leu Ser Val Pro Thr Leu
                325                 330                 335

Tyr Val Trp Leu Cys Met Phe Tyr Cys Phe Phe His Leu Trp Leu Asn
                340                 345                 350

Ile Val Ala Glu Leu Leu Cys Phe Gly Asp Arg Glu Phe Tyr Lys Asp
    355                 360                 365

Trp Trp Asn Ala Lys Thr Val Glu Glu Tyr Trp Arg Met Trp Asn Met
    370                 375                 380

```
Pro Val His Lys Trp Ile Ile Arg His Ile Tyr Phe Pro Cys Ile Arg
385                 390                 395                 400

Lys Gly Phe Ser Arg Val Ala Ile Leu Ile Ser Phe Leu Val Ser Ala
                405                 410                 415

Val Phe His Glu Ile Cys Ile Ala Val Pro Cys His Ile Phe Lys Phe
            420                 425                 430

Trp Ala Phe Ser Gly Ile Met Phe Gln Ile Pro Leu Val Phe Leu Thr
            435                 440                 445

Arg Tyr Leu His Ala Thr Phe Lys His Val Met Val Gly Asn Met Ile
        450                 455                 460

Phe Trp Phe Phe Ser Ile Val Gly Gln Pro Met Cys Val Leu Leu Tyr
465                 470                 475                 480

Tyr His Asp Val Met Asn Arg Gln Ala Gln Ala Ser Arg
                485                 490

<210> SEQ ID NO 120
<211> LENGTH: 4
<212> TYPE: PRT
<213> ORGANISM: Artificial Sequence
<220> FEATURE:
<223> OTHER INFORMATION: Construct

<400> SEQUENCE: 120

Gly Gly Gly Ser
1

<210> SEQ ID NO 121
<211> LENGTH: 26
<212> TYPE: PRT
<213> ORGANISM: Artificial Sequence
<220> FEATURE:
<223> OTHER INFORMATION: Construct

<400> SEQUENCE: 121

Met Ala Pro Pro Pro Gly Gly Gly Ser Pro Gln Gln Gln Gln Gly Gly
1               5                   10                  15

Gly Ser Gln Gln Gln Gln Gly Gly Gly Ser
            20                  25
```